(12) United States Patent
Arasappan et al.

(10) Patent No.: US 11,802,122 B2
(45) Date of Patent: Oct. 31, 2023

(54) 2-OXOIMIDAZOLIDINE-4-CARBOXAMIDES AS $Na_v1.8$ INHIBITORS

(71) Applicant: Merck Sharp & Dohme Corp., Rahway, NJ (US)

(72) Inventors: Ashok Arasappan, Bridgewater, NJ (US); Ian M. Bell, Harleysville, PA (US); Christopher James Bungard, Lansdale, PA (US); Christopher S. Burgey, Ambler, PA (US); Jason M. Cox, Flemington, NJ (US); Michael J. Kelly, III, Paoli, PA (US); Mark E. Layton, Harleysville, PA (US); Hong Liu, Hillsborough, NJ (US); Jian Liu, Edison, NJ (US); James J. Perkins, Churchville, PA (US); Akshay A. Shah, Robbinsville, NJ (US); Michael David VanHeyst, Harleysville, PA (US); Zhe Wu, Blue Bell, PA (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 0 days.

(21) Appl. No.: 17/347,639

(22) Filed: Jun. 15, 2021

(65) Prior Publication Data
US 2021/0403457 A1 Dec. 30, 2021

Related U.S. Application Data

(60) Provisional application No. 63/040,461, filed on Jun. 17, 2020.

(51) Int. Cl.

| | |
|---|---|
| *C07D 403/12* | (2006.01) |
| *C07D 233/32* | (2006.01) |
| *C07D 401/12* | (2006.01) |
| *C07D 401/14* | (2006.01) |
| *C07D 405/12* | (2006.01) |
| *C07D 413/12* | (2006.01) |
| *C07D 417/12* | (2006.01) |
| *C07D 417/14* | (2006.01) |
| *C07D 471/04* | (2006.01) |
| *C07D 471/08* | (2006.01) |
| *C07D 513/04* | (2006.01) |
| *A61K 31/4166* | (2006.01) |
| *A61P 25/00* | (2006.01) |
| *A61P 25/04* | (2006.01) |
| *A61P 29/00* | (2006.01) |

(52) U.S. Cl.
CPC ......... *C07D 403/12* (2013.01); *C07D 233/32* (2013.01); *C07D 401/12* (2013.01); *C07D 401/14* (2013.01); *C07D 405/12* (2013.01); *C07D 413/12* (2013.01); *C07D 417/12* (2013.01); *C07D 417/14* (2013.01); *C07D 471/04* (2013.01); *C07D 471/08* (2013.01); *C07D 513/04* (2013.01)

(58) Field of Classification Search
CPC .. C07D 403/12; C07D 233/32; C07D 401/12; C07D 401/14; C07D 405/12; C07D 413/12; C07D 417/12; C07D 417/14; C07D 471/04; C07D 471/08; C07D 513/04; A61K 31/4166; A61P 25/00; A61P 25/04; A61P 29/00
See application file for complete search history.

(56) References Cited

U.S. PATENT DOCUMENTS

| | | |
|---|---|---|
| 8,519,137 B2 | 8/2013 | Joshi et al. |
| 8,629,149 B2 | 1/2014 | Pajouhesh et al. |
| 9,051,270 B2 | 6/2015 | Hadida-Ruah et al. |

(Continued)

FOREIGN PATENT DOCUMENTS

| | | |
|---|---|---|
| EP | 3470404 A1 | 4/2019 |
| WO | 2008119825 A2 | 10/2008 |

(Continued)

OTHER PUBLICATIONS

Aoldin et al., Nomenclature of Voltage-Gated Sodium Channels, Neuron, 2000, 365-368, 28.

(Continued)

*Primary Examiner* — Bruck Kifle
(74) *Attorney, Agent, or Firm* — Baerbel R. Brown; Catherine D. Fitch

(57) ABSTRACT

Novel compounds of the structural formula (I), and the pharmaceutically acceptable salts thereof, are inhibitors of $Na_v1.8$ channel activity and may be useful in the treatment, prevention, management, amelioration, control and suppression of diseases mediated by $Na_v1.8$ channel activity. The compounds of the present invention may be useful in the treatment, prevention or management of pain disorders, cough disorders, acute itch disorders, and chronic itch disorders.

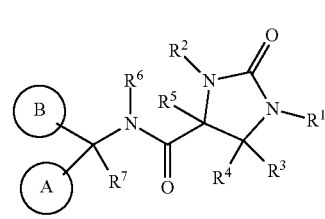

46 Claims, No Drawings

(56) References Cited

U.S. PATENT DOCUMENTS

| | | | |
|---|---|---|---|
| 9,108,903 | B2 | 8/2015 | Hadida-Ruah et al. |
| 9,163,042 | B2 | 10/2015 | Anderson et al. |
| 9,783,501 | B2 | 10/2017 | Hadida-Ruah et al. |
| 10,723,720 | B2 * | 7/2020 | Ashcraft .............. C07D 401/12 |
| 2016/0068541 | A1 | 3/2016 | Levine et al. |

FOREIGN PATENT DOCUMENTS

| | | | |
|---|---|---|---|
| WO | 2009049180 | A2 | 4/2009 |
| WO | 2009049181 | A1 | 4/2009 |
| WO | 2009049183 | A1 | 4/2009 |
| WO | 2011026240 | A1 | 3/2011 |
| WO | 2012177893 | A2 | 12/2012 |
| WO | 2012177896 | A1 | 12/2012 |
| WO | 2014120808 | A1 | 8/2014 |
| WO | 2014120815 | A1 | 8/2014 |
| WO | 2014120820 | A1 | 8/2014 |
| WO | 2015010065 | A1 | 1/2015 |
| WO | 2015089361 | A1 | 6/2015 |
| WO | 2017209322 | A1 | 12/2017 |
| WO | 2018213426 | A1 | 11/2018 |
| WO | 2019014352 | A1 | 1/2019 |
| WO | 2020092667 | A1 | 5/2020 |

OTHER PUBLICATIONS

Bagal, Sharan K. et al., Discovery and Optimization of Selective Nav1.8 Modulator Series That Demonstrate Efficacy in Preclinical Models of Pain, ACS Med. Chem. Lett., 2015, 650-654, 6.
Belkouch, Mounir et al., Functional up-regulation of Nav1.8 sodium channel in Aβ afferent fibers subjected to chronic peripheral inflammation, Journal of Neuroinflammation, 2014, 1-17, 11:45.
Bennett, David L. et al., Painful and painless channelopathies, Lancet Neurol., 2014, 587-599, 13(6).
Black, Joel A. et a., Multiple Sodium Channel Isoforms and Mitogen-Activated Protein Kinases Are Present in Painful Human Neuromas, Ann Neurol, 2008, 644-653, 64(6).
Carter et al., Advances in the Management of Neuropathic Pain, Physical Medicine and Rehabilitation Clinics of North America, 2001, 447-459, 12(2).
Catterall, William A. et al., The chemical basis for electrical signaling, Nature Chemical Biology, 2017, 455-463, 13(5).
Coward, K et al., Immunolocalizationof SNS/PN3 and NaN/SNS2 sodium channels in human pain states, Pain, 2000, 41-50, 85.
Emery, Edward C. et al., Novel SCN9A Mutations Underlying Extreme Pain Phenotypes: Unexpected Electrophysiological and Clinical Phenotype Correlations, Journal of Neuroscience, 2015, 7674-7681, 35(20).
Flaxman et al., Years Lived with Disability (YLDs) for 1160 Sequelae of 289 Diseases and Injuries 1990-2010: A Systematic Analysis for the Global Burden of Disease Study 2010, Lancet, 2012, 2163-2196, 380.
Goldin, Diveristy of Mammalian Voltage-Gated Sodium Channels, Ann NY Acad Sci., 1999, 38-50, 30, 868.
Han, Chongyang et al., The G1662S NaV1.8 mutation in small fibre neuropathy: impaired inactivation underlying DRG neuron hyperexcitability, J Neurol Neurosurg Psychiatry, 2014, 499-505, 85(5).
Han, Chongyang, et al., Sodium channel Nav1.8, Emerging links to human disease, Neurology, 2016, 473-483, 86.
Huang, Jianying et al., Small-Fiber Neuropathy Nav1.8 Mutation Shifts Activation to Hyperpolarized Potentials and Increases Excitability of Dorsal Root Ganglion Neurons, Journal of Neuroscience, 2013, 14087-14097, 33(35).
Jarvis, Michael F. et al., A-803467, a potent and selective Nav1.8 sodium channel blocker, attenuates neuropathic and inflammatory pain in the rat, PNAS, 2007, 8520-8525, 104.
Kist, Andreas M. et al., SCN10A Mutation in a Patient with Erythromelalgia Enhances C-Fiber Activity Dependent Slowing, PLOS One, 2016, pp. 1-19, 11(9):e0161789.
Kort, Michael E. et al., Discovery and Biological Evaluation of 5-Aryl-2-furfuramides, Potent and Selective Blockers of the Nav1.8 Sodium Channel with Efficacy in Models of Neuropathic and Inflammatory Pain, J. Med. Chem., 2008, 407-416, 51.
Liu, Yang et al., VGLUT2-Dependent Glutamate Release from Nociceptors Is Required to Sense Pain and Suppress Itch, Neuron, 2010, 543-556, 68(3).
McGaraughty, Steve et al., A Selective Nav1.8 Sodium Channel Blocker, A-803467 [5-(4-Chlorophenyl-N-(3,5-dimethoxyphenyl)furan-2-carboxamide], Attenuates Spinal Neuronal Activity in Neuropathic Rats, JPET, 2008, 1204-1211, 324.
Payne, Claire Elizabeth et al., A novel selective and orally bioavailable NAv1.8 channel blocker, PF-01247324, attenuates nociception and sensory neuron excitability, British Journal of Pharmacology, 2015, 2654-2670, 172.
Schreiber, Anne K. et al., Diabetic neuropathic pain: Physiopathology and treatment, World Journal of Diabetes, 2015, 432-444, 6(3).
Yiangou, Y. et al., SNS/PN3 and SNS2/NaN sodium channel-like immunoreactivity in human adult and neonate injured sensory nerves, FEBS Letters, 2000, 249-252, 467.
Yu et al., Overview of the Voltage-Gated Sodium Channel Family, Genome Biology, 2003, 207, 4.
Zeng, Chao et al., Relative efficacy and safety of topical non-steroidal anti-inflammatory drugs for osteoarthritis: a systematic review and network meta-analysis of randomised controlled trials and observational studies, Br J Sports Med, 2018, 642-650, 52.
Zhang, Xu-Feng et al., A-887826 is a structurally novel, potent and voltage-dependent Nav1.8 sodium channel blocker that attenuates neuropathic tactile allodynia in rats, Neuropharmacology, 2010, 201-207, 59.
International Preliminary Report on Patentability for PCT/US21/37303 dated Dec. 13, 2022, 7 pages.

* cited by examiner

2-OXOIMIDAZOLIDINE-4-CARBOXAMIDES AS NA$_v$1.8 INHIBITORS

CROSS-REFERENCE TO RELATED APPLICATIONS

This application is a U.S. Non Provisional application which claims priority from and the benefit of U.S. Provisional Application No. 63/040,461, filed Jun. 17, 2020.

BACKGROUND OF THE INVENTION

Voltage-gated sodium channels (VGSC) mediate the selective influx of sodium ions in excitable cells and play a central role in initiating and propagating action potentials (Yu et al., Genome Biology 4:207 (2003)). Voltage-gated sodium channels are ubiquitous in the central and peripheral nervous system where they play a central role in the initiation and propagation of action potentials, and also in skeletal and cardiac muscle where the action potential triggers cellular contraction (Goldin et al., Ann NY Acad Sci. 1999 Apr. 30; 868:38-50). Alterations in VGSC function or their expression can profoundly affect normal cell excitability (Huang et al., J Neurosci. 2013 Aug. 28; 33 (35):14087-97; Emery et al., J Neurosci. 2015 May 20; 35(20):7674-81; Kist et al., PLoS One. 2016 Sep. 6; 11(9):e0161789; and Schreiber et al., World J Diabetes. 2015 Apr. 15; 6(3):432-44).

Voltage-gated sodium channels are multimeric complexes characterized by one α-subunit, which forms an ion-conducting aqueous pore, and at least one β-subunit that modifies the kinetics and voltage-dependence of the channel gating. Nine different α-subunits have been identified and characterized in mammalian voltage-gated sodium channels, including Na$_v$1.8, also known as SNS, PN3 or Na$_v$1.8 (Goldin et al., Neuron. 2000 November; 28 (2):365-8).

Expression of sodium channels can be tissue specific. Na$_v$1.8 voltage-gated sodium ion channels are expressed primarily in sensory neurons, which are responsible for conveying information from the periphery (e.g. skin, muscle and joints) to the central nervous system via the spinal cord. Sodium channels are integral to this process as sodium channel activity is required for initiation and propagation of action potentials triggered by noxious stimuli (thermal, mechanical and chemical) activating peripheral nociceptors (Catterall et al., Nat Chem Biol. 2017 Apr. 13; 13(5):455-463). An increase in VGSC protein level at the cell surface or an alteration in activity of the VGSC channels can result in disease states such as migraine, neurodegeneration following ischemia, epilepsies, and chronic neuropathic and inflammatory pain states. Gain of function mutations in Na$_V$1.7, Na$_V$1.8, and Na$_V$1.9 manifest in a variety of pain syndromes where patients experience spontaneous pain without an external stimulus (Bennett et al., Lancet Neurol. 2014 June; 13(6):587-99; Huang et al., J Neurosci. 2013 Aug. 28; 33(35):14087-97; Kist et al., PLoS One. 2016 Sep. 6; 11(9):e0161789; Emery et al., J Neurosci. 2015 May 20; 35(20):7674-81; and Schreiber et al., World J Diabetes. 2015 Apr. 15; 6(3):432-44).

Na$_v$1.8 voltage-gated sodium ion channels are believed to play a role in various maladies, including neuropathic pain, chronic itch, and inflammatory pain perception (Belkouch et al., J Neuroinflammation. 2014 Mar. 7; 11:45; Coward et al., Pain. 2000 March; 85(1-2):41-50; Yiangou et al., FEBS Lett. 2000 Feb. 11; 467(2-3):249-52; Black et al., Ann Neurol. 2008 December; 64(6):644-53; Bird et al., Br J Pharmacol. 2015 May; 172(10):2654-70; Liu et al., Neuron. 2010 Nov. 4; 68(3):543-56; and Zhao et al., J Clin Invest. 2013).

Large portions of the voltage gated sodium ion channels are conserved among the various subtypes, therefore there is a potential for producing serious side effects when utilizing therapeutic agents that do not demonstrate subtype selectivity. Therefore, therapeutic agents suitable for use in addressing nociception, cough, or itch disorders, require specificity in their action, for example, discriminating between action upon Na$_v$1.5 sodium ion channels, thought to be important in regulation of cardiac function, and action upon Na$_v$1.8 sodium ion channels, thought to be central in inflammatory nociception, or itch and disorders arising from dysfunctional and/or upregulated Na$_v$1.8 sodium ion channels.

Accordingly, it is believed that inhibitors of Na$_v$1.8 voltage-gated sodium ion channel activity may useful to treat or prevent diseases, disorders and conditions involving Na$_v$1.8 receptors and/or stemming specifically from dysfunction of Na$_v$1.8 voltage-gated sodium ion channels (Han et al., J Neurol Neurosurg Psychiatry 2014 May; 85(5):499-505), including but not limited to, migraine, neurodegeneration following ischemia, epilepsy, inflammatory pain, spontaneous pain, acute pain, preoperative pain, perioperative pain, post-operative pain, neuropathic pain, chronic itch, and itch disorders.

There remains a need for potent Na$_v$1.8 sodium ion channel activity inhibitors with selective activity for Na$_v$1.8 sodium ion channels. As a result, the compounds of the present invention are useful for the treatment and prevention of diseases, disorders and conditions involving Na$_v$1.8 receptors and Na$_v$1.8 voltage-gated sodium ion channels.

The role of Nav1.8 sodium ion channels is discussed in: Bennett et al., Physical Medicine and Rehabilitation Clinics of North America, 2001, 12(2):447-459; Meissner et al., Br J Sports Med. 2018 May; 52(10):642-650; Legroux-Crespel et al., Neurology. 2016 Feb. 2; 86(5):473-83; and Flaxman et al., Lancet, 380:2163-2196 (2012).

Compounds useful to treat Na$_v$1.8 sodium ion channel related conditions are disclosed in: ACS Med. Chem. Lett. 2015, 6, 650; BJP 2015, 172, 2654; PNAS 2007, 104, 8520; J. Med. Chem. 2008, 51, 407; JPET 2008, 324, 1204; and Neuropharmacology 2010, 59, 201.

Na$_v$1.8 compounds are also disclosed in: WO 2009/049180, WO 2009/049181, WO 2009/049183, WO 2014/120808; WO 2014/120815; WO 2014/120820; WO 2015/010065; and WO 2015/089361; WO 2017/209322; U.S. Pat. Nos. 8,519,137; 9,051,270; 9,108,903; 9,163,042; 9,783,501; WO 2020/092667; WO2019/014352; WO2018/213426; U.S. Pat. No. 8,629,149; and WO2011/026240.

SUMMARY OF THE INVENTION

The present invention relates to novel compounds of structural formula I:

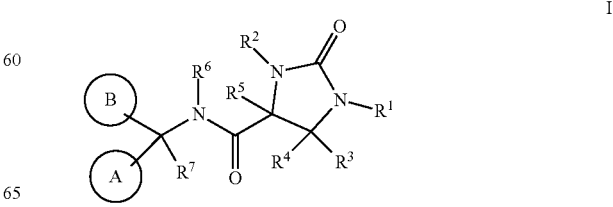

I and pharmaceutically acceptable salts thereof. The compounds of structural formula I, and embodiments thereof, are inhibitors of $Na_v1.8$ sodium ion channel activity (or $Na_v1.8$ inhibitors) and may be useful in the treatment and prevention of diseases, disorders and conditions mediated by $Na_v1.8$ sodium ion channel activity, such as nociception, osteoarthritis, peripheral neuropathy, inherited erythromelalgia, multiple sclerosis, asthma, itch, atopy, allergic or contact dermatitis, renal failure, cholestasis, pruritus, acute itch, chronic itch, migraine, neurodegeneration following ischemia, epilepsy, pain, inflammatory pain, spontaneous pain, acute pain, acute pain due to fractures, musculoskeletal damage, pancreatitis and renal colic, pen-operative pain, post-operative pain, neuropathic pain, postherpetic neuralgia, trigeminal neuralgia, diabetic neuropathy, chronic lower back pain, phantom limb pain, sciatica, pain caused by 2° or 3° burn injury, optic neuritis, pain resulting from cancer and chemotherapy, chronic pelvic pain, pain syndromes, and complex regional pain syndromes. In one embodiment of the present invention, the condition, disease or disorder is a pain disorder, an acute pain disorder or chronic pain disorder. In another embodiment of the present invention, the condition, disease or disorder is an acute pain disorder.

The present invention also relates to pharmaceutical compositions comprising the compounds of the present invention and a pharmaceutically acceptable carrier.

The present invention also relates to methods for the treatment, management, prevention, alleviation, amelioration, suppression or control of disorders, diseases, and conditions that may be responsive to inhibition of $Na_v1.8$ sodium ion channel activity in a subject in need thereof by administering the compounds and pharmaceutical compositions of the present invention.

The present invention also relates to the use of compounds of the present invention for manufacture of a medicament useful in treating diseases, disorders and conditions that may be responsive to the inhibition of $Na_v1.8$ sodium ion channel activity.

The present invention is also concerned with treatment or prevention of these diseases, disorders and conditions by administering the compounds of the present invention in combination with a therapeutically effective amount of another agent that may be useful to treat the disease, disorder and condition. The invention is further concerned with processes for preparing the compounds of this invention.

DETAILED DESCRIPTION OF THE INVENTION

The present invention is concerned with novel compounds of structural Formula I:

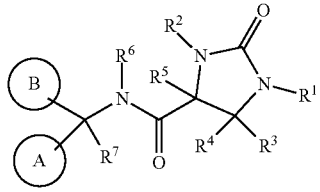

I or a pharmaceutically acceptable salt thereof, wherein
one of A and B is selected from:
1) aryl, and
2) heteroaryl, wherein aryl and heteroaryl are unsubstituted or substituted with one to five substituents selected from $R^a$, and
the other of A and B is selected from:
1) aryl,
2) heteroaryl,
3) —$C_{1-6}$alkyl-aryl,
4) —$C_{3-8}$cycloalkyl-aryl,
5) —$C_{2-8}$cycloheteroalkyl-aryl,
6) —$C_{1-6}$alkyl-heteroaryl,
7) —$C_{3-8}$cycloalkyl-heteroaryl,
8) —$C_{2-8}$cycloheteroalkyl-heteroaryl,
9) —$C_{1-6}$alkyl-O-aryl,
10) —$C_{1-6}$alkyl-O-heteroaryl,
11) —$C_{3-12}$cycloalkyl,
12) —$C_{2-12}$cycloheteroalkyl,
13) —$C_{1-6}$alkyl-$C_{3-12}$cycloalkyl,
14) —$C_{1-6}$alkyl-$C_{2-12}$cycloheteroalkyl,
15) —$C_{1-6}$alkyl-O—$C_{3-12}$cycloalkyl,
16) —$C_{1-6}$alkyl-O—$C_{2-12}$cycloheteroalkyl,
17) —$C_{0-6}$alkyl-aryl fused to a $C_{4-6}$cycloalkyl or $C_{4-6}$cycloheteroalkyl containing 1-3 heteroatoms independently selected from O, S and $N(R^h)_2$,
18) —$C_{0-6}$alkyl-aryl fused to a $C_{4-6}$cycloalkenyl or $C_{4-6}$cycloheteroalkenyl containing 1-3 heteroatoms independently selected from O, S and $N(R^h)_2$,
19) —$C_{0-6}$alkyl-heteroaryl fused to $C_{4-6}$cycloalkyl or $C_{4-6}$cycloheteroalkyl containing 1-3 heteroatoms independently selected from O, S and $N(R^h)_2$, and
20) —$C_{0-6}$alkyl-heteroaryl fused to $C_{4-6}$cycloalkenyl or $C_{4-6}$cycloheteroalkenyl containing 1-3 heteroatoms independently selected from O, S and $N(R^h)_2$, wherein alkyl, cycloalkyl, cycloheteroalkyl, cycloalkenyl, aryl and heteroaryl are unsubstituted or substituted with one to five substituents selected from $R^b$;

$R^1$ is selected from the group consisting of:
1) hydrogen,
2) —$C_{1-6}$alkyl,
3) —$C_{3-6}$alkenyl,
4) —$C_{3-6}$alkynyl,
5) —$C_{3-10}$cycloalkyl,
6) —$C_{2-10}$cycloheteroalkyl,
7) —$C_{1-6}$alkyl-O—$C_{1-6}$alkyl-,
8) —$(CH_2)_sC(O)R^j$,
9) —$(CH_2)_sC(O)NR^eR^j$,
10) —$(CH_2)_nNR^eC(O)R^j$,
11) —$(CH_2)_nNR^eC(O)OR^j$,
12) —$(CH_2)_nNR^eC(O)N(R^e)_2$,
13) —$(CH_2)_nNR^eC(O)NR^eR^j$,
14) —$(CH_2)_nNR^eS(O)_mR^j$,
15) —$(CH_2)_nNR^eS(O)mN(R^e)_2$,
16) —$(CH_2)_nNR^eS(O)mNR^eR^j$, and
17) —$(CH_2)_nNR^eR^j$, wherein each $CH_2$, alkyl, alkenyl, alkynyl, cycloalkyl and cycloheteroalkyl is unsubstituted or substituted with one to five substituents selected from $R^c$;

$R^2$ is selected from the group consisting of:
1) hydrogen,
2) —$C_{1-6}$alkyl,
3) —$C_{3-6}$alkenyl,
4) —$C_{3-6}$alkynyl,
5) —$C_{3-10}$cycloalkyl,
6) —$C_{2-10}$cycloheteroalkyl,
7) —$C_{1-6}$alkyl-O—$C_{1-6}$alkyl-,
8) —$(CH_2)_sC(O)R^j$,
9) —$(CH_2)_sC(O)NR^eR^j$,
10) —$(CH_2)_nNR^eC(O)R^j$,
11) —$(CH_2)_nNR^eC(O)OR^j$, 12) —$(CH_2)_nNR^eC(O)N(R^e)_2$,
13) —$(CH_2)_nNR^eC(O)NR^eR^j$,
14) —$(CH_2)_nNR^eS(O)_mR^j$,
15) —$(CH_2)_nNR^eS(O)mN(R^e)_2$,
16) —$(CH_2)_nNR^eS(O)mNR^eR^j$, and
17) —$(CH_2)_nNR^eR^j$, wherein each $CH_2$, alkyl, alkenyl, alkynyl, cycloalkyl, and cycloheteroalkyl is unsubstituted or substituted with one to five substituents selected from $R^d$;

$R^3$ is selected from the group consisting of:
1) hydrogen,
2) —$C_{1-6}$alkyl,
3) —$C_{2-6}$alkenyl,
4) —$C_{2-6}$alkynyl,
5) —$C_{3-10}$cycloalkyl,
6) —$C_{2-10}$cycloheteroalkyl,
7) —$C_{1-6}$alkyl-O—$C_{1-6}$alkyl-,
8) —$(CH_2)_sC(O)R^j$,
9) —$(CH_2)_sC(O)NR^eR^j$,
10) —$(CH_2)_sNR^eC(O)R^j$,
11) —$(CH_2)_sNR^eC(O)OR^j$,
12) —$(CH_2)_sNR^eC(O)N(R^e)_2$,
13) —$(CH_2)_sNR^eC(O)NR^eR^j$,
14) —$(CH_2)_sNR^eS(O)_mR^j$,
15) —$(CH_2)_sNR^eS(O)mN(R^e)_2$,
16) —$(CH_2)_sNR^eS(O)mNR^eR^j$, and
17) —$(CH_2)_sNR^eR^j$, wherein each $CH_2$, alkyl, alkenyl, alkynyl, cycloalkyl, and cycloheteroalkyl is unsubstituted or substituted with one to five substituents selected from $R^f$, and wherein $R^3$ and $R^4$ and the carbon atoms they are connected to can from a —$C_{3-5}$cycloalkyl ring;

$R^4$ is selected from the group consisting of:
1) hydrogen,
2) —$C_{1-6}$alkyl,
3) —$C_{2-6}$alkenyl,
4) —$C_{2-6}$alkynyl,
5) —$C_{3-10}$cycloalkyl,
6) —$C_{2-10}$cycloheteroalkyl,
7) —$C_{1-6}$alkyl-O—$C_{1-6}$alkyl-,
8) —$(CH_2)_sC(O)R^j$,
9) —$(CH_2)_sC(O)NR^eR^j$,
10) —$(CH_2)_sNR^eC(O)R^j$,
11) —$(CH_2)_sNR^eC(O)OR^j$,
12) —$(CH_2)_sNR^eC(O)N(R^e)_2$,
13) —$(CH_2)_sNR^eC(O)NR^eR^j$,
14) —$(CH_2)_sNR^eS(O)_mR^j$,
15) —$(CH_2)_sNR^eS(O)mN(R^e)_2$,
16) —$(CH_2)_sNR^eS(O)mNR^eR^j$, and
17) —$(CH_2)_sNR^eR^j$, wherein each $CH_2$, alkyl, alkenyl, alkynyl, cycloalkyl, and cycloheteroalkyl is unsubstituted or substituted with one to five substituents selected from $R^g$;

$R^5$ is selected from the group consisting of:
1) hydrogen, and
2) —$C_{1-6}$alkyl, wherein each alkyl is unsubstituted or substituted with one to five halogen substituents;

$R^6$ is selected from the group consisting of:
1) hydrogen,
2) —$C_{1-6}$alkyl,
3) —$C_{3-6}$cycloalkyl, and
4) —$C_{2-6}$cycloheteroalkyl, wherein each alkyl, cycloalkyl and cycloheteroalkyl is unsubstituted or substituted with one to five halogen substituents;

$R^7$ is selected from the group consisting of:
1) hydrogen,
2) —$C_{1-6}$alkyl,
3) —$C_{2-6}$alkenyl, and
4) —$C_{2-6}$alkynyl, wherein each alkyl, alkenyl and alkynyl is unsubstituted or substituted with one to five halogen substituents;

each $R^a$ is independently selected from the group consisting of:
1) —$CF_3$,
2) —$OCF_3$,
3) —$CHF_2$,
4) —$OCHF_2$,
5) —$CH_2CF_3$,
6) —$OCH_2CF_3$,
7) —$CF_2CH_3$,
8) CN,
9) oxo,
10) halogen,
11) —$S(O)_2C_{1-6}$alkyl,
12) —$C_{1-6}$alkyl,
13) —$C_{2-6}$alkenyl,
14) —$C_{2-6}$alkynyl,
15) —$C_{3-6}$cycloalkyl,
16) —$C_{2-6}$cycloheteroalkyl,
17) aryl,
18) heteroaryl,
19) —$C_{1-6}$alkyl-aryl,
20) —$C_{1-6}$alkyl-heteroaryl,
21) —$C_{1-6}$alkyl-$C_{3-6}$cycloalkyl,
22) —$C_{1-6}$alkyl-$C_{2-6}$cycloheteroalkyl,
23) —$C_{2-6}$alkenyl-$C_{3-6}$cycloalkyl,
24) —$C_{2-6}$alkenyl-$C_{2-6}$cycloheteroalkyl,
25) —$C_{2-6}$alkenyl-aryl,
26) —$C_{2-6}$alkenyl-heteroaryl,
27) —$C_{2-6}$alkynyl-$C_{3-6}$cycloalkyl,
28) —$C_{2-6}$alkynyl-$C_{2-6}$cycloheteroalkyl,
29) —$C_{2-6}$alkynyl-aryl,
30) —$C_{2-6}$alkynyl-heteroaryl,
31) —OH,
32) —$(CH_2)_p$—$OC_{1-6}$alkyl,
33) —$(CH_2)_p$—$OC_{2-6}$alkenyl,
34) —$(CH_2)_p$—$OC_{2-6}$alkynyl,
35) —$(CH_2)_p$—$OC_{3-6}$cycloalkyl,
36) —$(CH_2)_p$—$OC_{2-6}$heterocycloalkyl,
37) —$(CH_2)_p$—O-aryl,
38) —$(CH_2)_p$—O-heteroaryl,
39) —$OC_{1-6}$alkyl-$C_{3-6}$cycloalkyl,
40) —$OC_{1-6}$alkyl-$C_{2-6}$heterocycloalkyl,
41) —$OC_{1-6}$alkyl-aryl,
42) —$OC_{1-6}$alkyl-heteroaryl,
43) —$S(O)_mR^i$,
44) —$C_{1-6}$alkyl-$S(O)_mR^i$,
45) —$N(R^k)_2$, and
46) —$NR^kR^l$, wherein each $R^a$ is unsubstituted or substituted with one to six substituents selected from halogen, $CF_3$, OH, $C_{1-6}$alkyl, and —$OC_{1-6}$alkyl;

each $R^b$ is independently selected from the group consisting of:
1) —$CF_3$,
2) —$OCF_3$,
3) —$CHF_2$,
4) —$OCHF_2$,
5) —$CH_2CF_3$,
6) —$OCH_2CF_3$,
7) —$CF_2CH_3$,
8) CN, 9) oxo,
10) halogen,
11) —S(O)$_2$C$_{1-6}$alkyl,
12) —C$_{1-6}$alkyl,
13) —C$_{2-6}$alkenyl,
14) —C$_{2-6}$alkynyl,
15) —O—C$_{1-6}$alkyl,
16) —C$_{3-6}$cycloalkyl,
17) —O—C$_{3-6}$cycloalkyl,
18) —C$_{2-6}$cycloheteroalkyl,
19) aryl,
20) heteroaryl,
21) —C$_{1-6}$alkyl-aryl,
22) —C$_{1-6}$alkyl-heteroaryl,
23) —C$_{1-6}$alkyl-C$_{3-6}$cycloalkyl,
24) —C$_{1-6}$alkyl-C$_{2-6}$cycloheteroalkyl,
25) —C$_{2-6}$alkenyl-C$_{3-6}$cycloalkyl,
26) —C$_{2-6}$alkenyl-C$_{2-6}$cycloheteroalkyl,
27) —C$_{2-6}$alkenyl-aryl,
28) —C$_{2-6}$alkenyl-heteroaryl,
29) —C$_{2-6}$alkynyl-C$_{3-6}$cycloalkyl,
30) —C$_{2-6}$alkynyl-C$_{2-6}$cycloheteroalkyl,
31) —C$_{2-6}$alkynyl-aryl,
32) —C$_{2-6}$alkynyl-heteroaryl,
33) —OH,
34) —(CH$_2$)$_q$—OC$_{1-6}$alkyl,
35) —(CH$_2$)$_q$—OC$_{2-6}$alkenyl,
36) —(CH$_2$)$_q$—OC$_{2-6}$alkynyl,
37) —(CH$_2$)$_q$—OC$_{3-6}$cycloalkyl,
38) —(CH$_2$)$_q$—OC$_{2-6}$heterocycloalkyl,
39) —(CH$_2$)$_q$—O-aryl,
40) —(CH$_2$)$_q$—O-heteroaryl,
41) —OC$_{1-6}$alkyl-C$_{3-6}$cycloalkyl,
42) —OC$_{1-6}$alkyl-C$_{2-6}$heterocycloalkyl,
43) —OC$_{1-6}$alkyl-aryl,
44) —OC$_{1-6}$alkyl-heteroaryl,
45) —S(O)$_m$R$^i$,
46) —C$_{1-6}$alkyl-S(O)$_m$R$^i$,
47) —C(O)R$^L$, and
48) —NR$^k$R$^L$,
wherein each R$^b$ is unsubstituted or substituted with one to six substituents selected from halogen, CF$_3$, OCF$_3$, CN, CH$_2$CF$_3$, CF$_2$CH$_3$, —C$_{1-6}$alkyl, and —OC$_{1-6}$alkyl;
R$^c$ is selected from:
1) —C$_{1-6}$alkyl,
2) OH,
3) halogen, and
4) —OC$_{1-6}$alkyl,
wherein alkyl can be unsubstituted or substituted with one to three halogens;
R$^d$ is selected from:
1) —C$_{1-6}$alkyl,
2) OH,
3) halogen, and
4) —OC$_{1-6}$alkyl,
wherein alkyl can be unsubstituted or substituted with one to three halogens;
R$^e$ is selected from:
1) hydrogen, and
2) C$_{1-6}$alkyl;
R$^f$ is selected from:
1) —C$_{1-6}$alkyl,
2) OH,
3) halogen, and
4) —OC$_{1-6}$alkyl,
wherein alkyl can be unsubstituted or substituted with one to three halogens;

R$^g$ is selected from:
1) —C$_{1-6}$alkyl,
2) OH,
3) halogen, and
4) —OC$_{1-6}$alkyl,
wherein alkyl can be unsubstituted or substituted with one to three halogens;
R$^h$ is selected from:
1) hydrogen, and
2) C$_{1-6}$alkyl;
R$^i$ is selected from:
1) hydrogen,
2) C$_{1-6}$alkyl,
3) C$_{3-6}$cycloalkyl,
4) aryl, and
5) heteroaryl;
R$^j$ is selected from:
1) hydrogen,
2) C$_{1-6}$alkyl,
3) C$_{3-6}$alkenyl,
4) C$_{3-6}$alkynyl,
5) C$_{3-6}$cycloalkyl,
6) C$_{2-5}$cycloheteroalkyl,
7) aryl, and
8) heteroaryl;
R$^k$ is selected from:
1) hydrogen, and
2) C$_{1-6}$alkyl;
R$^L$ is selected from:
1) hydrogen,
2) C$_{1-6}$alkyl,
3) C$_{3-6}$cycloalkyl,
4) aryl, and
5) heteroaryl;
m is independently selected from 0 to 2;
n is independently selected from 2 to 6;
p is independently selected from 0 to 3;
q is independently selected from 0 to 3;
r is independently selected from 0 to 2; and
s is independently selected from 0 to 6.

The invention has numerous embodiments, which are summarized below. The invention includes the compounds as shown, and also includes individual diastereoisomers, enantiomers, and epimers of the compounds, and mixtures of diastereoisomers and/or enantiomers thereof including racemic mixtures.

In another embodiment of the present invention, one of A and B is selected from: aryl, and heteroaryl, wherein aryl and heteroaryl are unsubstituted or substituted with one to five substituents selected from R$^a$, and the other of A and B is selected from: aryl, heteroaryl, —C$_{1-6}$alkyl-aryl, —C$_{3-8}$cycloalkyl-aryl, —C$_{2-8}$cycloheteroalkyl-aryl, —C$_{1-6}$alkyl-heteroaryl, —C$_{3-8}$cycloalkyl-heteroaryl, —C$_{2-8}$cycloheteroalkyl-heteroaryl, —C$_{1-6}$alkyl-O-aryl, —C$_{1-6}$alkyl-O-heteroaryl, —C$_{3-12}$cycloalkyl, —C$_{2-12}$cycloheteroalkyl, —C$_{1-6}$alkyl-C$_{3-12}$cycloalkyl, —C$_{1-6}$alkyl-C$_{2-12}$cycloheteroalkyl, —C$_{1-6}$alkyl-O—C$_{3-12}$cycloalkyl, —C$_{1-6}$alkyl-O—C$_{2-12}$cycloheteroalkyl, —C$_{0-6}$alkyl-aryl fused to C$_{4-6}$cycloalkyl or C$_{4-6}$cycloheteroalkyl containing 1-3 heteroatoms independently selected from O, S and N(R$^h$)$_2$, —C$_{0-6}$alkyl-aryl fused to C$_{4-6}$cycloalkenyl or C$_{4-6}$cycloheteroalkenyl containing 1-3 heteroatoms independently selected from O, S and N(R$^h$)$_2$, —C$_{0-6}$alkyl-heteroaryl fused to C$_{4-6}$cycloalkyl or C$_{4-6}$cycloheteroalkyl containing 1-3 heteroatoms independently selected from O, S and N(R$^h$)$_2$, and —C$_{0-6}$alkyl-heteroaryl fused to C$_{4-6}$cycloalkenyl or C$_{4-6}$cycloheteroalkenyl containing 1-3 heteroatoms independently selected from O, S and N(R$^h$)$_2$, wherein alkyl, cycloalkyl, cycloheteroalkyl, cycloalkenyl, aryl and heteroaryl are unsubstituted or substituted with one to five substituents selected from R$^b$. In a class of this embodiment, A and B are independently substituted with 0-4 substituents selected from R$^b$. In another class of this embodiment, A and B are independently substituted with 0-3 substituents selected from R$^b$. In another class of this embodiment, A and B are independently substituted with 0-2 substituents selected from R$^b$.

In another embodiment, one of A and B is selected from: aryl, and heteroaryl, wherein aryl and heteroaryl are unsubstituted or substituted with one to five substituents selected from R$^a$, and the other of A and B is selected from: aryl, heteroaryl, —C$_{1-6}$alkyl-aryl, —C$_{1-6}$alkyl-O-aryl, —C$_{1-6}$alkyl-O-heteroaryl, —C$_{3-12}$cycloalkyl, —C$_{2-12}$cycloheteroalkyl, —C$_{1-6}$alkyl-C$_{3-12}$cycloalkyl, —C$_{1-6}$alkyl-C$_{2-12}$cycloheteroalkyl, —C$_{1-6}$alkyl-O—C$_{3-12}$cycloalkyl, and —C$_{0-6}$alkyl-aryl fused to a C$_{4-6}$cycloalkyl or C$_{4-6}$cycloheteroalkyl containing 1-3 heteroatoms independently selected from O, S and N(R$^h$)$_2$, wherein alkyl, cycloalkyl, cycloheteroalkyl, aryl and heteroaryl are unsubstituted or substituted with one to five substituents selected from R$^b$. In a class of this embodiment, A and B are independently substituted with 0-4 substituents selected from R$^b$. In another class of this embodiment, A and B are independently substituted with 0-3 substituents selected from R$^b$. In another class of this embodiment, A and B are independently substituted with 0-2 substituents selected from R$^b$.

In another embodiment, one of A and B is selected from: aryl, and heteroaryl, wherein aryl and heteroaryl are unsubstituted or substituted with one to five substituents selected from R$^a$, and the other of A and B is selected from: aryl, heteroaryl, —C$_{1-6}$alkyl-aryl, —C$_{1-6}$alkyl-O-aryl, —C$_{1-6}$alkyl-O-heteroaryl, —C$_{3-12}$cycloalkyl, —C$_{2-12}$cycloheteroalkyl, —C$_{1-6}$alkyl-C$_{3-12}$cycloalkyl, —C$_{1-6}$alkyl-C$_{2-12}$cycloheteroalkyl, —C$_{1-6}$alkyl-O—C$_{3-12}$cycloalkyl, and —C$_{0-6}$alkyl-aryl fused to a C$_{4-6}$cycloalkyl, wherein alkyl, cycloalkyl, cycloheteroalkyl, aryl and heteroaryl are unsubstituted or substituted with one to five substituents selected from R$^b$. In a class of this embodiment, A and B are independently substituted with 0-4 substituents selected from R$^b$. In another class of this embodiment, A and B are independently substituted with 0-3 substituents selected from R$^b$. In another class of this embodiment, A and B are independently substituted with 0-2 substituents selected from R$^b$.

In another embodiment, one of A and B is selected from: phenyl, and pyridine, wherein phenyl and pyridine are unsubstituted or substituted with one to five substituents selected from R$^a$, and the other of A and B is selected from: phenyl, pyridine, thiazole, pyrimidine, pyrazine, pyridazine, imidazole, pyrazole, oxazole, benzofuran, benzo[d]oxazole, benzo[d]thiazole, indazole, thiazolo[5,4-b]pyridine, pyrazolo[1,5-a]pyridine, indole, thiophene, furan, triazole, quinoline, isoquinoline, quinoxaline, quanazoline, pyrazolopyridine, pyrazolopyridine, imidazopyridine, oxazolopyridine, pyrazolopyrimidine, imidazopyrimidine, oxazolopyrimidine, thiazolopyrimidine, —(CH$_2$)$_2$-phenyl, —CH$_2$—O-phenyl, —CH$_2$—O-pyridine, cyclobutyl, cyclohexyl, bicyclo[1.1.1]pentane, spiro[3.3]heptane, azetidine, piperidine, tetrahydropyran, tetrahydrofuran, azabicyclo[3.1.0]hexane, —CH$_2$-cyclohexyl, —CH$_2$-tetrahydropyran, and bicyclo[4.2.0]octatriene, wherein alkyl, cycloalkyl, cycloheteroalkyl, aryl and heteroaryl are unsubstituted or substituted with one to five substituents selected from R$^b$. In a class of this embodiment, A and B are independently substituted with 0-4 substituents selected from R$^b$. In another class of this embodiment, A and B are independently substituted with 0-3 substituents selected from R$^b$. In another class of this embodiment, A and B are independently substituted with 0-2 substituents selected from R$^b$.

In another embodiment, one of A and B is selected from: phenyl, and pyridine, wherein phenyl and pyridine are unsubstituted or substituted with one to five substituents selected from R$^a$, and the other of A and B is selected from: phenyl, pyridine, thiazole, pyrimidine, pyrazine, pyridazine, imidazole, pyrazole, oxazole, benzofuran, benzo[d]oxazole, benzo[d]thiazole, indazole, thiazolo[5,4-b]pyridine, pyrazolo[1,5-a]pyridine, —(CH$_2$)$_2$-phenyl, —CH$_2$—O-phenyl, —CH$_2$—O-pyridine, cyclobutyl, cyclohexyl, bicyclo[1.1.1]pentane, spiro-[3.3]heptane, azetidine, piperidine, tetrahydropyran, tetrahydrofuran, azabicyclo[3.1.0]hexane, —CH$_2$-cyclohexyl, —CH$_2$-tetrahydropyran, and bicyclo[4.2.0]octatriene, wherein alkyl, cycloalkyl, cycloheteroalkyl, aryl and heteroaryl are unsubstituted or substituted with one to five substituents selected from R$^b$. In a class of this embodiment, A and B are independently substituted with 0-4 substituents selected from R$^b$. In another class of this embodiment, A and B are independently substituted with 0-3 substituents selected from R$^b$. In another class of this embodiment, A and B are independently substituted with 0-2 substituents selected from R$^b$.

In another embodiment, one of A and B is aryl, wherein aryl is unsubstituted or substituted with one to five substituents selected from R$^a$, and the other of A and B is selected from: aryl, heteroaryl, and —C$_{3-12}$cycloalkyl, wherein cycloalkyl, aryl and heteroaryl are unsubstituted or substituted with one to five substituents selected from R$^b$. In a class of this embodiment, A and B are independently substituted with 0-4 substituents selected from R$^b$. In another class of this embodiment, A and B are independently substituted with 0-3 substituents selected from R$^b$. In another class of this embodiment, A and B are independently substituted with 0-2 substituents selected from R$^b$.

In another embodiment, one of A and B is phenyl, wherein phenyl is unsubstituted or substituted with one to five substituents selected from R$^a$, and the other of A and B is selected from: phenyl, pyridine, thiazole, and cyclobutane, wherein phenyl, pyridine, thiazole and cyclobutene are unsubstituted or substituted with one to five substituents selected from R$^b$. In a class of this embodiment, A and B are independently substituted with 0-4 substituents selected from R$^b$. In another class of this embodiment, A and B are independently substituted with 0-3 substituents selected from R$^b$. In another class of this embodiment, A and B are independently substituted with 0-2 substituents selected from R$^b$.

In another embodiment of the present invention, A is selected from the group consisting of: aryl, and heteroaryl, wherein A is unsubstituted or substituted with one to five substituents selected from R$^a$. In a class of this embodiment, A is substituted with 0-4 substituents selected from R$^a$. In another class of this embodiment, A is substituted with 0-3 substituents selected from R$^a$. In another class of this embodiment, A is substituted with 0-2 substituents selected from R$^a$.

In another embodiment, A is selected from the group consisting of: phenyl, and pyridine, wherein A is unsubstituted or substituted with one to five substituents selected from R$^a$. In a class of this embodiment, A is substituted with 0-4 substituents selected from R$^a$. In another class of this embodiment, A is substituted with 0-3 substituents selected from $R^a$. In another class of this embodiment, A is substituted with 0-2 substituents selected from $R^a$.

In another embodiment, A is aryl, wherein aryl is unsubstituted or substituted with one to five substituents selected from $R^a$. In a class of this embodiment, aryl is substituted with 0-4 substituents selected from $R^a$. In another class of this embodiment, aryl is substituted with 0-3 substituents selected from $R^a$. In another class of this embodiment, aryl is substituted with 0-2 substituents selected from $R^a$.

In another embodiment, A is phenyl, wherein phenyl is unsubstituted or substituted with one to five substituents selected from $R^a$. In a class of this embodiment, phenyl is substituted with 0-4 substituents selected from $R^a$. In another class of this embodiment, phenyl is substituted with 0-3 substituents selected from $R^a$. In another class of this embodiment, phenyl is substituted with 0-2 substituents selected from $R^a$.

In another embodiment, A is independently selected from the group consisting of: aryl, heteroaryl, —$C_{1-6}$alkyl-aryl, —$C_{3-8}$cycloalkyl-aryl, —$C_{2-8}$cycloheteroalkyl-aryl, —$C_{1-6}$alkyl-heteroaryl, —$C_{3-8}$cycloalkyl-heteroaryl, —$C_{2-8}$cycloheteroalkyl-heteroaryl, —$C_{1-6}$alkyl-O-aryl, —$C_{1-6}$alkyl-O-heteroaryl, —$C_{3-12}$cycloalkyl, —$C_{2-12}$cycloheteroalkyl, —$C_{1-6}$alkyl-$C_{3-12}$cycloalkyl, —$C_{1-6}$alkyl-$C_{2-12}$cycloheteroalkyl, —$C_{1-6}$alkyl-O—$C_{3-12}$cycloalkyl, —$C_{1-6}$alkyl-O—$C_{2-12}$cycloheteroalkyl, —$C_{0-6}$alkyl-aryl fused to a $C_{4-6}$cycloalkyl or $C_{4-6}$cycloheteroalkyl containing 1-3 heteroatoms independently selected from O, S and $N(R^h)_2$, —$C_{0-6}$alkyl-aryl fused to a $C_{4-6}$cycloalkenyl or $C_{4-6}$cycloheteroalkenyl containing 1-3 heteroatoms independently selected from O, S and $N(R^h)_2$, —$C_{0-6}$alkyl-heteroaryl fused to $C_{4-6}$cycloalkyl or $C_{4-6}$cycloheteroalkyl containing 1-3 heteroatoms independently selected from O, S and $N(R^h)_2$, and —$C_{0-6}$alkyl-heteroaryl fused to $C_{4-6}$cycloalkenyl or $C_{4-6}$cycloheteroalkenyl containing 1-3 heteroatoms independently selected from O, S and $N(R^h)_2$, wherein A is unsubstituted or substituted with one to five substituents selected from $R^b$. In a class of this embodiment, A is substituted with 0-4 substituents selected from $R^b$. In another class of this embodiment, A is substituted with 0-3 substituents selected from $R^b$. In another class of this embodiment, A is substituted with 0-2 substituents selected from $R^b$.

In another embodiment, A is independently selected from the group consisting of: aryl, heteroaryl, —$C_{1-6}$alkyl-aryl, —$C_{3-8}$cycloalkyl-aryl, —$C_{2-8}$cycloheteroalkyl-aryl, —$C_{1-6}$alkyl-heteroaryl, —$C_{3-8}$cycloalkyl-heteroaryl, —$C_{2-8}$cycloheteroalkyl-heteroaryl, —$C_{1-6}$alkyl-O-aryl, —$C_{1-6}$alkyl-O-heteroaryl, —$C_{3-12}$cycloalkyl, —$C_{2-12}$cycloheteroalkyl, —$C_{1-6}$alkyl-$C_{3-12}$cycloalkyl, —$C_{1-6}$alkyl-$C_{2-12}$cycloheteroalkyl, —$C_{1-6}$alkyl-O—$C_{3-12}$cycloalkyl, —$C_{1-6}$alkyl-O—$C_{2-12}$cycloheteroalkyl, —$C_{0-6}$alkyl-aryl fused to a $C_{4-6}$cycloalkyl, —$C_{0-6}$alkyl-aryl fused to a $C_{4-6}$cycloalkenyl, —$C_{0-6}$alkyl-heteroaryl fused to $C_{4-6}$cycloalkyl, and —$C_{0-6}$alkyl-heteroaryl fused to $C_{4-6}$cycloalkenyl, wherein A is unsubstituted or substituted with one to five substituents selected from $R^b$. In a class of this embodiment, A is substituted with 0-4 substituents selected from $R^b$. In another class of this embodiment, A is substituted with 0-3 substituents selected from $R^b$. In another class of this embodiment, A is substituted with 0-2 substituents selected from $R^b$.

In another embodiment, A is independently selected from the group consisting of: aryl, heteroaryl, —$C_{1-6}$alkyl-aryl, —$C_{1-6}$alkyl-O-aryl, —$C_{1-6}$alkyl-O-heteroaryl, —$C_{3-12}$cycloalkyl, —$C_{2-12}$cycloheteroalkyl, —$C_{1-6}$alkyl-$C_{3-12}$cycloalkyl, —$C_{1-6}$alkyl-$C_{2-12}$cycloheteroalkyl, —$C_{1-6}$alkyl-O—$C_{3-12}$cycloalkyl, and —$C_{0-6}$alkyl-aryl fused to a $C_{4-6}$cycloalkyl or $C_{4-6}$cycloheteroalkyl containing 1-3 heteroatoms independently selected from O, S and $N(R^h)_2$, and wherein A is unsubstituted or substituted with one to five substituents selected from $R^b$. In a class of this embodiment, A is substituted with 0-4 substituents selected from $R^b$. In another class of this embodiment, A is substituted with 0-3 substituents selected from $R^b$. In another class of this embodiment, A is substituted with 0-2 substituents selected from $R^b$.

In another embodiment, A is independently selected from the group consisting of: aryl, heteroaryl, —$C_{1-6}$alkyl-aryl, —$C_{1-6}$alkyl-O-aryl, —$C_{1-6}$alkyl-O-heteroaryl, —$C_{3-12}$cycloalkyl, —$C_{2-12}$cycloheteroalkyl, —$C_{1-6}$alkyl-$C_{3-12}$cycloalkyl, —$C_{1-6}$alkyl-$C_{2-12}$cycloheteroalkyl, —$C_{1-6}$alkyl-O—$C_{3-12}$cycloalkyl, and —$C_{0-6}$alkyl-aryl fused to $C_{4-6}$cycloalkyl, and wherein A is unsubstituted or substituted with one to five substituents selected from $R^b$. In a class of this embodiment, A is substituted with 0-4 substituents selected from $R^b$. In another class of this embodiment, A is substituted with 0-3 substituents selected from $R^b$. In another class of this embodiment, A is substituted with 0-2 substituents selected from $R^b$.

In another embodiment, A is independently selected from the group consisting of: phenyl, pyridine, thiazole, pyrimidine, pyrazine, pyridazine, imidazole, pyrazole, oxazole, benzofuran, benzo[d]oxazole, benzo[d]thiazole, indazole, thiazolo[5,4-b]pyridine, pyrazolo[1,5-a]pyridine, indole, thiophene, furan, triazole, quinoline, isoquinoline, quinoxaline, quanazoline, pyrazolopyridine, pyrazolopyridine, imidazopyridine, oxazolopyridine, pyrazolopyrimidine, imidazopyrimidine, —$(CH_2)_2$-phenyl, —$CH_2$—O-phenyl, —$CH_2$—O-pyridine, cyclobutane, cyclohexane, bicyclo[1.1.1]pentane, spiro[3.3]heptane, azetidine, piperidine, tetrahydropyran, tetrahydrofuran, azabicyclo[3.1.0]hexane, —$CH_2$-cyclohexane, —$CH_2$-tetrahydropyran, —$CH_2$—O-cyclohexane, and bicyclo[4.2.0]octatriene, and wherein A is unsubstituted or substituted with one to five substituents selected from $R^b$. In a class of this embodiment, A is substituted with 0-4 substituents selected from $R^b$. In another class of this embodiment, A is substituted with 0-3 substituents selected from $R^b$. In another class of this embodiment, A is substituted with 0-2 substituents selected from $R^b$.

In another embodiment, A is independently selected from the group consisting of: phenyl, pyridine, thiazole, pyrimidine, pyrazine, pyridazine, imidazole, pyrazole, oxazole, benzofuran, benzo[d]oxazole, benzo[d]thiazole, indazole, thiazolo[5,4-b]pyridine, pyrazolo[1,5-a]pyridine, —$(CH_2)_2$-phenyl, —$CH_2$—O-phenyl, —$CH_2$—O-pyridine, cyclobutane, cyclohexane, bicyclo[1.1.1]pentane, spiro[3.3]heptane, azetidine, piperidine, tetrahydropyran, tetrahydrofuran, azabicyclo[3.1.0]hexane, —$CH_2$-cyclohexane, —$CH_2$-tetrahydropyran, —$CH_2$—O-cyclohexane, and bicyclo[4.2.0]octatriene, and wherein A is unsubstituted or substituted with one to five substituents selected from $R^b$. In a class of this embodiment, A is substituted with 0-4 substituents selected from $R^b$. In another class of this embodiment, A is substituted with 0-3 substituents selected from $R^b$. In another class of this embodiment, A is substituted with 0-2 substituents selected from $R^b$.

In another embodiment, A is independently selected from the group consisting of: aryl, heteroaryl, and —$C_{3-12}$cycloalkyl, wherein cycloalkyl, aryl and heteroaryl are unsubstituted or substituted with one to five substituents selected from $R^b$. In a class of this embodiment, A is substituted with 0-4 substituents selected from $R^b$. In another class of this embodiment, A is substituted with 0-3 substituents selected from $R^b$. In another class of this embodiment, A is substituted with 0-2 substituents selected from $R^b$.

In another embodiment, A is independently selected from the group consisting of: phenyl, pyridine, thiazole, pyrimidine, pyrazine, pyridazine, imidazole, pyrazole, oxazole, benzofuran, benzo[d]oxazole, benzo[d]thiazole, indazole, thiazolo[5,4-b]pyridine, pyrazolo[1,5-a]pyridine, cyclobutane, cyclohexane, bicyclo[1.1.1]pentane, and spiro[3.3]heptane, and wherein A is unsubstituted or substituted with one to five substituents selected from $R^b$. In a class of this embodiment, A is substituted with 0-4 substituents selected from $R^b$. In another class of this embodiment, A is substituted with 0-3 substituents selected from $R^b$. In another class of this embodiment, A is substituted with 0-2 substituents selected from $R^b$.

In another embodiment, A is independently selected from the group consisting of: phenyl, pyridine, thiazole, and cyclobutane, wherein A is unsubstituted or substituted with one to five substituents selected from $R^b$. In a class of this embodiment, A is substituted with 0-4 substituents selected from $R^b$. In another class of this embodiment, A is substituted with 0-3 substituents selected from $R^b$. In another class of this embodiment, A is substituted with 0-2 substituents selected from $R^b$.

In another embodiment of the present invention, B is independently selected from the group consisting of: aryl, heteroaryl, —$C_{1-6}$alkyl-aryl, —$C_{3-8}$cycloalkyl-aryl, —$C_{2-8}$cycloheteroalkyl-aryl, —$C_{1-6}$alkyl-heteroaryl, —$C_{3-8}$cycloalkyl-heteroaryl, —$C_{2-8}$cycloheteroalkyl-heteroaryl, —$C_{1-6}$alkyl-O-aryl, —$C_{1-6}$alkyl-O-heteroaryl, —$C_{3-12}$cycloalkyl, —$C_{2-12}$cycloheteroalkyl, —$C_{1-6}$alkyl-$C_{3-12}$cycloalkyl, —$C_{1-6}$alkyl-$C_{2-12}$cycloheteroalkyl, —$C_{1-6}$alkyl-O—$C_{3-12}$cycloalkyl, —$C_{1-6}$alkyl-O—$C_{2-12}$cycloheteroalkyl, —$C_{0-6}$alkyl-aryl fused to $C_{4-6}$cycloalkyl or $C_{4-6}$cycloheteroalkyl containing 1-3 heteroatoms independently selected from O, S and N($R^h$)$_2$, —$C_{0-6}$alkyl-aryl fused to $C_{4-6}$cycloalkenyl or $C_{4-6}$cycloheteroalkenyl containing 1-3 heteroatoms independently selected from O, S and N($R^h$)$_2$, —$C_{0-6}$alkyl-heteroaryl fused to $C_{4-6}$cycloalkyl or $C_{4-6}$cycloheteroalkyl containing 1-3 heteroatoms independently selected from O, S and N($R^h$)$_2$, and —$C_{0-6}$alkyl-heteroaryl fused to $C_{4-6}$cycloalkenyl or $C_{4-6}$cycloheteroalkenyl containing 1-3 heteroatoms independently selected from O, S and N($R^h$)$_2$, wherein alkyl, cycloalkyl, cycloheteroalkyl, cycloalkenyl, aryl and heteroaryl are unsubstituted or substituted with one to five substituents selected from $R^b$. In a class of this embodiment, wherein B is substituted with 0-4 substituents selected from $R^b$. In another class of this embodiment, B is substituted with 0-3 substituents selected from $R^b$. In another class of this embodiment, B is substituted with 0-2 substituents selected from $R^b$.

In another embodiment, B is independently selected from the group consisting of: aryl, heteroaryl, —$C_{1-6}$alkyl-aryl, —$C_{3-8}$cycloalkyl-aryl, —$C_{2-8}$cycloheteroalkyl-aryl, —$C_{1-6}$alkyl-heteroaryl, —$C_{3-8}$cycloalkyl-heteroaryl, —$C_{2-8}$cycloheteroalkyl-heteroaryl, —$C_{1-6}$alkyl-O-aryl, —$C_{1-6}$alkyl-O-heteroaryl, —$C_{3-12}$cycloalkyl, —$C_{2-12}$cycloheteroalkyl, —$C_{1-6}$alkyl-$C_{3-12}$cycloalkyl, —$C_{1-6}$alkyl-$C_{2-12}$cycloheteroalkyl, —$C_{1-6}$alkyl-O—$C_{3-12}$cycloalkyl, —$C_{1-6}$alkyl-O—$C_{2-12}$cyclo-heteroalkyl, —$C_{0-6}$alkyl-aryl fused to $C_{4-6}$cycloalkyl, —$C_{0-6}$alkyl-aryl fused to $C_{4-6}$cycloalkenyl, —$C_{0-6}$alkyl-heteroaryl fused to $C_{4-6}$cycloalkyl, and —$C_{0-6}$alkyl-heteroaryl fused to $C_{4-6}$cyclo-alkenyl, wherein alkyl, cycloalkyl, cycloheteroalkyl, cycloalkenyl, aryl and heteroaryl are unsubstituted or substituted with one to five substituents selected from $R^b$. In a class of this embodiment, B is substituted with 0-4 substituents selected from $R^b$. In another class of this embodiment, B is substituted with 0-3 substituents selected from $R^b$. In another class of this embodiment, B is substituted with 0-2 substituents selected from $R^b$.

In another embodiment, B is independently selected from the group consisting of: aryl, heteroaryl, —$C_{1-6}$alkyl-aryl, —$C_{1-6}$alkyl-O-aryl, —$C_{1-6}$alkyl-O-heteroaryl, —$C_{3-12}$cycloalkyl, —$C_{2-12}$cycloheteroalkyl, —$C_{1-6}$alkyl-$C_{3-12}$cycloalkyl, —$C_{1-6}$alkyl-$C_{2-12}$cycloheteroalkyl, —$C_{1-6}$alkyl-O—$C_{3-12}$cycloalkyl, and —$C_{0-6}$alkyl-aryl fused to $C_{4-6}$cycloalkyl containing 0-3 heteroatoms independently selected from O, S and N($R^h$)$_2$, wherein alkyl, cycloalkyl, cycloheteroalkyl, aryl and heteroaryl are unsubstituted or substituted with one to five substituents selected from $R^b$. In a class of this embodiment, B is substituted with 0-4 substituents selected from $R^b$. In another class of this embodiment, B is substituted with 0-3 substituents selected from $R^b$. In another class of this embodiment, B is substituted with 0-2 substituents selected from $R^b$.

In another embodiment, B is independently selected from the group consisting of: aryl, heteroaryl, —$C_{1-6}$alkyl-aryl, —$C_{1-6}$alkyl-O-aryl, —$C_{1-6}$alkyl-O-heteroaryl, —$C_{3-12}$cycloalkyl, —$C_{2-12}$cycloheteroalkyl, —$C_{1-6}$alkyl-$C_{3-12}$cycloalkyl, —$C_{1-6}$alkyl-$C_{2-12}$cycloheteroalkyl, —$C_{1-6}$alkyl-O—$C_{3-12}$cycloalkyl, and —$C_{0-6}$alkyl-aryl fused to $C_{4-6}$cycloalkyl, wherein alkyl, cycloalkyl, cycloheteroalkyl, aryl and heteroaryl are unsubstituted or substituted with one to five substituents selected from $R^b$. In a class of this embodiment, B is substituted with 0-4 substituents selected from $R^b$. In another class of this embodiment, B is substituted with 0-3 substituents selected from $R^b$. In another class of this embodiment, B is substituted with 0-2 substituents selected from $R^b$.

In another embodiment, B is independently selected from the group consisting of: phenyl, pyridine, thiazole, pyrimidine, pyrazine, pyridazine, imidazole, pyrazole, oxazole, benzofuran, benzo[d]oxazole, benzo[d]thiazole, indazole, thiazolo[5,4-b]pyridine, pyrazolo[1,5-a]pyridine, indole, thiophene, furan, triazole, quinoline, isoquinoline, quinoxaline, quanazoline, pyrazolopyridine, pyrazolopyridine, imidazopyridine, oxazolopyridine, pyrazolopyrimidine, imidazopyrimidine, —(CH$_2$)$_2$-phenyl, —CH$_2$—O-phenyl, —CH$_2$—O-pyridine, cyclobutane, cyclohexane, bicyclo[1.1.1]pentane, spiro[3.3]heptane, azetidine, piperidine, tetrahydropyran, tetrahydrofuran, azabicyclo[3.1.0]hexane, —CH$_2$-cyclohexane, —CH$_2$-tetrahydropyran, —CH$_2$—O-cyclohexane, and bicyclo[4.2.0]octatriene, and wherein B is unsubstituted or substituted with one to five substituents selected from $R^b$. In a class of this embodiment, B is substituted with 0-4 substituents selected from $R^b$. In another class of this embodiment, B is substituted with 0-3 substituents selected from $R^b$. In another class of this embodiment, B is substituted with 0-2 substituents selected from $R^b$.

In another embodiment, B is independently selected from the group consisting of: phenyl, pyridine, thiazole, pyrimidine, pyrazine, pyridazine, imidazole, pyrazole, oxazole, benzofuran, benzo[d]oxazole, benzo[d]thiazole, indazole, thiazolo[5,4-b]pyridine, pyrazolo[1,5-a]pyridine, —(CH$_2$)$_2$-phenyl, —CH$_2$—O-phenyl, —CH$_2$—O-pyridine, cyclobutane, cyclohexane, bicyclo[1.1.1]pentane, spiro[3.3]heptane, azetidine, piperidine, tetrahydropyran, tetrahydrofuran, azabicyclo[3.1.0]hexane, —CH$_2$-cyclohexane, —CH$_2$-tetrahydropyran, —CH$_2$—O-cyclohexane, and bicyclo[4.2.0]octatriene, and wherein B is unsubstituted or substituted with one to five substituents selected from $R^b$. In a class of this embodiment, B is substituted with 0-4 substituents selected from $R^b$. In another class of this embodiment, B is substituted with 0-3 substituents selected from $R^b$. In another class of this embodiment, B is substituted with 0-2 substituents selected from $R^b$.

In another embodiment, B is independently selected from the group consisting of: aryl, heteroaryl, and $C_{3-12}$cycloalkyl, wherein cycloalkyl, aryl and heteroaryl are unsubstituted or substituted with one to five substituents selected from $R^b$. In a class of this embodiment, B is substituted with 0-4 substituents selected from $R^b$. In another class of this embodiment, B is substituted with 0-3 substituents selected from $R^b$. In another class of this embodiment, B is substituted with 0-2 substituents selected from $R^b$.

In another embodiment, B is independently selected from the group consisting of: phenyl, pyridine, thiazole, pyrimidine, pyrazine, pyridazine, imidazole, pyrazole, oxazole, benzofuran, benzo[d]oxazole, benzo[d]thiazole, indazole, thiazolo[5,4-b]pyridine, pyrazolo[1,5-a]pyridine, cyclobutane, cyclohexane, bicyclo[1.1.1]pentane, and spiro[3.3]heptane, and wherein B is unsubstituted or substituted with one to five substituents selected from $R^b$. In a class of this embodiment, B is substituted with 0-4 substituents selected from $R^b$. In another class of this embodiment, B is substituted with 0-3 substituents selected from $R^b$. In another class of this embodiment, B is substituted with 0-2 substituents selected from $R^b$.

In another embodiment, B is independently selected from the group consisting of: phenyl, pyridine, thiazole, and cyclobutane, wherein B is unsubstituted or substituted with one to five substituents selected from $R^b$. In a class of this embodiment, B is substituted with 0-4 substituents selected from $R^b$. In another class of this embodiment, B is substituted with 0-3 substituents selected from $R^b$. In another class of this embodiment, B is substituted with 0-2 substituents selected from $R^b$.

In one embodiment, B is selected from the group consisting of: aryl, and heteroaryl, wherein B is unsubstituted or substituted with one to five substituents selected from $R^a$. In a class of this embodiment, B is substituted with 0-4 substituents selected from $R^a$. In another class of this embodiment, B is substituted with 0-3 substituents selected from $R^a$. In another class of this embodiment, B is substituted with 0-2 substituents selected from $R^a$.

In another embodiment, B is selected from the group consisting of: phenyl, and pyridine, wherein B is unsubstituted or substituted with one to five substituents selected from $R^a$. In a class of this embodiment, B is substituted with 0-4 substituents selected from $R^a$. In another class of this embodiment, B is substituted with 0-3 substituents selected from $R^a$. In another class of this embodiment, B is substituted with 0-2 substituents selected from $R^a$.

In another embodiment, B is aryl, wherein aryl is unsubstituted or substituted with one to five substituents selected from $R^a$. In a class of this embodiment, aryl is substituted with 0-4 substituents selected from $R^a$. In another class of this embodiment, aryl is substituted with 0-3 substituents selected from $R^a$. In another class of this embodiment, aryl is substituted with 0-2 substituents selected from $R^a$.

In another embodiment, B is phenyl, wherein phenyl is unsubstituted or substituted with one to five substituents selected from $R^a$. In a class of this embodiment, phenyl is substituted with 0-4 substituents selected from $R^a$. In another class of this embodiment, phenyl is substituted with 0-3 substituents selected from $R^a$. In another class of this embodiment, phenyl is substituted with 0-2 substituents selected from $R^a$.

In another embodiment of the present invention, $R^1$ is selected from the group consisting of: hydrogen, —$C_{1-6}$alkyl, —$C_{3-6}$alkenyl, —$C_{3-6}$alkynyl, —$C_{3-10}$cycloalkyl, —$C_{2-10}$cycloheteroalkyl, and —$C_{1-6}$alkyl-O—$C_{1-6}$alkyl-, wherein each alkyl, alkenyl, alkynyl, cycloalkyl, and cycloheteroalkyl is unsubstituted or substituted with one to five substituents selected from $R^c$. In another embodiment, $R^1$ is selected from the group consisting of: hydrogen, —$C_{1-6}$alkyl, —$C_{3-6}$alkenyl, and —$C_{3-6}$alkynyl, wherein each alkyl, alkenyl, and alkynyl is unsubstituted or substituted with one to five substituents selected from $R^c$.

In another embodiment, $R^1$ is selected from the group consisting of: hydrogen, and —$C_{1-6}$alkyl, wherein each alkyl is unsubstituted or substituted with one to five substituents selected from $R^c$. In another embodiment, $R^1$ is selected from the group consisting of: hydrogen, and —$CH_3$. In another embodiment, $R^1$ is —$C_{1-6}$alkyl, wherein each alkyl is unsubstituted or substituted with one to five substituents selected from $R^c$. In a class of this embodiment, $R^1$ is —$CH_3$. In another embodiment, $R^1$ is hydrogen.

In another embodiment of the present invention, $R^2$ is selected from the group consisting of: hydrogen, —$C_{1-6}$alkyl, —$C_{3-6}$alkenyl, —$C_{3-6}$alkynyl, —$C_{3-10}$cycloalkyl, —$C_{2-10}$cycloheteroalkyl, and —$C_{1-6}$alkyl-O—$C_{1-6}$alkyl-, wherein each alkyl, alkenyl, alkynyl, cycloalkyl, and cycloheteroalkyl is unsubstituted or substituted with one to five substituents selected from $R^d$. In another embodiment, $R^2$ is selected from the group consisting of: hydrogen, —$C_{1-6}$alkyl, —$C_{3-6}$alkenyl, and —$C_{3-6}$alkynyl, wherein each $CH_2$, alkyl, alkenyl and alkynyl is unsubstituted or substituted with one to five substituents selected from $R^d$.

In another embodiment, $R^2$ is selected from the group consisting of: hydrogen, and —$C_{1-6}$alkyl, wherein each alkyl is unsubstituted or substituted with one to five substituents selected from $R^d$. In another embodiment, $R^2$ is selected from the group consisting of: —$C_{1-6}$alkyl, wherein each alkyl is unsubstituted or substituted with one to five substituents selected from $R^d$. In a class of this embodiment, $R^2$ is selected from the group consisting of: —$CH_3$, and —$(CH_2)_2$—OH. In another embodiment of the present invention, $R^2$ is hydrogen.

In another embodiment of the present invention, $R^3$ is selected from the group consisting of: hydrogen, —$C_{1-6}$alkyl, —$C_{2-6}$alkenyl, —$C_{2-6}$alkynyl, —$C_{3-10}$cycloalkyl, —$C_{2-10}$cycloheteroalkyl, —$C_{1-6}$alkyl-O—$C_{1-6}$alkyl-, —$(CH_2)_sC(O)R^j$, —$(CH_2)_sC(O)NR^eR^j$, —$(CH_2)_sNR^eC(O)R^j$, —$(CH_2)_sNR^eC(O)OR^j$, —$(CH_2)_sNR^eC(O)N(R^e)_2$, —$(CH_2)_sNR^eC(O)NR^eR^j$, —$(CH_2)_sNR^eS(O)_mR^j$, —$(CH_2)_sNR^eS(O)_mN(R^e)_2$, —$(CH_2)_sNR^eS(O)_mNR^eR^j$, and —$(CH_2)_sNR^eR^j$, wherein each $CH_2$, alkyl, alkenyl, alkynyl, cycloalkyl, and cycloheteroalkyl is unsubstituted or substituted with one to five substituents selected from $R^f$.

In another embodiment, $R^3$ is selected from the group consisting of: hydrogen, —$C_{1-6}$alkyl, —$C_{2-6}$alkenyl, —$C_{2-6}$alkynyl, —$C_{3-10}$cycloalkyl, —$C_{2-10}$cycloheteroalkyl, —$C_{1-6}$alkyl-O—$C_{1-6}$alkyl-, wherein each alkyl, alkenyl, alkynyl, cycloalkyl and cycloheteroalkyl is unsubstituted or substituted with one to five substituents selected from $R^f$.

In another embodiment, $R^3$ is selected from the group consisting of: hydrogen, —$C_{1-4}$ alkyl, —$C_{2-4}$alkenyl, —$C_{2-4}$alkynyl, —$C_{3-6}$cycloalkyl, and —$C_{2-6}$cycloheteroalkyl, wherein each alkyl, alkenyl, alkynyl, cycloalkyl, and cycloheteroalkyl is unsubstituted or substituted with one to five substituents selected from $R^f$.

In another embodiment, $R^3$ is selected from the group consisting of: hydrogen, —$C_{1-6}$alkyl, —$C_{2-6}$alkenyl, and —$C_{2-6}$alkynyl, wherein each alkyl, alkenyl, and alkynyl is unsubstituted or substituted with one to five substituents selected from $R^f$.

In another embodiment, $R^3$ is selected from the group consisting of: hydrogen, and —$C_{1-6}$alkyl, wherein each alkyl is unsubstituted or substituted with one to five substituents selected from $R^f$. In another embodiment, $R^3$ is —$C_{1-6}$alkyl. In another embodiment, $R^3$ is hydrogen.

In another embodiment of the present invention, $R^4$ is selected from the group consisting of: hydrogen, —$C_{1-6}$alkyl, —$C_{2-6}$alkenyl, —$C_{2-6}$alkynyl, —$C_{3-10}$cycloalkyl, —$C_{2-10}$cycloheteroalkyl, and —$C_{1-6}$alkyl-O—$C_{1-6}$alkyl-, wherein each alkyl, alkenyl, alkynyl, cycloalkyl, and cycloheteroalkyl is unsubstituted or substituted with one to five substituents selected from $R^g$.

In another embodiment, $R^4$ is selected from the group consisting of: hydrogen, —$C_{1-6}$alkyl, —$C_{2-6}$alkenyl, —$C_{2-6}$alkynyl, —$C_{3-10}$cycloalkyl, and —$C_{2-6}$cycloheteroalkyl, wherein each alkyl, alkenyl, alkynyl, cycloalkyl, and cycloheteroalkyl is unsubstituted or substituted with one to five substituents selected from $R^g$.

In another embodiment, $R^4$ is selected from the group consisting of: hydrogen, —$C_{1-6}$alkyl, —$C_{2-6}$alkenyl, —$C_{2-6}$alkynyl, —$C_{3-10}$cycloalkyl, and —$C_{2-10}$cycloheteroalkyl, wherein each alkyl, alkenyl, alkynyl is unsubstituted or substituted with one to five substituents selected from $R^g$. In another embodiment, $R^4$ is selected from the group consisting of: hydrogen, —$C_{1-6}$alkyl, —$C_{2-6}$alkenyl, and —$C_{2-6}$alkynyl, wherein each alkyl, alkenyl, and alkynyl is unsubstituted or substituted with one to five substituents selected from $R^g$.

In another embodiment, $R^4$ is selected from the group consisting of: hydrogen, and —$C_{1-6}$alkyl, wherein each alkyl is unsubstituted or substituted with one to five substituents selected from $R^g$. In another embodiment, $R^4$ is —$C_{1-6}$alkyl, wherein each alkyl is unsubstituted or substituted with one to five substituents selected from $R^g$. In another embodiment, $R^4$ is hydrogen.

In another embodiment of the present invention, $R^5$ is selected from the group consisting of: hydrogen, and —$C_{1-6}$alkyl, wherein each alkyl is unsubstituted or substituted with one to three halogen substituents. In a class of this embodiment, halogen is selected from Cl and F. In another class of this embodiment, halogen is F. In another class of this embodiment, halogen is Cl.

In another embodiment, $R^5$ is selected from the group consisting of: hydrogen and —$CH_3$, wherein each —$CH_3$ is unsubstituted or substituted with one to three halogen substituents. In a class of this embodiment, halogen is selected from Cl and F. In another class of this embodiment, halogen is F. In another class of this embodiment, halogen is Cl. In another embodiment, $R^5$ is selected from the group consisting of: hydrogen, and —$CH_3$.

In another embodiment, $R^5$ is —$C_{1-6}$alkyl, wherein each alkyl is unsubstituted or substituted with one to three halogen substituents. In a class of this embodiment, halogen is selected from Cl and F. In another class of this embodiment, halogen is F. In another class of this embodiment, halogen is Cl. In another embodiment, $R^5$ is —$CH_3$. In another embodiment, $R^5$ is hydrogen.

In another embodiment of the present invention, $R^6$ is selected from the group consisting of: hydrogen, —$C_{1-6}$alkyl, —$C_{3-6}$cycloalkyl, and —$C_{2-6}$cycloheteroalkyl, wherein each alkyl, cycloalkyl and cycloheteroalkyl is unsubstituted or substituted with one to five halogen substituents. In another embodiment, $R^6$ is selected from the group consisting of: hydrogen, —$C_{1-6}$alkyl, —$C_{3-5}$cycloalkyl, and —$C_{2-5}$cycloheteroalkyl, wherein each alkyl, cycloalkyl and cycloheteroalkyl is unsubstituted or substituted with one to five halogen substituents. In a class of this embodiment, each alkyl, cycloalkyl and cycloheteroalkyl is unsubstituted or substituted with one to three halogen substituents.

In another embodiment, $R^6$ is selected from the group consisting of: hydrogen, and —$C_{1-6}$alkyl, wherein each alkyl is unsubstituted or substituted with one to five halogen substituents. In a class of this embodiment, each alkyl is unsubstituted or substituted with one to three halogen substituents. In another embodiment, $R^6$ is —$C_{1-6}$alkyl, wherein each alkyl is unsubstituted or substituted with one to five halogen substituents. In a class of this embodiment, each alkyl is unsubstituted or substituted with one to three halogen substituents. In another embodiment, $R^6$ is hydrogen.

In another embodiment of the present invention, $R^7$ is selected from the group consisting of: hydrogen, —$C_{1-6}$alkyl, —$C_{2-6}$alkenyl, and —$C_{2-6}$alkynyl, wherein each alkyl, alkenyl and alkynyl is unsubstituted or substituted with one to five halogen substituents. In another embodiment, $R^7$ is selected from the group consisting of: hydrogen, —$C_{1-6}$alkyl, —$C_{2-4}$alkenyl, and —$C_{2-4}$alkynyl, wherein each alkyl, alkenyl and alkynyl is unsubstituted or substituted with one to five halogen substituents. In a class of this embodiment, each alkyl, alkenyl and alkynyl is unsubstituted or substituted with one to three halogen substituents. In another embodiment, $R^7$ is selected from the group consisting of: hydrogen, —$C_{1-6}$alkyl, and —$C_{2-6}$alkenyl, wherein each alkyl and alkenyl is unsubstituted or substituted with one to five halogen substituents. In a class of this embodiment, each alkyl and alkenyl is unsubstituted or substituted with one to three halogen substituents.

In another embodiment, $R^7$ is selected from the group consisting of: hydrogen, and —$C_{1-6}$alkyl, wherein each alkyl is unsubstituted or substituted with one to five halogen substituents. In a class of this embodiment, each alkyl is unsubstituted or substituted with one to three halogen substituents. In another embodiment, $R^7$ is —$C_{1-6}$alkyl, wherein each alkyl is unsubstituted or substituted with one to five halogen substituents. In a class of this embodiment, each alkyl is unsubstituted or substituted with one to three halogen substituents. In another embodiment, $R^7$ is hydrogen.

In another embodiment of the present invention, each $R^a$ is independently selected from the group consisting of: —$CF_3$, —$OCF_3$, —$CHF_2$, —$OCHF_2$, —$CH_2CF_3$, —$OCH_2CF_3$, —$CF_2CH_3$, CN, oxo, halogen, —$S(O)_2C_{1-6}$alkyl, —$C_{1-6}$alkyl, —$C_{2-6}$alkenyl, —$C_{2-6}$alkynyl, —O—$C_{1-6}$alkyl, —$C_{3-6}$cycloalkyl, —O—$C_{3-6}$cycloalkyl, —$C_{2-6}$cycloheteroalkyl, aryl, heteroaryl, —$C_{1-6}$alkyl-aryl, —$C_{1-6}$alkyl-heteroaryl, —$C_{1-6}$alkyl-$C_{3-6}$cycloalkyl, —$C_{1-6}$alkyl-$C_{2-6}$cycloheteroalkyl, —$C_{2-6}$alkenyl-$C_{3-6}$cycloalkyl, —$C_{2-6}$alkenyl-$C_{2-6}$cycloheteroalkyl, —$C_{2-6}$alkenyl-aryl, —$C_{2-6}$alkenyl-heteroaryl, —$C_{2-6}$alkynyl-$C_{3-6}$cycloalkyl, —$C_{2-6}$alkynyl-$C_{2-6}$cycloheteroalkyl, —$C_{2-6}$alkynyl-aryl, —$C_{2-6}$alkynyl-heteroaryl, —OH, —$(CH_2)_p$—$OC_{1-6}$alkyl, —$(CH_2)_p$—$OC_{2-6}$alkenyl, —$(CH_2)_p$—$OC_{2-6}$alkynyl, —$(CH_2)_p$—$OC_{3-6}$cycloalkyl, —$(CH_2)_p$—$OC_{2-6}$heterocycloalkyl, —$(CH_2)_p$—O-aryl, —$(CH_2)_p$—O-heteroaryl, —$OC_{1-6}$alkyl-$C_{3-6}$cycloalkyl, —$OC_{1-6}$alkyl-$C_{2-6}$heterocycloalkyl, —$OC_{1-6}$alkyl-aryl, —$OC_{1-6}$alkyl-heteroaryl, —$S(O)_mR^i$, —$C_{1-6}$alkyl-$S(O)_mR^i$, —$N(R^k)_2$, and —$NR^kR^L$, wherein each $R^a$ is unsubstituted or substituted with one to six substituents selected from halogen, $CF_3$, OH, $C_{1-6}$alkyl, and $OC_{1-6}$alkyl. In a class of this embodiment, halogen is F or Cl. In another class of this embodiment, $R^a$ is unsubstituted or substituted with one to six substituents selected from halogen, $CF_3$ and $C_{1-6}$alkyl. In another class of this embodiment, $R^a$ is unsubstituted or substituted with one to six substituents selected from F, Cl, $CF_3$, and $CH_3$.

In another embodiment, each $R^a$ is independently selected from the group consisting of: —$CF_3$, —$OCF_3$, —$CHF_2$, —$OCHF_2$, —$CH_2CF_3$, —$OCH_2CF_3$, —$CF_2CH_3$, CN, oxo, halogen, —$S(O)_2C_{1-6}$alkyl, —$C_{1-6}$alkyl, —$C_{2-6}$alkenyl, —$C_{2-6}$alkynyl, —O—$C_{1-6}$alkyl, —$C_{3-6}$cycloalkyl, —O—$C_{3-6}$cycloalkyl, —$C_{2-6}$cycloheteroalkyl, aryl, heteroaryl, —$C_{1-6}$alkyl-aryl, —$C_{1-6}$alkyl-heteroaryl, —$C_{1-6}$alkyl-$C_{3-6}$cycloalkyl, —$C_{1-6}$alkyl-$C_{2-6}$cycloheteroalkyl, —$C_{2-6}$alkenyl-$C_{3-6}$cycloalkyl, —$C_{2-6}$alkenyl-$C_{2-6}$cycloheteroalkyl, —$C_{2-6}$alkenyl-aryl, —$C_{2-6}$alkenyl-heteroaryl, —$C_{2-6}$alkynyl-$C_{3-6}$cycloalkyl, —$C_{2-6}$alkynyl cycloheteroalkyl, —$C_{2-6}$alkynyl-aryl, —$C_{2-6}$alkynyl-heteroaryl, and —OH, wherein each $R^a$ is unsubstituted or substituted with one to six substituents selected from halogen, $CF_3$, OH, $C_{1-6}$alkyl, and $OC_{1-6}$alkyl. In a class of this embodiment, halogen is F or Cl. In another class of this embodiment, $R^a$ is unsubstituted or substituted with one to six substituents selected from halogen, $CF_3$ and $C_{1-6}$alkyl. In another class of this embodiment, $R^a$ is unsubstituted or substituted with one to six substituents selected from F, Cl, $CF_3$, and $CH_3$.

In another embodiment, each $R^a$ is independently selected from the group consisting of: —$CF_3$, —$OCF_3$, —$CHF_2$, —$OCHF_2$, —$CH_2CF_3$, —$OCH_2CF_3$, —$CF_2CH_3$, CN, oxo, halogen, —$S(O)_2C_{1-6}$alkyl, —$C_{1-6}$alkyl, —$C_{2-6}$alkenyl, —$C_{2-6}$alkynyl, —O—$C_{1-6}$alkyl, —$C_{3-6}$cycloalkyl, —O—$C_{3-6}$cycloalkyl, —$C_{2-6}$cycloheteroalkyl, aryl, heteroaryl, —$C_{1-6}$alkyl-aryl, —$C_{1-6}$alkyl-heteroaryl, —$C_{1-6}$alkyl-$C_{3-6}$cycloalkyl, —$C_{1-6}$alkyl-$C_{2-6}$cycloheteroalkyl, —$C_{2-6}$alkenyl-$C_{3-6}$cycloalkyl, —$C_{2-6}$alkenyl-$C_{2-6}$cycloheteroalkyl, —$C_{2-6}$alkenyl-aryl, —$C_{2-6}$alkenyl-heteroaryl, and —OH, wherein each $R^a$ is unsubstituted or substituted with one to six substituents selected from halogen, $CF_3$, OH, $C_{1-6}$alkyl, and $OC_{1-6}$alkyl. In a class of this embodiment, halogen is F or Cl. In another class of this embodiment, $R^a$ is unsubstituted or substituted with one to six substituents selected from halogen, $CF_3$ and $C_{1-6}$alkyl. In another class of this embodiment, $R^a$ is unsubstituted or substituted with one to six substituents selected from F, Cl, $CF_3$, and $CH_3$.

In another embodiment, each $R^a$ is independently selected from the group consisting of: —$CF_3$, —$OCF_3$, —$CHF_2$, —$OCHF_2$, —$CH_2CF_3$, —$OCH_2CF_3$, —$CF_2CH_3$, CN, oxo, halogen, —$S(O)_2C_{1-6}$alkyl, —$C_{1-6}$alkyl, —$C_{2-6}$alkenyl, —$C_{2-6}$alkynyl, —O—$C_{1-6}$alkyl, —$C_{3-6}$cycloalkyl, —O—$C_{3-6}$cycloalkyl, —$C_{2-6}$cycloheteroalkyl, aryl, heteroaryl, —$C_{1-6}$alkyl-aryl, —$C_{1-6}$alkyl-heteroaryl, —$C_{1-6}$alkyl-$C_{3-6}$cycloalkyl, —$C_{1-6}$alkyl-$C_{2-6}$cycloheteroalkyl, and —OH, wherein each $R^a$ is unsubstituted or substituted with one to six substituents selected from halogen, $CF_3$, OH, $C_{1-6}$alkyl, and $OC_{1-6}$alkyl. In a class of this embodiment, halogen is F or Cl. In another class of this embodiment, $R^a$ is unsubstituted or substituted with one to six substituents selected from halogen, $CF_3$ and $C_{1-6}$alkyl. In another class of this embodiment, $R^a$ is unsubstituted or substituted with one to six substituents selected from F, Cl, $CF_3$, and $CH_3$.

In another embodiment, each $R^a$ is independently selected from the group consisting of: —$CF_3$, —$OCF_3$, —$CHF_2$, —$OCHF_2$, —$CH_2CF_3$, —$OCH_2CF_3$, —$CF_2CH_3$, CN, oxo, halogen, —$S(O)_2C_{1-6}$alkyl, —$C_{1-6}$alkyl, —$C_{2-6}$alkenyl, —$C_{2-6}$alkynyl, —O—$C_{1-6}$alkyl, —$C_{3-6}$cycloalkyl, —O—$C_{3-6}$cycloalkyl, —$C_{2-6}$cycloheteroalkyl, and OH, wherein each $R^a$ is unsubstituted or substituted with one to six substituents selected from halogen, $CF_3$, OH, $C_{1-6}$alkyl, and $OC_{1-6}$alkyl. In a class of this embodiment, halogen is F or Cl. In another class of this embodiment, $R^a$ is unsubstituted or substituted with one to six substituents selected from halogen, $CF_3$ and $C_{1-6}$alkyl. In another class of this embodiment, $R^a$ is unsubstituted or substituted with one to six substituents selected from F, Cl, $CF_3$, and $CH_3$.

In another embodiment, each $R^a$ is independently selected from the group consisting of: —$CF_3$, —$OCF_3$, —$CHF_2$, —$OCHF_2$, —$CH_2CF_3$, —$OCH_2CF_3$, —$CF_2CH_3$, CN, oxo, halogen, —$C_{1-6}$alkyl, —$C_{2-6}$alkenyl, —$C_{2-6}$alkynyl, and OH, wherein each $R^a$ is unsubstituted or substituted with one to six substituents selected from halogen, $CF_3$, OH, $C_{1-6}$alkyl, and $OC_{1-6}$alkyl. In a class of this embodiment, halogen is F or Cl. In another class of this embodiment, $R^a$ is unsubstituted or substituted with one to six substituents selected from halogen, $CF_3$ and $C_{1-6}$alkyl. In another class of this embodiment, $R^a$ is unsubstituted or substituted with one to six substituents selected from F, Cl, $CF_3$, and $CH_3$. In another embodiment, each $R^a$ is independently selected from the group consisting of: —$CF_3$, —$OCF_3$, —$CHF_2$, —$OCHF_2$, —$CH_2CF_3$, —$OCH_2CF_3$, —$CF_2CH_3$, CN, oxo, halogen, —$C_{1-6}$alkyl, —$C_{2-6}$alkenyl, and OH, wherein each $R^a$ is unsubstituted or substituted with one to six substituents selected from halogen, $CF_3$, OH, $C_{1-6}$alkyl, and $OC_{1-6}$alkyl. In a class of this embodiment, halogen is F or Cl. In another class of this embodiment, $R^a$ is unsubstituted or substituted with one to six substituents selected from halogen, $CF_3$ and $C_{1-6}$alkyl. In another class of this embodiment, $R^a$ is unsubstituted or substituted with one to six substituents selected from F, Cl, $CF_3$, and $CH_3$.

In another embodiment, each $R^a$ is independently selected from the group consisting of: —$CF_3$, —$OCF_3$, —$CHF_2$, —$OCHF_2$, —$CH_2CF_3$, —$OCH_2CF_3$, —$CF_2CH_3$, CN, oxo, halogen, —$C_{1-6}$alkyl, and OH, wherein each $R^a$ is unsubstituted or substituted with one to six substituents selected from halogen, $CF_3$, OH, $C_{1-6}$alkyl, and $OC_{1-6}$alkyl. In a class of this embodiment, halogen is F or Cl. In another class of this embodiment, $R^a$ is unsubstituted or substituted with one to six substituents selected from halogen, $CF_3$ and $C_{1-6}$alkyl. In another class of this embodiment, $R^a$ is unsubstituted or substituted with one to six substituents selected from F, Cl, $CF_3$, and $CH_3$.

In another embodiment, each $R^a$ is independently selected from the group consisting of: —$CF_3$, —$OCF_3$, —$CHF_2$, —$OCHF_2$, —$CH_2CF_3$, —$OCH_2CF_3$, —$CF_2CH_3$, CN, halogen, and —$C_{1-6}$alkyl, wherein each $R^a$ is unsubstituted or substituted with one to six substituents selected from halogen, $CF_3$, OH, $C_{1-6}$alkyl, and $OC_{1-6}$alkyl. In a class of this embodiment, halogen is F or Cl. In another class of this embodiment, $R^a$ is unsubstituted or substituted with one to six substituents selected from halogen, $CF_3$ and $C_{1-6}$alkyl. In another class of this embodiment, $R^a$ is unsubstituted or substituted with one to six substituents selected from F, Cl, $CF_3$, and $CH_3$. In another embodiment, each $R^a$ is independently selected from the group consisting of: —$CF_3$, —$OCF_3$, —$CHF_2$, —$OCH_2CF_3$, CN, and halogen. In another embodiment, each $R^a$ is independently selected from the group consisting of: —$CF_3$, —$OCF_3$, —$CHF_2$, —$OCH_2CF_3$, CN, F, and Cl.

In another embodiment of the present invention, each $R^b$ is independently selected from the group consisting of: —$CF_3$, —$OCF_3$, —$CHF_2$, —$OCHF_2$, —$CH_2CF_3$, —$OCH_2CF_3$, —$CF_2CH_3$, CN, oxo, halogen, —$S(O)_2C_{1-6}$alkyl, —$C_{1-6}$alkyl, —$C_{2-6}$alkenyl, —$C_{2-6}$alkynyl, —O—$C_{1-6}$alkyl, —$C_{3-6}$cycloalkyl, —O—$C_{3-6}$cycloalkyl, —$C_{2-6}$cycloheteroalkyl, aryl, heteroaryl, —$C_{1-6}$alkyl-aryl, —$C_{1-6}$alkyl-heteroaryl, —$C_{1-6}$alkyl-$C_{3-6}$cycloalkyl, —$C_{1-6}$alkyl-$C_{2-6}$cycloheteroalkyl, —$C_{2-6}$alkenyl-$C_{3-6}$cycloalkyl, —$C_{2-6}$alkenyl-$C_{2-6}$cycloheteroalkyl, —$C_{2-6}$alkenyl-aryl, —C$_{2-6}$alkenyl-heteroaryl, —C$_{2-6}$alkynyl-C$_{3-6}$cycloalkyl, —C$_{2-6}$alkynyl-C$_{2-6}$cycloheteroalkyl, —C$_{2-6}$alkynyl-aryl, —C$_{2-6}$alkynyl-heteroaryl, —OH, —(CH$_2$)$_q$—OC$_{1-6}$alkyl, —(CH$_2$)$_q$—OC$_{2-6}$alkenyl, —(CH$_2$)$_q$—OC$_{2-6}$alkynyl, —(CH$_2$)$_q$—OC$_{3-6}$cycloalkyl, —(CH$_2$)$_q$—OC$_{2-6}$heterocycloalkyl, —(CH$_2$)$_q$—O-aryl, —(CH$_2$)$_q$—O-heteroaryl, —OC$_{1-6}$alkyl-C$_{3-6}$cycloalkyl, —OC$_{1-6}$alkyl-C$_{2-6}$heterocycloalkyl, —OC$_{1-6}$alkyl-aryl, —OC$_{1-6}$alkyl-heteroaryl, —S(O)$_m$R$^i$, —C$_{1-6}$alkyl-S(O)$_m$R$^i$, —C(O)R$^L$, and —NR$^k$R$^L$, wherein each R$^b$ is unsubstituted or substituted with one to six substituents selected from halogen, CF$_3$, OCF$_3$, CN, CH$_2$CF$_3$, CF$_2$CH$_3$, —C$_{1-6}$alkyl, and O—C$_{1-6}$alkyl. In a class of this embodiment, each R$^b$ is unsubstituted or substituted with one to six substituents selected from F, Cl, CF$_3$, and CH$_3$.

In another embodiment, each R$^b$ is independently selected from the group consisting of: —CF$_3$, —OCF$_3$, —CHF$_2$, —OCHF$_2$, —CH$_2$CF$_3$, —OCH$_2$CF$_3$, —CF$_2$CH$_3$, CN, oxo, halogen, —S(O)$_2$C$_{1-6}$alkyl, —C$_{1-6}$alkyl, —C$_{2-6}$alkenyl, —C$_{2-6}$alkynyl, —O—C$_{1-6}$alkyl, —C$_{3-6}$cycloalkyl, —O—C$_{3-6}$cycloalkyl, —C$_{2-6}$cycloheteroalkyl, aryl, heteroaryl, —C$_{1-6}$alkyl-aryl, —C$_{1-6}$alkyl-heteroaryl, —C$_{1-6}$alkyl-C$_{3-6}$cycloalkyl, —C$_{1-6}$alkyl-C$_{2-6}$cycloheteroalkyl, —C$_{2-6}$alkenyl-C$_{3-6}$cycloalkyl, —C$_{2-6}$alkenyl-C$_{2-6}$cycloheteroalkyl, —C$_{2-6}$alkenyl-aryl, —C$_{2-6}$alkenyl-heteroaryl, —C$_{2-6}$alkynyl-C$_{3-6}$cycloalkyl, —C$_{2-6}$alkynyl-C$_{2-6}$cycloheteroalkyl, —C$_{2-6}$alkynyl-aryl, —C$_{2-6}$alkynyl-heteroaryl, and —OH, wherein each R$^b$ is unsubstituted or substituted with one to six substituents selected from halogen, CF$_3$, OCF$_3$, CN, CH$_2$CF$_3$, CF$_2$CH$_3$, —C$_{1-6}$alkyl, and O—C$_{1-6}$alkyl. In a class of this embodiment, each R$^b$ is unsubstituted or substituted with one to six substituents selected from F, Cl, CF$_3$, and CH$_3$.

In another embodiment, each R$^b$ is independently selected from the group consisting of: —CF$_3$, —OCF$_3$, —CHF$_2$, —OCHF$_2$, —CH$_2$CF$_3$, —OCH$_2$CF$_3$, —CF$_2$CH$_3$, CN, oxo, halogen, —S(O)$_2$C$_{1-6}$alkyl, —C$_{1-6}$alkyl, —C$_{2-6}$alkenyl, —C$_{2-6}$alkynyl, —O—C$_{1-6}$alkyl, —C$_{3-6}$cycloalkyl, —O—C$_{3-6}$cycloalkyl, —C$_{2-6}$cycloheteroalkyl, aryl, heteroaryl, —C$_{1-6}$alkyl-aryl, —C$_{1-6}$alkyl-heteroaryl, —C$_{1-6}$alkyl-C$_{3-6}$cycloalkyl, —C$_{1-6}$alkyl-C$_{2-6}$cycloheteroalkyl, —C$_{2-6}$alkenyl-C$_{3-6}$cycloalkyl, —C$_{2-6}$alkenyl-C$_{2-6}$cycloheteroalkyl, —C$_{2-6}$alkenyl-aryl, —C$_{2-6}$alkenyl-heteroaryl, and —OH, wherein each R$^b$ is unsubstituted or substituted with one to six substituents selected from halogen, CF$_3$, OCF$_3$, CN, CH$_2$CF$_3$, CF$_2$CH$_3$, —C$_{1-6}$alkyl, and O—C$_{1-6}$alkyl. In a class of this embodiment, each R$^b$ is unsubstituted or substituted with one to six substituents selected from F, Cl, CF$_3$, and CH$_3$. In a class of this embodiment, each R$^b$ is unsubstituted or substituted with one to six substituents selected from F, Cl, CF$_3$, and CH$_3$.

In another embodiment, each R$^b$ is independently selected from the group consisting of: —CF$_3$, —OCF$_3$, —CHF$_2$, —OCHF$_2$, —CH$_2$CF$_3$, —OCH$_2$CF$_3$, —CF$_2$CH$_3$, CN, oxo, halogen, —S(O)$_2$C$_{1-6}$alkyl, —C$_{1-6}$alkyl, —C$_{2-6}$alkenyl, —C$_{2-6}$alkynyl, —O—C$_{1-6}$alkyl, —C$_{3-6}$cycloalkyl, —O—C$_{3-6}$cycloalkyl, —C$_{2-6}$cycloheteroalkyl, aryl, heteroaryl, and —OH, wherein each R$^b$ is unsubstituted or substituted with one to six substituents selected from halogen, CF$_3$, OCF$_3$, CN, CH$_2$CF$_3$, CF$_2$CH$_3$, —C$_{1-6}$alkyl, and O—C$_{1-6}$alkyl. In a class of this embodiment, each R$^b$ is unsubstituted or substituted with one to six substituents selected from F, Cl, CF$_3$, and CH$_3$.

In another embodiment, each R$^b$ is independently selected from the group consisting of: —CF$_3$, —OCF$_3$, —CHF$_2$, —OCHF$_2$, —CH$_2$CF$_3$, —OCH$_2$CF$_3$, —CF$_2$CH$_3$, CN, oxo, halogen, —S(O)$_2$C$_{1-6}$alkyl, —C$_{1-6}$alkyl, —C$_{2-6}$alkenyl, —C$_{2-6}$alkynyl, —C$_{3-6}$cycloalkyl, —C$_{2-6}$cycloheteroalkyl, aryl, heteroaryl, and —OH, wherein each R$^b$ is unsubstituted or substituted with one to six substituents selected from halogen, CF$_3$, OCF$_3$, CN, CH$_2$CF$_3$, CF$_2$CH$_3$, —C$_{1-6}$alkyl, and O—C$_{1-6}$alkyl. In a class of this embodiment, each R$^b$ is unsubstituted or substituted with one to six substituents selected from F, Cl, CF$_3$, and CH$_3$.

In another embodiment, each R$^b$ is independently selected from the group consisting of: —CF$_3$, —OCF$_3$, —CHF$_2$, —OCHF$_2$, —CH$_2$CF$_3$, —OCH$_2$CF$_3$, —CF$_2$CH$_3$, CN, oxo, halogen, —S(O)$_2$C$_{1-6}$alkyl, —C$_{1-6}$alkyl, —C$_{2-6}$alkenyl, —C$_{2-6}$alkynyl, —C$_{3-6}$cycloalkyl, —C$_{2-6}$cycloheteroalkyl and —OH, wherein each R$^b$ is unsubstituted or substituted with one to six substituents selected from halogen, CF$_3$, OCF$_3$, CN, CH$_2$CF$_3$, CF$_2$CH$_3$, —C$_{1-6}$alkyl, and O—C$_{1-6}$alkyl. In a class of this embodiment, each R$^b$ is unsubstituted or substituted with one to six substituents selected from F, Cl, CF$_3$, and CH$_3$.

In another embodiment, each R$^b$ is independently selected from the group consisting of: —CF$_3$, —OCF$_3$, —CHF$_2$, —OCHF$_2$, —CH$_2$CF$_3$, —OCH$_2$CF$_3$, —CF$_2$CH$_3$, CN, oxo, halogen, —S(O)$_2$C$_{1-6}$alkyl, —C$_{1-6}$alkyl, —C$_{2-6}$alkenyl, —C$_{3-6}$cycloalkyl, —C$_{2-6}$cycloheteroalkyl, and —OH, wherein each R$^b$ is unsubstituted or substituted with one to six substituents selected from halogen, CF$_3$, OCF$_3$, CN, CH$_2$CF$_3$, CF$_2$CH$_3$, —C$_{1-6}$alkyl, and O—C$_{1-6}$alkyl. In a class of this embodiment, each R$^b$ is unsubstituted or substituted with one to six substituents selected from F, Cl, CF$_3$, and CH$_3$.

In another embodiment, each R$^b$ is independently selected from the group consisting of: —CF$_3$, —OCF$_3$, —CHF$_2$, —OCHF$_2$, —CH$_2$CF$_3$, —OCH$_2$CF$_3$, —CF$_2$CH$_3$, CN, halogen, —S(O)$_2$C$_{1-6}$alkyl, —C$_{1-6}$alkyl, —C$_{2-6}$alkenyl, —C$_{2-6}$alkynyl, —C$_{3-6}$cycloalkyl, and —C$_{2-6}$cycloheteroalkyl, wherein each R$^b$ is unsubstituted or substituted with one to six substituents selected from halogen, CF$_3$, OCF$_3$, CN, CH$_2$CF$_3$, CF$_2$CH$_3$, —C$_{1-6}$alkyl, and O—C$_{1-6}$alkyl. In a class of this embodiment, each R$^b$ is unsubstituted or substituted with one to six substituents selected from F, Cl, CF$_3$, and CH$_3$.

In another embodiment, each R$^b$ is independently selected from the group consisting of: —CF$_3$, —OCF$_3$, —CHF$_2$, —OCHF$_2$, —CH$_2$CF$_3$, —OCH$_2$CF$_3$, —CF$_2$CH$_3$, CN, halogen, —S(O)$_2$C$_{1-6}$alkyl, —C$_{1-6}$alkyl, —C$_{2-6}$alkenyl, —C$_{3-6}$cycloalkyl, and —C$_{2-6}$cycloheteroalkyl, wherein each R$^b$ is unsubstituted or substituted with one to six substituents selected from halogen, CF$_3$, OCF$_3$, CN, CH$_2$CF$_3$, CF$_2$CH$_3$, —C$_{1-6}$alkyl, and O—C$_{1-6}$alkyl. In a class of this embodiment, each R$^b$ is unsubstituted or substituted with one to six substituents selected from F, Cl, CF$_3$, and CH$_3$.

In another embodiment, each R$^b$ is independently selected from the group consisting of: —CF$_3$, —OCF$_3$, —CHF$_2$, —OCHF$_2$, —CH$_2$CF$_3$, —CH(CF$_3$)CH$_3$, —OCH$_2$CF$_3$, —CF$_2$CH$_3$, CN, F, Cl, —S(O)$_2$CH$_3$, —CH$_3$, and cyclopropyl, wherein each R$^b$ is unsubstituted or substituted with one to six substituents selected from halogen, CF$_3$, OCF$_3$, CN, CH$_2$CF$_3$, CF$_2$CH$_3$, —C$_{1-6}$alkyl, and O—C$_{1-6}$alkyl. In a class of this embodiment, each R$^b$ is unsubstituted or substituted with one to six substituents selected from F, Cl, CF$_3$, and CH$_3$.

In another embodiment, each R$^b$ is independently selected from the group consisting of: —CF$_3$, —OCF$_3$, —CHF$_2$, —OCHF$_2$, —CH$_2$CF$_3$, —CH(CF$_3$)CH$_3$—OCH$_2$CF$_3$, CN, halogen, —S(O)$_2$C$_{1-6}$alkyl, —C$_{1-6}$alkyl, and —C$_{3-6}$cycloalkyl, wherein each R$^b$ is unsubstituted or substituted with one to six substituents selected from halogen, CF$_3$, OCF$_3$, CN, CH$_2$CF$_3$, CF$_2$CH$_3$, —C$_{1-6}$alkyl, and O—C$_{1-6}$alkyl. In a class of this embodiment, each $R^b$ is unsubstituted or substituted with one to six substituents selected from F, Cl, $CF_3$, and $CH_3$.

In another embodiment, each $R^b$ is independently selected from the group consisting of: $-CF_3$, $-OCF_3$, $-CHF_2$, $-OCHF_2$, $-CH_2CF_3$, $-CH(CF_3)CH_3$, $-OCH_2CF_3$, CN, F, Cl, $-S(O)_2CH_3$, $-CH_3$, and cyclopropyl, wherein each $R^b$ is unsubstituted or substituted with one to six substituents selected from halogen, $CF_3$, $OCF_3$, CN, $CH_2CF_3$, $CF_2CH_3$, $-C_{1-6}$alkyl, and $O-C_{1-6}$alkyl. In a class of this embodiment, each $R^b$ is unsubstituted or substituted with one to six substituents selected from F, Cl, $CF_3$, and $CH_3$.

In another embodiment, each $R^b$ is independently selected from the group consisting of: $-CF_3$, $-OCF_3$, $-OCH_2CF_3$, and halogen, wherein each $R^b$ is unsubstituted or substituted with one to six substituents selected from halogen, $CF_3$, $OCF_3$, CN, $CH_2CF_3$, $CF_2CH_3$, $-C_{1-6}$alkyl, and $O-C_{1-6}$alkyl. In a class of this embodiment, each $R^b$ is unsubstituted or substituted with one to six substituents selected from F, Cl, $CF_3$, and $CH_3$.

In another embodiment, each $R^b$ is independently selected from the group consisting of: $-CF_3$, $-OCF_3$, $-OCH_2CF_3$, F, and Cl, wherein each $R^b$ is unsubstituted or substituted with one to six substituents selected from halogen, $CF_3$, $OCF_3$, CN, $CH_2CF_3$, $CF_2CH_3$, $-C_{1-6}$alkyl, and $O-C_{1-6}$alkyl. In a class of this embodiment, each $R^b$ is unsubstituted or substituted with one to six substituents selected from F, Cl, $CF_3$, and $CH_3$.

In another embodiment of the present invention, $R^c$ is selected from: $-C_{1-6}$alkyl, OH, halogen, and $-OC_{1-6}$alkyl, wherein alkyl can be unsubstituted or substituted with one to three halogens. In another embodiment, $R^c$ is selected from: $-C_{1-6}$alkyl, OH, and halogen, wherein alkyl can be unsubstituted or substituted with one to three halogens. In another embodiment, $R^c$ is selected from: OH, and halogen. In a class of this embodiment, $R^c$ is selected from: OH, and F. In another embodiment, $R^c$ is OH. In another embodiment, $R^c$ is halogen. In a class of this embodiment, $R^c$ is F.

In another embodiment of the present invention, $R^d$ is selected from: $-C_{1-6}$alkyl, OH, halogen, and $-OC_{1-6}$alkyl, wherein alkyl can be unsubstituted or substituted with one to three halogens. In another embodiment, $R^d$ is selected from: $-C_{1-6}$alkyl, OH, and halogen, wherein alkyl can be unsubstituted or substituted with one to three halogens. In another embodiment, $R^d$ is selected from: OH, and halogen. In a class of this embodiment, $R^d$ is selected from: OH, and F. In another embodiment, $R^d$ is OH. In another embodiment, $R^d$ is halogen. In a class of this embodiment, $R^d$ is F.

In another embodiment of the present invention, $R^e$ is selected from: hydrogen and $C_{1-6}$alkyl. In another embodiment, $R^e$ is hydrogen. In another embodiment, $R^e$ is $C_{1-6}$alkyl.

In another embodiment of the present invention, $R^f$ is selected from: $-C_{1-6}$alkyl, OH, halogen, and $-OC_{1-6}$alkyl, wherein alkyl can be unsubstituted or substituted with one to three halogens. In another embodiment, $R^f$ is selected from: $-C_{1-6}$alkyl, OH, and halogen, wherein alkyl can be unsubstituted or substituted with one to three halogens. In another embodiment, $R^f$ is selected from: OH, and halogen. In a class of this embodiment, $R^f$ is selected from: OH, and F. In another embodiment, $R^f$ is OH. In another embodiment, $R^f$ is halogen. In a class of this embodiment, $R^f$ is F.

In another embodiment of the present invention, $R^g$ is selected from: $-C_{1-6}$alkyl, OH, halogen, and $-OC_{1-6}$alkyl, wherein alkyl can be unsubstituted or substituted with one to three halogens. In another embodiment, $R^g$ is selected from: $-C_{1-6}$alkyl, OH, and halogen, wherein alkyl can be unsubstituted or substituted with one to three halogens. In another embodiment, $R^g$ is selected from: OH, and halogen. In a class of this embodiment, $R^g$ is selected from: OH, and F. In another embodiment, $R^g$ is OH. In another embodiment, $R^g$ is halogen. In a class of this embodiment, $R^g$ is F.

In another embodiment of the present invention, $R^h$ is selected from: hydrogen and $C_{1-6}$alkyl. In another embodiment, $R^h$ is hydrogen. In another embodiment, $R^h$ is $C_{1-6}$alkyl.

In another embodiment of the present invention, $R^i$ is selected from: hydrogen, $C_{1-6}$alkyl, $C_{3-6}$cycloalkyl, aryl, and heteroaryl. In another embodiment, $R^i$ is selected from: hydrogen, $C_{1-6}$alkyl, and $C_{3-6}$cycloalkyl. In another embodiment, $R^i$ is selected from: hydrogen and $C_{1-6}$alkyl. In another embodiment, $R^i$ is hydrogen. In another embodiment, $R^i$ is $C_{1-6}$alkyl.

In another embodiment of the present invention, $R^j$ is selected from: hydrogen, $C_{1-6}$alkyl, C3-6alkenyl, C3-6alkynyl, $C_{3-6}$cycloalkyl, $C_{2-5}$cycloheteroalkyl, aryl, and heteroaryl. In another embodiment, $R^j$ is selected from: hydrogen, $C_{1-6}$alkyl, C3-6alkenyl, C3-6alkynyl, $C_{3-6}$cycloalkyl, and $C_{2-5}$cycloheteroalkyl. In another embodiment, $R^j$ is selected from: hydrogen, $C_{1-6}$alkyl, C3-6alkenyl, C3-6alkynyl, and $C_{3-6}$cycloalkyl. In another embodiment, $R^j$ is selected from: hydrogen, $C_{1-6}$alkyl, C3-6alkenyl, and C3-6alkynyl. In another embodiment, $R^j$ is selected from: hydrogen, $C_{1-6}$alkyl, and C3-6alkenyl. In another embodiment, $R^j$ is selected from: hydrogen, and $C_{1-6}$alkyl. In another embodiment, $R^j$ is $C_{1-6}$alkyl. In another embodiment, $R^j$ is hydrogen.

In another embodiment of the present invention, $R^k$ is selected from: hydrogen and $C_{1-6}$alkyl. In another embodiment, $R^k$ is hydrogen. In another embodiment, $R^k$ is $C_{1-6}$alkyl.

In another embodiment of the present invention, $R^L$ is selected from: hydrogen, $C_{1-6}$alkyl, $C_{3-6}$cycloalkyl, aryl, and heteroaryl. In another embodiment, $R^L$ is selected from: hydrogen, $C_{1-6}$alkyl, and $C_{3-6}$cycloalkyl. In another embodiment, $R^L$ is selected from: hydrogen, and $C_{1-6}$alkyl. In another embodiment, $R^L$ is hydrogen. In another embodiment, $R^L$ is $C_{1-6}$alkyl.

In one embodiment of the present invention, m is 0, 1 or 2. In another embodiment, m is 0 or 1. In another embodiment, m is 0 or 2. In another embodiment, m is 0. In another embodiment, m is 1. In another embodiment, m is 2.

In one embodiment of the present invention, n is 2, 3, 4, 5 or 6. In another embodiment, n is 2, 3, 4, or 5. In another embodiment, n is 2, 3, or 4. In another embodiment, n is 2 or 3. In another embodiment, n is 2 or 4. In another embodiment, n is 2, 3, 4, or 5. In another embodiment, n is 3. In another embodiment, n is 4. In another embodiment, n is 5. In another embodiment, n is 6.

In one embodiment of the present invention, p is 0, 1, 2 or 3. In another embodiment, p is 0, 1 or 2. In another embodiment, p is 0, 1 or 3. In another embodiment, p is 1, 2 or 3. In another embodiment, p is 1 or 2. In another embodiment, p is 1 or 3. In another embodiment, p is 0 or 1. In another embodiment, p is 0 or 2. In another embodiment, p is 0 or 3. In another embodiment, p is 0. In another embodiment, p is 1. In another embodiment, p is 2. In another embodiment, p is 3.

In one embodiment of the present invention, q is 0, 1, 2 or 3. In another embodiment, q is 1, 2 or 3. In another embodiment, q is 0, 1 or 2. In another embodiment, q is 0, 1 or 3. In another embodiment, q is 0, or 1. In another embodiment, q is 0 or 2. In another embodiment, q is 0. In another embodiment, q is 1. In another embodiment, q is 2. In another embodiment, q is 3.

In one embodiment of the present invention, r is 0, 1 or 2. In another embodiment, r is 1 or 2. In another embodiment, r is 0 or 1. In another embodiment, r is 0 or 2. In another embodiment, r is 0. In another embodiment, r is 1. In another embodiment, r is 2.

In one embodiment of the present invention, s is 0, 1, 2, 3, 4, 5 or 6. In another embodiment, s is 0, 1, 2, 3, 4, or 5. In another embodiment, s is 1, 2, 3, 4, 5 or 6. In another embodiment, s is 1, 2, 3, 4 or 5. In another embodiment, s is 0, 1, 2, 3, or 4. In another embodiment, s is 1, 2, 3, or 4. In another embodiment, s is 0, 1, 2, or 3. In another embodiment, s is 1, 2, or 3. In another embodiment, s is 0, 1 or 2. In another embodiment, s is 1 or 2. In another embodiment, s is 0. In another embodiment, s is 1. In another embodiment, s is 2. In another embodiment, s is 3. In another embodiment, s is 4. In another embodiment, s is 5. In another embodiment, s is 6.

In another embodiment of the present invention, the invention relates to compounds of structural formula Ia:

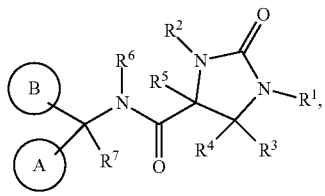

Ia wherein A is aryl; or a pharmaceutically acceptable salt thereof.

In another embodiment of the present invention, the invention relates to compounds of structural formula Ib:

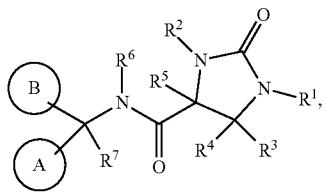

Ib wherein A is heteroaryl; or a pharmaceutically acceptable salt thereof.

In another embodiment of the present invention, the invention relates to compounds of structural formula Ic:

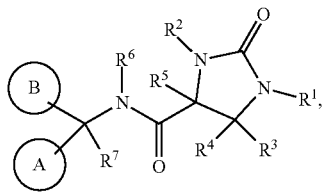

Ic wherein A is phenyl; or a pharmaceutically acceptable salt thereof.

In another embodiment of the present invention, the invention relates to compounds of structural formula Id:

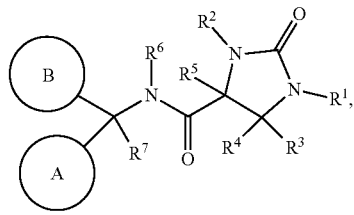

Id wherein A is pyridine; or a pharmaceutically acceptable salt thereof.

The compound of structural formula I, includes the compounds of structural formulas Ia, Ib, Ic, and Id, and pharmaceutically acceptable salts, hydrates and solvates thereof.

Another embodiment of the present invention relates to compounds of structural formula I wherein:

A is selected from the group consisting of:
1) aryl, and
2) heteroaryl,
wherein A is unsubstituted or substituted with one to five substituents selected from $R^a$;

B is independently selected from the group consisting of:
1) aryl,
2) heteroaryl,
3) —$C_{1-6}$alkyl-aryl,
4) —$C_{3-8}$cycloalkyl-aryl,
5) —$C_{2-8}$cycloheteroalkyl-aryl,
6) —$C_{1-6}$alkyl-heteroaryl,
7) —$C_{3-8}$cycloalkyl-heteroaryl,
8) —$C_{2-8}$cycloheteroalkyl-heteroaryl,
9) —$C_{1-6}$alkyl-O-aryl,
10) —$C_{1-6}$alkyl-O-heteroaryl,
11) —$C_{3-12}$cycloalkyl,
12) —$C_{2-12}$cycloheteroalkyl,
13) —$C_{1-6}$alkyl-$C_{3-12}$cycloalkyl,
14) —$C_{1-6}$alkyl-$C_{2-12}$cycloheteroalkyl,
15) —$C_{1-6}$alkyl-O—$C_{3-12}$cycloalkyl,
16) —$C_{1-6}$alkyl-O—$C_{2-12}$cycloheteroalkyl,
17) —$C_{0-6}$alkyl-aryl fused to $C_{4-6}$cycloalkyl or $C_{4-6}$cycloheteroalkyl containing 1-3 heteroatoms independently selected from O, S and $N(R^h)_2$,
18) —$C_{0-6}$alkyl-aryl fused to $C_{4-6}$cycloalkenyl or $C_{4-6}$cycloheteroalkenyl containing 1-3 heteroatoms independently selected from O, S and $N(R^h)_2$,
19) —$C_{0-6}$alkyl-heteroaryl fused to $C_{4-6}$cycloalkyl or $C_{4-6}$cycloheteroalkyl containing 1-3 heteroatoms independently selected from O, S and $N(R^h)_2$, and
20) —$C_{0-6}$alkyl-heteroaryl fused to $C_{4-6}$cycloalkenyl or $C_{4-6}$cycloheteroalkenyl containing 1-3 heteroatoms independently selected from O, S and $N(R^h)_2$, wherein alkyl, cycloalkyl, cycloheteroalkyl, cycloalkenyl, aryl and heteroaryl are unsubstituted or substituted with one to five substituents selected from $R^b$; or a pharmaceutically acceptable salt thereof.

$R^1$ is selected from the group consisting of:
1) hydrogen,
2) —$C_{1-6}$alkyl,
3) —$C_{3-6}$alkenyl,
4) —$C_{3-6}$alkynyl,
5) —$C_{3-10}$cycloalkyl,
6) —$C_{2-10}$cycloheteroalkyl,
7) —$C_{1-6}$alkyl-O—$C_{1-6}$alkyl-,
8) —$(CH_2)_sC(O)R^j$,
9) —$(CH_2)_sC(O)NR^eR^j$, 10) —$(CH_2)_nNR^eC(O)R^j$,
11) —$(CH_2)_nNR^eC(O)OR^j$,
12) —$(CH_2)_nNR^eC(O)N(R^e)_2$,
13) —$(CH_2)_nNR^eC(O)NR^eR^j$,
14) —$(CH_2)_nNR^eS(O)_mR^j$,
15) —$(CH_2)_nNR^eS(O)mN(R^e)_2$,
16) —$(CH_2)_nNR^eS(O)mNR^eR^j$, and
17) —$(CH_2)_nNR^eR^j$, wherein each $CH_2$, alkyl, alkenyl, alkynyl, cycloalkyl and cycloheteroalkyl is unsubstituted or substituted with one to five substituents selected from $R^c$;

$R^2$ is selected from the group consisting of:
1) hydrogen,
2) —$C_{1-6}$alkyl,
3) —$C_{3-6}$alkenyl,
4) —$C_{3-6}$alkynyl,
5) —$C_{3-10}$cycloalkyl,
6) —$C_{2-10}$cycloheteroalkyl,
7) —$C_{1-6}$alkyl-O—$C_{1-6}$alkyl-,
8) —$(CH_2)_sC(O)R^j$,
9) —$(CH_2)_sC(O)NR^eR^j$,
10) —$(CH_2)_nNR^eC(O)R^j$,
11) —$(CH_2)_nNR^eC(O)OR^j$,
12) —$(CH_2)_nNR^eC(O)N(R^e)_2$,
13) —$(CH_2)_nNR^eC(O)NR^eR^j$,
14) —$(CH_2)_nNR^eS(O)_mR^j$,
15) —$(CH_2)_nNR^eS(O)mN(R^e)_2$,
16) —$(CH_2)_nNR^eS(O)mNR^eR^j$, and
17) —$(CH_2)_nNR^eR^j$, wherein each $CH_2$, alkyl, alkenyl, alkynyl, cycloalkyl, and cycloheteroalkyl is unsubstituted or substituted with one to five substituents selected from $R^d$;

$R^3$ is selected from the group consisting of:
1) hydrogen,
2) —$C_{1-6}$alkyl,
3) —$C_{2-6}$alkenyl,
4) —$C_{2-6}$alkynyl,
5) —$C_{3-10}$cycloalkyl,
6) —$C_{2-10}$cycloheteroalkyl,
7) —$C_{1-6}$alkyl-O—$C_{1-6}$alkyl-,
8) —$(CH_2)_sC(O)R^j$,
9) —$(CH_2)_sC(O)NR^eR^j$,
10) —$(CH_2)_sNR^eC(O)R^j$,
11) —$(CH_2)_sNR^eC(O)OR^j$,
12) —$(CH_2)_sNR^eC(O)N(R^e)_2$,
13) —$(CH_2)_sNR^eC(O)NR^eR^j$,
14) —$(CH_2)_sNR^eS(O)_mR^j$,
15) —$(CH_2)_sNR^eS(O)mN(R^e)_2$,
16) —$(CH_2)_sNR^eS(O)mNR^eR^j$, and
17) —$(CH_2)_sNR^eR^j$, wherein each $CH_2$, alkyl, alkenyl, alkynyl, cycloalkyl, and cycloheteroalkyl is unsubstituted or substituted with one to five substituents selected from $R^f$, and wherein $R^3$ and $R^4$ and the carbon atoms they are connected to can from —$C_{3-5}$cycloalkyl ring $R^4$ is selected from the group consisting of:
1) hydrogen,
2) —$C_{1-6}$alkyl,
3) —$C_{2-6}$alkenyl,
4) —$C_{2-6}$alkynyl,
5) —$C_{3-10}$cycloalkyl,
6) —$C_{2-10}$cycloheteroalkyl,
7) —$C_{1-6}$alkyl-O—$C_{1-6}$alkyl-,
8) —$(CH_2)_sC(O)R^j$,
9) —$(CH_2)_sC(O)NR^eR^j$,
10) —$(CH_2)_sNR^eC(O)R^j$,
11) —$(CH_2)_sNR^eC(O)OR^j$,
12) —$(CH_2)_sNR^eC(O)N(R^e)_2$,
13) —$(CH_2)_sNR^eC(O)NR^eR^j$,
14) —$(CH_2)_sNR^eS(O)_mR^j$,
15) —$(CH_2)_sNR^eS(O)mN(R^e)_2$,
16) —$(CH_2)_sNR^eS(O)mNR^eR^j$, and
17) —$(CH_2)_sNR^eR^j$, wherein each $CH_2$, alkyl, alkenyl, alkynyl, cycloalkyl, and cycloheteroalkyl is unsubstituted or substituted with one to five substituents selected from $R^g$;

$R^5$ is selected from the group consisting of:
1) hydrogen, and
2) —$C_{1-6}$alkyl, wherein each alkyl is unsubstituted or substituted with one to five halogen substituents;

$R^6$ is selected from the group consisting of:
1) hydrogen,
2) —$C_{1-6}$alkyl,
3) —$C_{3-6}$cycloalkyl, and
4) —$C_{2-6}$cycloheteroalkyl, wherein each alkyl, cycloalkyl and cycloheteroalkyl is unsubstituted or substituted with one to five halogen substituents;

$R^7$ is selected from the group consisting of:
1) hydrogen,
2) —$C_{1-6}$alkyl,
3) —$C_{2-6}$alkenyl, and
4) —$C_{2-6}$alkynyl, wherein each alkyl, alkenyl and alkynyl is unsubstituted or substituted with one to five halogen substituents;

each $R^a$ is independently selected from the group consisting of:
1) —$CF_3$,
2) —$OCF_3$,
3) —$CHF_2$,
4) —$OCHF_2$,
5) —$CH_2CF_3$,
6) —$OCH_2CF_3$,
7) —$CF_2CH_3$,
8) CN,
9) oxo,
10) halogen,
11) —$S(O)_2C_{1-6}$alkyl,
12) —$C_{1-6}$alkyl,
13) —$C_{2-6}$alkenyl,
14) —$C_{2-6}$alkynyl,
15) —$C_{3-6}$cycloalkyl,
16) —$C_{2-6}$cycloheteroalkyl,
17) aryl,
18) heteroaryl,
19) —$C_{1-6}$alkyl-aryl,
20) —$C_{1-6}$alkyl-heteroaryl,
21) —$C_{1-6}$alkyl-$C_{3-6}$cycloalkyl,
22) —$C_{1-6}$alkyl-$C_{2-6}$cycloheteroalkyl,
23) —$C_{2-6}$alkenyl-$C_{3-6}$cycloalkyl,
24) —$C_{2-6}$alkenyl-$C_{2-6}$cycloheteroalkyl,
25) —$C_{2-6}$alkenyl-aryl,
26) —$C_{2-6}$alkenyl-heteroaryl,
27) —$C_{2-6}$alkynyl-$C_{3-6}$cycloalkyl,
28) —$C_{2-6}$alkynyl-$C_{2-6}$cycloheteroalkyl,
29) —$C_{2-6}$alkynyl-aryl,
30) —$C_{2-6}$alkynyl-heteroaryl,
31) —OH,
32) —$(CH_2)_p$—$OC_{1-6}$alkyl,
33) —$(CH_2)_p$—$OC_{2-6}$alkenyl,
34) —$(CH_2)_p$—$OC_{2-6}$alkynyl,
35) —$(CH_2)_p$—$OC_{3-6}$cycloalkyl,
36) —$(CH_2)_p$—$OC_{2-6}$heterocycloalkyl, 37) —(CH$_2$)$_p$—O-aryl,
38) —(CH$_2$)$_p$—O-heteroaryl,
39) —OC$_{1-6}$alkyl-C$_{3-6}$cycloalkyl,
40) —OC$_{1-6}$alkyl-C$_{2-6}$heterocycloalkyl,
41) —OC$_{1-6}$alkyl-aryl,
42) —OC$_{1-6}$alkyl-heteroaryl,
43) —S(O)$_m$R$^i$,
44) —C$_{1-6}$alkyl-S(O)$_m$R$^i$,
45) —N(R$^k$)$_2$, and
46) —NR$^k$R$^L$,
wherein each R$^a$ is unsubstituted or substituted with one to six substituents selected from halogen, CF$_3$, OH, C$_{1-6}$alkyl, and OC$_{1-6}$alkyl;
each R$^b$ is independently selected from the group consisting of:
1) —CF$_3$,
2) —OCF$_3$,
3) —CHF$_2$,
4) —OCHF$_2$,
5) —CH$_2$CF$_3$,
6) —OCH$_2$CF$_3$,
7) —CF$_2$CH$_3$,
8) CN,
9) oxo,
10) halogen,
11) —S(O)$_2$C$_{1-6}$alkyl,
12) —C$_{1-6}$alkyl,
13) —C$_{2-6}$alkenyl,
14) —C$_{2-6}$alkynyl,
15) —O—C$_{1-6}$alkyl,
16) —C$_{3-6}$cycloalkyl,
17) —O—C$_{3-6}$cycloalkyl,
18) —C$_{2-6}$cycloheteroalkyl,
19) aryl,
20) heteroaryl,
21) —C$_{1-6}$alkyl-aryl,
22) —C$_{1-6}$alkyl-heteroaryl,
23) —C$_{1-6}$alkyl-C$_{3-6}$cycloalkyl,
24) —C$_{1-6}$alkyl-C$_{2-6}$cycloheteroalkyl,
25) —C$_{2-6}$alkenyl-C$_{3-6}$cycloalkyl,
26) —C$_{2-6}$alkenyl-C$_{2-6}$cycloheteroalkyl,
27) —C$_{2-6}$alkenyl-aryl,
28) —C$_{2-6}$alkenyl-heteroaryl,
29) —C$_{2-6}$alkynyl-C$_{3-6}$cycloalkyl,
30) —C$_{2-6}$alkynyl-C$_{2-6}$cycloheteroalkyl,
31) —C$_{2-6}$alkynyl-aryl,
32) —C$_{2-6}$alkynyl-heteroaryl,
33) —OH,
34) —(CH$_2$)$_q$—OC$_{1-6}$alkyl,
35) —(CH$_2$)$_q$—OC$_{2-6}$alkenyl,
36) —(CH$_2$)$_q$—OC$_{2-6}$alkynyl,
37) —(CH$_2$)$_q$—OC$_{3-6}$cycloalkyl,
38) —(CH$_2$)$_q$—OC$_{2-6}$heterocycloalkyl,
39) —(CH$_2$)$_q$—O-aryl,
40) —(CH$_2$)$_q$—O-heteroaryl,
41) —OC$_{1-6}$alkyl-C$_{3-6}$cycloalkyl,
42) —OC$_{1-6}$alkyl-C$_{2-6}$heterocycloalkyl,
43) —OC$_{1-6}$alkyl-aryl,
44) —OC$_{1-6}$alkyl-heteroaryl,
45) —S(O)$_m$R$^i$,
46) —C$_{1-6}$alkyl-S(O)$_m$R$^i$,
47) —C(O)R$^L$, and
48) —NR$^k$R$^L$,
wherein each R$^b$ is unsubstituted or substituted with one to six substituents selected from halogen, CF$_3$, OCF$_3$, CN, CH$_2$CF$_3$, CF$_2$CH$_3$, —C$_{1-6}$alkyl, and —OC$_{1-6}$alkyl;

R$^c$ is selected from:
1) —C$_{1-6}$alkyl,
2) OH,
3) halogen, and
4) —OC$_{1-6}$alkyl,
wherein alkyl can be unsubstituted or substituted with one to three halogens;
R$^d$ is selected from:
1) —C$_{1-6}$alkyl,
2) OH,
3) halogen, and
4) —OC$_{1-6}$alkyl,
wherein alkyl can be unsubstituted or substituted with one to three halogens;
R$^e$ is selected from:
1) hydrogen, and
2) C$_{1-6}$alkyl;
R$^f$ is selected from:
1) —C$_{1-6}$alkyl,
2) OH,
3) halogen, and
4) —OC$_{1-6}$alkyl,
wherein alkyl can be unsubstituted or substituted with one to three halogens;
R$^g$ is selected from:
1) —C$_{1-6}$alkyl,
2) OH,
3) halogen, and
4) —OC$_{1-6}$alkyl,
wherein alkyl can be unsubstituted or substituted with one to three halogens;
R$^h$ is selected from:
1) hydrogen, and
2) C$_{1-6}$alkyl;
R$^i$ is selected from:
1) hydrogen,
2) C$_{1-6}$alkyl,
3) C$_{3-6}$cycloalkyl,
4) aryl, and
5) heteroaryl;
R$^j$ is selected from:
1) hydrogen,
2) C$_{1-6}$alkyl,
3) C$_{3-6}$alkenyl,
4) C$_{3-6}$alkynyl,
5) C$_{3-6}$cycloalkyl,
6) C$_{2-5}$cycloheteroalkyl,
7) aryl, and
8) heteroaryl;
R$^k$ is selected from:
1) hydrogen, and
2) C$_{1-6}$alkyl;
R$^L$ is selected from:
1) hydrogen,
2) C$_{1-6}$alkyl,
3) C$_{3-6}$cycloalkyl,
4) aryl, and
5) heteroaryl;
m is independently selected from 0 to 2;
n is independently selected from 2 to 6;
p is independently selected from 0 to 3;
q is independently selected from 0 to 3;
r is independently selected from 0 to 2; and
s is independently selected from 0 to 6;
or a pharmaceutically acceptable salt thereof.

Another embodiment of the present invention relates to compounds of structural formula I wherein:

A is selected from the group consisting of:
1) aryl, and
2) heteroaryl,
wherein A is unsubstituted or substituted with one to five substituents selected from $R^a$;
B is independently selected from the group consisting of:
1) aryl,
2) heteroaryl,
3) —$C_{1-6}$alkyl-aryl,
4) —$C_{1-6}$alkyl-O-aryl,
5) —$C_{1-6}$alkyl-O-heteroaryl,
6) —$C_{3-12}$cycloalkyl,
7) —$C_{2-12}$cycloheteroalkyl,
8) —$C_{1-6}$alkyl-$C_{3-12}$cycloalkyl,
9) —$C_{1-6}$alkyl-$C_{2-12}$cycloheteroalkyl,
10) —$C_{1-6}$alkyl-O—$C_{3-12}$cycloalkyl, and
11) —$C_{0-6}$alkyl-aryl fused to $C_{4-6}$cycloalkyl or $C_{4-6}$cycloheteroalkyl containing 1-3 heteroatoms independently selected from O, S and N($R^h$)$_2$, wherein alkyl, cycloalkyl, cycloheteroalkyl, aryl and heteroaryl are unsubstituted or substituted with one to five substituents selected from $R^b$;
$R^1$ is selected from the group consisting of:
1) hydrogen, and
2) —$C_{1-6}$alkyl,
wherein each alkyl is unsubstituted or substituted with one to five substituents selected from $R^c$;
$R^2$ is selected from the group consisting of:
1) hydrogen, and
2) —$C_{1-6}$alkyl,
wherein each alkyl is unsubstituted or substituted with one to five substituents selected from $R^d$;
$R^3$ is selected from the group consisting of:
1) hydrogen, and
2) —$C_{1-6}$alkyl,
wherein each alkyl is unsubstituted or substituted with one to five substituents selected from $R^f$;
$R^4$ is selected from the group consisting of:
1) hydrogen, and
2) —$C_{1-6}$alkyl,
wherein each alkyl is unsubstituted or substituted with one to five substituents selected from $R^g$;
$R^5$ is selected from the group consisting of:
1) hydrogen, and
2) —$C_{1-6}$alkyl,
wherein each alkyl is unsubstituted or substituted with one to five halogen substituents;
$R^6$ is selected from the group consisting of:
1) hydrogen, and
2) —$C_{1-6}$alkyl,
wherein each alkyl is unsubstituted or substituted with one to five halogen substituents;
$R^7$ is selected from the group consisting of:
1) hydrogen, and
2) —$C_{1-6}$alkyl,
wherein each alkyl is unsubstituted or substituted with one to five halogen substituents;
each $R^a$ is independently selected from the group consisting of:
1) —$CF_3$,
2) —$OCF_3$,
3) —$CHF_2$,
4) —$OCH_2CF_3$,
5) CN,
6) halogen, and
7) —$C_{2-6}$alkynyl, wherein each $R^a$ is unsubstituted or substituted with one to six substituents selected from halogen, $CF_3$, OH, $C_{1-6}$alkyl, and —$OC_{1-6}$alkyl; or a pharmaceutically acceptable salt thereof.
each $R^b$ is independently selected from the group consisting of:
1) —$CF_3$,
2) —$OCF_3$,
3) —$CHF_2$,
4) —$OCHF_2$,
5) —$CH_2CF_3$,
6) —$CH(CF_3)CH_3$,
7) —$OCH_2CF_3$,
8) CN,
9) halogen,
10) —$S(O)_2C_{1-6}$alkyl,
11) —$C_{1-6}$alkyl, and
12) —$C_{3-6}$cycloalkyl,
wherein each $R^b$ is unsubstituted or substituted with one to six substituents selected from halogen, $CF_3$, $OCF_3$, CN, $CH_2CF_3$, $CF_2CH_3$, —$C_{1-6}$alkyl, and —$OC_{1-6}$alkyl;
or a pharmaceutically acceptable salt thereof.

Another embodiment of the present invention relates to compounds of structural formula I wherein:
A is aryl, wherein aryl is unsubstituted or substituted with one to five substituents selected from $R^a$;
B is independently selected from the group consisting of:
1) aryl,
2) heteroaryl, and
3) $C_{3-12}$cycloalkyl,
wherein cycloalkyl, aryl and heteroaryl are unsubstituted or substituted with one to five substituents selected from $R^b$;
$R^1$, $R^2$, $R^3$, $R^4$, $R^5$, $R^6$ and $R^7$ are hydrogen;
each $R^a$ is independently selected from the group consisting of:
1) —$CF_3$,
2) —$OCF_3$, and
3) halogen;
each $R^b$ is independently selected from the group consisting of:
1) —$CF_3$,
2) —$OCF_3$,
3) —$OCH_2CF_3$, and
4) halogen,
wherein each $R^b$ is unsubstituted or substituted with one to six substituents selected from halogen, $CF_3$, $OCF_3$, CN, $CH_2CF_3$, $CF_2CH_3$, —$C_{1-6}$alkyl, and —$OC_{1-6}$alkyl;
or a pharmaceutically acceptable salt thereof.

Illustrative, but non-limiting, examples of the compounds of the present invention that are useful as inhibitors of $Na_v1.8$ channel activity are the following compounds:
1) (S)—N—((R)-2-(3-chloro-4-fluorophenoxy)-1-(3-chloro-4-fluorophenyl)ethyl)-2-oxoimidazolidine-4-carboxamide;
2) (S)—N—((S)-2-(3-chloro-4-fluorophenoxy)-1-(3-chloro-4-fluorophenyl)ethyl)-2-oxoimidazolidine-4-carboxamide;
3) (R)—N-(bis(4-chlorophenyl)methyl)-3-methyl-2-oxoimidazolidine-4-carboxamide and (S)—N-(bis(4-chlorophenyl)methyl)-3-methyl-2-oxoimidazolidine-4-carboxamide;
4) (S)—N—((R)-(5-chloro-6-(difluoromethyl)pyridin-2-yl)(5-chloro-6-(trifluoromethyl)pyridin-3-yl)methyl)-2-oxoimidazolidine-4-carboxamide;
5) (S)—N—((S)-(5-chloro-6-(difluoromethyl)pyridin-2-yl)(5-chloro-6-(trifluoromethyl)pyridin-3-yl)methyl)-2-oxoimidazolidine-4-carboxamide;

6) (S)—N—((R)-(3-chloro-4-fluorophenyl)(5-(trifluoromethyl)-1H-pyrazol-3-yl)methyl)-2-oxoimidazolidine-4-carboxamide;
7) (S)—N—((S)-(3-chloro-4-fluorophenyl)(5-(trifluoromethyl)-1H-pyrazol-3-yl)methyl)-2-oxoimidazolidine-4-carboxamide;
8) (S)—N—((R)-(3-chloro-2,4-difluorophenyl)(1-(1-(trifluoromethyl)cyclopropyl)piperidin-4-yl)methyl)-2-oxoimidazolidine-4-carboxamide;
9) (S)—N—((S)-(3-chloro-2,4-difluorophenyl)(1-(1-(trifluoromethyl)cyclopropyl)piperidin-4-yl)methyl)-2-oxoimidazolidine-4-carboxamide;
10) (S)—N-((5-chloro-4-(trifluoromethyl)pyrimidin-2-yl)(4-chlorophenyl)methyl)-2-oxoimidazolidine-4-carboxamide;
11) (S)—N—(R)-(5-fluoro-6-(trifluoromethyl)pyridin-2-yl)(4-(trifluoromethoxy)phenyl)-methyl)-2-oxoimidazolidine-4-carboxamide;
12) (S)—N—((S)-(5-fluoro-6-(trifluoromethyl)pyridin-2-yl)(4-(trifluoromethoxy)phenyl)-methyl)-2-oxoimidazolidine-4-carboxamide;
13) (S)—N—((R)-(3-chloro-2,4-difluorophenyl)((trans)-5-(trifluoromethyl)tetrahydro-2H-pyran-2-yl)methyl)-2-oxoimidazolidine-4-carboxamide;
14) (S)—N—((S)-(3-chloro-2,4-difluorophenyl)((trans)-5-(trifluoromethyl)tetrahydro-2H-pyran-2-yl)methyl)-2-oxoimidazolidine-4-carboxamide;
15) (S)—N—((R)-(3-chlorophenyl)(4-(trifluoromethoxy)phenyl)methyl)-2-oxoimidazolidine-4-carboxamide;
16) (S)—N—((S)-(3-chlorophenyl)(4-(trifluoromethoxy)phenyl)methyl)-2-oxoimidazolidine-4-carboxamide;
17) (R)—N-[bis(4-chlorophenyl)methyl]-1-methyl-2-oxoimidazolidine-4-carboxamide;
18) (S)—N-[bis(4-chlorophenyl)methyl]-1-methyl-2-oxoimidazolidine-4-carboxamide;
19) (4S)—N—{((R)-3-chloro-4-fluorophenyl)[5-fluoro-6-(2,2,2-trifluoro-ethoxy)pyridin-2-yl]methyl}-2-oxoimidazolidine-4-carboxamide;
20) (4S)—N—{((S)-3-chloro-4-fluorophenyl)[5-fluoro-6-(2,2,2-trifluoro-ethoxy)pyridin-2-yl]methyl}-2-oxoimidazolidine-4-carboxamide;
21) (4S)—N—[((R)-3-chloro-4-fluorophenyl)(6-cyanopyridin-2-yl)methyl]-2-oxoimidazolidine-4-carboxamide;
22) (4S)—N—[((S)-3-chloro-4-fluorophenyl)(6-cyanopyridin-2-yl)methyl]-2-oxoimidazolidine-4-carboxamide;
23) (4S)—N—[((R)-5-chloro-6-cyclopropylpyridin-3-yl)(3-chloro-2,4-difluoro-phenyl)methyl]-2-oxoimidazolidine-4-carboxamide;
24) (4S)—N—[((S)-5-chloro-6-cyclo-propylpyridin-3-yl)(3-chloro-2,4-difluoro-phenyl)methyl]-2-oxoimidazolidine-4-carboxamide;
25) (4S)—N—{[(R)-5-chloro-6-(trifluoromethyl)pyridin-3-yl][5-fluoro-6-(trifluoro-methyl)pyridin-2-yl]methyl}-2-oxoimidazolidine-4-carboxamide;
26) (4S)—N—{[(S)-5-chloro-6-(trifluoromethyl)pyridin-3-yl][5-fluoro-6-(trifluoro-methyl)pyridin-2-yl]methyl}-2-oxoimidazolidine-4-carboxamide;
27) (S)—N—((R)-(3-chloro-4-fluorophenyl)(cis-2,6-dimethyl-1-(2,2,2-trifluoroethyl)-piperidin-4-yl)methyl)-2-oxoimidazolidine-4-carboxamide;
28) (S)—N—((S)-(3-chloro-4-fluorophenyl)(cis-2,6-dimethyl-1-(2,2,2-trifluoroethyl)-piperidin-4-yl)methyl)-2-oxoimidazolidine-4-carboxamide;
29) (S)—N—((R)-(3-chloro-4-fluorophenyl)(2-(1-(trifluoromethyl)cyclopropyl)thiazol-4-yl)methyl)-2-oxoimidazolidine-4-carboxamide;
30) (S)—N—((S)-(3-chloro-4-fluorophenyl)(2-(1-(trifluoromethyl)cyclopropyl)thiazol-4-yl)methyl)-2-oxoimidazolidine-4-carboxamide;
31) (S)—N—((R)-(4-chlorophenyl)(4-fluoro-3-(trifluoromethyl)phenyl)methyl)-2-oxoimidazolidine-4-carboxamide;
32) (S)—N—((S)-(4-chlorophenyl)(4-fluoro-3-(trifluoromethyl)phenyl)methyl)-2-oxoimidazolidine-4-carboxamide;
33) (S)—N—((R)-(3-chloro-4-fluoro-phenyl)(4-cyano-phenyl)methyl)-2-oxoimidazolidine-4-carboxamide;
34) (S)—N—((S)-(3-chloro-4-fluoro-phenyl)(4-cyano-phenyl)methyl)-2-oxoimidazolidine-4-carboxamide;
35) (S)-2-oxo-N—((R)-(6-(trifluoromethyl)pyridin-3-yl)(2-(trifluoromethyl)thiazol-4-yl)methyl)imidazolidine-4-carboxamide;
36) (S)-2-oxo-N—((S)-(6-(trifluoromethyl)pyridin-3-yl)(2-(trifluoromethyl)thiazol-4-yl)methyl)imidazolidine-4-carboxamide;
37) (R)—N-(bis(4-chlorophenyl)methyl)-4-methyl-2,5-dioxoimidazolidine-4-carboxamide;
38) (S)—N-(bis(4-chlorophenyl)methyl)-4-methyl-2,5-dioxoimidazolidine-4-carboxamide;
39) (R)—N-(bis(4-chlorophenyl)methyl)-3-(2-hydroxyethyl)-2-oxoimidazolidine-4-carboxamide;
40) (S)—N-(bis(4-chlorophenyl)methyl)-3-(2-hydroxyethyl)-2-oxoimidazolidine-4-carboxamide;
41) (S)—N—((R)-(4-chlorophenyl)(2-(trifluoromethyl)-1H-imidazol-4-yl)methyl)-2-oxoimidazolidine-4-carboxamide;
42) (S)—N—((S)-(4-chlorophenyl)(2-(trifluoromethyl)-1H-imidazol-4-yl)methyl)-2-oxoimidazolidine-4-carboxamide;
43) (S)—N—((R)-1-(3-chloro-2,4-difluorophenyl)-2-((cis)-4-(trifluoromethyl)cyclohexyl)ethyl)-2-oxoimidazolidine-4-carboxamide;
44) (S)—N—((R)-1-(3-chloro-2,4-difluorophenyl)-2-((trans)-4-(trifluoromethyl)cyclohexyl)-ethyl)-2-oxoimidazolidine-4-carboxamide;
45) (S)—N—((S)-1-(3-chloro-2,4-difluorophenyl)-2-((trans)-4-(trifluoromethyl)cyclohexyl)-ethyl)-2-oxoimidazolidine-4-carboxamide;
46) (S)—N—((S)-1-(3-chloro-2,4-difluorophenyl)-2-((cis)-4-(trifluoromethyl)cyclohexyl)ethyl)-2-oxoimidazolidine-4-carboxamide;
47) (4S)—N—{(R)-(3-chloro-2,4-difluorophenyl)[6-(trifluoromethoxy)pyridin-3-yl]methyl}-2-oxoimidazolidine-4-carboxamide;
48) (4S)—N—{(S)-(3-chloro-2,4-difluorophenyl)[6-(trifluoromethoxy)pyridin-3-yl]methyl}-2-oxoimidazolidine-4-carboxamide;
49) (S)—N—((R)-1-(3-chloro-2,4-difluorophenyl)-2-(4,4-difluorocyclohexyl)ethyl)-2-oxoimidazolidine-4-carboxamide;
50) (S)—N—((S)-1-(3-chloro-2,4-difluorophenyl)-2-(4,4-difluorocyclohexyl)ethyl)-2-oxoimidazolidine-4-carboxamide;
51) (S)—N—((R)-1-(3-chloro-2,4-difluorophenyl)-2-((R)-tetrahydro-2H-pyran-3-yl)ethyl)-2-oxoimidazolidine-4-carboxamide;
52) (S)—N—((R)-1-(3-chloro-2,4-difluorophenyl)-2-((S)-tetrahydro-2H-pyran-3-yl)ethyl)-2-oxoimidazolidine-4-carboxamide;
53) (S)—N—((S)-1-(3-chloro-2,4-difluorophenyl)-2-((R)-tetrahydro-2H-pyran-3-yl)ethyl)-2-oxoimidazolidine-4-carboxamide;

54) (S)—N—((S)-1-(3-chloro-2,4-difluorophenyl)-2-((S)-tetrahydro-2H-pyran-3-yl)ethyl)-2-oxoimidazolidine-4-carboxamide;
55) (S)—N—((R)-3-chloro-2,4-difluorophenyl)(3-(trifluoromethyl)bicyclo[1.1.1]pentan-1-yl)methyl)-2-oxoimidazolidine-4-carboxamide;
56) (S)—N—((S)-(3-chloro-2,4-difluorophenyl)(3-(trifluoromethyl)bicyclo[1.1.1]pentan-1-yl)methyl)-2-oxoimidazolidine-4-carboxamide;
57) ((4S)—N—{(R)-(3-chloro-4-fluorophenyl)[1-(2,2,2-trifluoroethyl)-1H-pyrazol-3-yl]methyl}-2-oxoimidazolidine-4-carboxamide;
58) (4S)—N—{(S)-(3-chloro-4-fluorophenyl)[1-(2,2,2-trifluoroethyl)-1H-pyrazol-3-yl]methyl}-2-oxoimidazolidine-4-carboxamide;
59) (4S)—N—{((R)-3-chloro-4-fluorophenyl)-2-[(4,4-difluoro-cyclohexyl)oxy]ethyl}-2-oxoimidazolidine-4-carboxamide;
60) (4S)—N-{1-((S)-3-chloro-4-fluorophenyl)-2-[(4,4-difluoro-cyclohexyl)oxy]ethyl}-2-oxoimidazolidine-4-carboxamide;
61) (4S)—N—[(R)-(3-chloro-2,4-di-fluorophenyl)(3,3-dimethylcyclobutyl)methyl]-2-oxoimidazolidine-4-carboxamide;
62) (4S)—N—[(S)-(3-chloro-2,4-di-fluorophenyl)(3,3-dimethylcyclobutyl)methyl]-2-oxoimidazolidine-4-carboxamide;
63) (S)—N—((R)-(3-chloro-4-fluorophenyl)(1-methyl-3-(tri-fluoromethyl)-1H-pyrazol-5-yl)methyl)-2-oxoimidazolidine-4-carboxamide;
64) (S)—N—((S)-(3-chloro-4-fluorophenyl)(1-methyl-3-(tri-fluoromethyl)-1H-pyrazol-5-yl)methyl)-2-oxoimidazolidine-4-carboxamide;
65) (S)—N—((R)-(3-chloro-4-fluorophenyl)(trans-4-(trifluoromethyl)cyclohexyl)methyl)-2-oxoimidazolidine-4-carboxamide;
66) (S)—N—((S)-(3-chloro-4-fluorophenyl)(trans-4-(trifluoromethyl)cyclohexyl)methyl)-2-oxoimidazolidine-4-carboxamide;
67) (S)—N—((R)-(3-chloro-2,4-difluorophenyl)(6-(2,2,2-trifluoroethoxy)pyridin-3-yl)methyl)-2-oxoimidazolidine-4-carboxamide;
68) (S)—N—((S)-(3-chloro-2,4-difluorophenyl)(6-(2,2,2-trifluoroethoxy)pyridin-3-yl)methyl)-2-oxoimidazolidine-4-carboxamide;
69) (S)—N—((R)-(3-chloro-2,4-difluorophenyl)(trans-3-(trifluoromethyl)cyclobutyl)-methyl)-2-oxoimidazolidine-4-carboxamide;
70) (S)—N—((S)-(3-chloro-2,4-difluorophenyl)(trans-3-(trifluoromethyl)cyclobutyl)-methyl)-2-oxoimidazolidine-4-carboxamide;
71) (S)—N—((R)-(3-chloro-2,4-difluorophenyl)(2-(2,2,2-trifluoroethoxy)thiazol-5-yl)-methyl)-2-oxoimidazolidine-4-carboxamide;
72) (S)—N—((S)-(3-chloro-2,4-difluorophenyl)(2-(2,2,2-trifluoroethoxy)thiazol-5-yl)-methyl)-2-oxoimidazolidine-4-carboxamide;
73) (S)—N—((R)-(3-chloro-2,4-difluorophenyl)(2-(difluoromethoxy)thiazol-5-yl)methyl)-2-oxoimidazolidine-4-carboxamide;
74) (S)—N—((S)-(3-chloro-2,4-difluorophenyl)(2-(difluoromethoxy)thiazol-5-yl)methyl)-2-oxoimidazolidine-4-carboxamide;
75) (S)—N—((R)-(3-chloro-2,4-difluorophenyl)(6,6-difluorospiro[3.3]heptan-2-yl)methyl)-2-oxoimidazolidine-4-carboxamide;
76) (S)—N—((S)-(3-chloro-2,4-difluorophenyl)(6,6-difluorospiro[3.3]heptan-2-yl)methyl)-2-oxoimidazolidine-4-carboxamide;
77) (S)—N—((R)-(3-chloro-2,4-difluorophenyl)(5-chloro-6-(trifluoromethyl)pyridin-3-yl)methyl)-2-oxoimidazolidine-4-carboxamide;
78) (S)—N—((S)-(3-chloro-2,4-difluorophenyl)(5-chloro-6-(trifluoromethyl)pyridin-3-yl)methyl)-2-oxoimidazolidine-4-carboxamide;
79) (S)—N—((R)-(3-chloro-2,4-difluorophenyl)(trans-3-(trifluoromethyl)cyclobutyl)-methyl)-2-oxoimidazolidine-4-carboxamide;
80) (S)—N—((S)-(3-chloro-2,4-difluorophenyl)(trans-3-(trifluoromethyl)cyclobutyl)-methyl)-2-oxoimidazolidine-4-carboxamide;
81) (S)—N—((R)-3-chloro-4-(trifluoromethoxy)phenyl)(5-(trifluoromethoxy)pyridin-2-yl)methyl)-2-oxoimidazolidine-4-carboxamide;
82) (S)—N—((S)-3-chloro-4-(trifluoromethoxy)phenyl)(5-(trifluoromethoxy)pyridin-2-yl)methyl)-2-oxoimidazolidine-4-carboxamide;
83) (S)—N—((R)-(5-chloro-6-cyclopropylpyridin-2-yl)(4-(trifluoromethoxy)phenyl)-methyl)-2-oxoimidazolidine-4-carboxamide;
84) (S)—N—((S)-(5-chloro-6-cyclopropylpyridin-2-yl)(4-(trifluoromethoxy)phenyl)-methyl)-2-oxoimidazolidine-4-carboxamide;
85) (S)—N—((R)-(3-chloro-4-(trifluoromethoxy)phenyl)(1-(trifluoromethyl)-1H-pyrazol-4-yl)-l3-methyl)-2-oxoimidazolidine-4-carboxamide;
86) (S)—N—((S)-(3-chloro-4-(trifluoromethoxy)phenyl)(1-(trifluoromethyl)-1H-pyrazol-4-yl)-l3-methyl)-2-oxoimidazolidine-4-carboxamide;
87) (S)—N—((R)-(3-chloro-2,4-difluorophenyl)(6-(difluoromethoxy)-5-fluoropyridin-3-yl)methyl)-2-oxoimidazolidine-4-carboxamide;
88) (S)—N—((S)-(3-chloro-2,4-difluorophenyl)(6-(difluoromethoxy)-5-fluoropyridin-3-yl)methyl)-2-oxoimidazolidine-4-carboxamide;
89) (S)—N—((R)-(3-chloro-2,4-difluorophenyl)(6-(difluoromethyl)pyridin-3-yl)methyl)-2-oxoimidazolidine-4-carboxamide;
90) (S)—N—((S)-(3-chloro-2,4-difluorophenyl)(6-(difluoromethyl)pyridin-3-yl)methyl)-2-oxoimidazolidine-4-carboxamide;
91) (S)—N—((R)-(3-chloro-2,4-difluorophenyl)(5-fluoro-6-(trifluoromethyl)pyridin-3-yl)methyl)-2-oxoimidazolidine-4-carboxamide;
92) (S)—N—((S)-(3-chloro-2,4-difluorophenyl)(5-fluoro-6-(trifluoromethyl)pyridin-3-yl)methyl)-2-oxoimidazolidine-4-carboxamide;
93) (S)—N—((R)-(5-fluoro-6-(trifluoro-methyl)pyridin-2-yl)(6-(trifluoromethoxy)pyridin-3-yl)methyl)-2-oxoimidazolidine-4-carboxamide;
94) (S)—N—((S)-(5-fluoro-6-(trifluoromethyl)pyridin-2-yl)(6-(trifluoromethoxy)pyridin-3-yl)methyl)-2-oxoimidazolidine-4-carboxamide;
95) (S)—N—((R)-(5-fluoro-6-(2,2,2-trifluoroethoxy)pyridin-3-yl)(5-fluoro-6-(trifluoro-methyl)pyridin-2-yl)methyl)-2-oxoimidazolidine-4-carboxamide;
96) (S)—N—((S)-(5-fluoro-6-(2,2,2-trifluoroethoxy)pyridin-3-yl)(5-fluoro-6-(trifluoro-methyl)-pyridin-2-yl)methyl)-2-oxoimidazolidine-4-carboxamide;
97) (S)—N—((R)-(3-chloro-4-(trifluoromethoxy)phenyl)(2-(trifluoromethyl)oxazol-4-yl)methyl)-2-oxoimidazolidine-4-carboxamide 98) (S)—N—((S)-(3-chloro-4-(trifluoromethoxy)phenyl)(2-(trifluoromethyl)oxazol-4-yl)methyl)-2-oxoimidazolidine-4-carboxamide;
99) (S)—N—((R)-(3-chloro-2,4-difluorophenyl)(2-(trifluoromethyl)pyrimidin-5-yl)methyl)-2-oxoimidazolidine-4-carboxamide;
100) (S)—N—((S)-(3-chloro-2,4-difluorophenyl)(2-(trifluoromethyl)pyrimidin-5-yl)methyl)-2-oxoimidazolidine-4-carboxamide;
101) (S)—N—((R)-3-chloro-4-(trifluoromethoxy)phenyl)(2-(trifluoromethyl)pyrimidin-4-yl)methyl)-2-oxoimidazolidine-4-carboxamide;
102) (S)—N—((S)-3-chloro-4-(trifluoromethoxy)phenyl)(2-(trifluoromethyl)pyrimidin-4-yl)methyl)-2-oxoimidazolidine-4-carboxamide;
103) (4S)—N—((R)-(3-chloro-2,4-difluorophenyl)(6-(2,2,2-trifluoroethoxy)pyridazin-3-yl)-methyl)-2-oxoimidazolidine-4-carboxamide;
104) (4S)—N—((S)-(3-chloro-2,4-difluorophenyl)(6-(2,2,2-trifluoroethoxy)pyridazin-3-yl)-methyl)-2-oxoimidazolidine-4-carboxamide;
105) (4S)—N—((R)-(3-chloro-2,4-difluorophenyl)(5-(2,2,2-trifluoroethoxy)pyrazin-2-yl)methyl)-2-oxoimidazolidine-4-carboxamide;
106) (4S)—N—((S)-(3-chloro-2,4-difluorophenyl)(5-(2,2,2-trifluoroethoxy)pyrazin-2-yl)methyl)-2-oxoimidazolidine-4-carboxamide;
107) (S)—N—((R)-1-(3-chloro-2,4-difluorophenyl)-3-(4-chlorophenyl)propyl)-2-oxo-imidazolidine-4-carboxamide;
108) (S)—N—((S)-1-(3-chloro-2,4-difluorophenyl)-3-(4-chlorophenyl)propyl)-2-oxo-imidazolidine-4-carboxamide;
109) (4S)—N-(1-(3-chloro-4-fluorophenyl)-2-((6-(trifluoromethyl)pyridin-3-yl)oxy)ethyl)-2-oxoimidazolidine-4-carboxamide;
110) (S)—N—((R)-1-(3-chloro-2,4-difluorophenyl)-2-cyclohexylethyl)-2-oxoimidazolidine-4-carboxamide;
111) (S)—N—((S)-1-(3-chloro-2,4-difluorophenyl)-2-cyclohexylethyl)-2-oxoimidazolidine-4-carboxamide;
112) (4S)—N—((R)-(3-chloro-2,4-difluorophenyl)(2-(difluoromethoxy)pyrimidin-5-yl)methyl)-2-oxoimidazolidine-4-carboxamide;
113) (4S)—N—((S)-(3-chloro-2,4-difluorophenyl)(2-(difluoromethoxy)pyrimidin-5-yl)methyl)-2-oxoimidazolidine-4-carboxamide;
114) (S)—N—((R)-(5-chloro-6-(trifluoromethyl)pyridin-2-yl)(5-chloro-6-(trifluoromethyl)-pyridin-3-yl)methyl)-2-oxoimidazolidine-4-carboxamide;
115) (S)—N—((S)-(5-chloro-6-(trifluoromethyl)pyridin-2-yl)(5-chloro-6-(trifluoromethyl)-pyridin-3-yl)methyl)-2-oxoimidazolidine-4-carboxamide;
116) (S)—N—((R)-(4-chloro-3-cyanophenyl)(4-(trifluoromethoxy)phenyl)methyl)-2-oxoimidazolidine-4-carboxamide;
117) (S)—N—((S)-(4-chloro-3-cyanophenyl)(4-(trifluoromethoxy)phenyl)methyl)-2-oxoimidazolidine-4-carboxamide;
118) (S)—N—((R)-(3-chloro-2,4-difluorophenyl)((R)-1-(2,2,2-trifluoroethyl)piperidin-2-yl)methyl)-2-oxoimidazolidine-4-carboxamide;
119) (S)—N—((R)-(3-chloro-2,4-difluorophenyl)((S)-1-(2,2,2-trifluoroethyl)piperidin-2-yl)methyl)-2-oxoimidazolidine-4-carboxamide;
120) (S)—N—((S)-(3-chloro-2,4-difluorophenyl)((S)-1-(2,2,2-trifluoroethyl)piperidin-2-yl)methyl)-2-oxoimidazolidine-4-carboxamide;
121) (S)—N—((S)-(3-chloro-4-fluoro-phenyl)((S)-2-chlorobicyclo[4.2.0]-octa-1(6),2,4-trien-7-yl)methyl)-2-oxoimidazolidine-4-carboxamide;
122) (S)—N—((R)-(4-chlorophenyl)(5-fluoro-4-(trifluoromethyl)pyridin-2-yl)methyl)-2-oxo-imidazolidine-4-carboxamide;
123) (S)—N—((S)-(4-chlorophenyl)(5-fluoro-4-(trifluoromethyl)pyridin-2-yl)methyl)-2-oxo-imidazolidine-4-carboxamide;
124) (S)—N—((R)-(4-chloro-3-(trifluoromethyl)-phenyl)(4-cyanophenyl)-methyl)-2-oxo-imidazolidine-4-carboxamide;
125) (S)—N—((S)-(4-chloro-3-(trifluoromethyl)-phenyl)(4-cyanophenyl)-methyl)-2-oxo-imidazolidine-4-carboxamide;
126) (S)—N-(bis(3-chloro-4-fluorophenyl)methyl)-2-oxo-imidazolidine-4-carboxamide;
127) (S)—N—((R)-(3-chloro-4-fluorophenyl)(5-chloro-6-(trifluoromethyl)pyridin-2-yl)methyl)-2-oxoimidazolidine-4-carboxamide;
128) (S)—N—((S)-(3-chloro-4-fluorophenyl)(5-chloro-6-(trifluoromethyl)pyridin-2-yl)methyl)-2-oxoimidazolidine-4-carboxamide;
129) (S)—N—((R)-(3-chloro-2,4-difluorophenyl)(6-(difluoromethyl)-5-fluoropyridin-2-yl)methyl)-2-oxoimidazolidine-4-carboxamide;
130) (S)—N—((S)-(3-chloro-2,4-difluorophenyl)(6-(difluoromethyl)-5-fluoropyridin-2-yl)methyl)-2-oxoimidazolidine-4-carboxamide;
131) (S)—N—((R)-(3-chloro-2,4-difluorophenyl)(2-(difluoromethoxy)pyrimidin-5-yl)methyl)-2-oxoimidazolidine-4-carboxamide;
132) (S)—N—((S)-(3-chloro-2,4-difluorophenyl)(2-(difluoromethoxy)pyrimidin-5-yl)methyl)-2-oxoimidazolidine-4-carboxamide;
133) (S)—N—((R)-(3-chloro-2,4-difluorophenyl)(3-methyl-1-((S)-1,1,1-trifluoropropan-2-yl)azetidin-3-yl)methyl)-2-oxoimidazolidine-4-carboxamide;
134) (S)—N—((R)-(3-chloro-2,4-difluorophenyl)(3-methyl-1-((R)-1,1,1-trifluoropropan-2-yl)azetidin-3-yl)methyl)-2-oxoimidazolidine-4-carboxamide;
135) (S)—N—((S)-(3-chloro-2,4-difluorophenyl)(3-methyl-1-((S)-1,1,1-trifluoropropan-2-yl)azetidin-3-yl)methyl)-2-oxoimidazolidine-4-carboxamide;
136) (S)—N—((S)-(3-chloro-2,4-difluorophenyl)(3-methyl-1-((R)-1,1,1-trifluoropropan-2-yl)azetidin-3-yl)methyl)-2-oxoimidazolidine-4-carboxamide;
137) (S)—N—((R)-(3-chloro-4-fluorophenyl)(2-methylbenzo[d]thiazol-5-yl)methyl)-2-oxoimidazolidine-4-carboxamide;
138) (S)—N—((S)-(3-chloro-4-fluorophenyl)(2-methylbenzo[d]thiazol-5-yl)methyl)-2-oxoimidazolidine-4-carboxamide;
139) (S)—N—((R)-(3-chloro-4-fluorophenyl)(trans-2-(trifluoromethyl)cyclobutyl)methyl)-2-oxoimidazolidine-4-carboxamide;
140) (S)—N—((S)-(3-chloro-4-fluorophenyl)(trans-2-(trifluoromethyl)cyclobutyl)methyl)-2-oxoimidazolidine-4-carboxamide;
141) (4S)—N-((3-chloro-4-fluorophenyl)(3,3-dimethyl-2-(trifluoromethyl)cyclobutyl)methyl)-2-oxoimidazolidine-4-carboxamide;
142) (4S)—N-((3-chloro-4-fluorophenyl)(4-fluorobicyclo[4.2.0]octa-1(6),2,4-trien-7-yl)methyl)-2-oxoimidazolidine-4-carboxamide;

143) (S)—N—((R)-(3-chloro-4-fluoro-phenyl)((R)-2-chlorobicyclo[4.2.0]-octa-1(6),2,4-trien-7-yl)methyl)-2-oxo-imidazolidine-4-carboxamide;
144) (S)—N—((R)-(3-chloro-4-fluoro-phenyl)((S)-2-chlorobicyclo[4.2.0]-octa-1(6),2,4-trien-7-yl)methyl)-2-oxo-imidazolidine-4-carboxamide;
145) (S)—N—((S)-(3-chloro-4-fluoro-phenyl)((R)-2-chlorobicyclo[4.2.0]-octa-1(6),2,4-trien-7-yl)methyl)-2-oxo-imidazolidine-4-carboxamide;
146) (S)—N—((S)-(3-chloro-4-fluoro-phenyl)((S)-2-chlorobicyclo[4.2.0]-octa-1(6),2,4-trien-7-yl)methyl)-2-oxo-imidazolidine-4-carboxamide;
147) (S)—N—((R)-(3-chloro-4-fluoro-phenyl)((R)-2-chlorobicyclo[4.2.0]-octa-1(6),2,4-trien-7-yl)methyl)-2-oxo-imidazolidine-4-carboxamide;
148) (S)—N—((R)-(3-chloro-4-fluoro-phenyl)((S)-2-chlorobicyclo[4.2.0]-octa-1(6),2,4-trien-7-yl)methyl)-2-oxo-imidazolidine-4-carboxamide;
149) (S)—N—((S)-(3-chloro-4-fluoro-phenyl)((R)-2-chlorobicyclo[4.2.0]-octa-1(6),2,4-trien-7-yl)methyl)-2-oxo-imidazolidine-4-carboxamide;
150) (S)—N—((S)-(3-chloro-4-fluoro-phenyl)((S)-2-chlorobicyclo[4.2.0]-octa-1(6),2,4-trien-7-yl)methyl)-2-oxo-imidazolidine-4-carboxamide;
151) (4S)—N-((3-chloro-4-fluorophenyl)(4-chlorobicyclo[4.2.0]-octa-1(6),2,4-trien-7-yl)-methyl)-2-oxoimidazolidine-4-carboxamide;
152) (4S)—N-((3-chloro-4-fluorophenyl)(thiazolo[5,4-b]pyridin-2-yl)methyl)-2-oxo-imidazolidine-4-carboxamide;
153) (S)—N—((R)-(3-chloro-4-fluorophenyl)(5-chlorobenzofuran-2-yl)methyl)-2-oxo-imidazolidine-4-carboxamide;
154) (S)—N—((S)-(3-chloro-4-fluorophenyl)(5-chlorobenzofuran-2-yl)methyl)-2-oxo-imidazolidine-4-carboxamide;
155) (S)—N—((R)-(4-chlorophenyl)(6-(difluoromethoxy)pyridin-2-yl)methyl)-2-oxo-imidazolidine-4-carboxamide;
156) (S)—N—((S)-(4-chlorophenyl)(6-(difluoromethoxy)pyridin-2-yl)methyl)-2-oxo-imidazolidine-4-carboxamide;
157) (S)—N—((R)-(4-chlorophenyl)(1-methyl-5-(trifluoromethyl)-1H-pyrazol-3-yl)methyl)-2-oxoimidazolidine-4-carboxamide;
158) (S)—N—((S)-(4-chlorophenyl)(1-methyl-5-(trifluoromethyl)-1H-pyrazol-3-yl)methyl)-2-oxoimidazolidine-4-carboxamide;
159) (4S)—N-((4-chlorophenyl)(4-methyl-2-(trifluoromethyl)thiazol-5-yl)methyl)-2-oxoimidazolidine-4-carboxamide;
160) (4S)—N-((1(R))-(3-chloro-4-fluorophenyl)(3-(2,2,2-trifluoroethyl)-3-azabicyclo-[3.1.0]hexan-6-yl)methyl)-2-oxoimidazolidine-4-carboxamide;
161) (4S)—N-((1(S))-(3-chloro-4-fluorophenyl)(3-(2,2,2-trifluoroethyl)-3-azabicyclo-[3.1.0]-hexan-6-yl)methyl)-2-oxoimidazolidine-4-carboxamide;
162) (S)—N—((R)-(3-chloro-2,4-difluorophenyl)((cis-1-methyl-2-(trifluoro-methyl)piperidin-4-yl)methyl)-2-oxoimidazolidine-4-carboxamide;
163) (S)—N—((R)-(3-chloro-2,4-difluorophenyl)((trans)-1-methyl-2-(trifluoro-methyl)piperidin-4-yl)methyl)-2-oxoimidazolidine-4-carboxamide;
164) (S)—N—((S)-(3-chloro-2,4-difluorophenyl)((cis)-1-methyl-2-(trifluoro-methyl)-piperidin-4-yl)methyl)-2-oxoimidazolidine-4-carboxamide;
165) (S)—N—((S)-(3-chloro-2,4-difluorophenyl)((trans)-1-methyl-2-(trifluoro-methyl)-piperidin-4-yl)methyl)-2-oxoimidazolidine-4-carboxamide;
166) (S)—N—((R)-(3-chloro-2,4-difluorophenyl)((cis-5-(trifluoromethyl)-tetrahydrofuran-3-yl)methyl)-2-oxo-imidazolidine-4-carboxamide;
167) S)—N—((R)-(3-chloro-2,4-difluorophenyl)((trans-5-(trifluoromethyl)-tetrahydrofuran-3-yl)methyl)-2-oxo-imidazolidine-4-carboxamide;
168) (S)—N—((S)-(3-chloro-2,4-difluorophenyl)((cis-5-(trifluoromethyl)-tetrahydrofuran-3-yl)methyl)-2-oxo-imidazolidine-4-carboxamide;
169) (S)—N—((S)-(3-chloro-2,4-difluorophenyl)((trans-5-(trifluoromethyl)-tetrahydrofuran-3-yl)methyl)-2-oxo-imidazolidine-4-carboxamide;
170) (S)—N—((R)-(4-chlorophenyl)(pyrazolo[1,5-a]pyridin-5-yl)methyl)-2-oxo-imidazolidine-4-carboxamide;
171) (S)—N—((S)-(4-chlorophenyl)(pyrazolo[1,5-a]pyridin-5-yl)methyl)-2-oxo-imidazolidine-4-carboxamide;
172) (4S)—N-(benzo[d]thiazol-6-yl(4-chlorophenyl)methyl)-2-oxoimidazolidine-4-carboxamide;
173) (S)—N—((R)-(4-chlorophenyl)(1H-indazol-6-yl)methyl)-2-oxoimidazolidine-4-carboxamide;
174) (S)—N—((S)-(4-chlorophenyl)(1H-indazol-6-yl)methyl)-2-oxoimidazolidine-4-carboxamide;
175) (S)—N—((R)-(4-chlorophenyl)(pyrazolo[1,5-a]pyridin-5-yl)methyl)-2-oxo-imidazolidine-4-carboxamide;
176) (S)—N—((S)-(4-chlorophenyl)(pyrazolo[1,5-a]pyridin-5-yl)methyl)-2-oxo-imidazolidine-4-carboxamide;
177) (S)—N—((R)-(4-chlorophenyl)(2-methylbenzo[d]oxazol-6-yl)methyl)-2-oxo-imidazolidine-4-carboxamide;
178) (S)—N—((S)-(4-chlorophenyl)(2-methylbenzo[d]oxazol-6-yl)methyl)-2-oxo-imidazolidine-4-carboxamide;
179) (S)—N—((R)-(4-chlorophenyl)(2-methylbenzo[d]thiazol-6-yl)methyl)-2-oxo-imidazolidine-4-carboxamide;
180) (S)—N—((S)-(4-chlorophenyl)(2-methylbenzo[d]thiazol-6-yl)methyl)-2-oxo-imidazolidine-4-carboxamide;
181) (S)—N—((R)-(3-chloro-4-fluorophenyl)(4-(methylsulfonyl)phenyl)methyl)-2-oxoimidazolidine-4-carboxamide;
182) (S)—N—((S)-(3-chloro-4-fluorophenyl)(4-(methylsulfonyl)phenyl)methyl)-2-oxo-imidazolidine-4-carboxamide;
183) (4S)—N-[(3-chloro-4-fluorophenyl)(5-cyanopyridin-2-yl)methyl]-2-oxoimidazolidine-4-carboxamide;
184) (S)—N—((R)-benzo[d]thiazol-2-yl(3-chloro-4-fluorophenyl)methyl)-2-oxo-imidazolidine-4-carboxamide;
185) (S)—N—((S)-benzo[d]thiazol-2-yl(3-chloro-4-fluorophenyl)methyl)-2-oxo-imidazolidine-4-carboxamide;
186) (S)—N—((R)-benzo[d]oxazol-2-yl(3-chloro-4-fluorophenyl)methyl)-2-oxo-imidazolidine-4-carboxamide;
187) (S)—N—((S)-benzo[d]oxazol-2-yl(3-chloro-4-fluorophenyl)methyl)-2-oxo-imidazolidine-4-carboxamide;
188) (S)—N—((R)-(8,8-difluorobicyclo[4.2.0]octa-1(6),2,4-trien-3-yl)(4-(trifluoromethoxy)-phenyl)methyl)-2-oxoimidazolidine-4-carboxamide;
189) (S)—N—((S)-(8,8-difluorobicyclo[4.2.0]octa-1(6),2,4-trien-3-yl)(4-(trifluoromethoxy)-phenyl)methyl)-2-oxoimidazolidine-4-carboxamide;
190) (S)—N—((R)-(4-chlorophenyl)(7,7-difluorobicyclo[4.2.0]octa-1(6),2,4-trien-3-yl)methyl)-2-oxoimidazolidine-4-carboxamide;
191) (S)—N—((S)-(4-chlorophenyl)(7,7-difluorobicyclo[4.2.0]octa-1(6),2,4-trien-3-yl)methyl)-2-oxoimidazolidine-4-carboxamide;

192) (4S)—N—((R)(4-chlorophenyl)((R)2,2-dimethyl-1-(2,2,2-trifluoroethyl)piperidin-4-yl)methyl)-2-oxoimidazolidine-4-carboxamide;
193) (4S)—N—((R)(4-chlorophenyl)((S)2,2-dimethyl-1-(2,2,2-trifluoroethyl)piperidin-4-yl)methyl)-2-oxoimidazolidine-4-carboxamide;
194) (4S)—N—((S)(4-chlorophenyl)((S)2,2-dimethyl-1-(2,2,2-trifluoroethyl)piperidin-4-yl)methyl)-2-oxoimidazolidine-4-carboxamide; and
195) (4S)—N—((S)(4-chlorophenyl)((R)2,2-dimethyl-1-(2,2,2-trifluoroethyl)piperidin-4-yl)methyl)-2-oxoimidazolidine-4-carboxamide;
or a pharmaceutically acceptable salt thereof.

Additional illustrative, but non-limiting, examples of the compounds of the present invention that are useful as inhibitors of Na$_v$1.8 channel activity are the following compounds:

1) (S)—N—((R)-(5-fluoro-6-(trifluoromethyl)pyridin-2-yl)(4-(trifluoromethoxy)-phenyl)-methyl)-2-oxoimidazolidine-4-carboxamide;
2) (S)—N—((S)-(5-fluoro-6-(trifluoromethyl)pyridin-2-yl)(4-(trifluoromethoxy)-phenyl)-methyl)-2-oxoimidazolidine-4-carboxamide;
3) (S)—N—((R)-(3-chlorophenyl)(4-(trifluoromethoxy)phenyl)methyl)-2-oxoimidazolidine-4-carboxamide;
4) (S)—N—((S)-(3-chlorophenyl)(4-(trifluoromethoxy)phenyl)methyl)-2-oxoimidazolidine-4-carboxamide;
5) (S)—N—((R)-(3-chloro-2,4-difluorophenyl)(6-(2,2,2-trifluoroethoxy)pyridin-3-yl)methyl)-2-oxoimidazolidine-4-carboxamide;
6) (S)—N—((S)-(3-chloro-2,4-difluorophenyl)(6-(2,2,2-trifluoroethoxy)pyridin-3-yl)methyl)-2-oxoimidazolidine-4-carboxamide;
7) (S)—N—((R)-(3-chloro-2,4-difluorophenyl)(trans-3-(trifluoromethyl)cyclobutyl)-methyl)-2-oxoimidazolidine-4-carboxamide; and
8) (S)—N—((S)-(3-chloro-2,4-difluorophenyl)(trans-3-(trifluoromethyl)cyclobutyl)-methyl)-2-oxoimidazolidine-4-carboxamide;
or pharmaceutically acceptable salts thereof.

Although the specific stereochemistries described above are preferred, other stereoisomers, including diastereoisomers, enantiomers, epimers, and mixtures of these may also have utility in treating Na$_v$1.8 mediated diseases.

Synthetic methods for making the compounds are disclosed in the Examples shown below. Where synthetic details are not provided in the examples, the compounds are readily made by a person of ordinary skill in the art of medicinal chemistry or synthetic organic chemistry by applying the synthetic information provided herein. Where a stereochemical center is not defined, the structure represents a mixture of stereoisomers at that center. For such compounds, the individual stereoisomers, including enantiomers, diastereoisomers, and mixtures of these are also compounds of the invention.

Definitions

"Ac" is acetyl, which is CH$_3$C(=O)—.

"Alkyl" means saturated carbon chains which may be linear or branched or combinations thereof, unless the carbon chain is defined otherwise. Other groups having the prefix "alk", such as alkoxy and alkanoyl, also may be linear or branched, or combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like.

"Alkenyl" means carbon chains which contain at least one carbon-carbon double bond, and which may be linear or branched, or combinations thereof, unless otherwise defined. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched, or combinations thereof, unless otherwise defined. Examples of alkynyl include ethynyl, propargyl, 3-methyl-1-pentynyl, 2-heptynyl and the like. In one embodiment, —C$_{2-6}$alkenyl is ethenyl or propenyl. In another embodiment, —C$_{2-6}$alkenyl is ethenyl. In another embodiment, —C$_{2-6}$alkenyl is propenyl.

"Cycloalkyl" means a saturated monocyclic, bicyclic, spirocyclic or bridged carbocyclic ring, having a specified number of carbon atoms. Examples of cycloalkyl include cyclopropyl, cyclobutyl, cyclopentyl, cyclohexyl, cycloheptyl, and the like. In one embodiment of the present invention, cycloalkyl is selected from: cyclopropyl, cyclobutyl and cyclohexyl. In another embodiment, cycloalkyl is cyclopropyl, cyclobutyl or cyclopentyl. In another embodiment, cycloalkyl is cyclopropyl or cyclobutyl. In another embodiment, cycloalkyl is cyclopropyl. In another embodiment, cycloalkyl is cyclobutyl. In another embodiment, cycloalkyl is cyclopentyl. In another embodiment, cycloalkyl is cyclohexyl. In another embodiment, cycloalkyl is cycloheptyl. In one embodiment, C$_{3-12}$cycloalkyl is cyclopropyl, cyclobutyl, cyclohexyl, bicyclo[1.1.1]pentyl, or spiro[3.3]heptyl. In another embodiment, C$_{3-12}$cycloalkyl is cyclobutyl, cyclohexyl, bicyclo[1.1.1]pentyl, or spiro[3.3]heptyl. In another embodiment, C$_{3-12}$cycloalkyl is -cyclopropyl. In another embodiment, C$_{3-12}$cycloalkyl is cyclobutyl. In another embodiment, C$_{3-12}$cycloalkyl is cyclohexyl.

"Cycloalkenyl" means a monocyclic, bicyclic, spirocyclic or bridged carbocyclic ring, having a specified number of carbon atoms with at least one double bond. Examples of cycloalkenyl include cyclopropene, cyclobutene, cyclopentene, cyclohexene, cycloheptene, and the like. In one embodiment, cycloalkenyl is cyclobutene.

"Cycloheteroalkyl" means a saturated or partly unsaturated non-aromatic monocyclic, bicyclic, spirocyclic or bridged ring or ring system having a specified number of carbon atoms and containing at least one ring heteroatom selected from N, NH, S (including SO and SO$_2$) and O. The cycloheteroalkyl ring may be substituted on the ring carbons and/or the ring nitrogen or sulfur. Examples of cycloheteroalkyl include tetrahydrofuranyl, pyrrolidinyl, tetrahydrothiophenyl, azetidinyl, piperazinyl, piperidinyl, morpholinyl, oxetanyl and tetrahydropyranyl. In one embodiment of the present invention, cycloheteroalkyl is selected from: pyrrolidinyl, azetidinyl, piperidinyl, piperazinyl, azepanyl, azocanyl, morpholinyl, thiomorpholinyl, thiomorpholine dionyl, oxazepanyl, 1,4-thiazepanyl, isoindolinyl, dihydroisoquinolinyl, tetra-hydroisoquinolinyl, octahydro-isoindolyl, azabicyclo[2.2.1]heptanyl, oxa-azabicyclo[2.2.1]-yl, azabicyclo[3.1.1]heptanyl, azabicyclo[4.1.0]heptanyl, azabicyclo[3.2.1]octanyl, diazabicyclo[3.2.1]octanyl, oxa-azabicyclo-[3.2.1]octanyl, azabicyclo[3.2.0]heptanyl, oxa-azabicyclo[3.2.0]heptanyl, azaspiro[2.5]octanyl, azaspiro[2.6]nonanyl, azaspiro[3.5]nonanyl, oxa-azaspiro[3.5]nonanyl, oxaazaspiro-[4.5]decanyl, dihydrothieno[3,2-c]pyridinyl, dihydro-thiazolo[4,5-c]pyridinyl, dihydrooxazolo[4,5-c]pyridiyl, dihydroimidazo[1,2-a]pyrazinyl, hexahydrofuro[3,2-b]pyrrolyl, hexahydrocyclopenta[c]pyrrolyl, octahydrocyclpenta[c]pyrrolyl, and azatricyclo

[4.3.1.1³,⁸]-undecanyl. In another embodiment, cycloheteroalkyl is selected from: pyrrolidine, azetidine, piperidine, piperazine, azepane, morpholine, thiomorpholine, oxazepane, isoindoline, dihydroisoquinoline, azabicyclo[2.2.1]heptane, azabicyclo[3.1.1]-heptane, azabicyclo[4.1.0]-heptane, azabicyclo[3.2.1]octane, azabicyclo[3.2.0]heptane, azaspiro[2.5]octane, dihydrothieno-[3,2-c]pyridine, dihydroimidazo[1,2-a]pyrazine, and hexahydrofuro[3,2-b]pyrrole. In another embodiment, cycloheteroalkyl is selected from: azepane, morpholine and piperidine. In another embodiment, cycloheteroalkyl is azepane. In another embodiment, cycloheteroalkyl is morpholine. In another embodiment, cycloheteroalkyl is piperidine. In another embodiment, cycloheteroalkyl is azetidine, piperidine, tetrahydropyran, tetrahydrofuran, or azabicyclo[3.1.0]hexane. In another embodiment, cycloheteroalkyl is azetidine, piperidinyl, tetrahydropyranyl, or tetrahydrofuranyl, In another embodiment, $C_{2-12}$cycloheteroalkyl is tetrahydropyranyl.

"Cycloheteroalkenyl" means a monocyclic, bicyclic, spirocyclic or bridged ring or ring system having a specified number of carbon atoms and containing at least one double bond and at least one heteroatom. Examples of cycloheteroalkenyl include dihydropyran and dihydrofuran, and the like.

"Aryl" means a monocyclic, bicyclic or tricyclic carbocyclic aromatic ring or ring system containing 6-14 carbon atoms, wherein at least one of the rings is aromatic. Examples of aryl include phenyl and naphthyl. In one embodiment, aryl is phenyl or naphthalenyl. In another embodiment, aryl is naphthalenyl. In another embodiment, aryl is phenyl.

"Heteroaryl" means a monocyclic, bicyclic or tricyclic ring or ring system containing 5-14 ring atoms and containing at least one ring heteroatom selected from N, NH, S (including SO and $SO_2$) and O, wherein at least one of the heteroatom containing rings is aromatic. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzisoxazolyl, benzoxazolyl, benzothiazolyl, benzimidazolyl, benzofuranyl, benzothiophenyl, quinolyl, indolyl, isoquinolyl, quinazolinyl, dibenzofuranyl, and the like. In one embodiment of the present invention, heteroaryl is a 5 or 6 membered heteroaryl ring. In another embodiment, heteroaryl is selected from: pyrazolyl, pyridyl, isoxazolyl and thiazolyl. In another embodiment of the present invention, heteroaryl is selected from: pyridinyl, pyrimidinyl, pyrazinyl, pyridazinyl, indazolyl, imidazo[1,2-a]pyridinyl, 1,3-dihydro-2H-imidazo[4,5-b]pyridin-2-one, 1H-[1,2,3]triazolo[4,5-b]pyridinyl, 1H-pyrazolo[4,3-b]pyridinyl, pyrrolo[3,2-c]pyridinyl, pyrrolo[2,3-b]pyridinyl, benzimidazolyl, imidazolyl, pyrazolyl, thiophenyl, furan, 1,2,4-oxadiazolyl, 1,3,4-oxadiazolyl, oxazolyl, isoxazolyl, isothiazolyl, thiazolyl, 1,2,4-thiadiazolyl, 1,3,4-thiadiazolyl; 4H-pyrido[2,3-e][1,2,4]thiadiazinyl 1,1-dioxidyl, 2H-pyrido[2,3-e][1,2]thiazinyl 1,1-dioxide, 2,3-dihydroisothiazolo[4,5-b]pyridinyl 1,1-dioxide, and 3,4-dihydro-2H-pyrido[2,3-e][1,2]thiazine 1,1-dioxide. In another embodiment of the present invention, heteroaryl is selected from: pyridinyl, pyrimidinyl, and pyridazinyl. In another embodiment of the present invention, heteroaryl is pyridinyl.

In another embodiment, heteroaryl is pyridine, thiazole, pyrimidine, pyrazine, pyridazine, imidazole, pyrazole, oxazole, benzofuran, benzo[d]oxazole, benzo[d]thiazole, indole, indazole, thiazolo[5,4-b]pyridine, pyrazolo[1,5-a]pyridine, thiophene, furan, triazole, quinoline, isoquinoline, quinoxaline, quanazoline, pyrazolopyridine, pyrazolopyridine, imidazopyridine, oxazolopyridine, pyrazolopyrimidine, imidazopyrimidine, oxazolopyrimidine, or thiazolopyrimidine. In another embodiment, heteroaryl is pyridine, thiazole, pyrimidine, pyrazine, pyridazine, imidazole, pyrazole, oxazole, benzofuran, benzo[d]oxazole, benzo[d]thiazole, indazole, thiazolo[5,4-b]pyridine, pyrazolo[1,5-a]pyridine, thiophene, furan, triazole or indole. In another embodiment, heteroaryl is pyridine, thiazole, pyrimidine, pyrazine, pyridazine, imidazole, pyrazole, oxazole, benzofuran, benzo[d]oxazole, benzo[d]thiazole, indazole, thiazolo[5,4-b]pyridine, or pyrazolo[1,5-a]pyridine. In another embodiment, heteroaryl is pyrimidine, pyrazine, pyridazine, imidazole, pyrazole, oxazole, benzofuran, benzo[d]oxazole, benzo[d]thiazole, indazole, thiazolo[5,4-b]pyridine, or pyrazolo[1,5-a]pyridine.

In another embodiment of the present invention, heteroaryl is selected from: pyridine, pyrimidine, pyrazine, pyridazine, imidazole, pyrazole, thiazole, oxazole, benzofuran, benzoxazole, benzothiazole, indole, indazole, thiazolopyridine, thiophene, furan, triazole, quinoline, isoquinoline, quinoxaline, quanazoline, pyrazolopyridine, pyrazolopyridine, imidazopyridine, oxazolopyridine, pyrazolopyrimidine, imidazopyrimidine, oxazolopyrimidine, and thiazolopyrimidine.

In another embodiment of the present invention, heteroaryl is selected from: pyridine, pyrimidine, pyrazine, pyridazine, imidazole, pyrazole, thiazole, oxazole, benzofuran, benzoxazole, benzothiazole, indole, indazole, and thiazolopyridine.

In another embodiment of the present invention, heteroaryl is selected from: pyridine, and thiazole. In another embodiment of the present invention, heteroaryl is pyridine. In another embodiment of the present invention, heteroaryl is thiazole.

"Halogen" includes fluorine, chlorine, bromine and iodine. In one embodiment, halogen is fluorine, chorine or bromine. In another embodiment, halogen is fluorine or chlorine. In another embodiment, halogen is chlorine or bromine. In another embodiment, halogen is fluorine or bromine. In another embodiment, halogen is fluorine. In another embodiment, halogen is chlorine. In another embodiment, halogen is bromine.

"Me" represents methyl.

"Oxo" represents =O.

"Saturated" means containing only single bonds.

"Unsaturated" means containing at least one double or triple bond. In one embodiment, unsaturated means containing at least one double bond. In another embodiment, unsaturated means containing at least one triple bond.

When any variable (e.g., $R^1$, $R^a$, etc.) occurs more than one time in any constituent or in formula I, its definition on each occurrence is independent of its definition at every other occurrence. Also, combinations of substituents and/or variables are permissible only if such combinations result in stable compounds. A squiggly line across a bond in a substituent variable represents the point of attachment.

Under standard nomenclature used throughout this disclosure, the terminal portion of the designated side chain is described first, followed by the adjacent functionality toward the point of attachment. For example, a $C_{1-5}$ alkylcarbonylamino $C_{1-6}$ alkyl substituent is equivalent to:

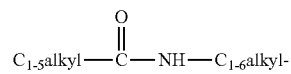

In choosing compounds of the present invention, one of ordinary skill in the art will recognize that the various substituents, i.e. $R^1$, $R^2$, etc., are to be chosen in conformity with well-known principles of chemical structure connectivity and stability.

The term "substituted" shall be deemed to include multiple degrees of substitution by a named substituent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

The phrase "pharmaceutically acceptable" is employed herein to refer to those compounds, materials, compositions, salts and/or dosage forms which are, using sound medical judgment, and following all applicable government regulations, safe and suitable for administration to a human being or an animal.

Compounds of Formula I may contain one or more asymmetric centers and can thus occur as racemates and racemic mixtures, single enantiomers, diastereomeric mixtures and individual diastereomers. The present invention is meant to encompass all such isomeric forms of the compounds of Formula I.

The independent syntheses of optical isomers and diastereoisomers or their chromatographic separations may be achieved as known in the art by appropriate modification of the methodology disclosed herein. Their absolute stereochemistry may be determined by the X-ray crystallography of crystalline products or crystalline intermediates which are derivatized, if necessary, with a reagent containing an asymmetric center of known absolute configuration or sufficient heavy atoms to make an absolute assignment.

If desired, racemic mixtures of the compounds may be separated so that the individual enantiomers are isolated. The separation can be carried out by methods well-known in the art, such as the coupling of a racemic mixture of compounds to an enantiomerically pure compound to form a diastereoisomeric mixture, followed by separation of the individual diastereoisomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

Some of the compounds described herein contain olefinic double bonds, and unless specified otherwise, are meant to include both E and Z geometric isomers.

Tautomers are defined as compounds that undergo rapid proton shifts from one atom of the compound to another atom of the compound. Some of the compounds described herein may exist as tautomers with different points of attachment of hydrogen. Such an example may be a ketone and its enol form known as keto-enol tautomers. The individual tautomers as well as mixture thereof are encompassed with compounds of Formula I.

In the compounds of general formula I, the atoms may exhibit their natural isotopic abundances, or one or more of the atoms may be artificially enriched in a particular isotope having the same atomic number, but an atomic mass or mass number different from the atomic mass or mass number predominately found in nature. The present invention is meant to include all suitable isotopic variations of the compounds of structural formula I. For example, different isotopic forms of hydrogen (H) include protium ($^1$H), deuterium ($^2$H), and tritium ($^3$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Tritium is radioactive and may therefore provide for a radiolabeled compound, useful as a tracer in metabolic or kinetic studies. Isotopically-enriched compounds within structural formula I, can be prepared without undue experimentation by conventional techniques well known to those skilled in the art or by processes analogous to those described in the Schemes and Examples herein using appropriate isotopically-enriched reagents and/or intermediates.

Furthermore, some of the crystalline forms for compounds of the present invention may exist as polymorphs and as such are intended to be included in the present invention. In addition, some of the compounds of the instant invention may form solvates with water or common organic solvents. Such solvates are encompassed within the scope of this invention.

It is generally preferable to administer compounds of the present invention as enantiomerically pure formulations. Racemic mixtures can be separated into their individual enantiomers by any of a number of conventional methods. These include chiral chromatography, derivatization with a chiral auxiliary followed by separation by chromatography or crystallization, and fractional crystallization of diastereomeric salts.

Salts

It will be understood that, as used herein, references to the compounds of the present invention are meant to also include the pharmaceutically acceptable salts, and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylars-anilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate, diphosphate, polygalacturonate, salicylate, stearate, sulfate, subacetate, succinate, tannate, tartrate, teoclate, tosylate, triethiodide, trifluoroacetate and valerate. Where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed. Included are those esters and acyl groups known in the art for modifying the solubility or hydrolysis characteristics for use as sustained-release or prodrug formulations.

The term "prodrug" means compounds that are rapidly transformed, for example, by hydrolysis in blood, in vivo to the parent compound, e.g., conversion of a prodrug of Formula I to a compound of Formula I, or to a salt thereof; a thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference. This invention includes prodrugs of the novel compounds of this invention.

Solvates, and in particular, the hydrates of the compounds of the present invention are included in the present invention as well.

Utilities

The compound of the present invention are selective inhibitors of $Na_v1.8$ sodium ion channel activity or have selective activity as $Na_v1.8$ sodium ion channel blockers. In one embodiment, the compounds of the present invention exhibit at least 10-fold selectivity for $Na_v1.8$ sodium channels over $Na_v1.5$ sodium channels, and in some embodiments exhibit at least 100-fold selectivity for $Na_v1.8$ sodium channels over $Na_v1.5$ sodium channels based on functional potency ($IC_{50}$ values) for each channel in Qube® assay system.

The compounds of the present invention are potent inhibitors of $Na_v1.8$ channel activity. The compounds, and pharmaceutically acceptable salts thereof, may be efficacious in the treatment of diseases, disorders and conditions that are mediated by the inhibition of $Na_v1.8$ sodium ion channel activity and/or $Na_v1.8$ receptors.

Diseases, disorders or conditions mediated by $Na_v1.8$ sodium ion channel activity and/or $Na_v1.8$ receptors, include but are not limited to nociception, osteoarthritis, peripheral neuropathy, inherited erythromelalgia, multiple sclerosis, asthma, pruritus, acute itch, chronic itch, migraine, neurodegeneration following ischemia, epilepsy, inflammatory pain, spontaneous pain, acute pain, pen-operative pain, post-operative pain, neuropathic pain, postherpetic neuralgia, trigeminal neuralgia, diabetic neuropathy, chronic lower back pain, phantom limb pain, pain resulting from cancer and chemotherapy, chronic pelvic pain, pain syndromes, and complex regional pain syndromes.

One or more of these conditions or diseases may be treated, managed, prevented, reduced, alleviated, ameliorated or controlled by the administration of a therapeutically effective amount of a compound of the present invention, or a pharmaceutically acceptable salt thereof, to a patient in need of treatment. Also, the compounds of the present invention may be used for the manufacture of a medicament which may be useful for treating, preventing, managing, alleviating, ameliorating or controlling one or more of these conditions, diseases or disorders: nociception, osteoarthritis, peripheral neuropathy, inherited erythromelalgia, multiple sclerosis, asthma, pruritus, acute itch, chronic itch, migraine, neurodegeneration following ischemia, epilepsy, inflammatory pain, spontaneous pain, acute pain, pen-operative pain, post-operative pain, neuropathic pain, postherpetic neuralgia, trigeminal neuralgia, diabetic neuropathy, chronic lower back pain, phantom limb pain, pain resulting from cancer and chemotherapy, chronic pelvic pain, pain syndromes, and complex regional pain syndromes.

Preferred uses of the compounds may be for the treatment of one or more of the following diseases by administering a therapeutically effective amount to a patient in need of treatment. The compounds may be used for manufacturing a medicament for the treatment of one or more of these diseases:

1) pain conditions,
2) pruritic conditions, and
3) cough conditions.

In one embodiment of the present invention, the pain condition is an acute pain or chronic pain disorder. In another embodiment of the present invention, the the pain condition is an acute pain disorder.

The compounds of the present invention may be effective in treating nociception. Nociception or pain is essential for survival and often serves a protective function. However, the pain associated with surgical procedures and current therapies to relieve that pain, can delay recovery after surgery and increase the length of hospital stays. As many as 80% of surgical patients experience post-operative pain due to tissue damage, and damage to peripheral nerves and subsequent inflammation. Approximately 10-50% of surgical patients will develop chronic pain after surgery often because the nerve damage results in lasting neuropathic pain once the wound has healed.

The compounds of the present invention may be effective in treating osteoarthritis. Osteoarthritis is type of arthritis caused by inflammation, breakdown, and eventual loss of cartilage in the joints. The standards of care for pain associated with osteoarthritis are non-steroidal anti-inflammatory drugs (NSAIDs), for example celecoxib and diclofenac (reviewed in Zeng et al., 2018). Patients that do not respond to NSAID therapies are typically treated with low dose opiates, such as hydrocodone. Patients that are refractory to the above therapies will usually opt for total joint replacement.

The compounds of the present invention may be effective in treating peripheral neuropathy. Peripheral neuropathy is nerve damage caused by chronically high blood sugar and diabetes. It leads to numbness, loss of sensation, and sometimes pain in distal limbs such as feet, legs, or hands. It is the most common complication of diabetes. The standards of care for the treatment of painful diabetic neuropathy are gabapentinoids, for example gabapentin and pregabalin.

Some patients will respond well to tricyclic antidepressants such as amitriptyline, while other patients get significant relief using SRI/NRI drugs such as duloxetine (Schreiber et al., World J Diabetes. 2015 Apr. 15; 6(3):432-44). Many options are available, however side-effects are common (e.g. dizziness, nausea) which limit their full potential.

The compounds of the present invention may be effective in treating inherited erythromelalgia. Inherited erythromelalgia (IEM) is a chronic pain syndrome which has been linked to mutations in several voltage-gated sodium channels, including $Na_v1.8$ (Kist et al., PLoS One. 2016 Sep. 6; 11(9):e0161789). Patients present with the classic "gloves and stocking" flare pattern on distal regions such as hands and feet, typically brought on with warm temperatures and exercise. Some patients find relief from the burning pain associated with flares by cold water immersion. Although medications that affect voltage-gated sodium channels (eg, lidocaine and mexiletine) show promise, there is no current standard of care to treat IEM.

The compounds of the present invention may be effective in treating neuropathic pain. Neuropathic pain is pain caused by damage or disease affecting the somatosensory nervous system. It has been demonstrated in human patients, as well as in animal models of neuropathic pain, that damage to primary afferent sensory neurons can lead to neuroma formation and spontaneous activity, as well as evoked activity in response to normally innocuous stimuli. (Colloca et al., Nat Rev Dis Primers. 2017 Feb. 16; 3:17002; Coward et al., Pain. 2000 March; 85(1-2):41-50; Yiangou et al., FEBS Lett. 2000 Feb. 11; 467(2-3):249-52; Carter et al., Phys Med Rehabil Clin N Am. 2001 May; 12(2):447-59). Some nerve injuries result in an increase in Nav1.8 expression, which is believed to be an underlying mechanism for pathological pain. (Black et al., Ann Neurol. 2008 December; 64(6):644-53; Bird et al., Br J Pharmacol. 2015 May; 172(10):2654-70). Injuries of the peripheral nervous system often result in neuropathic pain persisting long after an initial injury resolves. Examples of neuropathic pain include, but are not limited to, post herpetic neuralgia, trigeminal neuralgia, diabetic neuropathy, chronic lower back pain, lumbar radiculopathy, phantom limb pain, pain resulting from cancer and chemotherapy, chronic pelvic pain, complex regional pain syndrome and related neuralgias, and painful conditions that arise due to gain-of-function mutations in Nav1.8 (Huang et al., J Neurosci. 2013 Aug. 28; 33(35): 14087-97; Kist et al., PLoS One. 2016 Sep. 6; 11(9): e0161789; Emery et al., J Neurosci. 2015 May 20; 35(20): 7674-81; and Schreiber et al., World J Diabetes. 2015 Apr. 15; 6(3):432-44.

The ectopic activity of normally silent sensory neurons is thought to contribute to the generation and maintenance of neuropathic pain, which is generally assumed to be associated with an increase in sodium channel activity in the injured nerve. (Wood et al., Curr Opin Pharmacol. 2001 February; 1(1):17-21; Baker et al., TRENDS in Pharmacological Sciences, 2001, 22(1): 27-31). Standards of care for neuropathic pain vary considerably depending on the particular condition, but first line therapies are typically pregabalin, gabapentin, tricyclic antidepressants (e.g. amitriptyline), and SRI/NRI drugs (e.g. duloxetine). Patients refractory to these therapies are usually prescribed low dose opiates (e.g. hydrocodone).

The compounds of the present invention may be effective in treating multiple sclerosis. Recent evidence points to a potential role for Nav1.8 in multiple sclerosis. Nav1.8 expression in cerebellum has been identified in tissues taken from animal models of multiple sclerosis (EAE model) and in postmortem brains from patients suffering from multiple sclerosis (MS) (Shields et al., Ann Neurol. 2012 February; 71(2):186-94; Black et al., Proc Natl Acad Sci USA. 2000 Oct. 10; 97(21):11598-602). Also, two SCN10A polymorphisms showed significant association with MS (Roostaei et al., Neurology. 2016 Feb. 2; 86 (5):410-7). When Nav1.8 is overexpressed in cerebellum, mice develop ataxic-related motor deficits which are ameliorated with oral delivery of a selective small molecule Nav1.8 antagonist (Shields et al., PLoS One. 2015 Mar. 6; 10(3)). These studies suggest that a Nav1.8 antagonist may be a useful therapy to treat symptoms related to multiple sclerosis.

The compounds of the present invention may be effective in treating asthma. Asthma is caused by airway inflammation in which a person's airways become hyper-responsive, narrow and swollen, which makes it difficult to breathe. These symptoms are typically triggered through an allergic reaction (Nair P et al., J Allergy Clin Immunol Pract. 2017 May-June; 5(3):649-659). In a preclinical model of asthma, deletion of Nav1.8-containing neurons, or inhibition of nerve fibers via small molecules reduces airway inflammation and immune cell infiltration (Talbot et al., Neuron. 2015 Jul. 15; 87(2):341-54). Selective Nav1.8 antagonists may be a useful therapy to prevent airway hypersensitivity caused by immune cell infiltration.

The compounds of the present invention may be effective in treating pruritus. Pruritus, also commonly known as itch, affects approximately 4% of the global population is an unpleasant sensation that elicits the desire or reflex to scratch, and is regarded as closely related to pain (Luo et al., Cell Mol Life Sci. 2015 September; 72 (17): 3201-23). Theories on the origin of itch implicate the subtle, low-frequency activation of nociceptors (pain-sensing neurons); however, it has been described that some afferents preferentially respond to histamine, which induces itch (Schmelz et al., J Neurosci. 1997 Oct. 15; 17(20):8003-8). At the same time, it has been found that histamine-responding neurons also respond to capsaicin which produces pain (McMahon et al., Trends in Neuroscience 1992, 15:497-501). Members of the transient receptor potential (TRP) family, and nerve growth factor (NGF) are both known to play a role in itch and pain, and clinically, both maladies are treated with therapeutic agents such as gabapentin and antidepressants. Therefore, it continues to be accepted that the underlying mechanisms of pain and itch are highly interwoven and complex, and distinguishing pan-selective or itch-selective pathways remains ambiguous (Ikoma et al., Nat Rev Neurosci. 2006 July; 7(7):535-47). A role for Nav1.8 in pruritis was studied using a mouse transgenically expressing a constitutively active form of the serine/threonine kinase BRAF was expressed in Nav1.8-expressing neurons. This resulted in enhanced pruriceptor excitability, and heightened evoked and spontaneous scratching behavior (Zhao et al., 2013). In skin, pruritogens are released from keratinocytes, lymphocytes, mast cells, and eosinophils during inflammation. These molecules act directly on free nerve endings which express Nav1.8 to induce itch (Riol-Blanco et al., Nature. 2014 Jun. 5; 510 (7503):157-61). Chronic and acute itch can arise from many different insults, diseases and disorders, and may be classified as dermal or pruriceptive, neurogenic, neuropathic, or psychogenic: itch can arise from both systemic disorders, skin disorders, as well as physical or chemical insult to the dermis. Pathologically, conditions such as dry skin, eczema, psoriasis, varicella zoster, urticaria, scabies, renal failure, cirrhosis, lymphoma, iron deficiency, diabetes, menopause, polycythemia, uremia, and hyperthyroidism can cause itch, as can diseases of the nervous system such as tumors, multiple sclerosis, peripheral neuropathy, nerve compression, and delusions related to obsessive-compulsive disorders. Medicines such as opioids and chloroquine can also trigger itch (Ikoma et al., Nat Rev Neurosci. 2006 July; 7(7):535-47). Itching following burn is also an extremely serious clinical problem as it hampers the healing process, resulting in permanent scaring, and negatively impacting quality of life (Van Loey et al., Br J Dermatol. 2008 January; 158(1):95-100).

The invention also includes pharmaceutically acceptable salts of the compounds, and pharmaceutical compositions comprising the compounds and a pharmaceutically acceptable carrier.

The compounds, or pharmaceutically acceptable salts thereof, may be useful in treating pain conditions, pruritic conditions, and cough conditions.

A compound of the present invention, or a pharmaceutically acceptable salt thereof, may be used in the manufacture of a medicament for the treatment of pain conditions, pruritic conditions, and cough conditions in a human or other mammalian patient.

A method of treating a pain conditions comprises the administration of a therapeutically effective amount of a compound of the present invention, or a pharmaceutically acceptable salt thereof, or a pharmaceutical composition comprising the compound, to a patient in need of treatment. A method of treating a pruritic condition comprises the administration of a therapeutically effective amount of a compound of the present invention, or a pharmaceutically acceptable salt thereof, or a pharmaceutical composition comprising the compound, to a patient in need of treatment. A method of treating a cough condition comprises the administration of a therapeutically effective amount of a compound of the present invention, or a pharmaceutically acceptable salt thereof, or a pharmaceutical composition comprising the compound, to a patient in need of treatment. Other medical uses of the compounds of the present invention are described herein.

The term "pain condition" as used herein includes, but is not limited to, acute pain, perioperative pain, pre-operative pain, post-operative pain, neuropathic pain, post herpetic neuralgia, trigeminal neuralgia, diabetic neuropathy, chronic lower back pain, phantom limb pain, chronic pelvic pain, vulvodynia, complex regional pain syndrome and related neuralgias, pain associated with cancer and chemotherapy, pain associated with HIV, and HIV treatment-induced neuropathy, nerve injury, root avulsions, painful traumatic mononeuropathy, painful polyneuropathy, erythromyelalgia, paroxysmal extreme pain disorder, small fiber neuropathy, burning mouth syndrome, central pain syndromes (potentially caused by virtually any lesion at any level of the nervous system), postsurgical pain syndromes (e.g., post mastectomy syndrome, post thoracotomy syndrome, stump pain)), bone and joint pain (osteoarthritis), repetitive motion pain, dental pain, myofascial pain (muscular injury, fibromyalgia), perioperative pain (general surgery, gynecological), chronic pain, dysmennorhea, pain associated with angina, inflammatory pain of varied origins (e.g. osteoarthritis, rheumatoid arthritis, rheumatic disease, teno-synovitis and gout), shoulder tendonitis or bursitis, gouty arthritis, and aolymyalgia rheumatica, primary hyperalgesia, secondary hyperalgesia, primary allodynia, secondary allodynia, or other pain caused by central sensitization, complex regional pain syndrome, chronic arthritic pain and related neuralgias acute pain, migraine, migraine headache, headache pain, cluster headache, non-vascular headache, traumatic nerve injury, nerve compression or entrapment, and neuroma pain, The term "pruritic condition" or "pruritic disorder" as used herein includes, but is not limited to, conditions with an unpleasant sensation that provokes the desire to scratch, such as chronic itch.

The term "cough condition" or "cough disorder" as used herein includes, but is not limited to, chronic cough, neuropathic cough or cough due to neurological conditions.

Treatment of a disease, disorder or condition mediated by $Na_v1.8$ sodium ion channel activity or $Na_v1.8$ receptors refers to the administration of the compounds of the present invention to a subject with the disease, disorder or condition. One outcome of treatment may be reducing the disease, disorder or condition mediated by $Na_v1.8$ sodium ion channel activity or $Na_v1.8$ receptors. Another outcome of treatment may be alleviating the disease, disorder or condition mediated by $Na_v1.8$ sodium ion channel activity or $Na_v1.8$ receptors. Another outcome of treatment may be ameliorating the disease, disorder or condition mediated by $Na_v1.8$ sodium ion channel activity or $Na_v1.8$ receptors. Another outcome of treatment may be suppressing the disease, disorder or condition mediated by $Na_v1.8$ sodium ion channel activity or $Na_v1.8$ receptors. Another outcome of treatment may be managing the disease, disorder or condition mediated by $Na_v1.8$ sodium ion channel activity or $Na_v1.8$ receptors.

Another outcome of treatment may be preventing the disease, disorder or condition mediated by $Na_v1.8$ sodium ion channel activity or $Na_v1.8$ receptors.

Prevention of the disease, disorder or condition mediated by $Na_v1.8$ sodium ion channel activity or $Na_v1.8$ receptors refers to the administration of the compounds of the present invention to a subject at risk of the disease, disorder or condition. One outcome of prevention may be reducing the disease, disorder or condition mediated by $Na_v1.8$ sodium ion channel activity or $Na_v1.8$ receptors in a subject at risk of the disease, disorder or condition. Another outcome of prevention may be suppressing the disease, disorder or condition mediated by $Na_v1.8$ sodium ion channel activity or $Na_v1.8$ receptors in a subject at risk of the disease, disorder or condition. Another outcome of prevention may be ameliorating the disease, disorder or condition mediated by $Na_v1.8$ sodium ion channel activity or $Na_v1.8$ receptors in a subject at risk of the disease, disorder or condition. Another outcome of prevention may be alleviating the disease, disorder or condition mediated by $Na_v1.8$ sodium ion channel activity or $Na_v1.8$ receptors in a subject at risk of the disease, disorder or condition. Another outcome of prevention may be managing the disease, disorder or condition mediated by $Na_v1.8$ sodium ion channel activity or $Na_v1.8$ receptors in a subject at risk of the disease, disorder or condition.

One outcome of treatment may be reducing the amount of pain experienced by a subject relative to that subject's pain immediately before the administration of the compounds of the present invention. Another outcome of treatment may be alleviating the amount of pain experienced by a subject relative to that subject's pain immediately before the administration of the compounds of the present invention. Another outcome of treatment may be ameliorating the amount of pain experienced by a subject relative to that subject's pain immediately before the administration of the compounds of the present invention. Another outcome of treatment may be suppressing the amount of pain experienced by a subject relative to that subject's pain immediately before the administration of the compounds of the present invention. Another outcome of treatment may be managing the amount of pain experienced by a subject relative to that subject's pain immediately before the administration of the compounds of the present invention. Another outcome of treatment may be ameliorating the amount of pain experienced by a subject relative to that subject's pain immediately before the administration of the compounds of the present invention.

Another outcome of treatment may be preventing further pain experienced by a subject after the administration of the compounds of the present invention.

Prevention of pain refers to the administration of the compounds of the present invention to reduce the pain of a subject at risk of pain. Prevention includes, but is not limited to, the administration to a subject prior to surgery or other expected painful event. One outcome of prevention may be reducing pain in a subject at risk of pain. Another outcome of prevention may be suppressing pain in a subject at risk of pain. Another outcome of prevention may be ameliorating pain in a subject at risk of pain. Another outcome of prevention may be alleviating pain in a subject at risk of pain. Another outcome of prevention may be managing pain in a subject at risk of pain.

The terms "administration of" and or "administering a" compound should be understood to mean providing a compound of the invention or a prodrug of a compound of the invention to the individual or mammal in need of treatment.

The administration of the compound of structural formula I in order to practice the present methods of therapy is carried out by administering an effective amount of the compound of structural formula I to the mammal in need of such treatment or prophylaxis. The need for a prophylactic administration according to the methods of the present invention is determined via the use of well known risk factors. The effective amount of an individual compound is determined, in the final analysis, by the physician or veterinarian in charge of the case, but depends on factors such as the exact disease to be treated, the severity of the disease and other diseases or conditions from which the patient suffers, the chosen route of administration other drugs and treatments which the patient may concomitantly require, and other factors in the physician's judgment.

The usefulness of the present compounds in these diseases or disorders may be demonstrated in animal disease models that have been reported in the literature.

Administration and Dose Ranges

Any suitable route of administration may be employed for providing a mammal, especially a human, with an effective dose of a compound of the present invention. For example, oral, intravenous, infusion, subcutaneous, transcutaneous, intramuscular, intradermal, transmucosal, intramucosal, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of the present invention are administered orally.

In the treatment or prevention of disorders, diseases and/or conditions which require inhibition of $Na_v1.8$ sodium ion channel activity, a suitable dosage level will generally be about 0.0001 to 500 mg per kg patient body weight per day which can be administered in single or multiple doses. In one embodiment, a suitable dosage level may be about 0.001 to 500 mg per kg patient body weight per day. In another embodiment, a suitable dosage level may be about 0.001 to about 250 mg/kg per day. In another embodiment, a suitable dosage level may be about 0.01 to about 250 mg/kg per day. In another embodiment, a suitable dosage level may be about 0.1 to about 100 mg/kg per day. In another embodiment, a suitable dosage level may be about 0.05 to 100 mg/kg per day. In another embodiment, a suitable dosage level may be about 0.1 to 50 mg/kg per day. In another embodiment, a suitable dosage level may be about 0.05 to 0.5 mg/kg per day. In another embodiment, a suitable dosage level may be about 0.5 to 5 mg/kg per day. In another embodiment, a suitable dosage level may be about 5 to 50 mg/kg per day. For oral administration, the compositions are preferably provided in the form of tablets containing 0.01 to 1000 mg of the active ingredient, particularly 0.01, 0.025, 0.05, 0.075, 0.1, 0.25, 0.5, 0.75, 1.0, 2.5, 5.0, 7.5, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 mg of the active ingredient for the symptomatic adjustment of the dosage to the patient to be treated. The compounds may be administered on a regimen of 1 to 8 times per day; preferably, 1 to 4 times a day; more preferably once or twice per day. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The compounds of this invention may be used in pharmaceutical compositions comprising (a) the compound(s) or pharmaceutically acceptable salts thereof, and (b) a pharmaceutically acceptable carrier. The compounds of this invention may be used in pharmaceutical compositions that include one or more other active pharmaceutical ingredients. The compounds of this invention may also be used in pharmaceutical compositions in which the compound of the present invention or a pharmaceutically acceptable salt thereof is the only active ingredient.

The term "composition," as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

Compounds of the present invention may be used in combination with other drugs that may also be useful in the treatment or amelioration of the diseases or conditions for which compounds of the present invention are useful. Such other drugs may be administered, by a route and in an amount commonly used therefor, contemporaneously or sequentially with a compound of the present invention. In the treatment of patients who have pain conditions, pruritic conditions and cough conditions, more than one drug is commonly administered. The compounds of this invention may generally be administered to a patient who is already taking one or more other drugs for these conditions. Often the compounds will be administered to a patient who is already being treated with one or more anti-pain compounds when the patient's pain is not adequately responding to treatment.

The combination therapy also includes therapies in which the compound of the present invention and one or more other drugs are administered on different overlapping schedules. It is also contemplated that when used in combination with one or more other active ingredients, the compound of the present invention and the other active ingredients may be used in lower doses than when each is used singly. Accordingly, the pharmaceutical compositions of the present invention include those that contain one or more other active ingredients, in addition to a compound of the present invention.

Examples of other active ingredients that may be administered in combination with a compound of the present invention, and either administered separately or in the same pharmaceutical composition, include but are not limited to:
 (i) an opioid agonist;
 (ii) an opioid antagonist;
 (iii) a calcium channel antagonist;
 (iv) a NMDA receptor agonist;
 (v) a NMDA receptor antagonist;
 (vi) a COX-2 selective inhibitor;
 (vii) a NSAID (non-steroidal anti-inflammatory drug);
 (viii) an analgesic;
 (ix) a sodium channel inhibitor;
 (x) an anti-NGF antibody;
 (xi) a $Na_v1.7$ inhibitor;
 (xii) a HCN inhibitor;
 (xiii) a TRPV1 antagonist;
 (xiv) a $Na_v1.7$ biological; and
 (xv) a $Na_v1.8$ biological; and
pharmaceutically acceptable salts thereof.

In another embodiment of the present invention, the pharmaceutical composition comprises:
 (1) a compound of Claim 1 or a pharmaceutically acceptable salt thereof;
 (2) one or more compounds, or pharmaceutically acceptable salts thereof, selected from the group consisting of:
  (i) an opioid agonist;
  (ii) an opioid antagonist;
  (iii) a calcium channel antagonist;
  (iv) a NMDA receptor agonist;
  (v) a NMDA receptor antagonist;
  (vi) a COX-2 selective inhibitor;
  (vii) a NSAID (non-steroidal anti-inflammatory drug);
  (viii) an analgesic;
  (ix) a sodium channel inhibitor;
  (x) an anti-NGF antibody;
  (xi) a $Na_v1.7$ inhibitor;
  (xii) a HCN inhibitor;
  (xiii) a TRPV1 antagonist;
  (xiv) a $Na_v1.7$ biological; and
  (xv) a $Na_v1.8$ biological; and
 pharmaceutically acceptable salts thereof; and
 (3) a pharmaceutically acceptable carrier.

A Nav 1.7 biological means a protein, including, but not limited to, antibodies, nanobodies and peptides, that inhibits the function of the Nav1.7 channel. A Nav 1.8 biological means a protein, including, but not limited to, antibodies, nanobodies and peptides, that inhibits the function of the Nav1.8 channel.

Specific compounds of use in combination with a compound of the present invention include: sodium channel inhibitors, including but not limited to, lidocaine including the lidocaine patch; tricyclic antidepressants including, but not limited to, amitriptyline; and SRI/NRI drugs, including but not limited to, duloxetine.

Suitable opioid agonists include, but are not limited to, codeine, fentanyl, hydrocodone, hydromorphone, levorphanol, meperidine, methadone, morphine, oxycodone, oxymorphone, buprenorphine, butorphanol, dezocine, nalbuphine, pentazocine, and tramadol.

Suitable opioid antagonists include, but are not limited to, naltrexone and naloxone.

Suitable calcium channel antagonists include, but are not limited to, Amlodipine, Diltiazem, Felodipine, gabapentin, Isradipine, Nicardipine, Nifedipine, Nisoldipine, pregabalin, Verapamil, and ziconitide.

Suitable NMDA receptor antagonists include, but are not limited to, ketamine, methadone, memantine, amantadine, and dextromethorphan.

Suitable COX-2 inhibitors include, but are not limited to, celecoxib, etoricoxib and parecoxib.

Suitable NSAIDs or non-steroidal anti-inflammatory drugs include, but are not limited to, aspirin, diclofenac, diflunisal, etodolac, fenoprofin, flurbiprofen, ibuprofen, indomethacin, ketoprofen, meclofenamic acid, mefenamic acid, meloxicam, naproxen, naproxen sodium, oxaprozin, piroxicam, sulindac, and tolmetin.

Suitable analgesics include, but are not limited to, acetaminophen and duloxetine.

The above combinations include combinations of a compound of the present invention not only with one other active compound, but also with two or more other active compounds. Non-limiting examples include combinations of compounds with two or more active compounds selected from: opioid agonists; opioid antagonists; calcium channel antagonists; NMDA receptor agonists; NMDA receptor antagonists; COX-2 selective inhibitors; NSAIDs (non-steroidal anti-inflammatory drugs); and an analgesic.

The compounds of the present invention, or a pharmaceutically acceptable salt thereof, may also be used in combination with spinal cord stimulation therapy and cutaneous stimulation therapy.

The present invention also provides a method for the treatment or prevention of a $Na_v1.8$ sodium ion channel activity mediated disease, disorder or condition, which method comprises administration to a patient in need of such treatment or at risk of developing a $Na_v1.8$ sodium ion channel activity mediated disease with a therapeutically effective amount of a $Na_v1.8$ sodium ion channel activity inhibitor and an amount of one or more active ingredients, such that together they give effective relief.

In a further aspect of the present invention, there is provided a pharmaceutical composition comprising a $Na_v1.8$ sodium ion channel activity inhibitor and one or more active ingredients, together with at least one pharmaceutically acceptable carrier or excipient.

Thus, according to a further aspect of the present invention there is provided the use of a $Na_v1.8$ sodium ion channel activity inhibitor and one or more active ingredients for the manufacture of a medicament for the treatment or prevention of a $Na_v1.8$ sodium ion channel activity mediated disease, disorder or condition. In a further or alternative aspect of the present invention, there is therefore provided a product comprising a $Na_v1.8$ sodium ion channel activity inhibitor and one or more active ingredients as a combined preparation for simultaneous, separate or sequential use in the treatment or prevention of a $Na_v1.8$ sodium ion channel activity mediated disease, disorder or condition. Such a combined preparation may be, for example, in the form of a twin pack.

It will be appreciated that for the treatment or prevention of pain conditions, pruritic conditions and cough conditions, a compound of the present invention may be used in conjunction with another pharmaceutical agent effective to treat that disease, disorder or condition.

The present invention also provides a method for the treatment or prevention of pain conditions, pruritic conditions and cough conditions, which method comprises administration to a patient in need of such treatment an amount of a compound of the present invention and an amount of another pharmaceutical agent effective to threat that disorder, disease or condition, such that together they give effective relief.

The present invention also provides a method for the treatment or prevention of pain conditions, pruritic conditions and cough conditions, which method comprises administration to a patient in need of such treatment an amount of a compound of the present invention and an amount of another pharmaceutical agent useful in treating that particular condition, disorder or disease, such that together they give effective relief.

The term "therapeutically effective amount" means the amount the compound of structural formula I that will elicit the biological or medical response of a cell, tissue, system, animal or human that is being sought by the researcher, veterinarian, medical doctor or other clinician, which includes alleviation of the symptoms of the disorder being treated. The novel methods of treatment of this invention are for disorders known to those skilled in the art. The term "mammal" includes humans, and companion animals such as dogs and cats.

The weight ratio of the compound of the Formula I to the second active ingredient may be varied and will depend upon the effective dose of each ingredient. Generally, an effective dose of each will be used. Thus, for example, when a compound of the Formula I is combined with a COX-2 inhibitor the weight ratio of the compound of the Formula I to the COX-2 inhibitor will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

Methods of Synthesis

The following reaction schemes and Examples illustrate methods which may be employed for the synthesis of the compounds of structural formula I described in this invention. These reaction schemes and Examples are provided to illustrate the invention and are not to be construed as limiting the invention in any manner. All substituents are as defined above unless indicated otherwise. Several strategies based upon synthetic transformations known in the literature of organic synthesis may be employed for the preparation of the compounds of structural formula I. The scope of the invention is defined by the appended claims.

Instrumentation

Reverse phase chromatography was carried out on a Gilson GX-281 equipped with a column selected from the following: Phenomenex Synergi C18 (150 mm×30 mm×4 micron), YMC-Actus Pro C18 (150 mm×30 mm×5 micron), Xtimate C18 (150 mm×25 mm×5 micron), Boston Green ODS (150 mm×30 mm×5 micron), XSELECT C18 (150 mm×30 mm×5 micron), and Waters XSELECT C18 (150 mm×30 mm×5 micron). Conditions included either high pH (0-100% acetonitrile/water eluent comprising 0.1% v/v 10 mM $NH_4CO_3$ or 0.05% $NH_4OH$) or low pH (0-95% acetonitrile/water eluent comprising 0.1% v/v TFA) and are noted for some examples.

SFC chiral resolution was carried out on a Sepiate Prep SFC 100, Multigram II (MG II), THAR80 prep SFC, or a Waters SFC (80, 200, or 350) using the following conditions: Chiral Method A: AD-H column, 30% EtOH (0.1% $NH_3 \cdot H_2O$)/$CO_2$; Chiral Method B: IC column, 45% EtOH (0.1% $NH_3 \cdot H_2O$)/$CO_2$; Chiral Method C: AD-H column, 30% EtOH/$CO_2$; Chiral Method D: AD-H column, 25% EtOH (0.1% $NH_3 \cdot H_2O$)/$CO_2$; Chiral Method E: AD-H column, 5-40% EtOH (0.05% DEA)/$CO_2$; Chiral Method F: WHELK-01 column, 30% EtOH (0.1% $NH_3 \cdot H_2O$)/$CO_2$; Chiral Method G: AD-H column, 20% MeOH/$CO_2$; Chiral Method H: OJ-H column, 25% EtOH (0.1% $NH_3 \cdot H_2O$)/$CO_2$; Chiral Method I: AD-H column, 40% EtOH/$CO_2$; Chiral Method J: OJ-H column, 15% EtOH (0.1% $NH_3 \cdot H_2O$)/$CO_2$; Chiral Method K: IG-3 column, 40% EtOH/$CO_2$; Chiral Method L: AD-H column, 30% MeOH/$CO_2$; Chiral Method M: AD-H column, 30% MeOH (0.05% DEA)/$CO_2$; Chiral Method N: OJ-H column, 20% EtOH (0.1% $NH_3 \cdot H_2O$)/$CO_2$; Chiral Method O: AD-H column, 15% MeOH (0.1% $NH_3 \cdot H_2O$)/$CO_2$; Chiral Method P: AD-H column, 30% MeOH (0.1% $NH_3 \cdot H_2O$)/$CO_2$; Chiral Method Q: AD-H column, 25% MeOH (0.1% $NH_3 \cdot H_2O$)/$CO_2$; Chiral Method R: OD-H column, 25% EtOH (0.1% $NH_3 \cdot H_2O$)/$CO_2$; Chiral Method S: WHELK-01 column, 50% EtOH (0.1% $NH_3 \cdot H_2O$)/$CO_2$; Chiral Method T: AD-H column, 20% EtOH/$CO_2$; Chiral Method U: AS-H column, 25% MeOH/$CO_2$; Chiral Method V: AD-H column, 40% MeOH/$CO_2$; Chiral Method W: OJ-H column, 15% MeOH/$CO_2$; Chiral Method X: IA column, 40% MeOH/$CO_2$; Chiral Method Y: AD-H column, 40% MeOH (0.05% DEA)/$CO_2$; Chiral Method Z: AS-H column, 20% MeOH/$CO_2$; Chiral Method AA: AD-H column, 35% EtOH (0.1% $NH_3 \cdot H_2O$)/$CO_2$; Chiral Method AB: AD-H column, 35% MeOH (0.1% $NH_3 \cdot H_2O$)/$CO_2$; Chiral Method AC: IC column, 30% EtOH (0.1% $NH_3 \cdot H_2O$)/$CO_2$; Chiral Method AD: OD-H column, 40% EtOH (0.1% $NH_3 \cdot H_2O$)/$CO_2$; Chiral Method AE: OD-H column, 30% EtOH/$CO_2$; Chiral Method AF: AD-H column, 35% EtOH/$CO_2$; Chiral Method AG: AD-H column, 13% MeOH/$CO_2$; Chiral Method AH: AD-H column, 15-25% MeOH/$CO_2$; Chiral Method AI: OJ-H column, 15-25% MeOH/$CO_2$; Chiral Method AJ: IC column, 20% MeOH/$CO_2$; Chiral Method AK: Chiral Technologies SFC-B (P4VP), 10% MeOH/$CO_2$; Chiral Method AL: OJ-H column, 10% MeOH/$CO_2$; Chiral Method AM: AD-H column, 10% MeOH/$CO_2$; Chiral Method AN: AD-H column, 35% MeOH/$CO_2$; Chiral Method AO: AD-H column, 5% MeOH/$CO_2$; Chiral Method AP: AD-H column, 25% EtOH/$CO_2$; Chiral Method AQ: WHELK-01 column, 20% EtOH/$CO_2$; Chiral Method AR: OD-H column, 15% EtOH/$CO_2$.

LC/MS determinations were carried out on a Waters Classing Aquity system equipped with TUV and MS detectors and a Waters SQD mass spectrometer, a Shimadzu 20 UV 254 and 220 nM with Shimadzu 2010 or 2020 mass spectrometer, or an Agilent 1200 HPLC quipped with DAD/ELSD and G6110 MSD using one of the following conditions: 1) Ascentis Express C18 (3×50 mm) 2.7 μm column using mobile phase containing A: 0.05% TFA in water and B: 0.05% TFA in acetonitrile with a gradient from 90:10 (A:B) to 5:95 (A:B) over 6 min at a flow rate of 1.8 mL/min, UV detection at 210 nm; 2) Aquity BEH C18, (1.0×50 mm) 1.7 μm column using mobile phase containing A: 0.05% TFA in water and B: 0.05% TFA in acetonitrile with a gradient from 90:10 (A:B) to 5:95 (A:B) over 2 min at a flow rate of 0.3 mL/min, UV detection at 215 nm; 3) Agilent YMC J'Sphere H-80 (3×50 mm) 5 μm column using mobile phase containing A: 0.1% TFA in water and B: acetonitrile with a gradient from 95:5 (A:B) to 0:100 (A:B) over 3.6 min and 0:100 (A:B) for 0.4 min at a flow rate of 1.4 mL/min, UV detection at 254 and 220 nm and Agilent 1100 quadrupole mass spectrometer; 4) an Agilent TC-C18 (2.1×50 mm) 5 μm column using mobile phase containing A: 0.0375% TFA in water and B: 0.01875% TFA in acetonitrile with a gradient from 90:10 (A:B) for 0.4 min to 90:10 to 0:100

(A:B) over 3 min and 10:90 (A:B) for 0.6 min at a flow rate of 0.8 mL/min, UV detection at 254 and 220 nm and Agilent 6110 quadrupole mass spectrometer.

Proton or $^1$H NMR was acquired using a Varian Unity-Inova 400 MHz NMR spectrometer equipped with a Varian 400 ATB PFG 5 mm, Nalorac DBG 400-5 or a Nalorac IDG 400-5 probe, a Varian-400 MHz MR spectrometer equipped with an Auto X ID PFG Probe 5 mm, a Varian 400 MHz VNMRS spectrometer equipped with a PFG 4Nuc Probe 5 mm, or a Bruker AvanceIII 500 MHz spectrometer equipped with a PABBO Probe 5 mm in accordance with standard analytical techniques, unless specified otherwise, and results of spectral analysis are reported. Chemical shift (δ) values are reported in delta (δ) units, parts per million (ppm). Chemical shifts for $^1$H NMR spectra are given relative to signals for residual non-deuterated solvent (CDCl$_3$ referenced at δ 7.26 ppm; DMSO d-6 referenced at δ 2.50 ppm and CD$_3$OD referenced at δ 3.31 ppm). Multiples are reported by the following abbreviations: s=singlet, d=doublet, t=triplet, q=quartet, dd=doublet of doublets, m=multiplet or overlap of nonequivalent resonances. Coupling constants (J) are reported in Hertz (Hz).

Abbreviations

AcOH is acetic acid; aq. is aqueous; OAc is acetate; BH$_3$ DMS is Borane dimethylsulfide; Boc is tert-butoxycarbonyl; Calc'd is calculated; CDI is 1,1'-carbonyl-diimidazole, DAST is diethylaminosulfur trifluoride; DCE is dichloroethane; DCM is dichloromethane; DEA is diethanolamine; Deoxoflour is Bis(2-methoxyethyl)aminosulfur Trifluoride; DIEA is N,N-diisopropylethylamine; DMA is dimethylacetamide; DME is dimethoxyethane; DMF is dimethylformamide; DMSO is dimethylsulfoxide; dppf is 1,1'-bis(diphenylphosphino)-ferrocene; EDC is 1-ethyl-3-(3-dimethylaminopropyl)-carbodiimide; Et$_2$O is diethyl ether; EtOAc is ethyl acetate; EtOH is ethanol; g is grams; h or hr(s) is hour(s); HATU is 1-[bis(dimethyl-amino)-methylene]-1H-1,2,3-triazolo[4,5-b]pyridinium-3-oxide-hexafluoro-phosphate; Hex is hexanes; HOAt is 1-Hydroxy-7-azabenzotriazole; HPLC is high-performance liquid chromatography; IPA is isopropyl alcohol; iPrMgCl is isopropylmagnesium chloride; iPrMgCl—LiCl is isopropylmagnesium chloride lithium chloride complex; L is liter; LAH is lithium aluminum hydride; LC/MS is liquid chromatography/mass spectrometry; LRMS is low resolution mass spectrometry; M is molar; Me is methyl; MeOH is methanol; MeCN is acetonitrile; mg is milligrams; mL is milliliter; mmol is millimolar; NaHMDS is Sodium bis(trimethylsilyl)amide; NH$_4$OAc is ammonium acetate, NMO is 4-Methylmorpholine N-oxide; NMP is N-methylpyrrolidone; PCC is pyridinium chlorochromate; Pd/C is palladium on carbon; Pd(dppf)Cl$_2$ is [1,1'-bis(diphenylphosphino)-ferrocene]dichloropalladium(II); Pd(PPh$_3$)$_4$ is tetrakis(triphenylphosphine)palladium(0); Pd(tBu$_3$P)$_2$ is Bis(tri-tert-butylphosphine)palladium(0); PE is petroleum ether; PG is protecting group; prep is preparative; rt or RT is room temperature; sat is saturated; SFC is Supercritical Fluid Chromatography; T3P is 2,4,6-Tripropyl-1,3,5,2,4,6-trioxatriphosphorinane-2,4,6-trioxide; TBAF is tetrabutylammonium fluoride; tBuXPhos Pd G3 is [(2-Di-tert-butylphosphino-2',4',6'-triisopropyl-1,1'-biphenyl)-2-(2'-amino-1,1'-biphenyl)] palladium(II) methanesulfonate; TEA is triethylamine; THF is tetrahydrofuran; Ti(OEt)$_4$ is titanium (IV) ethoxide; Ti(OiPr)$_4$ is titanium (IV) isopropoxide; TLC is thin layer chromatography; TMS-Diazomethane is trimethylsilyl-diazomethane; and UV is ultraviolet.

As illustrated in Scheme A, in general, compounds of the invention can be prepared by condensation between an appropriately functionalized aldehyde A-1 and tert-butanesulfinamide, utilizing dehydrating agents such as Ti(OEt)$_4$ or Ti(OiPr)$_4$, to afford intermediate A-2. Intermediate A-2 can then be reacted with a variety of organometallic nucleophiles A-3 to give intermediate A-4 which can be deprotected under acidic conditions to give amines of formula A-5. Amine A-5 can then be brought together with imidazolidinone A-6, utilizing amide coupling conditions (Z=OH) or nucleophilic displacement reactions (Z=Cl) to deliver compounds of formula A-7. In some embodiments, a protecting group, such as Boc, may need to be removed throughout the course of synthesis. Aldehydes of type A-1 and organometallics of type A-3 are commercially available or may be synthesized from appropriate intermediates.

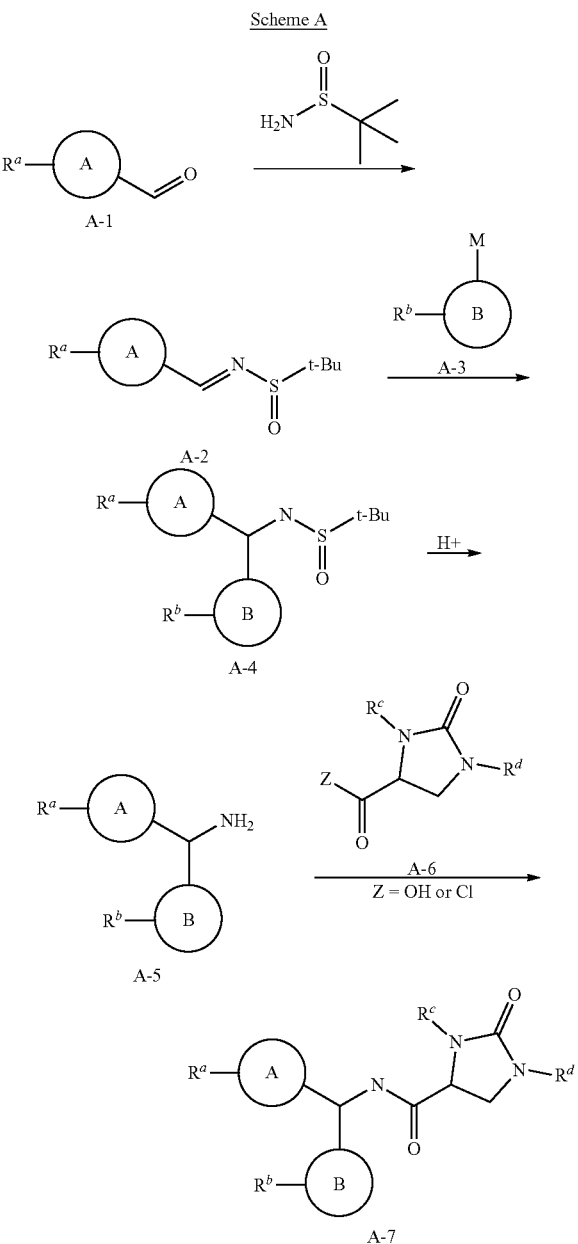

Scheme A

As illustrated in Scheme B, in general, compounds of the invention can be prepared by activation of appropriately functionalized carboxylic acid B-1 with either (COCl)$_2$ or amide coupling with amine B-2 to give intermediates of B-3. These intermediates are then suitable to for reaction with a variety of organometallic nucleophiles A-3 to give intermediate B-4. Intermediate B-4 can then undergo reductive amination reaction in the presence of an amine source and reductant to yield intermediates of A-5. In some cases, tert-butanesulfinamide was used as the amine source and would require deprotection (in an acidic environment) following reductive amination. Amine A-5 can then be brought together with imidazolidinone A-6, utilizing amide coupling conditions (Z=OH) or nucleophilic displacement reactions (Z=Cl) to deliver compounds of formula A-7. In some embodiments, a protecting group, such as Boc, may need to be removed throughout the course of synthesis. Carboxylic acid of type B-1 and organometallics of type A-3 are commercially available or may be synthesized from appropriate intermediates.

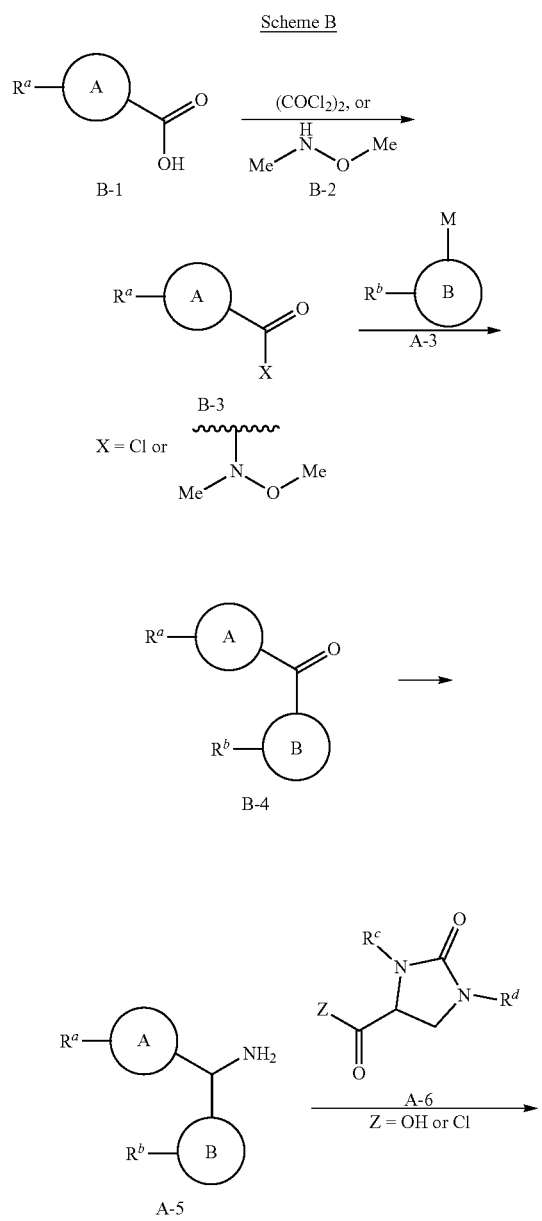

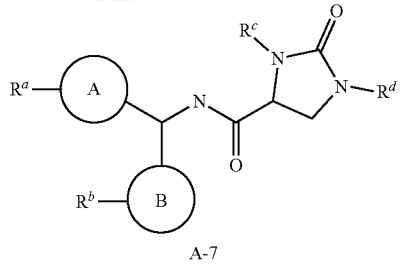

INTERMEDIATES

Intermediate 1

(3-chloro-4-fluorophenyl)(2-(1-(trifluoromethyl) cyclopropyl)thiazol-4-yl)methanamine hydrochloride

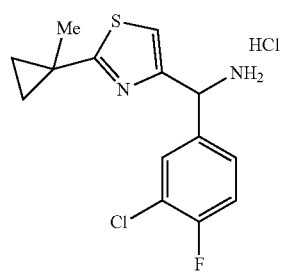 [SMILES: CC1(c2nc(C(N)c3ccc(F)c(Cl)c3)cs2)CC1 ; Cl]

Step 1: (R)—N-((2-chlorothiazol-4-yl)methylene)-2-methylpropane-2-sulfinamide. 2-chlorothiazole-4-carbaldehyde (2.00 g, 13.6 mmol) and (R)-2-methylpropane-2-sulfinamide (1.64 g, 13.6 mmol) was taken up in THF (68 mL) and then Ti(OEt)$_4$ (5.68 mL, 27.1 mmol) was added. The mixture was stirred for 2 hours, then diluted with brine, filtered through sand and extracted with EtOAc. The combined organic layers were washed with saturated NH$_4$Cl, brine, dried over Na$_2$SO$_4$, filtered, and concentrated in vacuo to give the title compound.

Step 2: (R)—N-((3-chloro-4-fluorophenyl)(2-chlorothiazol-4-yl)methyl)-2-methylpropane-2-sulfinamide. 2-chloro-1-fluoro-4-iodobenzene (3.1 mL, 24 mmol) was dissolved in THF (20 mL) and cooled to 0° C., then iPrMgCl (8.0 mL, 16 mmol, 2 M in THF) was added slowly over 5 min. This mixture was stirred for 15 min, then a solution of (R)—N-((2-chlorothiazol-4-yl)methylene)-2-methylpropane-2-sulfinamide (2.0 g, 8.0 mmol) in toluene (100 mL) was slowly added at −25° C. The mixture was then allowed to warm to rt and stirred for 1 h at rt. The mixture was quenched with 1 N HCl and stirred for 10 min. Then the mixture was extracted with EtOAc. The combined organic layers were washed with brine, dried over MgSO$_4$, filtered, and concentrated in vacuo. The resulting residue was purified by silica gel chromatography (0-100% EtOAc:hex) to give the title compound.

Step 3: (R)—N-((3-chloro-4-fluorophenyl)(2-(3,3,3-trifluoroprop-1-en-2-yl)thiazol-4-yl)methyl)-2-methylpropane-2-sulfinamide. (R)—N-((3-chloro-4-fluorophenyl)(2-chlorothiazol-4-yl)methyl)-2-methylpropane-2-sulfinamide (1.1 g, 3.0 mmol), Na$_2$CO$_3$ (0.95 g, 9.0 mmol), Pd(dppf)Cl$_2$ (1.1 mg, 1.5 mmol) and 4,4,6-trimethyl-2-(3,3,3-trifluoroprop-1- en-2-yl)-1,3,2-dioxaborinane (1.3 mL, 6.0 mmol) was dissolved THF (12 mL) and water (3 mL), and degassed by bubbling $N_2$ through the solution for 10 min. The mixture was then heated to 110° C. via microwave irradiation for 1 h. Then the mixture was diluted with sat. $Na_2CO_3$ and extracted with EtOAc. The combined organic layers were washed with brine, dried over $Na_2SO_4$, filtered, and concentrated in vacuo. The resulting residue was purified by silica gel chromatography (0-75% EtOAc:hex) to give the title compound.

Step 4: (R)—N-((3-chloro-4-fluorophenyl)(2-(1-(trifluoromethyl)cyclopropyl)thiazol-4-yl)methyl)-2-methylpropane-2-sulfinamide. A solution of (R)—N-((3-chloro-4-fluorophenyl)(2-(3,3,3-trifluoroprop-1-en-2-yl)thiazol-4-yl)methyl)-2-methylpropane-2-sulfinamide (0.50 g, 1.1 mmol) and diphenyl-(methyl)sulfonium tetrafluoroborate (0.42 g, 1.5 mmol) in THF (12 mL) was cooled to 0° C. Then NaHMDS (0.91 mL, 1.8 mmol) was added over 5 min to 0° C., and the reaction was allowed to warm to rt. The mixture was quenched by the addition of MeOH and concentrated in vacuo. The resulting residue was subjected to silica gel chromatography (0-80% EtOAc:hex) to give the title compound.

Step 5: (3-chloro-4-fluorophenyl)(2-(1-(trifluoromethyl)cyclopropyl)thiazol-4-yl)methanamine hydrochloride. A solution of (R)—N-((3-chloro-4-fluorophenyl)(2-(1-(trifluoromethyl)cyclopropyl)thiazol-4-yl)methyl)-2-methylpropane-2-sulfinamide (0.52 g, 0.85 mmol) in EtOAc (12 mL) was cooled to 0° C. Then HCl gas was bubbled through the mixture for 15 seconds until saturated. The mixture was then concentrated in vacuo to give the title compound.

Intermediate 2A (R or S)-6-(amino(3-chloro-4-fluorophenyl)methyl) picolinonitrile hydrochloride

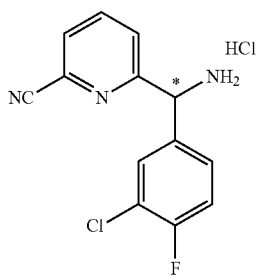 [SMILES: N#Cc1cccc(C(N)c2ccc(F)c(Cl)c2)n1 ; Cl]

Step 1: (R)—N-((6-bromopyridin-2-yl)methylene)-2-methylpropane-2-sulfinamide. To a mixture of 6-bromopicolinaldehyde (1.0 g, 5.4 mmol) and (R)-2-methylpropane-2-sulfinamide (0.78 g, 6.4 mmol) in THF (20 mL) was added Ti(OEt)$_4$ (2.2 mL, 11 mmol) at 0° C. The resulting mixture was stirred at rt for 3 h, then diluted with EtOAc, washed with brine and filtered. The filtrate was extracted with EtOAc. The combined organic layers were dried over $Na_2SO_4$, filtered, and the filtrate was concentrated in vacuo to give the title compound.

Step 2: (R)—N-((6-bromopyridin-2-yl)(3-chloro-4-fluorophenyl)methyl)-2-methylpropane-2-sulfinamide. To a solution of (R)—N-((6-bromopyridin-2-yl)methylene)-2-methylpropane-2-sulfinamide (0.75 g, 2.6 mmol) in toluene (20 mL) was added (3-chloro-4-fluorophenyl)-magnesium bromide (7.8 mL, 7.8 mmol, 1 M) at −45° C. The mixture was stirred at −45° C. for 2 h, then quenched with sat. $NH_4Cl$. The mixture was then extracted with EtOAc, dried over $Na_2SO_4$, filtered and concentrated in vacuo. The resulting residue was purified by prep. silica gel TLC (2:1 EtOAc:PE) to give the title compound.

Step 3: (R)—N-(-(3-chloro-4-fluorophenyl)(6-cyanopyridin-2-yl)methyl)-2-methylpropane-2-sulfinamide. To a mixture of (R)—N-((6-bromopyridin-2-yl)(3-chloro-4-fluorophenyl)methyl)-2-methylpropane-2-sulfinamide (0.13 g, 0.32 mmol) and Zn(CN)$_2$ (0.19 g, 1.6 mmol) in NMP (6 mL) was added Pd(tBu$_3$P)$_2$ (45 mg, 0.089 mmol). The mixture was heated to 130° C. for 10 min by microwave. Then the reaction was filtered. Water was added to the filtrate, and the mixture was extracted with EtOAc. The combined organic layers were washed with brine, dried over $Na_2SO_4$, filtered and concentrated in vacuo. The resulting residue was purified by reverse phase HPLC (55:45 to 35:65; water (0.1% TFA):MeCN (0.1% TFA)), followed by lyophilization to give the title compound: first eluted diastereomer 2A1 (R)—N—((R or S)-(3-chloro-4-fluorophenyl)(6-cyanopyridin-2-yl)methyl)-2-methylpropane-2-sulfinamide Step 4: (R or S)-6-(amino(3-chloro-4-fluorophenyl) methyl)picolinonitrile. A solution of 2A1 (R)—N-(-(3-chloro-4-fluorophenyl)(6-cyanopyridin-2-yl)methyl)-2-methylpropane-2-sulfinamide (0.22 g, 0.60 mmol) in HCl (0.50 mL, 2.0 mmol, 4 N in MeOH) and THF (3 mL) was stirred at 15° C. for 1 h. Then the reaction mixture was concentrated in vacuo to give the title compound as the hydrochloride salt.

Intermediate 2B (R or S)-6-(amino(3-chloro-4-fluorophenyl)methyl) picolinonitrile hydrochloride

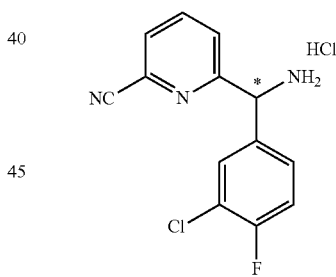

Step 1: (R)—N—((R or S)-(3-chloro-4-fluorophenyl)(6-cyanopyridin-2-yl)methyl)-2-methylpropane-2-sulfinamide. To a mixture of (R)—N-((6-bromopyridin-2-yl)(3-chloro-4-fluorophenyl)methyl)-2-methylpropane-2-sulfinamide (0.13 g, 0.32 mmol, as prepared in intermediate 2A) and Zn(CN)$_2$ (0.19 g, 1.6 mmol) in NMP (6 mL) was added Pd(tBu$_3$P)$_2$ (45 mg, 0.089 mmol). The mixture was heated to 130° C. for 10 min by microwave. The reaction was filtered and to the filtrate was added water, followed by extraction with EtOAc. The combined organic layers were washed with brine, dried over $Na_2SO_4$, filtered and concentrated in vacuo. The resulting residue was purified by reverse phase HPLC (55:45 to 35:65; water (0.1% TFA):MeCN (0.1% TFA)), followed by lyophilization to give the title compound: second eluted diastereomer 2B1 (R)—N—((R or S)-3-chloro-4-fluorophenyl)(6-cyanopyridin-2-yl)methyl)-2-methylpropane-2-sulfinamide.

Step 2: (R or S)-6-(amino(3-chloro-4-fluorophenyl)methyl)picolinonitrile. A solution of 2B1 (R)—N—((R or S)-(3-chloro-4-fluorophenyl)(6-cyanopyridin-2-yl)methyl)-2-methylpropane-2-sulfinamide (0.22 g, 0.60 mmol) in HCl (0.50 mL, 2.0 mmol, 4 N in MeOH) and THF (3 mL) was stirred at 15° C. for 1 h. The reaction was concentrated in vacuo to give intermediate 2B (R or S)-6-(amino(3-chloro-4-fluorophenyl)methyl)picolinonitrile as the hydrochloride salt.

Intermediate 3

6-(difluoromethyl)-5-fluoropicolinaldehyde

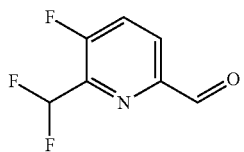

Step 1: 6-chloro-2-(difluoromethyl)-3-fluoropyridine. To a solution of 6-chloro-3-fluoro-picolinaldehyde (2.0 g, 12 mmol) in CHCl₃ (35 mL) was slowed added DAST (5.0 mL, 7.6 mmol) at 0° C. The mixture was degassed and backfilled with N₂ (three times). Then the mixture was stirred at rt for 12 h, quenched with water and extracted with DCM. The combined organic phases were concentrated in vacuo to give the title compound.

Step 2: 2-(difluoromethyl)-3-fluoro-6-vinylpyridine. To a mixture of 6-chloro-2-(difluoro-methyl)-3-fluoropyridine (2.2 g, 12 mmol), potassium trifluoro(vinyl)borate (3.2 g, 24 mmol) and K₂CO₃ (3.4 g, 24 mmol) in THF (25 mL) and water (0.1 mL) was add Pd(dppf)Cl₂ (0.89 g, 1.21 mmol). The mixture was stirred at 80° C. for 12 h. The mixture was then filtered, and the filtrate was concentrated in vacuo to give the title compound.

Step 3: 6-(difluoromethyl)-5-fluoropicolinaldehyde. A mixture of 2-(difluoromethyl)-3-fluoro-6-vinylpyridine (1.8 g crude), NMO (2.4 g, 21 mmol) and OsO₄ (0.033 mL, 0.10 mmol) in THF (25 mL) and water (5 mL) was stirred at rt for 2 h. Then NaIO₄ (11 g, 52 mmol) was added to the mixture and the reaction was stirred at rt for 2 h. The mixture was then diluted with water and extracted with EtOAc. The combined organic layers were washed with brine, dried over Na₂SO₄, filtered and concentrated in vacuo to give the title compound.

Intermediate 4

(3-chloro-4-fluorophenyl)(5-fluoro-6-(2,2,2-trifluoroethoxy)pyridin-2-yl)methanamine

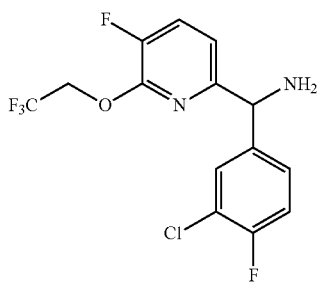 [SMILES: NC(c1ccc(F)c(Cl)c1)c1ccc(F)c(OCC(F)(F)F)n1]

Step 1: 6-chloro-5-fluoro-N-methoxy-N-methylpicolinamide. To a mixture of 6-chloro-5-fluoropicolinic acid (5.0 g, 28 mmol) in DCM (20 mL) was added CDI (5.5 g, 34 mmol). The mixture was stirred for 1 h. Then N,O-dimethylhydroxylamine hydrochloride (3.3 g, 34 mmol) and TEA (12 mL, 85 mmol) were added. The mixture was stirred at rt for 16 h, then diluted with water and extracted with DCM. The combined organic layers were washed with brine, dried over Na₂SO₄, filtered and concentrated in vacuo. The resulting residue was purified by silica gel chromatography (0-30% EtOAc:PE) to give the title compound.

Step 2: 5-fluoro-N-methoxy-N-methyl-6-(2,2,2-trifluoroethoxy)picolinamide. To a mixture of 6-chloro-5-fluoro-N-methoxy-N-methylpicolinamide (3.0 g, 14 mmol), tBuXPhos Pd G3 (1.0 g, 1.4 mmol) and Cs₂CO₃ (9.4 g, 29 mmol) in toluene (20 mL) was added 2,2,2-trifluoro (1.1 g, 11 mmol). The mixture was stirred at 80° C. for 16 h. Then the mixture was filtered, and the filtrate was concentrated in vacuo. The resulting residue was purified by silica gel chromatography (0-30% EtOAc:PE) to give the title compound.

Step 3: (3-chloro-4-fluorophenyl)(5-fluoro-6-(2,2,2-trifluoroethoxy)pyridin-2-yl)methanone. To a solution of 4-bromo-2-chloro-1-fluorobenzene (2.4 g, 12 mmol) in THF (5 mL) was added iPrMgCl (6.5 mL, 8.5 mmol) at 0° C. and the mixture was stirred at rt for 1 h. Then a solution of 5-fluoro-N-methoxy-N-methyl-6-(2,2,2-trifluoroethoxy)picolinamide (1.5 g, 5.3 mmol) in THF (5 mL) was added, and the resulting mixture was stirred at rt for 16 h. Then sat. NH₄Cl was added, and the mixture was extracted with EtOAc. The combined organic layers were dried under Na₂SO₄, filtered and concentrated in vacuo. The resulting residue was purified by silica gel chromatography (0-30% EtOAc:PE) to give title compound.

Step 4: (3-chloro-4-fluorophenyl)(5-fluoro-6-(2,2,2-trifluoroethoxy)pyridin-2-yl)methanamine. NH₄OAc (0.99 g, 13 mmol) and NaBH₃CN (80 mg, 1.3 mmol) were added to a solution of (3-chloro-4-fluorophenyl)(5-fluoro-6-(2,2,2-trifluoroethoxy)pyridin-2-yl)methanone (0.30 g, 0.85 mmol) in EtOH (5 mL) in a 30 mL microwave vial. The mixture was stirred and heated at 130° C. for 10 min in a microwave reactor. Then the reaction mixture was concentrated in vacuo followed by treatment 2 N NaOH until the pH >10. The solution was then extracted with EtOAc. The organic layer was dried over Na₂SO₄, filtered, and concentrated in vacuo. The resulting residue was purified by silica gel chromatography (0-30% EtOAc:PE) to give the title compound.

Intermediate 5

1-(2,2,2-trifluoroethyl)-1H-pyrazole-3-carboxylic acid

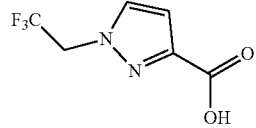

Step 1: ethyl 1-(2,2,2-trifluoroethyl)-1H-pyrazole-3-carboxylate. To a mixture of methyl 1H-pyrazole-3-carboxylate (1.0 g, 7.1 mmol) and K₂CO₃ (2.0 g, 14 mmol) in MeCN (10 mL) was added 2,2,2-trifluoroethyl trifluoromethanesulfonate (2.5 g, 11 mmol). The resulting mixture was stirred at 80° C. for 18 h. Then the reaction was quenched by the addition of water, and the resulting mixture was extracted with EtOAc. The combined organic layers were washed with brine, dried over $Na_2SO_4$, filtered and concentrated in vacuo. The resulting crude product was purified by silica gel chromatography (31% EtOAc:PE) to give the title compound.

Step 2: 1-(2,2,2-trifluoroethyl)-1H-pyrazole-3-carboxylic acid. To a mixture of ethyl 1-(2,2,2-trifluoroethyl)-1H-pyrazole-3-carboxylate (1.0 g, 4.5 mmol) in a solution of EtOH (5 mL) and water (5 mL) was added NaOH (0.36 g, 9.0 mmol). The resulting mixture was stirred at 80° C. for 30 min. Then the mixture was concentrated in vacuo. The resulting residue was taken up in EtOAc, and washed with hydrochloric acid (0.5 M). The organic was separated, dried over $Na_2SO_4$, filtered and the filtrate was concentrated in vacuo to give the title compound.

Intermediate 6

5-fluoro-4-(trifluoromethyl)picolinaldehyde

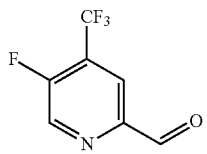 [SMILES: O=Cc1cc(C(F)(F)F)c(F)cn1]

Step 1: 5-fluoro-4-(trifluoromethyl)-2-vinylpyridine. To a mixture of 2-chloro-5-fluoro-4-(trifluoromethyl)pyridine (1.0 g, 5.0 mmol), potassium trifluoro(vinyl)borate (1.0 g, 7.5 mmol) and $K_2CO_3$ (1.4 g, 10 mmol) in dioxane (15 mL) and water (1.5 mL) was add $Pd(dppf)Cl_2$ (0.37 g, 0.50 mmol). The mixture was stirred at 100° C. for 12 h. Then water was added, and the mixture was extracted with EtOAc. The combined organic layers were dried over $Na_2SO_4$, filtered and concentrated in vacuo to give the title compound.

Step 2: 5-fluoro-4-(trifluoromethyl)picolinaldehyde. A mixture of 5-fluoro-4-(trifluoromethyl)-2-vinylpyridine (0.96 g crude), NMO (1.2 g, 10 mmol) and $OsO_4$ (2.5 mL, 0.25 mmol) in THF (20 mL) and water (10 mL) was stirred at rt for 12 h. Then $NaIO_4$ (3.2 g, 15 mmol) was added, and the mixture was stirred at rt for 2 h. To the mixture was added water followed by extraction with DCM. The combined organic layers were dried over $Na_2SO_4$, filtered and concentrated in vacuo to give the title compound.

Intermediate 7

(3-chloro-2,4-difluorophenyl)(5-chloro-6-cyclopropylpyridin-3-yl)methanamine hydrochloride

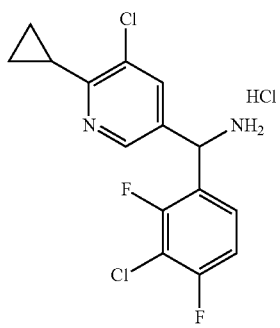 [SMILES: NC(c1cnc(C2CC2)c(Cl)c1)c1ccc(F)c(Cl)c1F ; Cl]

Step 1: 5-bromo-3-chloro-2-cyclopropylpyridine. Zinc chloride (0.55 g, 4.0 mmol) in THF (15 mL) was added to a solution of cyclopropylmagnesium bromide (8.1 mL, 4.0 mmol) in THF (15 mL). The reaction mixture was stirred at rt for 1 h, then 2,5-dibromo-3-chloropyridine (1.0 g, 3.7 mmol) and $Pd(PPh_3)_4$ (0.43 g, 0.37 mmol) were added in one portion. The mixture was stirred at rt for 10 h, then diluted with water and extracted with EtOAc. The combined organic layers were washed with brine, dried over $Na_2SO_4$, filtered and concentrated in vacuo. The resulting residue was purified by silica gel chromatography (0-10% EtOAc:PE) to give the title compound.

Step 2: (R)—N-((3-chloro-2,4-difluorophenyl)(5-chloro-6-cyclopropylpyridin-3-yl)methyl)-2-methylpropane-2-sulfinamide. To a solution of 5-bromo-3-chloro-2-cyclopropylpyridine (0.38 g, 1.7 mmol) in THF (3 mL) was added iPrMgCl—LiCl (1.2 mL, 1.5 mmol, 1.3 M in THF) at 0° C. The mixture was stirred for 2 h, then a mixture of (R)—N-(3-chloro-2,4-difluorobenzylidene)-2-methylpropane-2-sulfinamide (0.42 g, 1.5 mmol, from step one of example 52A and 52B) in THF (3 mL) was added. The reaction mixture was stirred at 0° C. for 2 h, then diluted with $NH_4Cl$ and extracted with EtOAc. The combined organic layers were washed with brine, dried over $Na_2SO_4$, filtered and concentrated in vacuo. The resulting residue was purified by silica gel chromatography (0-15% EtOAc:PE) to give the title compound.

Step 3: (3-chloro-2,4-difluorophenyl)(5-chloro-6-cyclopropylpyridin-3-yl)methanamine hydrochloride. To a solution of (R)—N-((3-chloro-2,4-difluorophenyl)(5-chloro-6-cyclo-propylpyridin-3-yl)methyl)-2-methylpropane-2-sulfinamide (0.20 g, 0.46 mmol) in MeOH (2 mL) was added HCl (2.0 mL, 8.0 mmol, 4 N in MeOH). The reaction mixture was stirred at rt for 1 h, then concentrated in vacuo to give the title compound.

Intermediate 8

5-chloro-6-(trifluoromethyl)picolinaldehyde

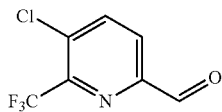

Intermediate 8 was prepared according to a similar procedure to that of Intermediate 6 starting from 3,6-dichloro-2-(trifluoromethyl)pyridine.

Intermediate 9

(5-chloro-6-(trifluoromethyl)pyridin-3-yl)(5-fluoro-6-(trifluoromethyl)pyridin-2-yl)methanamine hydrochloride

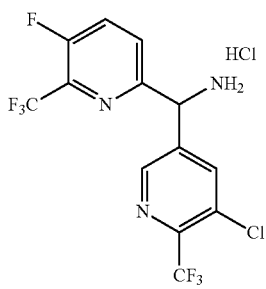 [SMILES: NC(c1cnc(C(F)(F)F)c(Cl)c1)c1ccc(F)c(C(F)(F)F)n1 ; Cl]

Step 1: 3-chloro-5-(4,4,5,5-tetramethyl-1,3,2-dioxaborolan-2-yl)-2-(trifluoromethyl)pyridine. To a solution of 3-chloro-2-(trifluoromethyl)pyridine (2.0 g, 11 mmol) and 4,4,4',4',5,5,5',5'-octamethyl-2,2'-bi(1,3,2-dioxaborolane) (4.2 g, 17 mmol) in hexane (30 mL) was added 4,4'-di-tert-butyl-2,2'-bipyridine (0.30 g, 1.1 mmol) and bis(1,5-cyclooctadiene)rhodium(I) tetrafluoroborate (0.37 g, 0.55 mmol). The mixture was stirred at 65° C. for 18 h, then diluted with water and extracted with DCM. The combined organic layers were washed with brine, dried over $Na_2SO_4$, filtered and concentrated in vacuo. The resulting residue was purified by silica gel chromatography (0-8% EtOAc:PE) to give the title compound.

Step 2: 3-chloro-5-iodo-2-(trifluoromethyl)pyridine. To a solution of compound 3-chloro-5-(4,4,5,5-tetramethyl-1,3,2-dioxaborolan-2-yl)-2-(trifluoromethyl)pyridine (1.0 g, 3.2 mmol) in DME (15 mL) was added 1-iodopyrrolidine-2,5-dione (2.2 g, 9.8 mmol), CuI (0.062 g, 0.32 mmol), 1,10-phenanthroline (0.059 g, 0.32 mmol) and $K_2CO_3$ (0.90 g, 6.5 mmol). The mixture was stirred at 50° C. for 12 h, then diluted with water and extracted with DCM. The combined organic layers were washed with brine, dried over $Na_2SO_4$, filtered and concentrated in vacuo. The resulting residue was purified by preparative silica gel TLC (0-1% EtOAc:PE) to give the title compound.

Step 3: (R)—N-((5-chloro-6-(trifluoromethyl)pyridin-3-yl)(5-fluoro-6-(trifluoromethyl)pyridin-2-yl)methyl)-2-methylpropane-2-sulfinamide. To a solution of 3-chloro-5-iodo-2-(trifluoro-methyl)pyridine (0.28 g, 0.91 mmol) in toluene (3 mL) was added iPrMgCl—LiCl complex (0.65 mL, 0.85 mmol, 1.3 M in THF) at −40° C. The mixture was stirred at −40° C. for 1 h. Then (R)—N-((5-fluoro-6-(trifluoromethyl)pyridin-2-yl)methylene)-2-methylpropane-2-sulfinamide (0.18 g, 0.61 mmol, from Step 3 of Example 7A and 7B) in toluene (2 mL) was added. The mixture was stirred at −40° C. and then slowly warmed to 29° C., and stirred at 29° C. for 4 h. The mixture was then quenched with sat. $NH_4Cl$ and extracted with EtOAc. The combined organic layers were washed with brine, dried over $Na_2SO_4$, filtered and concentrated in vacuo. The resulting residue was purified by preparative silica gel TLC (33% EtOAc:PE) to give the title compound.

Step 4: (5-chloro-6-(trifluoromethyl)pyridin-3-yl)(5-fluoro-6-(trifluoromethyl)pyridin-2-yl)methanamine hydrochloride. To a solution of (R)—N-((5-chloro-6-(trifluoromethyl)pyridin-3-yl)(5-fluoro-6-(trifluoromethyl)pyridin-2-yl)methyl)-2-methylpropane-2-sulfinamide (0.24 g, 0.50 mmol) in MeOH (2 mL) was added HCl (2.0 mL, 8.0 mmol, 4 N in MeOH). The mixture was stirred at rt for 11 h, then concentrated in vacuo to give the title compound.

Intermediate 10

(3-chloro-4-fluorophenyl)(cis-2,6-dimethyl-1-(2,2,2-trifluoroethyl)piperidin-4-yl)methanamine

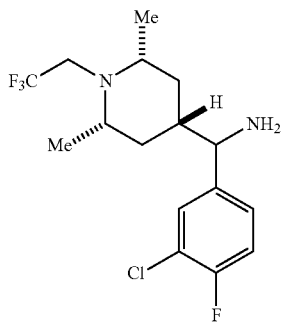 [SMILES: C[C@@H]1C[C@H](C(N)c2ccc(F)c(Cl)c2)C[C@H](C)N1CC(F)(F)F]

Step 1: methyl cis-2,6-dimethyl-1-(2,2,2-trifluoroethyl)piperidine-4-carboxylate. To a mixture of methyl cis-2,6-dimethylpiperidine-4-carboxylate (0.20 g, 1.2 mmol) and $K_2CO_3$ (0.32 g, 2.3 mmol) in MeCN (10 mL) was added 2,2,2-trifluoroethyl trifluoromethanesulfonate (0.41 g, 1.7 mmol). The resulting mixture was stirred at 100° C. for 12 h. Then water was added, and the mixture was extracted with EtOAc. The combined organic layers were washed with brine, dried over $Na_2SO_4$, filtered and concentrated in vacuo. The resulting crude product was purified by silica gel chromatography (0-10% EtOAc:PE) to give the title compound.

Step 2: cis-2,6-dimethyl-1-(2,2,2-trifluoroethyl)piperidine-4-carboxylic acid. To a mixture of methyl cis-2,6-dimethyl-1-(2,2,2-trifluoroethyl)piperidine-4-carboxylate (0.31 g, 1.2 mmol) in MeOH (2.5 mL) and THF (2.5 mL) was added aq. NaOH (0.61 mL, 3.7 mmol, 6 M) at 25° C. The reaction was stirred at 25° C. for 12 h, concentrated in vacuo, and taken up in water. The mixture was extracted with DCM. Then HCl (1 M) was added to the aqueous mixture until pH~3, and the mixture was extracted with EtOAc. The combined EtOAc layers were separated and concentrated in vacuo to give the title compound.

Step 3: cis-N-methoxy-N,2,6-trimethyl-1-(2,2,2-trifluoroethyl)piperidine-4-carboxamide. To a mixture of cis-2,6-dimethyl-1-(2,2,2-trifluoroethyl)piperidine-4-carboxylic acid (0.29 g, 1.2 mmol) in DCM (15 mL) was added di(1H-imidazol-1-yl)methanone (0.24 g, 1.5 mmol). The mixture was stirred at rt for 1 h, then N,O-dimethyl hydroxylamine hydrochloride (0.14 g, 1.4 mmol) and TEA (0.32 mL, 2.3 mmol) were added. The resulting mixture was stirred for 12 h, then concentrated in vacuo. The resulting residue was purified by silica gel chromatography (0-30% EtOAc:PE) to give the title compound.

Step 4: (3-chloro-4-fluorophenyl)(cis-2,6-dimethyl-1-(2,2,2-trifluoroethyl)piperidin-4-yl)methanone. To a mixture of cis-N-methoxy-N,2,6-trimethyl-1-(2,2,2-trifluoroethyl)piperidine-4-carboxamide (0.30 g, 1.0 mmol) in THF (5 mL) was added (3-chloro-4-fluorophenyl) magnesium bromide (0.71 g, 3.0 mmol) at 0° C. The mixture was stirred at 0° C. for 1.5 h, then quenched with sat. $NH_4Cl$ and extracted with EtOAc. The combined organic layers were washed with brine, dried over $Na_2SO_4$, filtered and concentrated in vacuo. The resulting residue was purified by silica gel chromatography (0-20% EtOAc:PE) to give the title compound.

Step 5: (3-chloro-4-fluorophenyl)(cis-2,6-dimethyl-1-(2,2,2-trifluoroethyl)piperidin-4-yl)methanamine. To a mixture of (3-chloro-4-fluorophenyl)(cis-2,6-dimethyl-1-(2,2,2-trifluoroethyl)piperidin-4-yl)methanone (0.28 g, 0.77 mmol), and $NH_4OAc$ (0.89 g, 12 mmol) in EtOH (8 mL) was added $NaCNBH_3$ (73 mg, 1.2 mmol) at 25° C. The mixture was stirred under microwave at 130° C. for 15 min. Then the mixture was concentrated in vacuo, and the resulting residue was purified by prep. silica gel TLC (10% DCM:MeOH) to give the title compound.

Intermediate 11

1-(3-chloro-4-fluorophenyl)-2-((4,4-difluorocyclohexyl)oxy)ethan-1-one

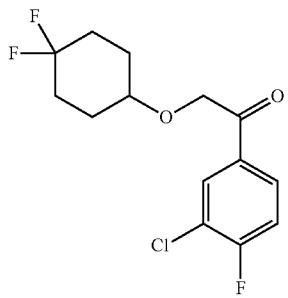

Step 1: 1-(3-chloro-4-fluorophenyl)-2-diazoethan-1-one. A mixture of 3-chloro-4-fluorobenzoic acid (1.0 g, 5.7 mmol) in SOCl$_2$ (10 mL) was stirred at 90° C. for 2 h. Then the solvent was evaporated under reduced pressure. The resulting crude residue was dissolved in THF (10 mL), and MeCN (10 mL), and cooled to 0° C. Then TMS-Diazomethane (5.7 mL, 11 mmol) was added, and the reaction mixture was warmed to rt and stirred for 1 h. Water was added and the mixture was extracted with EtOAc. The combined organic layers were washed with brine, dried over Na$_2$SO$_4$, filtered and concentrated in vacuo to give the title compound.

Step 2: 1-(3-chloro-4-fluorophenyl)-2-((4,4-difluorocyclohexyl)oxy)ethan-1-one. To a mixture of 1-(3-chloro-4-fluorophenyl)-2-diazoethan-1-one (0.10 g crude) and 4,4-difluorocyclohexanol (0.10 g, 0.76 mmol) in toluene (2 mL) was added indium(iii) trifluoromethanesulfonate (28 mg, 0.050 mmol). The resulting mixture was stirred at 20° C. for 18 h. The mixture was concentrated in vacuo and then purified by prep. silica gel TLC (1:5 EtOAc:PE) to give the title compound.

Intermediate 12

2-(tetrahydro-2H-pyran-3-yl)acetic acid

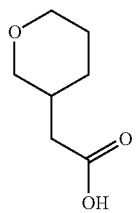

Step 1: 2-(tetrahydro-2H-pyran-3-yl)acetic acid. Methyl 2-(tetrahydro-2H-pyran-3-yl)acetate (0.60 g, 3.8 mmol) was dissolved in MeOH (10 mL), then LiOH·H$_2$O (0.32 g, 7.6 mmol) in water (2 mL) was added. The reaction was stirred at rt for 10 h, then acidified with 3 M HCl until pH=2, and extracted with EtOAc. The combined organic layers were dried over Na$_2$SO$_4$, filtered and concentrated in vacuo to give the title compound.

Intermediate 13

1-(2,2,2-trifluoroethyl)piperidine-2-carbaldehyde

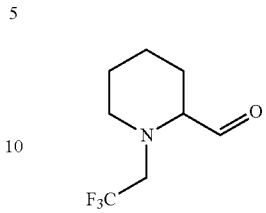

Step 1: tert-butyl 2-(methoxy(methyl)carbamoyl)piperidine-1-carboxylate. To a solution of CDI (1.4 g, 8.7 mmol) in DCM (10 mL) was added 1-(boc)piperidine-2-carboxylic acid (1.0 g, 4.4 mmol) at rt for 1 h. Then DIEA (2.3 mL, 13 mmol) and N,O-dimethyl hydroxylamine hydrochloride (0.64 g, 6.5 mmol) were added, and the resulting mixture was stirred at rt for 2 h. Then water was added, and mixture was extracted with DCM. The combined organic layers were washed with brine, dried over Na$_2$SO$_4$, filtered and concentrated in vacuo. The crude product was purified by silica gel chromatography (26% EtOAC:PE) to give the title compound.

Step 2: N-methoxy-N-methylpiperidine-2-carboxamide. To a mixture of tert-butyl 2-(methoxy-(methyl)carbamoyl)piperidine-1-carboxylate (0.40 g, 1.5 mmol) in DCM (2 mL) was added TFA (3.0 mL, 39 mmol). The resulting mixture was stirred at rt for 90 min, then concentrated in vacuo to give the title compound.

Step 3: N-methoxy-N-methyl-1-(2,2,2-trifluoroethyl)piperidine-2-carboxamide. To a mixture of N-methoxy-N-methylpiperidine-2-carboxamide (0.22 g crude) and K$_2$CO$_3$ (0.35 g, 2.6 mmol) in MeCN (6 mL) was added 2,2,2-trifluoroethyl trifluoromethanesulfonate (0.89 g, 3.8 mmol). The resulting mixture was stirred at rt for 4 h. Then water was added, and the mixture was extracted with EtOAc. The combined organic layers were washed with brine, dried over Na$_2$SO$_4$, filtered and concentrated in vacuo. The resulting crude product was purified by silica gel chromatography (15% EtOAc:PE) to give the title compound.

Step 4: 1-(2,2,2-trifluoroethyl)piperidine-2-carbaldehyde. To a mixture of N-methoxy-N-methyl-1-(2,2,2-trifluoroethyl)piperidine-2-carboxamide (1.2 g, 4.7 mmol) in THF (20 mL) was added LAH (0.27 g, 7.1 mmol) at 0° C. The resulting mixture was stirred at 0° C. for 1 h, then filtered and concentrated to dryness. The resulting residue was diluted with water and the mixture was extracted with EtOAc. The combined organic layers were washed with brine, dried over Na$_2$SO$_4$, filtered and concentrated in vacuo to give the title compound.

Intermediate 14

7,7-difluorobicyclo[4.2.0]octa-1(6),2,4-triene-3-carbaldehyde

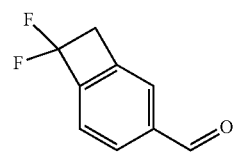

Step 1: 7,7-difluoro-3-iodobicyclo[4.2.0]octa-1(6),2,4-triene. The title compound was prepared according to a procedure similar to the synthesis of Example 30 starting from 4-iodo-2-methylbenzoic acid.

Step 2: 7,7-difluorobicyclo[4.2.0]octa-1(6),2,4-triene-3-carbaldehyde. To a stirred solution of 7,7-difluoro-3-iodobicyclo[4.2.0]octa-1(6),2,4-triene (1.0 g, 4.0 mmol) and THF (20 mL) at 0° C. was added iPrMgCl (3.0 mL, 6.0 mmol, 2.0 M in THF). The solution was stirred for 20 minutes at 0° C., then DMF (0.92 mL, 12 mmol) was added. The reaction was stirred for 30 minutes at 0° C., then quenched with aq. HCl (1 N) and then extracted with EtOAc. The organic layer was washed with sat. NaHCO$_3$, brine, dried over MgSO$_4$, filtered and concentrated in vacuo to give the title compound.

Intermediate 15

4-(amino(3-chloro-4-fluorophenyl)methyl)benzonitrile hydrochloride

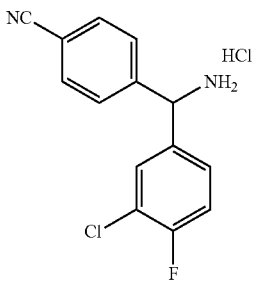 [SMILES: N#Cc1ccc(C(N)c2ccc(F)c(Cl)c2)cc1 ; Cl]

Step 1: (S)—N-(4-cyanobenzylidene)-2-methylpropane-2-sulfinamide. 4-formylbenzonitrile (1.3 g, 10 mmol) and (S)-2-methylpropane-2-sulfinamide (1.2 g, 10 mmol) were taken up in THF (50 mL) and then Ti(OiPr)$_4$ (5.9 mL, 20 mmol) was added. This mixture was stirred for 2 h, then diluted with brine, filtered through sand and extracted with EtOAc. The combined organic layers were washed with sat NH$_4$Cl, brine, dried over Na$_2$SO$_4$, filtered, and concentrated in vacuo to give the title compound.

Step 2: 4-(amino(3-chloro-4-fluorophenyl)methyl)benzonitrile hydrochloride. The title compound was prepared according to a procedure similar to the synthesis of Example 29 starting from (S)—N-(4-cyanobenzylidene)-2-methylpropane-2-sulfinamide.

Intermediate 16

N-methoxy-N,1-dimethyl-3-(trifluoromethyl)-1H-pyrazole-5-carboxamide

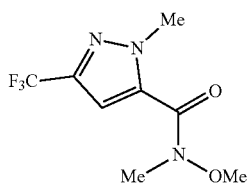 [SMILES: CON(C)C(=O)c1cc(C(F)(F)F)nn1C]

The title compound was prepared according to a procedure similar to the synthesis in Examples 66A and 66B starting from 1-methyl-3-(trifluoromethyl)-1H-pyrazole-5-carboxylic acid.

Intermediate 17

N-methoxy-N,1-dimethyl-5-(trifluoromethyl)-1H-pyrazole-3-carboxamide

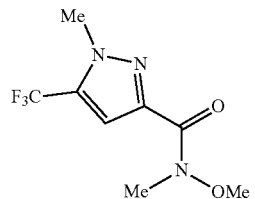 [SMILES: CON(C)C(=O)c1cc(C(F)(F)F)n(C)n1]

T$_3$P® (6.1 mL, 10 mmol) was added to a solution of 1-methyl-5-(trifluoromethyl)-1H-pyrazole-3-carboxylic acid (1.0 g, 5.2 mmol) and N,O-dimethylhydroxylamine HCl (0.50 g, 5.2 mmol) in EtOAc (26 mL). Then DIEA (2.7 mL, 15 mmol) was added, and the reaction was stirred for 12 h. Then the reaction mixture was diluted with sat. potassium phosphate monobasic and extracted with EtOAc. The combined organic layers were washed with brine, dried over Na$_2$SO$_4$, filtered, and concentrated in vacuo to give the title compound.

Intermediate 18

N-methoxy-N,4-dimethyl-2-(trifluoromethyl)thiazole-5-carboxamide

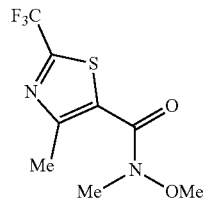 [SMILES: CON(C)C(=O)c1sc(C(F)(F)F)nc1C]

N-methoxy-N,4-dimethyl-2-(trifluoromethyl)thiazole-5-carboxamide was prepared according to a procedure similar to the synthesis of Intermediate 17 starting from 4-methyl-2-(trifluoromethyl)thiazole-5-carboxylic acid.

Intermediate 19

1-methyl-2-(trifluoromethyl)piperidine-4-carboxylic acid

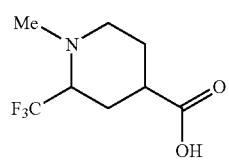

To a solution of 2-(trifluoromethyl)piperidine-4-carboxylic acid (0.25 g, 1.3 mmol) in EtOH (15 mL) was added acetic acid (0.36 mL, 6.3 mmol, glacial) and formaldehyde (0.38 g, 13 mmol) at rt. The reaction mixture was heated at 70° C. for 2 h. Then the mixture was cooled to rt and NaBH₃CN (0.24 g, 3.8 mmol) added. The reaction was stirred at rt for 15 h, and then quenched by the addition of water. The mixture was extracted with EtOAc. Organic layers were combined, dried over Na₂SO₄, filtered and concentrated in vacuo to give the title compound.

Intermediate 20

6-(difluoromethoxy)-5-fluoronicotinaldehyde

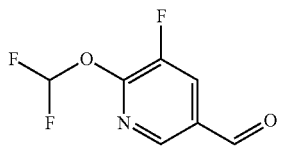

Step 1: 5-bromo-2-(difluoromethoxy)-3-fluoropyridine. To a solution of 5-bromo-3-fluoropyridin-2-ol (2.0 g, 10 mmol) in MeCN (20 mL) was added NaH (0.54 g, 14 mmol, 60% in mineral oil). The mixture was stirred at rt for 20 minutes, then CsF (0.16 g, 1.0 mmol) was added, followed by the dropwise addition of trimethylsilyl 2,2-difluoro-2-(fluorosulfonyl)acetate (2.3 mL, 11 mmol). The reaction was stirred at rt for 2 h, then quenched with H₂O and extracted with Et₂O. The organic layer was dried over Na₂SO₄, filtered and concentrated in vacuo. The resulting residue was purified by silica gel chromatography (0-20% EtOAc:hex) to give the title compound.

Step 2: 6-(difluoromethoxy)-5-fluoronicotinaldehyde. The title compound was prepared according to a procedure similar to the synthesis of Intermediate 6 starting from 5-bromo-2-(difluoromethoxy)-3-fluoropyridine.

Intermediate 21

(R)—N-((6-(difluoromethyl)pyridin-3-yl)methylene)-2-methylpropane-2-sulfinamide

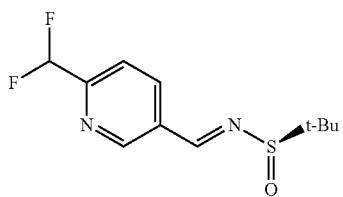 [SMILES: CC(C)(C)[S@@](=O)/N=C/c1ccc(C(F)F)nc1]

A microwave tube was charged with 6-(difluoromethyl) nicotinaldehyde (1.0 g, 6.4 mmol), (R)-2-methylpropane-2-sulfinamide (0.93 g, 7.6 mmol) and Ti(OEt)₄ (4.0 mL, 19 mmol). The mixture was heated via microwave irradiation at 90° C. for 25 min. Then water was added, and the mixture stirred for 30 min, followed by filtering through a pad of the Celite®. The filtrate was extracted with EtOAc. The organic layer was dried over Na₂SO₄, filtered and concentrated in vacuo. The resulting residue was purified by silica gel chromatography (0-50% EtOAc:hex) to give the title compound.

Intermediate 22

(R)—N-((5-fluoro-6-(trifluoromethyl)pyridin-3-yl)methylene)-2-methylpropane-2-sulfinamide

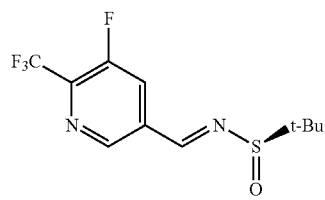 [SMILES: CC(C)(C)[S@@](=O)/N=C/c1cnc(C(F)(F)F)c(F)c1]

The title compound was prepared according to a procedure similar to the synthesis of Intermediate 21 starting from 5-fluoro-6-(trifluoromethyl)nicotinaldehyde.

Intermediate 23

(R)-2-methyl-N-((2-(trifluoromethyl)pyrimidin-5-yl)methylene)propane-2-sulfinamide

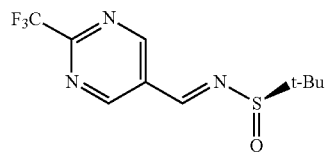 [SMILES: CC(C)(C)[S@@](=O)/N=C/c1cnc(C(F)(F)F)nc1]

The title compound was prepared according to a procedure similar to the synthesis of Intermediate 21 starting from 2-(trifluoromethyl)pyrimidine-5-carbaldehyde.

Intermediate 24

3-fluoro-5-iodo-2-(2,2,2-trifluoroethoxy)pyridine

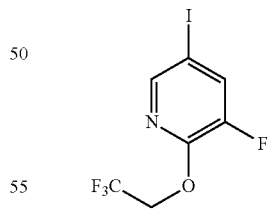

To a solution of 2,3-difluoro-5-iodopyridine (3.1 g, 13 mmol) and 2,2,2-trifluoroethan-1-ol (1.1 mL, 14 mmol) in THF (20 mL) at 0° C. was added NaH (0.62 g, 16 mmol, 60% in mineral oil). The mixture was stirred at 0° C. for 30 min, then warmed to rt and stirred for 3 h. Then the mixture was partitioned between EtOAc and brine. The separated organic layer was dried over Na₂SO₄, filtered and concentrated in vacuo. The resulting residue was purified by silica gel chromatography (0-20% EtOAc:hex) to give the title compound.

Intermediate 25

5-chloro-6-cyclopropylpicolinic acid

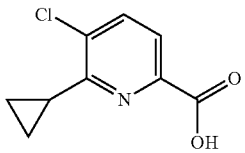 [SMILES: O=C(O)c1ccc(Cl)c(C2CC2)n1]

Step 1: methyl 5-chloro-6-cyclopropylpicolinate. To a solution of methyl 6-bromo-5-chloropyridine-2-carboxylate (0.60 g, 2.4 mmol) in 1,4-dioxane (8 mL) were added cyclopropylboronic acid (0.23 g, 2.6 mmol), $Cs_2CO_3$ (1.6 g, 4.8 mmol) and water (0.2 mL). The mixture was purged with $N_2$ for 5 min. Then $Pd(dppf)Cl_2$ (0.16 g, 0.24 mmol) was added, and the mixture was heated to 80° C. and stirred for 5 h. The reaction was quenched with water and extracted with EtOAc. The organic layer was dried over $Na_2SO_4$, filtered and concentrated in vacuo. The resulting residue was purified by silica gel chromatography (0-10% EtOAc:hex) to give the title compound.

Step 2: 5-chloro-6-cyclopropylpicolinic acid. To a solution of methyl 5-chloro-6-cyclopropylpicolinate (0.30 g, 1.4 mmol) in THF (3 mL) was added water (0.5 mL) and NaOH (0.12 g, 2.9 mmol). The mixture was stirred at rt for 2 h, then heated to 40° C. and stirred for 30 min. The mixture was then cooled to rt, and 1 M HCl in $H_2O$ (2.9 mL, 2.9 mmol) was added. Then the reaction mixture was extracted with $Et_2O$, dried over $Na_2SO_4$, filtered and concentrated in vacuo to give the title compound.

Intermediate 26

2-(difluoromethoxy)pyrimidine-5-carbaldehyde

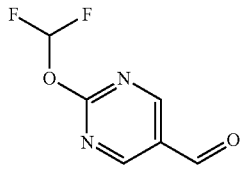

Step 1: 5-bromo-2-(difluoromethoxy)pyrimidine. To a solution of 5-bromopyrimidin-2-ol (2.0 g, 11 mmol) in MeCN (50 mL) were added $K_2CO_3$ (6.4 g, 46 mmol) and ethyl 2-bromo-2,2-difluoroacetate (4.6 g, 23 mmol). The reaction mixture was stirred at 80° C. for 13 h, then diluted with water and extracted with EtOAc. The combined organic layers were washed with brine, dried over $Na_2SO_4$, filtered and concentrated in vacuo. The resulting residue was purified by silica gel chromatography (0-10% EtOAc:PE) to give the title compound.

Step 2: 2-(difluoromethoxy)pyrimidine-5-carbaldehyde. Title compound was prepared in a similar manner to that of Intermediate 6 starting from 5-bromo-2-(difluoromethoxy)pyrimidine.

EXAMPLES

Examples 1A and 1B (S)—N—((R)-2-(3-chloro-4-fluorophenoxy)-1-(3-chloro-4-fluorophenyl)ethyl)-2-oxoimidazolidine-4-carboxamide and (S)—N—((S)-2-(3-chloro-4-fluorophenoxy)-1-(3-chloro-4-fluorophenyl)ethyl)-2-oxoimidazolidine-4-carboxamide

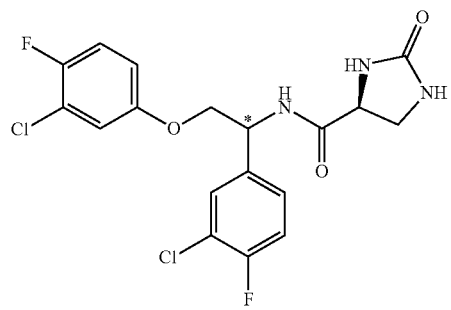 [SMILES: O=C1NC[C@@H](C(=O)NC(COc2ccc(F)c(Cl)c2)c2ccc(F)c(Cl)c2)N1]

Step 1: 2-bromo-1-(3-chloro-4-fluorophenyl)ethan-1-one. A mixture of 3-chloro-4-fluorobenzoic acid (5.0 g, 29 mmol) in $SOCl_2$ (30 mL) was stirred at 90° C. for 2 h. Then the solvent was evaporated in vacuo. The resulting residue was dissolved in DCM (50 mL) and cooled to 0° C. prior to the addition of TMS-Diazomethane (43 mL, 86 mmol). The reaction mixture was warmed to rt, stirred 3 h at rt, and then cooled to 0° C. Then HBr (20 mL, 120 mmol) was added, carefully accompanied by gas evolution ($N_2$). After stirring for 30 minutes, the excess acid was neutralized by the addition of solid $Na_2CO_3$. Then aqueous $NaHCO_3$ was added, and the mixture was extracted with DCM. The combined organic layers were washed with brine, dried over $Na_2SO_4$, filtered, and the solvent was evaporated in vacuo. The resulting crude product was purified by silica gel chromatography (0-100% EtOAc:PE) to give the title compound.

Step 2. 2-(3-chloro-4-fluorophenoxy)-1-(3-chloro-4-fluorophenyl)ethan-1-one. To a mixture of 2-bromo-1-(3-chloro-4-fluorophenyl)ethan-1-one (0.21 g, 0.82 mmol) and 3-chloro-4-fluorophenol (0.10 g, 0.68 mmol) in MeCN (3 mL) was added $K_2CO_3$ (19 g, 1.4 mmol). The resulting mixture was stirred at 15° C. for 8 h. Then the reaction mixture was diluted with water and extracted with EtOAc. The combined organic layers were washed with brine, dried over $Na_2SO_4$, filtered, and the solvent was concentrated in vacuo. The resulting residue was purified by prep. silica gel TLC (10% EtOAc:PE) to give the title compound.

Step 3: 2-(3-chloro-4-fluorophenoxy)-1-(3-chloro-4-fluorophenyl)ethan-1-amine. $NH_4OAc$ (0.44 g, 5.7 mmol) and $NaBH_3CN$ (0.036 g, 0.57 mmol) were added to a solution of 2-(3-chloro-4-fluorophenoxy)-1-(3-chloro-4-fluorophenyl)ethan-1-one (0.12 g, 0.38 mmol) in EtOH (3 mL) in a 40 mL microwave vial. The mixture was stirred at 130° C. for 10 min in a microwave reactor. Then the reaction mixture was concentrated to remove most of the EtOH, treated with 2 N NaOH until pH >10, and extracted with EtOAc. The organic layer was separated, dried over $Na_2SO_4$, filtered, and concentrated in vacuo to give the title compound.

Step 4: (S)—N—((R and S)-2-(3-chloro-4-fluorophenoxy)-1-(3-chloro-4-fluorophenyl)ethyl)-2-oxoimidazolidine-4-carboxamide. To a mixture of 2-(3-chloro-4-fluorophenoxy)-1-(3-chloro-4-fluorophenyl)ethan-1-amine. (0.12 g crude), (S)-2-oxoimidazolidine-4-carboxylic acid (59 mg, 0.45 mmol) and DIEA (0.20 mL, 1.1 mmol) in DMF (4 mL) was added T₃P® (0.48 g, 0.75 mmol) at 0° C. The resulting mixture was stirred at 15° C. for 1 h. The resulting residue was purified by reverse phase HPLC (40:60 to 30:70; water (0.1% TFA):MeCN (0.1% TFA)), followed by lyophilization to give the title compound.

Step 5: (S)—N—((R or S)-2-(3-chloro-4-fluorophenoxy)-1-(3-chloro-4-fluorophenyl)ethyl)-2-oxoimidazolidine-4-carboxamide. (S)—N—((R and S)-2-(3-chloro-4-fluorophenoxy)-1-(3-chloro-4-fluorophenyl)ethyl)-2-oxoimidazolidine-4-carboxamide was separated by chiral-SFC (method A) to give the title compounds: first eluted diastereomer 1A (S)—N—((R or S)-2-(3-chloro-4-fluorophenoxy)-1-(3-chloro-4-fluorophenyl)ethyl)-2-oxoimidazolidine-4-carboxamide, and second eluted diastereomer 1B (S)—N—((R or S)-2-(3-chloro-4-fluorophenoxy)-1-(3-chloro-4-fluorophenyl)ethyl)-2-oxoimidazolidine-4-carboxamide. Diastereomer 1A: LRMS m/z (M+H): calculated 430.1, observed 430.0. $^1$H NMR (500 MHz, CD₃OD) δ 7.61 (dd, J=2.0, 7.0 Hz, 1H), 7.39-7.46 (m, 1H), 7.26 (t, J=9.0 Hz, 1H), 7.16 (t, J=9.0 Hz, 1H), 7.09 (dd, J=3.0, 6.0 Hz, 1H), 6.91 (td, J=3.5, 9.0 Hz, 1H), 5.36 (t, J=6.0 Hz, 1H), 4.37 (dd, J=6.5, 10.0 Hz, 1H), 4.27 (d, J=6.0 Hz, 2H), 3.83 (t, J=9.5 Hz, 1H), 3.45 (dd, J=6.5, 9.0 Hz, 1H). Diastereomer 1B: LRMS m/z (M+H): calculated 430.1, observed 430.0. $^1$H NMR (500 MHz, CD₃OD) δ 7.46 (d, J=7.0 Hz, 1H), 7.27-7.31 (m, 1H), 7.14 (t, J=9.0 Hz, 1H), 7.04 (t, J=9.0 Hz, 1H), 6.97 (dd, J=3.0, 6.0 Hz, 1H), 6.77-7.81 (m, 1H), 5.21 (t, J=6.0 Hz, 1H), 4.25 (dd, J=6.0, 10.0 Hz, 1H), 4.13 (d, J=6.0 Hz, 2H), 3.68 (t, J=9.5 Hz, 1H), 3.32 (dd, J=6.0, 9.0 Hz, 1H).

Examples 2A and 2B (R)—N-(bis(4-chlorophenyl)methyl)-3-methyl-2-oxoimidazolidine-4-carboxamide and (S)—N-(bis(4-chlorophenyl)methyl)-3-methyl-2-oxoimidazolidine-4-carboxamide

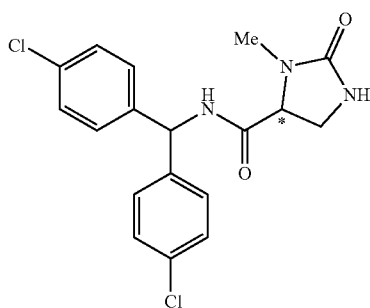 [SMILES: CN1C(=O)NCC1C(=O)NC(c1ccc(Cl)cc1)c1ccc(Cl)cc1]

Step 1: (R and S)—N-(bis(4-chlorophenyl)methyl)-3-methyl-2-oxoimidazolidine-4-carboxamide. To a solution of 3-methyl-2-oxoimidazolidine-4-carboxylic acid (0.15 g, 1.0 mmol), bis (4-chlorophenyl)methanamine (0.30 g, 1.2 mmol) and DIEA (0.57 mL, 3.2 mmol) in DMF (4 mL) was added T₃P® (1.3 g, 2.1 mmol, 50% in DMF) at 0° C. The mixture was stirred at rt for 12 h, then water was added, and the mixture was extracted with EtOAc. The combined organic layers were washed with saturated brine, dried over by Na₂SO₄, filtered and concentrated. The resulting residue was purified by reverse phase HPLC (5:95 to 95:5; water (0.1% TFA):MeCN (0.1% TFA)), followed by lyophilization to give the title compound.

Step 2: (R or S)—N-(bis(4-chlorophenyl)methyl)-3-methyl-2-oxoimidazolidine-4-carboxamide. (R and S)—N-(bis(4-chlorophenyl)methyl)-3-methyl-2-oxoimidazolidine-4-carboxamide was resolved by chiral-SFC (method B) to give the title compounds: first eluted enantiomer 2A (R or S)—N-(bis(4-chlorophenyl)methyl)-3-methyl-2-oxoimidazolidine-4-carboxamide, and second eluted enantiomer 2B (R or S)—N-(bis(4-chlorophenyl)methyl)-3-methyl-2-oxoimidazolidine-4-carboxamide. Enantiomer 2A: LRMS m/z (M+H): calculated 378.1, observed 378.1. $^1$H NMR (500 MHz, CD₃CN) δ 7.47-7.53 (m, 1H), 7.34-7.40 (m, 4H), 7.23-7.28 (m, 4H), 6.13-6.19 (m, 1H), 4.83 (s, 1H), 4.04-4.10 (m, 1H), 3.54-3.59 (m, 1H), 3.14-3.22 (m, 1H), 2.62-2.66 (m, 3H). Enantiomer 2B: LRMS m/z (M+H): calculated 378.1, observed 378.1. $^1$H NMR (500 MHz, CD₃CN) δ 7.47-7.53 (m, 1H), 7.34-7.40, (m, 4H) 7.23-7.27 (m, 4H), 6.13-6.19 (m, 1H), 4.83 (s, 1H), 4.03-4.10 (m, 1H), 3.57 (t, J=9.5 Hz, 1H), 3.16-3.20 (m, 1H), 2.61-2.65 (m, 3H).

Examples 3A and 3B (S)—N—((R)-(5-chloro-6-(difluoromethyl)pyridin-2-yl)(5-chloro-6-(trifluoromethyl)pyridin-3-yl)methyl)-2-oxoimidazolidine-4-carboxamide and
(S)—N—((S)-(5-chloro-6-(difluoromethyl)pyridin-2-yl)(5-chloro-6-(trifluoromethyl)pyridin-3-yl)methyl)-2-oxoimidazolidine-4-carboxamide

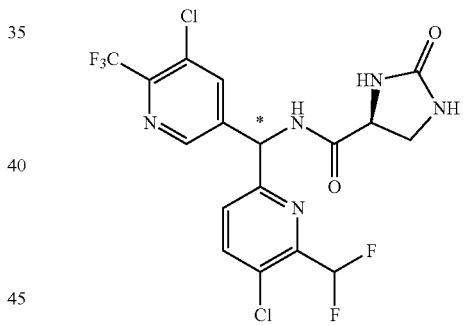

Step 1: 3,6-dichloro-2-(difluoromethyl)pyridine. To a mixture of 3,6-dichloropicolinaldehyde (1.5 g, 8.5 mmol) in CHCl₃ (35 mL) was slowly added DAST (3.4 mL, 26 mmol) at 0° C. The mixture was degassed and backfilled with N₂ (×3). The mixture was stirred at rt for 12 h, then quenched with NaHCO₃ and water. The resulting mixture was extracted with EtOAc. The combined organic layers were washed with brine, dried over Na₂SO₄, filtered and concentrated in vacuo to give the title compound.

Step 2: 3-chloro-2-(difluoromethyl)-6-vinylpyridine. To a mixture of 3,6-dichloro-2-(difluoromethyl)pyridine (2.0 g crude) and K₂CO₃ (1.7 g, 12 mmol) in dioxane (21 mL) and water (4.2 mL) was added Pd(dppf)Cl₂ (0.44 g, 0.61 mmol). The mixture was stirred at 100° C. for 2 h, then filtered and concentrated to give the title compound.

Step 3: 5-chloro-6-(difluoromethyl)picolinaldehyde. A solution of 3-chloro-2-(difluoromethyl)-6-vinylpyridine (1.5 g crude), NMO (1.9 g, 16 mmol) and OsO₄ (0.025 mL, 0.079 mmol) in THF (25 mL) and water (5 mL) was stirred at rt for 2 h. Then NaIO₄ (8.5 g, 40 mmol) was added, and the mixture was stirred at rt for 2 h. The mixture was then diluted with water and extracted with EtOAc. The combined organic layers were washed with brine, dried over Na₂SO₄, filtered and the solvent was concentrated in vacuo to give the title compound.

Step 4: (R)—N-((5-chloro-6-(difluoromethyl)pyridin-2-yl)methylene)-2-methylpropane-2-sulfinamide. To a mixture of 5-chloro-6-(difluoromethyl)picolinaldehyde (1.1 g crude) and (R)-2-methylpropane-2-sulfinamide (1.0 g, 8.6 mmol) in THF (25 mL) was added Ti(OEt)₄ (2.8 mL, 14 mmol) at 0° C. The resulting mixture was stirred at rt for 18 h, then diluted with EtOAc, and washed with brine. The mixture was filtered, and the filtrate was concentrated to dryness. The resulting crude product was purified by silica gel chromatography (23% EtOAc:PE) to give the title compound.

Step 5: (R)—N-((5-chloro-6-(difluoromethyl)pyridin-2-yl)(5-chloro-6-(trifluoromethyl)pyridin-3-yl)methyl)-2-methylpropane-2-sulfinamide. To a solution of 3-chloro-5-iodo-2-(trifluoro-methyl)pyridine (1.4 g, 4.5 mmol) in toluene (3 mL) was added iPrMgCl—LiCl (3.1 mL, 4.1 mmol, 1.3 M in THF) at 0° C. The reaction was stirred for 2 h, then a mixture of (R)—N-((5-chloro-6-(difluoromethyl)pyridin-2-yl)methylene)-2-methylpropane-2-sulfinamide (0.60 g, 2.0 mmol) in toluene (3 mL) was added at −40° C. The reaction mixture was stirred at −40° C. for 2 h, then concentrated. The concentrate was purified by silica gel chromatography (25% EtOAc:PE) to give the title compound.

Step 6: (5-chloro-6-(difluoromethyl)pyridin-2-yl)(5-chloro-6-(trifluoromethyl)pyridin-3-yl)methanamine hydrochloride. (R)—N-((5-chloro-6-(difluoromethyl)pyridin-2-yl)(5-chloro-6-(trifluoromethyl)pyridin-3-yl)methyl)-2-methylpropane-2-sulfinamide (1.0 g, 2.1 mmol) was taken up in HCl (5 mL, 20 mmol, 4 N in MeOH) and stirred at rt for 1 h. Then the mixture was concentrated in vacuo to give the title compound Step 7: (S)—N—((R and S)-(5-chloro-6-(difluoromethyl)pyridin-2-yl)(5-chloro-6-(trifluoromethyl)-pyridin-3-yl)methyl)-2-oxoimidazolidine-4-carboxamide. To a mixture of (5-chloro-6-(difluoro-methyl)pyridin-2-yl)(5-chloro-6-(trifluoromethyl)pyridin-3-yl)methanamine hydrochloride (0.10 g crude), (S)-2-oxoimidazolidine-4-carboxylic acid (0.038 g, 0.29 mmol) and DIEA (0.13 mL, 0.73 mmol) in DMF (2 mL) was added T₃P® (0.31 g, 0.49 mmol, 50% in EtOAc) at 0° C. The resulting mixture was stirred at rt for 1 h. The residue was purified by reverse phase HPLC (35:65 to 65:35; water (0.1% TFA):MeCN (0.1% TFA)), followed by lyophilization to give the title compound.

Step 8: (S)—N—((R or S)-(5-chloro-6-(difluoromethyl)pyridin-2-yl)(5-chloro-6-(trifluoromethyl)-pyridin-3-yl)methyl)-2-oxoimidazolidine-4-carboxamide. (S)—N—((R and S)-(5-chloro-6-(di-fluoromethyl)pyridin-2-yl)(5-chloro-6-(trifluoromethyl)pyridin-3-yl)methyl)-2-oxoimidazolidine-4-carboxamide was separated by chiral-SFC (method C) to give the title compounds: first eluted diastereomer 3A, (S)—N—((R or S)-(5-chloro-6-(difluoromethyl)pyridin-2-yl)(5-chloro-6-(trifluoromethyl)pyridin-3-yl)methyl)-2-oxoimidazolidine-4-carboxamide, and second eluted diastereomer 3B (S)—N—((R or S)-(5-chloro-6-(difluoromethyl)pyridin-2-yl)(5-chloro-6-(trifluoromethyl)pyridin-3-yl)methyl)-2-oxoimidazolidine-4-carboxamide. Diastereomer 3A: LRMS m/z (M+H): calculated 484.0, observed 484.0. ¹H NMR (400 MHz, CD₃OD) δ 9.10-9.14 (m, 1H), 8.66 (d, J=1.6 Hz, 1H), 8.14 (s, 1H), 8.03 (d, J=8.4 Hz, 1H), 7.66 (d, J=8.4 Hz, 1H), 6.81-7.14 (m, 1H), 6.42-6.48 (m, 1H), 4.40 (m, 1H), 3.80 (t, J=9.6 Hz, 1H), 3.47 (m, 1H). Diastereomer 3B: LRMS m/z (M+H): calculated 484.0, observed 483.9. ¹H NMR (400 MHz, CD₃OD) δ 8.65 (d, J=1.6 Hz, 1H), 8.13 (s, 1H), 8.03 (d, J=8.4 Hz, 1H), 7.66 (d, J=8.4 Hz, 1H), 6.82-7.15 (m, 1H), 6.44 (s, 1H), 4.38-4.42 (m, 1H), 3.79 (t, J=9.6 Hz, 1H), 3.43-3.47 (m, 1H).

Examples 4A and 4B (S)—N—((R)-(3-chloro-4-fluorophenyl)(5-(trifluoromethyl)-1H-pyrazol-3-yl)methyl)-2-oxoimidazolidine-4-carboxamide and (S)—N—((S)-(3-chloro-4-fluorophenyl)(5-(trifluoromethyl)-1H-pyrazol-3-yl)methyl)-2-oxoimidazolidine-4-carboxamide

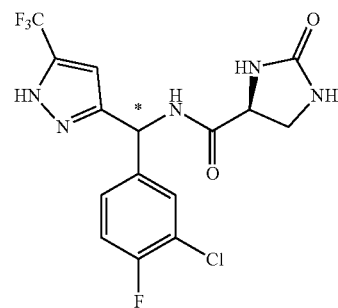 [SMILES: O=C1NC[C@@H](C(=O)NC(c2ccc(F)c(Cl)c2)c2cc(C(F)(F)F)[nH]n2)N1]

Step 1: N-methoxy-N-methyl-5-(trifluoromethyl)-1H-pyrazole-3-carboxamide. To a solution of 5-(trifluoromethyl)-1H-pyrazole-3-carboxylic acid (1.5 g, 8.3 mmol) in DMF (30 mL) was added DIEA (4.4 mL, 25 mmol) and HATU (6.3 g, 17 mmol) at 0° C. The mixture was stirred for 0.5 h, then N,O-dimethylhydroxylamine hydrochloride (1.2 g, 12 mmol) was added, and the resulting mixture was stirred at rt for another 2 h. Water was added, and the mixture was extracted with EtOAc. The combined organic layers were washed with brine, dried over Na₂SO₄, filtered and the solvent was evaporated in vacuo. The resulting crude product was purified by silica gel chromatography (10-100% EtOAc:PE) to give the title compound.

Step 2: (3-chloro-4-fluorophenyl)(5-(trifluoromethyl)-1H-pyrazol-3-yl)methanone. To a mixture of N-methoxy-N-methyl-5-(trifluoromethyl)-1H-pyrazole-3-carboxamide (0.60 g, 2.7 mmol) in THF (3 mL) was added (3-chloro-4-fluorophenyl)magnesium bromide (13 mL, 13 mmol, in THF 1 M). The mixture was stirred at 0° C. for 2 h. Then aqueous NH₄Cl was added and the mixture was extracted with EtOAc. The combined organic layers were washed with brine, dried over Na₂SO₄, filtered and the solvent was evaporated in vacuo to give the title compound.

Step 3: (R)—N-((3-chloro-4-fluorophenyl)(5-(trifluoromethyl)-1H-pyrazol-3-yl)methyl)-2-methylpropane-2-sulfinamide. To a microwave tube charged with (3-chloro-4-fluorophenyl)(5-(trifluoromethyl)-1H-pyrazol-3-yl)methanone (0.40 g, 1.4 mmol), (R)-2-methylpropane-2-sulfinamide (0.25 g, 2.0 mmol) in toluene (3 mL) was added Ti(OEt)₄ (0.56 mL, 2.7 mmol). The mixture was microwaved at 105° C. for 30 min and then cooled to rt. The mixture was dissolved in THF (5 mL) and water (0.01 mL) and cooled to −78° C., followed by the addition of NaBH₄ (57 mg, 1.5 mmol). The mixture was stirred at −78° C. for 1 h, then gradually warmed to 0° C. over 1 h, and stirred at 0° C. for 1 h. The mixture was then warmed to rt, aq. NaHCO₃ was added and the mixture was extracted with EtOAc. The combined organic layers were washed with brine, dried over Na$_2$SO$_4$, filtered and the solvent was evaporated in vacuo. The resulting residue was purified by prep. silica gel TLC (50% EtOAc:PE) to give the title compound.

Step 4: (3-chloro-4-fluorophenyl)(5-(trifluoromethyl)-1H-pyrazol-3-yl)methanamine hydrochloride. To a mixture of (R)—N-((3-chloro-4-fluorophenyl)(5-(trifluoromethyl)-1H-pyrazol-3-yl)methyl)-2-methylpropane-2-sulfinamide (0.30 g, 0.75 mmol) in MeOH (1 mL) was added HCl (3.0 mL, 12 mmol, 4 M in MeOH). The resulting mixture was stirred at rt for 1 h, and then concentrated in vacuo to give the title compound.

Step 5: (S)—N—((R and S)-(3-chloro-4-fluorophenyl)(5-(trifluoromethyl)-1H-pyrazol-3-yl)methyl)-2-oxoimidazolidine-4-carboxamide. To a mixture of (3-chloro-4-fluorophenyl)(5-(trifluoromethyl)-1H-pyrazol-3-yl)methanamine hydrochloride (0.15 g crude), (S)-2-oxoimidazolidine-4-carboxylic acid (89 mg, 0.68 mmol) and DIEA (0.24 mL, 1.4 mmol) in DMF (3 mL) was added T$_3$P® (0.58 g, 0.91 mmol, 50% in EtOAc) at 0° C. The resulting mixture was stirred at rt for 1 h. The residue was purified by reverse phase HPLC (35:65 to 55:45; water (0.1% TFA):MeCN (0.1% TFA)), followed by lyophilization to give the title compound.

Step 6: (S)—N—((R or S)-(3-chloro-4-fluorophenyl)(5-(trifluoromethyl)-1H-pyrazol-3-yl)methyl)-2-oxoimidazolidine-4-carboxamide. (S)—N—((R and S)-(3-chloro-4-fluorophenyl)(5-(trifluoro-methyl)-1H-pyrazol-3-yl)methyl)-2-oxoimidazolidine-4-carboxamide was separated by chiral-SFC (method A) to give the title compounds: first eluted diastereomer 4A (S)—N—((R or S)-(3-chloro-4-fluorophenyl)(5-(trifluoromethyl)-1H-pyrazol-3-yl)methyl)-2-oxoimidazolidine-4-carboxamide, and second eluted diastereomer 4B (S)—N—((R or S)-(3-chloro-4-fluorophenyl)(5-(trifluoromethyl)-1H-pyrazol-3-yl)methyl)-2-oxoimidazolidine-4-carboxamide. Diastereomer 4A: LRMS m/z (M+H): calculated 406.1, observed 406.0. $^1$H NMR (400 MHz, CD$_3$OD) δ 7.49 (dd, J=2.0, 6.8 Hz, 1H), 7.21-7.37 (m, 2H), 6.44-6.46 (m, 1H), 6.35 (s, 1H), 4.36 (dd, J=6.0, 10.0 Hz, 1H), 3.78 (t, J=9.6 Hz, 1H), 3.45 (dd, J=6.4, 9.2 Hz, 1H). Diastereomer 4B: LRMS m/z (M+H): calculated 406.1, observed 406.0. $^1$H NMR (400 MHz, CD$_3$OD) δ 7.42-7.51 (m, 1H), 7.22-7.34 (m, 2H), 6.45 (s, 1H), 6.37 (s, 1H), 4.37 (dd, J=6.0, 10.0 Hz, 1H), 3.79 (t, J=9.6 Hz, 1H), 3.47 (m, 1H).

Examples 5A and 5B (S)—N—((R)-(3-chloro-2,4-difluorophenyl)(1-(1-(trifluoromethyl)cyclopropyl)piperidin-4-yl)methyl)-2-oxoimidazolidine-4-carboxamide and (S)—N—((S)-(3-chloro-2,4-difluorophenyl)(1-(1-(trifluoromethyl)cyclopropyl)piperidin-4-yl)methyl)-2-oxoimidazolidine-4-carboxamide

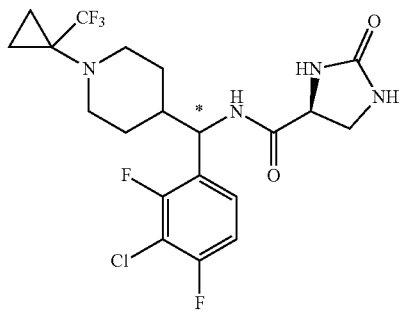 [SMILES: O=C1NC[C@@H](C(=O)NC(c2ccc(F)c(Cl)c2F)C2CCN(C3(C(F)(F)F)CC3)CC2)N1]

Step 1: benzyl cyclopent-3-ene-1-carboxylate. To a stirred solution of cyclopent-3-ene-1-carboxylic acid (1.0 g, 8.9 mmol) and K$_2$CO$_3$ (2.5 g, 18 mmol) in DMF (10 mL) was added (bromomethyl)benzene (1.6 g, 9.4 mmol). The reaction was stirred at rt for 3 h, then diluted with EtOAc and washed with water, and brine. The organic layer was separated, dried over Na$_2$SO$_4$, filtered and concentrated in vacuo to give the title compound.

Step 2: benzyl 3,4-dihydroxycyclopentane-1-carboxylate. To a stirred solution of benzyl cyclopent-3-ene-1-carboxylate (1.8 g, 8.9 mmol) and NMO (1.3 g, 11 mmol) in THF (24 mL) and water (6 mL) was added OsO$_4$ (0.28 mL, 0.89 mmol). The reaction was stirred at rt for 12 h, then quenched with sat. Na$_2$SO$_3$ and extracted with DCM. The combined organic layers were dried over Na$_2$SO$_4$, filtered and concentrated in vacuo to give a residue, which was purified by silica gel chromatography (50% EtOAc:PE) to give the title compound.

Step 3: benzyl 4-oxo-2-(2-oxoethyl)butanoate. To a stirred solution of benzyl 3,4-dihydroxy-cyclopentane-1-carboxylate (0.28 g, 1.2 mmol) in THF (6 mL) and water (2 mL) was added NaIO$_4$ (0.38 g, 1.8 mmol). The reaction was stirred at rt for 3 h, then diluted with water and extracted with DCM. The combined organic layers were dried over Na$_2$SO$_4$, filtered and concentrated in vacuo to give the title compound.

Step 4: benzyl 1-(1-(trifluoromethyl)cyclopropyl)piperidine-4-carboxylate. To a stirred solution of benzyl 4-oxo-2-(2-oxoethyl)butanoate (0.30 g, 1.3 mmol) and 1-(trifluoromethyl)cyclo-propanamine hydrochloride (0.21 g, 1.3 mmol) in EtOH (15 mL) was added NaHCO$_3$ (0.22 g, 2.6 mmol). The reaction was stirred at rt for 15 min, then NaCNBH$_3$ (80 mg, 1.3 mmol) was added to the mixture at rt. Then the reaction was stirred at 50° C. for 48 h, quenched with water and extracted with DCM. The combined organic layers were washed with brine, dried over Na$_2$SO$_4$, filtered and concentrated in vacuo to give a residue, which was purified by prep. silica gel TLC (15% EtOAc:PE) to give the title compound.

Step 5: 1-(1-(trifluoromethyl)cyclopropyl)piperidine-4-carboxylic acid. To a stirred solution of benzyl 1-(1-(trifluoromethyl)cyclopropyl)piperidine-4-carboxylate (0.21 g, 0.64 mmol) in MeOH (3 mL) and water (1.5 mL) was added NaOH (0.13 g, 3.2 mmol) at rt. The reaction was stirred at rt for 2 h. The pH of the reaction mixture was adjusted to pH 3 with 1 M HCl, then the solvent was removed through freeze-drying to give the title compound.

Step 6: N-methoxy-N-methyl-1-(1-(trifluoromethyl)cyclopropyl)piperidine-4-carboxamide. To a stirred solution of 1-(1-(trifluoromethyl)cyclopropyl)piperidine-4-carboxylic acid (0.15 g, crude), N,O-dimethylhydroxylamine hydrochloride (0.12 g, 1.3 mmol) and DIPEA (0.44 mL, 2.5 mmol) in DMF (3.0 mL) was added HATU (0.36 g, 0.95 mmol) at rt. The reaction was stirred at rt for 12 h, then diluted with EtOAc, washed with water and brine, dried over Na$_2$SO$_4$, filtered and concentrated in vacuo to give the title compound.

Step 7: (3-chloro-2,4-difluorophenyl)(1-(1-(trifluoromethyl)cyclopropyl)piperidin-4-yl)-methanone. To a stirred solution of N-methoxy-N-methyl-1-(1-(trifluoromethyl)cyclopropyl)-piperidine-4-carboxamide (0.14 g crude) in THF (6.0 mL) was added (3-chloro-2,4-difluorophenyl)magnesium bromide (1.0 mL, 1.0 mmol) at 0° C. The reaction was stirred at 0° C. for 1 h, and stirred at rt for 2 h. Then the reaction mixture was quenched with saturated NH$_4$Cl, diluted with EtOAc, and washed with brine. The organic layer was separated, dried over Na$_2$SO$_4$, filtered and concentrated in vacuo to give a residue, which was purified by preparative silica gel TLC (15% EtOAc:PE) to give the title compound.

Step 8: (R)—N-((3-chloro-2,4-difluorophenyl)(1-(1-(trifluoromethyl)cyclopropyl)piperidin-4-yl)methylene)-2-methylpropane-2-sulfinamide. To a stirred solution of (3-chloro-2,4-difluorophenyl)(1-(1-(trifluoromethyl)cyclopropyl)piperidin-4-yl)methanone (0.12 g, 0.31 mmol) in toluene (1.0 mL) were added (R)-2-methylpropane-2-sulfinamide (57 mg, 0.47 mmol) and Ti(OEt)$_4$ (0.43 g, 1.9 mmol) at rt. The reaction mixture was stirred at 100° C. for 1 h, then cooled to rt and quenched with brine (2.0 mL). The mixture was then diluted with EtOAc and filtered through a Celite®. The filtrate was washed with brine. The organic layer was separated, dried over Na$_2$SO$_4$, filtered and concentrated in vacuo to give the title compound.

Step 9. (R)—N-((3-chloro-2,4-difluorophenyl)(1-(1-(trifluoromethyl)cyclopropyl)piperidin-4-yl)methyl)-2-methylpropane-2-sulfinamide. To a stirred solution of (R)—N-((3-chloro-2,4-difluorophenyl)(1-(1-(trifluoromethyl)cyclopropyl)piperidin-4-yl)methylene)-2-methylpropane-2-sulfinamide (0.12 g crude) in THF (3.0 mL) was added NaBH$_4$ (10 mg, 0.26 mmol) at −78° C. The reaction was stirred at −78° C. for 2 h. Then the reaction mixture was diluted with EtOAc, washed with brine, dried over Na$_2$SO$_4$, filtered and concentrated in vacuo to give the title compound.

Step 10: (3-chloro-2,4-difluorophenyl)(1-(1-(trifluoromethyl)cyclopropyl)piperidin-4-yl)methanamine hydrochloride. A mixture of (R)—N-((3-chloro-2,4-difluorophenyl)(1-(1-(trifluoromethyl)cyclopropyl)piperidin-4-yl)methyl)-2-methylpropane-2-sulfinamide (0.12 g crude) and HCl (1.0 mL, 2.0 mmol, 2 N in MeOH) was stirred at rt for 2 h. Then the mixture was concentrated in vacuo to give the title compound.

Step 11: (S)—N—((R and S)-(3-chloro-2,4-difluorophenyl)(1-(1-(trifluoromethyl)cyclopropyl)-piperidin-4-yl)methyl)-2-oxoimidazolidine-4-carboxamide. To a stirred solution of (3-chloro-2,4-difluorophenyl)(1-(1-(trifluoromethyl)cyclopropyl)piperidin-4-yl)methanamine hydrochloride (70 mg crude), DIPEA (89 mg, 0.69 mmol) and ((S)-2-oxoimidazolidine-4-carboxylic acid (28 mg, 0.22 mmol) in DMF (2.0 mL) was added T$_3$P® (0.22 g, 0.34 mmol, 50% wt in EtOAc) at rt. The reaction was stirred at rt for 6 h. The residue was purified by reverse phase HPLC (42:58 to 72:28; water (0.1% TFA):MeCN (0.1% TFA)), followed by lyophilization to give the title compound.

Step 12: (S)—N—((R or S)-(3-chloro-2,4-difluorophenyl)(1-(1-(trifluoromethyl)cyclopropyl)-piperidin-4-yl)methyl)-2-oxoimidazolidine-4-carboxamide. (S)—N—((R and S)-(3-chloro-2,4-difluorophenyl)(1-(1-(trifluoromethyl)cyclopropyl)piperidin-4-yl)methyl)-2-oxoimidazolidine-4-carboxamide was separated by chiral-SFC (method D) to give the title compounds: first eluted diastereomer 5A (S)—N—((R or S)-(3-chloro-2,4-difluorophenyl)(1-(1-(trifluoromethyl)-cyclopropyl)piperidin-4-yl)methyl)-2-oxoimidazolidine-4-carboxamide, and second eluted diastereomer 5B (S)—N—((R or S)-(3-chloro-2,4-difluorophenyl)(1-(1-(trifluoromethyl)-cyclopropyl)piperidin-4-yl)methyl)-2-oxoimidazolidine-4-carboxamide. Diastereomer 5A: LRMS m/z (M+H): calculated 481.1, observed 481.0. $^1$H NMR (400 MHz, CD$_3$OD) δ 7.29-7.43 (m, 1H), 7.01-7.09 (m, 1H), 4.89 (d, J=9.6 Hz, 1H), 4.26 (dd, J=10.0, 6.4 Hz, 1H), 3.74 (t, J=9.6 Hz, 1H), 3.29-3.38 (m, 1H), 3.07 (d, J=11.2 Hz, 1H), 2.97 (d, J=10.8 Hz, 1H), 2.55-2.77 (m, 2H), 1.72-1.92 (m, 2H), 1.03-1.30 (m, 3H), 0.92-1.03 (m, 2H), 0.74-0.83 (m, 2H). Diastereomer 5B: LRMS m/z (M+H): calculated 481.1, observed 481.0. $^1$H NMR (400 MHz, CD$_3$OD) δ 8.43 (d, J=8.0 Hz, 1H) 7.25-7.33 (m, 1H), 7.06-7.15 (m, 1H), 4.89 (d, J=9.6 Hz, 1H), 4.28 (dd, J=10.0, 6.4 Hz, 1H), 3.74 (t, J=9.6 Hz, 1H), 3.29-3.37 (m, 1H), 3.08 (d, J=12.4 Hz, 1H), 2.97 (d, J=11.6 Hz, 1H), 2.73 (t, J=11.2 Hz, 1H), 2.62 (t, J=11.2 Hz, 1H), 1.88 (d, J=12.4 Hz, 1H), 1.79 (d, J=11.6 Hz, 1H), 1.06-1.28 (m, 3H), 0.92-1.03 (m, 2H), 0.74-0.83 (m, 2H).

Example 6

(S)—N-((5-chloro-4-(trifluoromethyl)pyrimidin-2-yl)(4-chlorophenyl)methyl)-2-oxoimidazolidine-4-carboxamide

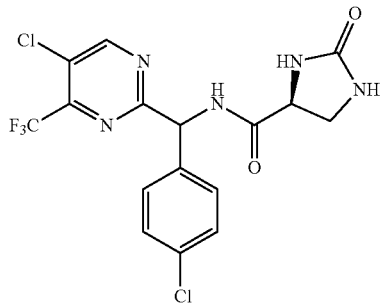 [SMILES: O=C1NC[C@@H](C(=O)NC(c2ccc(Cl)cc2)c2ncc(Cl)c(C(F)(F)F)n2)N1]

Step 1: 5-chloro-4-(trifluoromethyl)-2-vinylpyrimidine. To a mixture of 2,5-dichloro-4-(trifluoromethyl)pyrimidine (0.20 g, 0.92 mmol), potassium trifluoro(vinyl)borate (0.12 g, 0.92 mmol) and cesium carbonate (0.90 g, 2.8 mmol) in THF (5 mL) and water (0.5 mL) was added PdCl$_2$(PPh$_3$)$_2$ (32 mg, 0.046 mmol). The mixture was stirred at 85° C. for 12 h, then water was added, and the mixture was extracted with EtOAc. The combined organic layers were dried over Na$_2$SO$_4$, and filtered. The filtrate was concentrated under vacuum to give the title compound.

Step 2: 5-chloro-4-(trifluoromethyl)pyrimidine-2-carbaldehyde. A mixture of 5-chloro-4-(trifluoromethyl)-2-vinylpyrimidine (0.16 g, 0.77 mmol), NMO (0.18 g, 1.5 mmol) and OsO$_4$ (2.3 mL, 0.23 mmol) in THF (3 mL) and water (1.5 mL) was stirred at rt for 12 h. Then NaIO$_4$ (0.49 mg, 2.3 mmol) was added, and the mixture was stirred at rt for 2 h. Then water was added, and the mixture was extracted with EtOAc. The combined organic layers were dried over Na$_2$SO$_4$ and filtered. The filtrate was concentrated in vacuo to give the title compound.

Step 3: (R)—N-((5-chloro-4-(trifluoromethyl)pyrimidin-2-yl)methylene)-2-methylpropane-2-sulfinamide. To a mixture of 5-chloro-4-(trifluoromethyl)pyrimidine-2-carbaldehyde (0.11 g, 0.52 mmol) and (R)-2-methylpropane-2-sulfinamide (95 mg, 0.78 mmol) in THF (5 mL) was added Ti(OEt)$_4$ (0.36 g, 1.6 mmol). The mixture was stirred at 80° C. for 2 h, followed by the addition of water and filtration. The filtrate was extracted with EtOAc, and the EtOAc layer was washed with brine, dried with Na$_2$SO$_4$, filtered. The filtrate was concentrated, and the resulting residue was purified by silica gel chromatography (20% EtOAc:PE) to give the title compound.

Step 4: (R)—N-((5-chloro-4-(trifluoromethyl)pyrimidin-2-yl)(4-chlorophenyl)methyl)-2-methylpropane-2-sulfinamide. A solution of (R)—N-((5-chloro-4-(trifluoromethyl)pyrimidin-2-yl)methylene)-2-methylpropane-2-sulfinamide (60 mg, 0.17 mmol) in THF (5 mL) was cooled to −40° C., then (4-chlorophenyl)magnesium bromide (0.41 mL, 0.41 mmol) was slowly added. The reaction was stirred at −40° C. for 5 h, then quenched with saturated NH₄Cl. The mixture was extracted with EtOAc, washed with brine, dried with Na₂SO₄, filtered and concentrated. The resulting residue was purified by prep. silica gel TLC (33% EtOAc:PE) to give title compound.

Step 5: (5-chloro-4-(trifluoromethyl)pyrimidin-2-yl)(4-chlorophenyl)methanamine. To a mixture of (R)—N-((5-chloro-4-(trifluoromethyl)pyrimidin-2-yl)(4-chlorophenyl)methyl)-2-methyl-propane-2-sulfinamide (35 mg, 0.073 mmol) in MeOH (2 mL) was added hydrogen chloride (2.0 mL, 8.0 mmol in MeOH) at rt. The reaction was stirred at rt for 3 h, then concentrated to give the title compound, which was used in the next step without further purification.

Step 6: (S)—N-((5-chloro-4-(trifluoromethyl)pyrimidin-2-yl)(4-chlorophenyl)methyl)-2-oxoimidazolidine-4-carboxamide. To a solution of (S)-2-oxoimidazolidine-4-carboxylic acid (5.8 mg, 0.045 mmol), (5-chloro-4-(trifluoromethyl)pyrimidin-2-yl)(4-chlorophenyl)methanamine (20 mg, 0.045 mmol) and TEA (0.019 mL, 0.13 mmol) in DMF (5 mL) was added T₃P® (57 mg, 0.089 mmol) at rt. The resulting mixture was stirred at 40° C. for 1.5 h, then concentrated to give a residue. The residue was purified by reverse phase HPLC (30:70 to 60:40; water (0.1% TFA):MeCN (0.1% TFA)), followed by lyophilization to give the title compound. LRMS m/z (M+H): calculated 434.0, observed 434.1. ¹H NMR (CD₃OD, 500 MHz) δ 9.18-9.01 (m, 1H), 7.45-7.35 (m, 4H), 6.48-6.14 (m, 1H), 4.48-4.31 (m, 1H), 3.82 (dt, J=9.7, 4.1 Hz, 1H), 3.60-3.43 (m, 1H)

Examples 7A and 7B (S)—N—((R)-(5-fluoro-6-(trifluoromethyl)pyridin-2-yl)(4-(trifluoromethoxy)phenyl)methyl)-2-oxoimidazolidine-4-carboxamide and (S)—N—((S)-(5-fluoro-6-(trifluoromethyl)pyridin-2-yl)(4-(trifluoromethoxy)phenyl)methyl)-2-oxoimidazolidine-4-carboxamide

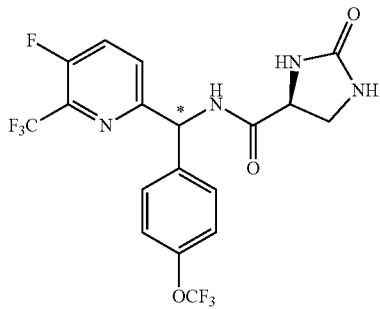

Step 1: 3-fluoro-2-(trifluoromethyl)-6-vinylpyridine. To a mixture of 6-chloro-3-fluoro-2-(trifluoromethyl)pyridine (0.20 g, 1.0 mmol), potassium trifluoro (vinyl)borate (0.13 g, 1.0 mmol) and potassium carbonate (0.42 g, 3.0 mmol) in THF (3 mL) and water (0.3 mL) was added PdCl₂(PPh₃)₂ (35 mg, 0.050 mmol). The mixture was stirred at 70° C. for 12 h. Then water was added, and the mixture was extracted with DCM. The combined organic layers were dried over Na₂SO₄, and filtered. The filtrate was concentrated in vacuo to give the title compound.

Step 2: 5-fluoro-6-(trifluoromethyl)picolinaldehyde. A mixture of 3-fluoro-2-(trifluoromethyl)-6-vinylpyridine (0.16 g, 0.75 mmol), NMO (0.18 g, 1.5 mmol) and OsO₄ (0.075 mL, 0.075 mmol) in THF (5 mL) and water (2.5 mL) was stirred at rt for 12 h. Then NaIO₄ (0.48 g, 2.3 mmol) was added, and the mixture was stirred at rt for 2 h. Then water was added, and the mixture was extracted by DCM. The combined organic layers were dried over Na₂SO₄, filtered, and the filtrate was concentrated in vacuo to give the title compound.

Step 3: (R)—N-((5-fluoro-6-(trifluoromethyl)pyridin-2-yl)methylene)-2-methylpropane-2-sulfinamide. To a mixture of 5-fluoro-6-(trifluoromethyl)picolinaldehyde (0.15 g, 0.66 mmol) and (R)-2-methylpropane-2-sulfinamide (0.12 g, 0.99 mmol) in THF (10 mL) was added Ti(OEt)₄ (0.41 mL, 2.0 mmol) at 15° C. The resulting mixture was stirred at 80° C. for 2 h, then diluted with EtOAc and brine, and filtered. The filtrate was extracted with EtOAc. The organic layer was dried over Na₂SO₄, filtered and concentrated in vacuo. The resulting residue was purified by silica gel chromatography (20% EtOAc:PE) to give the title compound Step 4: (R)—N-((5-fluoro-6-(trifluoromethyl)pyridin-2-yl)(4-(trifluoromethoxy)phenyl)methyl)-2-methylpropane-2-sulfinamide. To a mixture of (R)—N-((5-fluoro-6-(trifluoromethyl)pyridin-2-yl)methylene)-2-methylpropane-2-sulfinamide (0.14 g, 0.42 mmol) in THF (5 mL) was added (4-(trifluoromethoxy)phenyl)magnesium bromide (1.3 mL, 1.3 mmol) at −78° C. The mixture was stirred at −78° C. for 1.5 h, then quenched with sat. NH₄Cl and extracted with EtOAc. The combined organic layers were washed with brine, dried over Na₂SO₄, and filtered. The filtrate was concentrated in vacuo. The resulting residue was purified by silica gel chromatography (25% EtOAc:PE) to give the title compound.

Step 5: (5-fluoro-6-(trifluoromethyl)pyridin-2-yl)(4-(trifluoromethoxy)phenyl)methanamine hydrochloride. To a solution of (R)—N-((5-fluoro-6-(trifluoromethyl)pyridin-2-yl)(4-(trifluoromethoxy)phenyl)methyl)-2-methylpropane-2-sulfinamide (0.18 g, 0.37 mmol) in MeOH (1 mL) was added HCl (3.0 mL, 6.0 mmol, 2 M in MeOH). The resulting mixture was stirred at rt for 2 h, then directly concentrated to give the title compound.

Step 6: (S)—N—((R and S)-(5-fluoro-6-(trifluoromethyl)pyridin-2-yl)(4-(trifluoromethoxy)-phenyl)methyl)-2-oxo-imidazolidine-4-carboxamide. To a solution of (5-fluoro-6-(trifluoro-methyl)pyridin-2-yl)(4-(trifluoromethoxy)phenyl)methanamine hydrochloride (0.12 g crude), (S)-2-oxoimidazolidine-4-carboxylic acid (34 mg, 0.26 mmol) and DIEA (0.14 mL, 0.80 mmol) in DMF (8 mL) was added T₃P® (0.25 g, 0.40 mmol) at 0° C. The mixture was stirred at rt for 2 h, then directly concentrated in vacuo. The resulting residue was purified by reverse phase HPLC (30:70 to 60:40; water (0.1% TFA):MeCN (0.1% TFA)), followed by lyophilization to give the title compound.

Step 7: (S)—N—((R or S)-(5-fluoro-6-(trifluoromethyl)pyridin-2-yl)(4-(trifluoromethoxy)-phenyl)methyl)-2-oxo-imidazolidine-4-carboxamide. (S)—N—((R and S)-(5-fluoro-6-(trifluoro-methyl)pyridin-2-yl)(4-(trifluoromethoxy)phenyl)methyl)-2-oxoimidazolidine-4-carboxamide was separated by chiral-SFC (method E) to give the title compounds: first eluted diastereomer 7A (S)—N—((R or S)-(5-fluoro-6-(trifluoromethyl)pyridin-2-yl)(4-(trifluoromethoxy)phenyl)-methyl)-2-oxoimidazolidine-4-carboxamide and second eluted diastereomer 7B (S)—N—((R or S)-(5-fluoro-6-(trifluoromethyl)pyridin-2-yl)(4-(trifluoromethoxy)phenyl)methyl)-2-oxo-imidazolidine-4-carboxamide. Diastereomer 7A: LRMS m/z (M+H): calculated 467.1, observed 467.2. ¹H NMR (500 MHz, CD₃OD) δ 8.98 (d, J=7.5 Hz, 1H), 7.91-7.82 (m, 1H), 7.75 (dd, J=3.5, 9.0 Hz, 1H), 7.48 (d, J=8.5 Hz, 2H), 7.29 (d, J=8.0 Hz, 2H), 6.38-6.29 (m, 1H), 4.42 (dd, J=6.0, 10.0 Hz, 1H), 3.82 (t, J=9.5 Hz, 1H), 3.50 (dd, J=6.0, 9.5 Hz, 1H). Diastereomer 7B: LRMS m/z (M+H): calculated 467.1, observed 466.5. ¹H NMR (500 MHz, CD₃OD) δ 8.93 (d, J=7.5 Hz, 1H), 7.92-7.83 (m, 1H), 7.76 (dd, J=3.5, 9.0 Hz, 1H), 7.50 (d, J=8.5 Hz, 2H), 7.29 (d, J=8.1 Hz, 2H), 6.39-6.32 (m, 1H), 4.41 (dd, J=6.5, 10.1 Hz, 1H), 3.82 (t, J=9.5 Hz, 1H), 3.49 (dd, J=6.5, 9.0 Hz, 1H).

Examples 8A, 8B and 8C (S)—N—((R or S)-(3-chloro-2,4-difluorophenyl) ((trans)-5-(trifluoromethyl)tetrahydro-2H-pyran-2-yl)methyl)-2-oxoimidazolidine-4-carboxamide

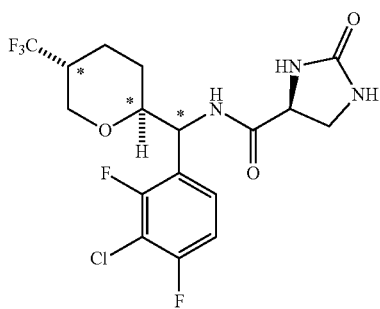 [SMILES: O=C1NC[C@@H](C(=O)NC(c2ccc(F)c(Cl)c2F)[C@@H]2CC[C@@H](C(F)(F)F)CO2)N1]

Step 1: 6-((benzyloxy)methyl)tetrahydro-2H-pyran-3-ol. To a solution of 2-((benzyloxy)methyl)-3,4-dihydro-2H-pyran (6.0 g, 38 mmol) in THF (80 mL) was added BH₃.DMS (5.1 mL, 54 mmol) at 0° C. The mixture was stirred at 18° C. for 2 h, then cooled at 0° C. Then NaOAc (3.2 g, 38 mmol) was added, followed by hydrogen peroxide (13 g, 0.12 mol). The mixture was stirred at 18° C. for 12 h, diluted with water and extracted with EtOAc. The combined organic layers were washed with sat. Na₂SO₃, dried over Na₂SO₄, filtered, and the filtrate was concentrated in vacuo to give the title compound.

Step 2: 6-((benzyloxy)methyl)dihydro-2H-pyran-3(4H)-one. To a solution of 6-((benzyloxy)-methyl)tetrahydro-2H-pyran-3-ol (5.0 g crude) in DCM (100 mL) was added PCC (9.7 g, 45 mmol) at 0° C. The mixture was stirred at 18° C. for 10 h. Then the reaction mixture was filtered. The filtrate was diluted with water and extracted with EtOAc. The combined organic layers were washed with brine, dried over Na₂SO₄, and concentrated in vacuo. The resulting residue was purified by silica gel chromatography (0-20% EtOAc:PE) to give the title compound.

Step 3: 6-((benzyloxy)methyl)-3-(trifluoromethyl)tetrahydro-2H-pyran-3-ol. To a solution of 6-((benzyloxy) methyl)dihydro-2H-pyran-3(4H)-one (3.0 g, 14 mmol) and trimethyl(trifluoro-methyl)silane (4.8 g, 34 mmol) in THF (80 mL) was added TBAF (29 mL, 29 mmol) dropwise at 0° C. The mixture was stirred at 18° C. for 18 h. Then a HCl solution (34 mL, 0.20 mol, 6 M) was added. The mixture was stirred at 18° C. for 2 h, filtered, and the filtrate was diluted with water and extracted with EtOAc. The combined organic layers were washed with brine, dried over Na₂SO₄, filtered, and the filtrate was concentrated in vacuo. The resulting residue was purified by silica gel chromatography (0-30% EtOAc:PE) to give the title compound.

Step 4: 2-((benzyloxy)methyl)-5-(trifluoromethyl)-3,4-dihydro-2H-pyran. To a solution of 6-((benzyloxy)methyl)-3-(trifluoromethyl)tetrahydro-2H-pyran-3-ol (1.2 g, 4.1 mmol), N,N-dimethylpyridin-4-amine (0.20 g, 1.7 mmol) and pyridine (11 g, 0.14 mol) in THF (50 mL) was added sulfurous dichloride (4.9 g, 41 mmol). The reaction mixture was heated at 80° C. to reflux. After 24 h, the reaction mixture was cooled to 0° C. in an ice bath, and TEA (10 g, 0.10 mmol) was added dropwise over 5 min. Water was added dropwise over 2 minutes, then water was added to the reaction mixture, and the mixture was extracted with EtOAc. The combined organic layers were concentrated in vacuo and washed with brine. The organic layer was dried with Na₂SO₄, filtered and the filtrate was concentrated in vacuo. The resulting residue was purified by silica gel chromatography (0-5% EtOAc:PE) to give the title compound.

Step 5: (trans)-2-((benzyloxy)methyl)-5-(trifluoromethyl)tetrahydro-2H-pyran. To a solution of 2-((benzyloxy)methyl)-5-(trifluoromethyl)-3,4-dihydro-2H-pyran (1.8 g, 6.6 mmol) in MeOH (20 mL) was added Pd/C (0.70 g). The mixture was stirred at 18° C. for 16 h under an atmosphere of H₂ (30 psi). Then the mixture was filtered, and the filtrate was concentrated in vacuo. The resulting residue purified by silica gel chromatography (0-5% EtOAc:PE) to give the title compound.

Step 6: ((trans)-5-(trifluoromethyl)tetrahydro-2H-pyran-2-yl)methanol. To a solution of (trans)-2-((benzyloxy)methyl)-5-(trifluoromethyl)tetrahydro-2H-pyran (0.50 g, 1.8 mmol) in MeOH (12 mL) was added Pd/C (0.19 g). The mixture was stirred at rt for 16 h under an atmosphere of H₂ (30 psi). Then the mixture was filtered, and the filtrate was concentrated in vacuo to give the title compound.

Step 7: (trans)-5-(trifluoromethyl)tetrahydro-2H-pyran-2-carbaldehyde. To a solution of oxalyl dichloride (1.0 g, 8.2 mmol) in DCM (10 mL) was added (methylsulfinyl)methane (0.21 g, 2.7 mmol) at −70° C. The mixture was stirred at −70° C. for 30 min, ((trans)-5-(trifluoromethyl)-tetrahydro-2H-pyran-2-yl)methanol (0.50 g crude) in DCM (20 mL) was added dropwise. The mixture was stirred at −70° C. for 2 h, then TEA (2.8 g, 27 mmol) was added. The reaction mixture was stirred at −70° C. for 30 min, then warmed to rt and stirred at rt for 1 h. Then the mixture was diluted with water and extracted with DCM. The combined organic layers were washed with brine, dried over Na₂SO₄, filtered, and the filtrate was concentrated in vacuo to give the title compound.

Step 8: (R)-2-methyl-N-((E)-((trans)-5-(trifluoromethyl) tetrahydro-2H-pyran-2-yl)methylene)-propane-2-sulfinamide. To a solution of (trans)-5-(trifluoromethyl)tetrahydro-2H-pyran-2-carbaldehyde (0.40 g crude) in THF (15 mL) was added (R)-2-methylpropane-2-sulfinamide (0.53 g, 4.4 mmol) and Ti(OEt)₄ (1.0 g, 4.4 mmol). The mixture was stirred at 55° C. for 2 h. Then brine was added, and the mixture was filtered. The filtrate was diluted with water, extracted with EtOAc and washed with brine. The combined organic layers were dried with Na₂SO₄ and concentrated in vacuo. The resulting residue was purified by prep. silica gel TLC (20%, EtOAc:PE) to give title compound.

Step 9: (R)—N-((3-chloro-2,4-difluorophenyl)((trans)-5-(trifluoromethyl)tetrahydro-2H-pyran-2-yl)methyl)-2-methylpropane-2-sulfinamide. To a solution of 1-bromo-3-chloro-2,4-difluorobenzene (0.16 g, 0.70 mmol) in THF (5 mL) was added isopropyl magnesium chloride (72 mg, 0.70 mmol) at 0° C. The mixture was stirred at rt for 6 h. Then (R)-2-methyl-N-((E)-((trans)-5-(trifluoromethyl)tetrahydro-2H-pyran-2-yl)methylene)propane-2-sulfinamide (0.20 g, 0.70 mmol) in THF (5 mL) was added to the reaction, and the mixture was stirred at rt for 6 h. To the reaction solution was added sat. NH₄Cl, then diluted with water and extracted with EtOAc. The combined organic layers were washed with brine, dried with Na₂SO₄, filtered and concentrated in vacuo. The resulting residue was purified by prep. silica gel TLC (25% EtOAc:PE) to give the title compound.

Step 10: (3-chloro-2,4-difluorophenyl)((trans)-5-(trifluoromethyl)tetrahydro-2H-pyran-2-yl)methanamine hydrochloride. To a solution of (R)—N-((3-chloro-2,4-difluorophenyl)((trans)-5-(trifluoromethyl)tetrahydro-2H-pyran-2-yl)methyl)-2-methylpropane-2-sulfinamide (0.16 g, 0.37 mmol) in MeOH (2 mL) was added HCl (2.0 mL, 8.0 mmol, 4 N in MeOH). The mixture was stirred at rt for 11 h. Then the mixture was concentrated to give the title compound.

Step 11: (S)—N—((R and S)-(3-chloro-2,4-difluorophenyl)((trans)-5-(trifluoromethyl)tetrahydro-2H-pyran-2-yl)methyl)-2-oxoimidazolidine-4-carboxamide. To a solution of (3-chloro-2,4-difluorophenyl)((trans)-5-(trifluoromethyl)tetrahydro-2H-pyran-2-yl)methanamine hydrochloride (50 mg crude) in DMF (1.5 mL) was added (S)-2-oxoimidazolidine-4-carboxylic acid (40 mg, 0.30 mmol) and TEA (31 mg, 0.30 mmol). T₃P® (0.19 g, 0.30 mmol) was added. The mixture was stirred at rt for 1 h. Then the mixture was purified by reverse phase HPLC (34:66 to 64:36; water (0.1% TFA):MeCN (0.1% TFA)), followed by lyophilization to give the title compound.

Step 12: (S)—N—((R or S)-(3-chloro-2,4-difluorophenyl)((trans)-5-(trifluoromethyl)tetrahydro-2H-pyran-2-yl)methyl)-2-oxoimidazolidine-4-carboxamide. The mixture of (4S)—N-((3-chloro-2,4-difluorophenyl)(5-(trifluoromethyl)tetrahydro-2H-pyran-2-yl)methyl)-2-oxoimidazolidine-4-carboxamide were purified by chiral-SFC (method F) to give the title compounds: first eluted peak (showed to be a mixture of two compounds) 8A (S)—N—((R or S)-(3-chloro-2,4-difluorophenyl)((trans)-5-(trifluoromethyl)tetrahydro-2H-pyran-2-yl)methyl)-2-oxoimidazolidine-4-carboxamide, second eluted peak 8B (S)—N—((R or S)-(3-chloro-2,4-difluorophenyl)((trans)-5-(trifluoromethyl)tetrahydro-2H-pyran-2-yl)methyl)-2-oxoimidazolidine-4-carboxamide, and third eluted peak 8C (S)—N—((R or S)-(3-chloro-2,4-difluorophenyl)((trans)-5-(trifluoromethyl)tetrahydro-2H-pyran-2-yl)methyl)-2-oxoimidazolidine-4-carboxamide. Isomer 8A: LRMS m/z (M+H): calculated 442.1, observed 442.0. ¹H NMR (400 MHz, CD₃OD): δ 7.46-7.31 (m, 1H), 7.16-6.96 (m, 1H), 5.23-5.09 (m, 1H), 4.42-4.30 (m, 1H), 4.22-4.08 (m, 1H), 3.83-3.61 (m, 2H), 3.46-3.33 (m, 2H), 2.56-2.32 (m, 2H), 2.13-1.93 (m, 1H), 1.68-1.49 (m, 2H). Isomer 8B: LRMS m/z (M+H): calculated 442.1, observed 442.0. ¹H NMR (400 MHz, CD₃OD) δ 7.45-7.36 (m, 1H), 7.17-7.03 (m, 1H), 5.17 (d, J=5.2 Hz, 1H), 4.33-4.35 (m, 1H), 4.13-4.17 (m, 1H), 3.74-3.79 (m, 1H), 3.63-3.67 (m, 1H), 3.47-3.36 (m, 2H), 2.42-2.52 (m, 1H), 2.03-2.10 (m, 1H), 1.71-1.49 (m, 3H). Isomer 8C: LRMS m/z (M+H): calculated 442.1, observed 442.0. ¹H NMR (400 MHz, CD₃OD) δ 7.48-7.34 (m, 1H), 7.07-7.12 (m, 1H), 5.23 (d, J=6.0 Hz, 1H), 4.27-4.31 (m, 1H), 4.08-4.12 (m, 1H), 3.79-3.65 (m, 2H), 3.47-3.33 (m, 2H), 2.45-2.30 (m, 1H), 2.45-2.30 (m, 1H), 2.03-2.08 (m, 1H), 1.87-1.92 (m, 1H), 1.73-1.59 (m, 1H), 1.40-1.12 (m, 1H).

Examples 9A and 9B (S)—N—((R)-(3-chlorophenyl)(4-(trifluoromethoxy)phenyl)methyl)-2-oxoimidazolidine-4-carboxamide and (S)—N—((S)-(3-chlorophenyl)(4-(trifluoromethoxy)phenyl)methyl)-2-oxoimidazolidine-4-carboxamide

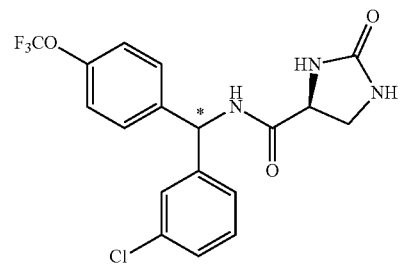 [SMILES: O=C1NC[C@@H](C(=O)NC(c2ccc(OC(F)(F)F)cc2)c2cccc(Cl)c2)N1]

Step 1: (4S)—N—((R and S)-(3-chlorophenyl)(4-(trifluoromethoxy)phenyl)methyl)-2-oxoimidazolidine-4-carboxamide. T₃P® (1.2 mL, 2.0 mmol) was added to a solution of (S)-2-oxoimidazolidine-4-carboxylic acid (0.13 g, 1.0 mmol) and (R and S)-(3-chlorophenyl)(4-(trifluoromethoxy)phenyl)methanamine (0.30 g, 1.0 mmol) in EtOAc (5 mL). Then DIEA (0.35 mL, 2.0 mmol) was added and the reaction was stirred for 2 hours. The mixture was then concentrated in vacuo and purified by silica gel chromatography (0-100% (3:1 EtOAc:EtOH):hex) to give the title compound.

Step 2: (S)—N—((R or S)-(3-chlorophenyl)(4-(trifluoromethoxy)phenyl)methyl)-2-oxoimidazolidine-4-carboxamide. (4S)—N—((R and S)-(3-chlorophenyl)(4-(trifluoromethoxy)phenyl)methyl)-2-oxoimidazolidine-4-carboxamide was separated by chiral-SFC (method G) to give the title compounds: first eluted diastereomer 9A (4S)—N—((R or S)-(3-chlorophenyl)(4-(trifluoromethoxy)phenyl)methyl)-2-oxoimidazolidine-4-carboxamide, and second eluted diastereomer 9B (4S)—N—((R or S)-(3-chlorophenyl)(4-(trifluoromethoxy)-phenyl)methyl)-2-oxoimidazolidine-4-carboxamide. Diastereomer 9A: LRMS m/z (M+H): calculated 414.1, observed 414.3. ¹H NMR (500 MHz, DMSO-d₆) δ 8.86 (d, J=8.3 Hz, 1H), 7.45-7.26 (m, 8H), 6.57 (s, 1H), 6.29 (s, 1H), 6.20 (d, J=8.2 Hz, 1H), 4.22 (dd, J=9.0, 6.1 Hz, 1H), 3.56 (t, J=9.2 Hz, 1H), 3.29-3.17 (m, 1H). Diastereomer 9B: LRMS m/z (M+H): calculated 414.1, observed 414.3. ¹H NMR (500 MHz, DMSO-d₆) δ 8.85 (d, J=8.3 Hz, 1H), 7.44-7.33 (m, 7H), 7.29 (d, J=7.5 Hz, 1H), 6.57 (s, 1H), 6.29 (s, 1H), 6.20 (d, J=8.3 Hz, 1H), 4.21 (dd, J=9.1, 6.3 Hz, 1H), 3.55 (t, J=9.3 Hz, 1H), 3.27-3.17 (m, 1H).

TABLE 1

The compounds of Examples 10A-18B were prepared according to a synthetic procedure similar to the synthetic procedure for Examples 9A and 9B.

| Example | Structure | Name | Calc'd [M + H]+ | Observed [M + H]+ | Conditions |
|---------|-----------|------|-----------------|-------------------|------------|
| 10A | 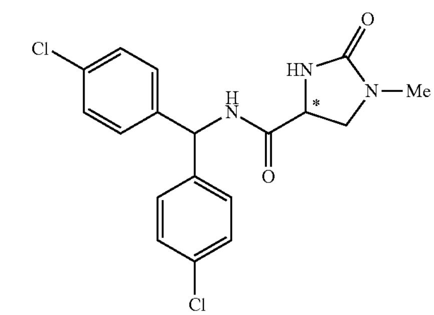 [SMILES: CN1CC(C(=O)NC(c2ccc(Cl)cc2)c2ccc(Cl)cc2)NC1=O] | (R or S)-N-[bis(4-chlorophenyl)methyl]-1-methyl-2-oxoimidazolidine-4-carboxamide | 378.1 | 378.1 | Chiral method B, Peak 1 |
| 10B | 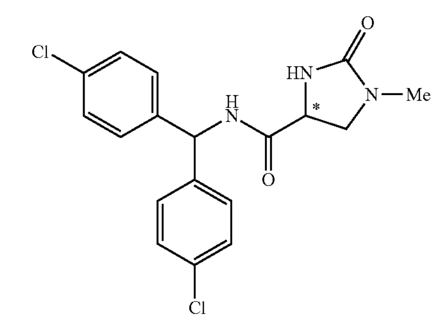 [SMILES: CN1CC(C(=O)NC(c2ccc(Cl)cc2)c2ccc(Cl)cc2)NC1=O] | (R or S)-N-[bis(4-chlorophenyl)methyl]-1-methyl-2-oxoimidazolidine-4-carboxamide | 378.1 | 378.1 | Chiral method B, Peak 2 |
| 11A | 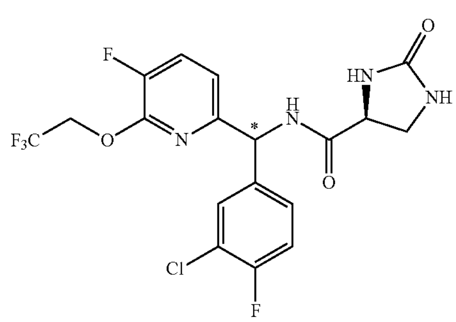 [SMILES: O=C1NC[C@@H](C(=O)NC(c2ccc(F)c(Cl)c2)c2ccc(F)c(OCC(F)(F)F)n2)N1] | (4S)-N-{((R or S)-3-chloro-4-fluorophenyl)[5-fluoro-6-(2,2,2-trifluoroethoxy)pyridin-2-yl]methyl}-2-oxoimidazolidine-4-carboxamide | 465.1 | 465.1 | Chiral method H, Peak 1 |
| 11B | 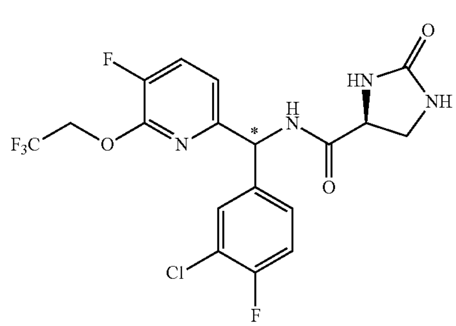 [SMILES: O=C1NC[C@@H](C(=O)NC(c2ccc(F)c(Cl)c2)c2ccc(F)c(OCC(F)(F)F)n2)N1] | (4S)-N-{((R or S)-3-chloro-4-fluorophenyl)[5-fluoro-6-(2,2,2-trifluoroethoxy)pyridin-2-yl]methyl}-2-oxoimidazolidine-4-carboxamide | 465.1 | 465.1 | Chiral method H, Peak 2 |

TABLE 1-continued

The compounds of Examples 10A-18B were prepared according to a synthetic procedure similar to the synthetic procedure for Examples 9A and 9B.

| Example | Structure | Name | Calc'd [M + H]+ | Observed [M + H]+ | Conditions |
|---|---|---|---|---|---|
| 12A | 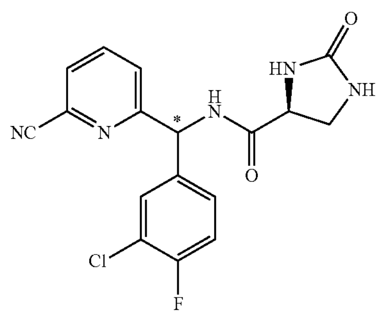 [SMILES: N#Cc1cccc(C(NC(=O)[C@@H]2CNC(=O)N2)c2ccc(F)c(Cl)c2)n1] | (4S)-N-[((R or S)-3-chloro-4-fluorophenyl)(6-cyanopyridin-2-yl)methyl]-2-oxoimidazolidine-4-carboxamide | 374.1 | 374.1 | separated prior (intermediate 2A) |
| 12B | 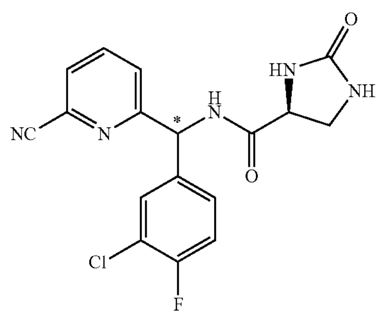 [SMILES: N#Cc1cccc(C(NC(=O)[C@@H]2CNC(=O)N2)c2ccc(F)c(Cl)c2)n1] | (4S)-N-[((R or S)-3-chloro-4-fluorophenyl)(6-cyanopyridin-2-yl)methyl]-2-oxoimidazolidine-4-carboxamide | 374.1 | 374.1 | Separated prior (intermediate 2B) |
| 13A | 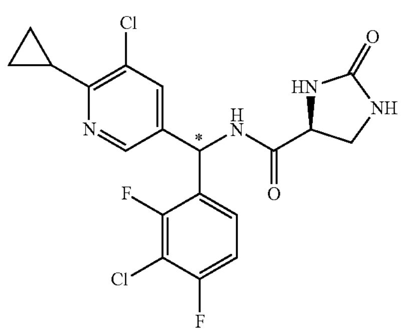 [SMILES: O=C1NC[C@@H](C(=O)NC(c2cnc(C3CC3)c(Cl)c2)c2ccc(F)c(Cl)c2F)N1] | (4S)-N-[((R or S)-5-chloro-6-cyclopropylpyridin-3-yl)(3-chloro-2,4-difluorophenyl)methyl]-2-oxoimidazolidine-4-carboxamide | 441.1 | 441.1 | Chiral method I, Peak 1 |
| 13B | 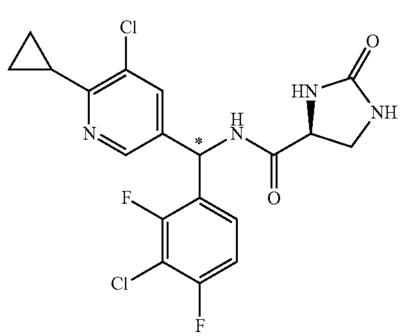 [SMILES: O=C1NC[C@@H](C(=O)NC(c2cnc(C3CC3)c(Cl)c2)c2ccc(F)c(Cl)c2F)N1] | (4S)-N-[((R or S)-5-chloro-6-cyclopropylpyridin-3-yl)(3-chloro-2,4-difluorophenyl)methyl]-2-oxoimidazolidine-4-carboxamide | 441.1 | 441.1 | Chiral method I, Peak 2 |

TABLE 1-continued

The compounds of Examples 10A-18B were prepared according to a synthetic procedure similar to the synthetic procedure for Examples 9A and 9B.

| Example | Structure | Name | Calc'd [M + H]+ | Observed [M + H]+ | Conditions |
|---|---|---|---|---|---|
| 14A | 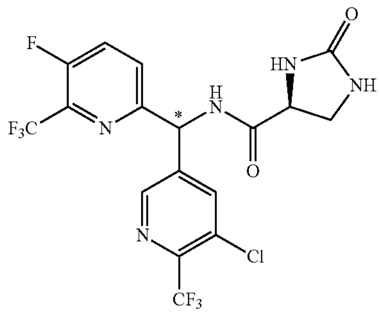 [SMILES: O=C1NC[C@@H](C(=O)NC(c2cnc(C(F)(F)F)c(Cl)c2)c2ccc(F)c(C(F)(F)F)n2)N1] | (4S)-N-{[(R or S)-5-chloro-6-(trifluoromethyl)pyridin-3-yl][5-fluoro-6-(trifluoromethyl)pyridin-2-yl]methyl}-2-oxoimidazolidine-4-carboxamide | 486.1 | 486.0 | Chiral method J, Peak 1 |
| 14B | 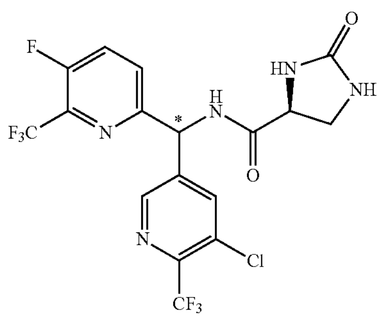 [SMILES: O=C1NC[C@@H](C(=O)NC(c2cnc(C(F)(F)F)c(Cl)c2)c2ccc(F)c(C(F)(F)F)n2)N1] | (4S)-N-{[R or S]-5-chloro-6-(trifluoromethyl)pyridin-3-yl][5-fluoro-6-(trifluoromethyl)pyridin-2-yl]methyl}-2-oxoimidazolidine-4-carboxamide | 486.1 | 486.0 | Chiral method J, Peak 2 |
| 15A | 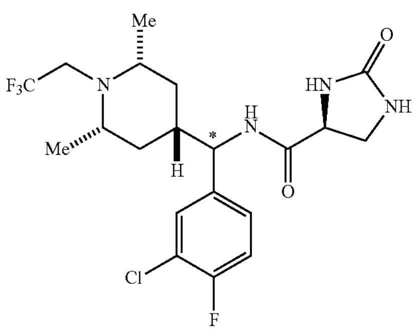 [SMILES: C[C@@H]1C[C@H](C(NC(=O)[C@@H]2CNC(=O)N2)c2ccc(F)c(Cl)c2)C[C@H](C)N1CC(F)(F)F] | (S)-N-((R or S)-(3-chloro-4-fluorophenyl)(cis-2,6-dimethyl-1-(2,2,2-trifluoroethyl)piperidin-4-yl)methyl)-2-oxoimidazolidine-4-carboxamide | 465.2 | 465.1 | Chiral method K, Peak 1 |
| 15B | 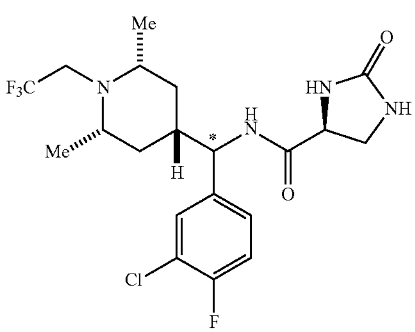 [SMILES: C[C@@H]1C[C@H](C(NC(=O)[C@@H]2CNC(=O)N2)c2ccc(F)c(Cl)c2)C[C@H](C)N1CC(F)(F)F] | (S)-N-((R or S)-(3-chloro-4-fluorophenyl)(cis-2,6-dimethyl-1-(2,2,2-trifluoroethyl)piperidin-4-yl)methyl)-2-oxoimidazolidine-4-carboxamide | 465.2 | 465.1 | Chiral method K, Peak 2 |

TABLE 1-continued

The compounds of Examples 10A-18B were prepared according to a synthetic procedure similar to the synthetic procedure for Examples 9A and 9B.

| Example | Structure | Name | Calc'd [M + H]+ | Observed [M + H]+ | Conditions |
|---|---|---|---|---|---|
| 16A | 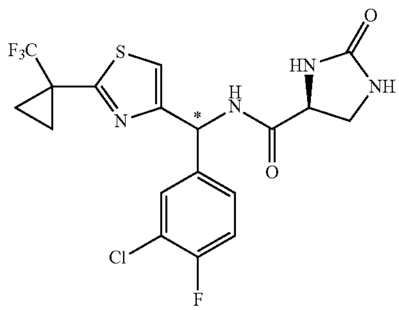 [SMILES: O=C1NC[C@@H](C(=O)NC(c2ccc(F)c(Cl)c2)c2csc(C3(C(F)(F)F)CC3)n2)N1] | (S)-N-((R or S)-(3-choro-4-fluoro-phenyl)(2-(1-(trifluoromethyl)cyclopro-pyl)thiazol-4-yl)methyl)-2-oxoimidazolidine-4-carboxamide | 463.1 | 463.1 | Chiral method L, Peak 1 |
| 16B | 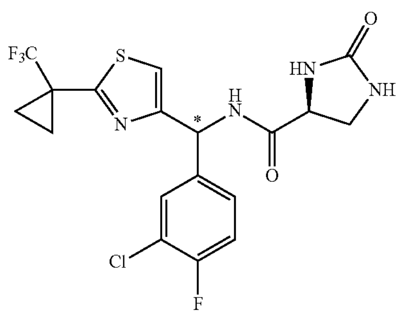 [SMILES: O=C1NC[C@@H](C(=O)NC(c2ccc(F)c(Cl)c2)c2csc(C3(C(F)(F)F)CC3)n2)N1] | (S)-N-((R or S)-(3-chloro-4-fluoro-phenyl)(2-(1-(trifluoromethyl)cyclopro-pyl)thiazol-4-yl)methyl)-2-oxoimidazolidine-4-carboxamide | 463.1 | 463.1 | Chiral method L, Peak 2 |
| 17A | 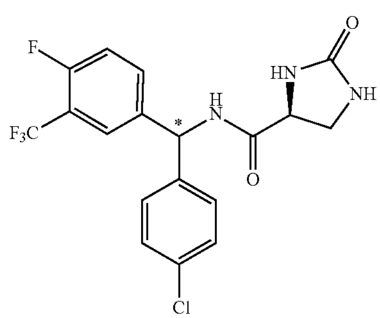 [SMILES: O=C1NC[C@@H](C(=O)NC(c2ccc(Cl)cc2)c2ccc(F)c(C(F)(F)F)c2)N1] | (S)-N-((R or S)-(4-chlorophenyl)(4-fluoro-3-(trifluoro-methyl)phenyl)methyl)-2-oxoimidazolidine-4-carboxamide | 416.1 | 416.1 | Chiral method M, Peak 1 |
| 17B | 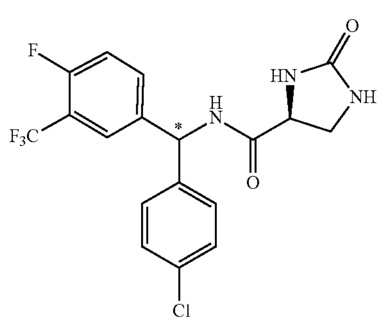 [SMILES: O=C1NC[C@@H](C(=O)NC(c2ccc(Cl)cc2)c2ccc(F)c(C(F)(F)F)c2)N1] | (S)-N-((R or S)-(4-chloropehnyl)(4-fluoro-3-(trifluoro-methyl)phenyl)methyl)-2-oxoimidazolidine-4-carboxamide | 416.1 | 416.2 | Chiral method M, Peak 2 |

TABLE 1-continued

The compounds of Examples 10A-18B were prepared according to a synthetic procedure similar to the synthetic procedure for Examples 9A and 9B.

| Example | Structure | Name | Calc'd [M + H]+ | Observed [M + H]+ | Conditions |
|---|---|---|---|---|---|
| 18A | 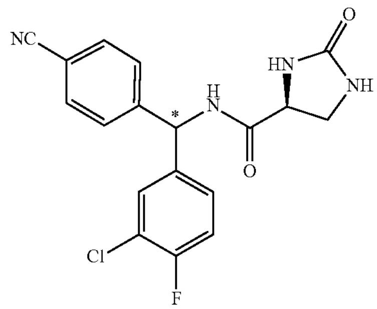 [SMILES: N#Cc1ccc(C(NC(=O)[C@@H]2CNC(=O)N2)c2ccc(F)c(Cl)c2)cc1] | (S)-N-((R or S)-(3-chloro-4-fluoro-phenyl)(4-cyano-phenyl)methyl)-2-oxoimidazolidine-4-carboxamide | 373.1 | 373.2 | Chiral method M, Peak 1 |
| 18B | 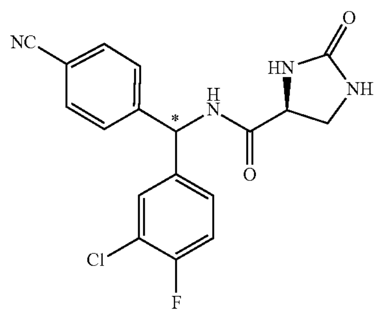 [SMILES: N#Cc1ccc(C(NC(=O)[C@@H]2CNC(=O)N2)c2ccc(F)c(Cl)c2)cc1] | (S)-N-((R or S)-(3-chloro-4-fluoro-phenyl)(4-cyano-phenyl)methyl)-2-oxoimidazolidine-4-carboxamide | 373.1 | 373.2 | Chiral method M, Peak 2 |

Example 19

(S)-2-oxo-N—((R and S)-(6-(trifluoromethyl)pyridin-3-yl)(2-(trifluoromethyl)thiazol-4-yl)methyl)imidazolidine-4-carboxamide

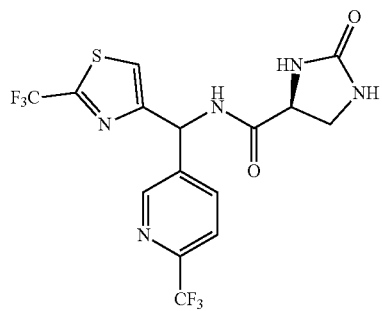 [SMILES: O=C1NC[C@@H](C(=O)NC(c2ccc(C(F)(F)F)nc2)c2csc(C(F)(F)F)n2)N1]

Step 1: (S)-2-methyl-N-((2-(trifluoromethyl)thiazol-4-yl)methylene)propane-2-sulfinamide. 2-(trifluoromethyl)thiazole-4-carbaldehyde (3.0 g, 17 mmol) and (S)-2-methylpropane-2-sulfinamide (2.0 g, 17 mmol) were taken up in THF (83 mL), and then Ti(OEt)$_4$ (9.8 mL, 33 mmol) was added. This mixture was allowed to stir for 2 hours, then diluted with brine, filtered through sand and extracted with EtOAc. The combined organic layers were washed with sat. NH$_4$Cl, brine, dried over Na$_2$SO$_4$, filtered, and concentrated in vacuo to give the title compound.

Step 2: (S)-2-methyl-N-((6-(trifluoromethyl)pyridin-3-yl)(2-(trifluoromethyl)thiazol-4-yl)methyl)propane-2-sulfinamide. 5-bromo-2-(trifluoromethyl)pyridine (0.45 g, 2.0 mmol) was taken up in THF (10 mL) and cooled to −78° C. To this solution was slowly added n-butyllithium (0.88 mL, 2.1 mmol) over 5 min. The mixture was stirred for 15 min, then slowly added to a solution of (S)-2-methyl-N-((2-(trifluoromethyl)thiazol-4-yl)methylene)propane-2-sulfinamide (0.28 g, 1.0 mmol) in THF (10 mL) at −78° C. After stirring for 1 h, the reaction was quenched with sat. NH$_4$Cl, stirred for 10 min, then filtered through a pad of Celite® and concentrated in vacuo. The resulting residue was purified by reverse phase HPLC (75:25 to 5:95; water (0.1% TFA): MeCN (0.1% TFA)), and then lyophilized to give the title compound.

Step 3: (6-(trifluoromethyl)pyridin-3-yl)(2-(trifluoromethyl)thiazol-4-yl)methanamine hydrochloride. (S)-2-methyl-N—((S and R)-(6-(trifluoromethyl)pyridin-3-yl)(2-(trifluoro-methyl)thiazol-4-yl)methyl)propane-2-sulfinamide (0.43 g, 1.0 mmol) was taken up in EtOAc (20 mL), and HCl gas was bubbled through until saturated (~15 seconds). Then the mixture was concentrated in vacuo to give title compound.

Step 4: (S)-2-oxo-N—((R and S)-(6-(trifluoromethyl)pyridin-3-yl)(2-(trifluoromethyl)thiazol-4-yl)methyl)imidazolidine-4-carboxamide. To as solution of (S)-2-oxoimidazolidine-4-carboxylic acid (10 mg, 0.08 mmol), (6-(trifluoromethyl)pyridin-3-yl)(2-(trifluoromethyl)thiazol-4-yl)methanamine hydrochloride (26 mg, 0.080 mmol) and HATU (30 mg, 0.080 mmol) in DMSO (0.53 mL) was added 4-methylmorpholine (18 µl, 0.16 mmol). The reaction was stirred for 2 h at 23° C. Then the mixture was filtered and purified by mass directed reverse phase HPLC to give the title compound. LRMS m/z (M+H): calculated 440.1, observed 440.1. $^1$H NMR (500 MHz, DMSO-d$_6$) δ 9.17 (d, J=8.0 Hz, 1H), 8.79 (s, 1H), 8.08 (s, 1H), 8.05 (d, J=8.1 Hz, 1H), 7.94 (d, J=8.2 Hz, 1H), 6.57 (s, 0.7H) 6.32 (s, 0.3H), 6.52 (d, J=8.0 Hz, 1H), 4.24 (dd, J=9.3, 5.8 Hz, 1H), 3.55 (t, 0.3H), 3.46 (t, 0.7H), 3.27-3.21 (m, 1H).

Examples 20A and 20B (R)—N-(bis(4-chlorophenyl)methyl)-4-methyl-2,5-dioxoimidazolidine-4-carboxamide and (S)—N-(bis(4-chlorophenyl)methyl)-4-methyl-2,5-dioxoimidazolidine-4-carboxamide

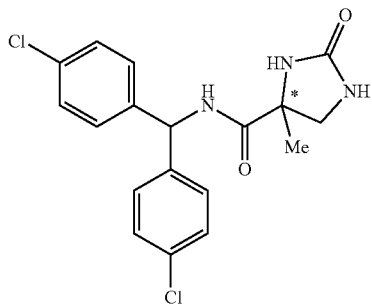 [SMILES: CC1(C(=O)NC(c2ccc(Cl)cc2)c2ccc(Cl)cc2)CNC(=O)N1]

Step 1: Ethyl 3-((bis(4-chlorophenyl)methyl)amino)-2-((boc)amino)-3-oxopropanoate. To a solution of 2-((boc)amino)-3-ethoxy-3-oxopropanoic acid (0.80 g, 3.2 mmol), bis(4-chlorophenyl)methanamine (0.98 g, 3.9 mmol) and TEA (1.4 mL, 9.7 mmol) in DMF (10 mL) was added T₃P® (3.1 g, 4.9 mmol, 50% in DMF) at 0° C. The mixture was stirred at rt for 1 h. Then the mixture was washed with water, and extracted with EtOAc. The combined organic layers were washed with brine, dried over $Na_2SO_4$, and filtered. The filtrate was concentrated in vacuo. The resulting residue was purified silica gel chromatography (25% EtOAc:PE) to give the title compound.

Step 2: Ethyl 3-((bis(4-chlorophenyl)methyl)amino)-2-((boc)amino)-2-methyl-3-oxopropanoate. To a mixture of ethyl 3-((bis(4-chlorophenyl)methyl)amino)-2-((boc)amino)-3-oxopropanoate (1.0 g, 2.0 mmol) and $K_2CO_3$ (0.86 g, 6.2 mmol) in DMF (10 mL) was added MeI (0.16 mL, 2.5 mmol). The mixture was stirred at rt for 12 h, then water was added, and the mixture was extracted with EtOAc. The combined organic layers were washed with brine, dried over $Na_2SO_4$, filtered and concentrated in vacuo. The resulting residue was purified by silica gel chromatography (20-46% EtOAc:PE) to give the title compound.

Step 3: Ethyl 2-amino-3-((bis(4-chlorophenyl)methyl)amino)-2-methyl-3-oxopropanoate. To a mixture of ethyl 3-((bis(4-chlorophenyl)methyl)amino)-2-((boc)amino)-2-methyl-3-oxopropanoate (0.79 g, 1.6 mmol) in EtOAc (10 mL) was added HCl (8.0 mL, 32 mmol, 4 N in EtOAc). The mixture was stirred at rt for 1 h, concentrated in vacuo to give title compound.

Step 4: Ethyl 3-((bis(4-chlorophenyl)methyl)amino)-2-methyl-3-oxo-2-ureidopropanoate. A solution of ethyl 2-amino-3-((bis(4-chlorophenyl)methyl)amino)-2-methyl-3-oxopropanoate (0.85 g, 2.2 mmol) and potassium cyanate (0.23 g, 2.8 mmol) in THF (7 mL) and water (3.5 mL) was stirred at 50° C. for 12 h. Then the mixture was concentrated in vacuo. The resulting residue was purified by reverse phase HPLC (55:45 to 31:69; water (0.1% TFA):MeCN (0.1% TFA)), followed by lyophilization to give the title compound.

Step 5: (R and S)—N-(bis(4-chlorophenyl)methyl)-4-methyl-2,5-dioxoimidazolidine-4-carboxamide. To a stirred refluxing solution of ethyl 3-((bis(4-chlorophenyl)methyl)amino)-2-methyl-3-oxo-2-ureidopropanoate (0.16 g, 0.36 mmol) in EtOH (3 mL) was added sodium ethanolate (0.76 mL, 0.38 mmol). The mixture was stirred at 90° C. for 12 h, then concentrated in vacuo. The solid was filtered off, and the filtrate was purified by reverse phase HPLC (51:49 to 31:69; water (0.1% TFA):MeCN (0.1% TFA)), followed by lyophilization to give the title compound.

Step 6: (R or S)—N-(bis(4-chlorophenyl)methyl)-4-methyl-2,5-dioxoimidazolidine-4-carboxamide. (R and S)—N-(bis(4-chlorophenyl)methyl)-4-methyl-2,5-dioxoimidazolidine-4-carboxamide was resolved by chiral-SFC (method N) to give the title compounds: first eluted enantiomer 20A (R or S)—N-(bis(4-chlorophenyl)methyl)-4-methyl-2,5-dioxoimidazolidine-4-carboxamide, and second eluted enantiomer 20B (R or S)—N-(bis(4-chlorophenyl)methyl)-4-methyl-2,5-dioxoimidazolidine-4-carboxamide. Enantiomer 20A: LRMS m/z (M+H): calculated 392.1, observed 392.2. ¹H NMR (500 MHz, $CD_3CN$) δ 7.55-7.61 (m, 1H), 7.29-7.42 (m, 4H), 7.13-7.26 (m, 4H), 6.54 (s, 1H), 6.06-6.12 (m, 1H), 1.57-1.65 (m, 3H). Enantiomer 20B: LRMS m/z (M+H): calculated 392.1, observed 392.2. ¹H NMR (500 MHz, $CD_3CN$) δ 7.55-7.63 (m, 1H), 7.33-7.39 (m, 4H), 7.20-7.26 (m, 4H), 6.54 (s, 1H), 6.06-6.12 (m, 1H), 1.61 (s, 3H).

Examples 21A and 21B (R)—N-(bis(4-chlorophenyl)methyl)-3-(2-hydroxyethyl)-2-oxoimidazolidine-4-carboxamide and (S)—N-(bis(4-chlorophenyl)methyl)-3-(2-hydroxyethyl)-2-oxoimidazolidine-4-carboxamide

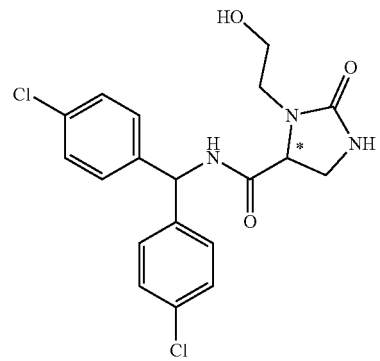 [SMILES: O=C(NC(c1ccc(Cl)cc1)c1ccc(Cl)cc1)C1CNC(=O)N1CCO]

Step 1: 3-(((benzyloxy)carbonyl)amino)-2-((boc)amino)propanoic acid. A solution of 3-amino-2-((boc)amino)propanoic acid (4.0 g, 20 mmol) and $Na_2CO_3$ (4.6 g, 43 mmol) in water (30 mL) was stirred for 3 min, then 1,4-Dioxane (30 mL) was added. After 5 min, benzyl carbonochloridate (3.1 mL, 22 mmol) was added dropwise at 0° C. Then reaction mixture was stirred at rt for 3 h, then poured into water and washed with EtOAc. Then 2 N HCl was added until pH~2, and the mixture was extracted with EtOAc. The organic layer was separated, washed with brine, dried over $Na_2SO_4$ and filtered. The filtrate was concentrated in vacuo to give the title compound.

Step 2. Benzyl tert-butyl (3-((bis(4-chlorophenyl)methyl)amino)-3-oxopropane-1,2-diyl)dicarbamate. To a mixture of 3-(((benzyloxy)carbonyl)amino)-2-((boc)amino)propanoic acid (2.0 g, 5.9 mmol), bis(4-chlorophenyl)methanamine (1.6 g, 6.2 mmol) and DIEA (3.1 mL, 18 mmol) in DMF (25 mL) was added $T_3P$® (5.6 g, 8.9 mmol, 50% in DMF) at 0° C. The mixture was stirred at rt for 2 h. Then water was added, and the mixture was extracted with EtOAc. The combined organic layers were filtered, and the resulting solid was washed with PE and the filtrate was dried in vacuo to give the title compound.

Step 3. Benzyl (2-amino-3-((bis(4-chlorophenyl)methyl)amino)-3-oxopropyl)carbamate hydrochloride. To a mixture of benzyl tert-butyl (3-((bis(4-chlorophenyl)methyl)amino)-3-oxopropane-1,2-diyl)dicarbamate (2.0 g, 3.5 mmol) in EtOAc (10 mL) was added HCl (8.0 mL, 32 mmol, 4 N in EtOAc). The mixture was stirred at rt for 5 h, then concentrated in vacuo to give the title compound.

Step 4: benzyl (3-((bis(4-chlorophenyl)methyl)amino)-2-((2-hydroxyethyl)amino)-3-oxo-propyl)carbamate. A mixture of benzyl (2-amino-3-((bis(4-chlorophenyl)methyl)amino)-3-oxopropyl)carbamate hydrochloride (0.50 g, 1.1 mmol), 2-bromoethanol (0.19 mL, 2.6 mmol) and $K_2CO_3$ (0.29 g, 2.1 mmol) in MeCN (6 mL) was stirred at 80° C. for 24 h. The mixture was then filtered and purified by reverse phase HPLC (66:34 to 46:54; water (0.1% TFA):MeCN (0.1% TFA)), followed by lyophilization to give the title compound.

Step 5: (R and S)—N-(bis(4-chlorophenyl)methyl)-3-(2-hydroxyethyl)-2-oxoimidazolidine-4-carboxamide. To a solution of benzyl (3-((bis(4-chlorophenyl)methyl)amino)-2-((2-hydroxy-ethyl)amino)-3-oxopropyl)carbamate (0.30 g, 0.58 mmol) in MeCN (4 mL) was added potassium 2-methylpropan-2-olate (1.2 mL, 1.2 mmol). The reaction was stirred at 80° C. for 2 h, then the mixture was filtered and purified by reverse phase HPLC (61:39 to 46:54; water (0.1% TFA):MeCN (0.1% TFA)), followed by lyophilization to give the title compound.

Step 6: (R or S)—N-(bis(4-chlorophenyl)methyl)-3-(2-hydroxyethyl)-2-oxoimidazolidine-4-carboxamide. The (R and S)—N-(bis(4-chlorophenyl)methyl)-3-(2-hydroxyethyl)-2-oxoimidazolidine-4-carboxamide was resolved by chiral-SFC (Phenomenex-Amylose-1, co-solvent: 45% EtOH (0.1% $NH_3·H_2O$)) to give the title compounds: first eluted enantiomer 21A (R or S)—N-(bis(4-chlorophenyl)methyl)-3-(2-hydroxyethyl)-2-oxoimidazolidine-4-carboxamide, and second eluted enantiomer 21B (R or S)—N-(bis(4-chlorophenyl)methyl)-3-(2-hydroxyethyl)-2-oxoimidazolidine-4-carboxamide. Enantiomer 21A: LRMS m/z (M+H): calculated 408.1, observed 408.0. $^1$H NMR (500 MHz, $CD_3CN$) δ 7.90-7.98 (m, 1H), 7.34-7.39 (m, 4H), 7.23-7.28 (m, 4H), 6.11-6.17 (m, 1H), 4.90 (br s, 1H), 4.23-4.29 (m, 1H), 3.60-3.69 (m, 2H), 3.46-3.52 (m, 1H), 3.36 (t, J=5.5 Hz, 1H), 3.18-3.26 (m, 1H), 3.16-3.19 (m, 2H). Enantiomer 21B: LRMS m/z (M+H): calculated 408.1, observed 408.0. $^1$H NMR (500 MHz, $CD_3CN$) δ 7.91-7.99 (m, 1H), 7.34-7.38 (m, 4H), 7.23-7.29 (m, 4H), 6.11-6.17 (m, 1H), 4.91 (br s, 1H), 4.24-4.30 (m, 1H), 3.59-3.69 (m, 2H), 3.43-3.53 (m, 1H), 3.37 (br s, 1H), 3.18-3.26 (m, 1H), 3.16-3.19 (m, 2H).

Examples 22A and 22B (S)—N—((R)-(4-chlorophenyl)(2-(trifluoromethyl)-1H-imidazol-4-yl)methyl)-2-oxoimidazolidine-4-carboxamide and (S)—N—((S)-(4-chlorophenyl)(2-(trifluoromethyl)-1H-imidazol-4-yl)methyl)-2-oxoimidazolidine-4-carboxamide

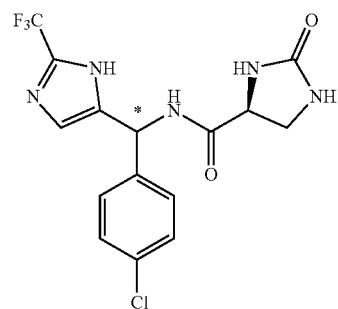 [SMILES: O=C1NC[C@@H](C(=O)NC(c2ccc(Cl)cc2)c2cnc(C(F)(F)F)[nH]2)N1]

Step 1: 2-(4-chlorophenyl)-2-(1,3-dioxoisoindolin-2-yl) acetic acid. A solution of 2-amino-2-(4-chlorophenyl)acetic acid (3.0 g, 16 mmol), AcOH (42 mL) and pyridine (28 mL) was stirred at 120° C. for 10 h. Then the reaction was filtered, and the filtrate was diluted with water and extracted with EtOAc. The combined organic layers were washed with brine, dried over $Na_2SO_4$, filtered and concentrated in vacuo. The resulting residue was purified by silica gel chromatography (0-15% DCM:MeOH) to give the title compound.

Step 2: 2-(3-bromo-1-(4-chlorophenyl)-2-oxopropyl) isoindoline-1,3-dione. To a solution of 2-(4-chlorophenyl)-2-(1,3-dioxoisoindolin-2-yl)acetic acid (1.0 g, 3.2 mmol) in DCM (15 mL) was added oxalyl dichloride (0.80 g, 6.3 mmol). The mixture was stirred at 16° C. for 11, then concentrated in vacuo. The resulting residue was suspended in DCM (15 mL), and then (diazomethyl) trimethylsilane (6.3 mL, 13 mmol) was added at −20° C. The mixture was stirred at 16° C. for 2 h, then cooled to −20° C. followed by the dropwise addition of hydrogen bromide (3.0 mL, 3.2 mmol). The reaction was stirred at 16° C. for 2 h, then quenched with sat. $NaHCO_3$ solution at 0° C., and extracted with EtOAc. The combined organic layers were dried over $Na_2SO_4$, filtered, and the filtrate was concentrated in vacuo to give the title compound.

Step 3: 2-((4-chlorophenyl)(2-(trifluoromethyl)-1H-imidazol-4-yl)methyl)isoindoline-1,3-dione. To a solution of 2-(3-bromo-1-(4-chlorophenyl)-2-oxopropyl)isoindoline-1,3-dione (1.0 g crude) and $NaHCO_3$ (0.40 g, 4.8 mmol) in THF (10 mL) was added 2,2,2-trifluoroacetimidamide (0.27 g, 2.4 mmol). The mixture was stirred at 60° C. for 11 h, then diluted with water and extracted with EtOAc. The combined organic layers were dried over $Na_2SO_4$, filtered, and the filtrate was concentrated in vacuo. The resulting residue was purified by prep. silica gel TLC (25% EtOAc:PE) to give the title compound.

Step 4: (4-chlorophenyl)(2-(trifluoromethyl)-1H-imidazol-5-yl)methanamine 2,2,2-trifluoroacetate. To a solution of 2-((4-chlorophenyl)(2-(trifluoromethyl)-1H-imidazol-4-yl)methyl)-isoindoline-1,3-dione (0.20 g, 0.49 mmol) in EtOH (3 mL) was added $N_2H_4·H_2O$ (74 mg, 1.5 mmol). The mixture was stirred at 16° C. for 11 h, then diluted with water and MeCN. The residue was purified by reverse phase HPLC (80:20 to 50:50; water (0.1% TFA):MeCN (0.1% TFA)), followed by lyophilization to give the title compound.

Step 5: (S)—N—((R and S)-(4-chlorophenyl)(2-(trifluoromethyl)-1H-imidazol-4-yl)methyl)-2-oxoimidazolidine-4-carboxamide. To a solution of (4-chlorophenyl)(2-(trifluoromethyl)-1H-imidazol-5-yl)methanamine 2,2,2-trifluoroacetate (58 mg, 0.21 mmol) in DMF (2 mL) was added (S)-2-oxoimidazolidine-4-carboxylic acid (27 mg, 0.21 mmol) and TEA (43 mg, 0.42 mmol). Then T$_3$P® (0.13 g, 0.42 mmol) was added, and the mixture was stirred at 16° C. for 11 h. The mixture was then diluted with MeCN and purified by reverse phase HPLC (83:17 to 53:47; water (0.1% TFA):MeCN (0.1% TFA)), followed by lyophilization to give the title compound.

Step 6: (S)—N—((R or S)-(4-chlorophenyl)(2-(trifluoromethyl)-1H-imidazol-4-yl)methyl)-2-oxoimidazolidine-4-carboxamide. (S)—N—((R and S)-(4-chlorophenyl)(2-(trifluoromethyl)-1H-imidazol-4-yl)methyl)-2-oxoimidazolidine-4-carboxamide was subject to chiral-SFC (method H) to give the title compounds: first eluted diastereomer 22A (S)—N—((R or S)-(4-chlorophenyl)(2-(trifluoromethyl)-1H-imidazol-4-yl)methyl)-2-oxoimidazolidine-4-carboxamide, and second eluted diastereomer 22B (S)—N—((R or S)-(4-chlorophenyl)(2-(trifluoromethyl)-1H-imidazol-4-yl)methyl)-2-oxoimidazolidine-4-carboxamide. Diastereomer 22A: LRMS m/z (M+H): calculated 388.1, observed 388.0. $^1$H NMR (400 MHz, CD$_3$OD) δ 7.33-7.39 (m, 4H), 6.98 (s, 1H), 6.10-6.28 (m, 1H), 4.33-4.38 (m, 1H), 3.75-3.80 (m, 1H), 3.45-3.49 (m, 1H). Diastereomer 22B: LRMS m/z (M+H): calculated 388.1, observed 388.0. $^1$H NMR (400 MHz, CD$_3$OD) δ 7.29-7.45 (m, 4H), 6.99 (s, 1H), 6.18 (s, 1H), 4.33-4.38 (m, 1H), 3.75-3.80 (m, 1H), 3.45-3.49 (m, 1H).

Examples 23A, 23B, 23C and 23D (S)—N—((R)-1-(3-chloro-2,4-difluorophenyl)-2-((cis)-4-(trifluoromethyl)cyclohexyl)ethyl)-2-oxoimidazolidine-4-carboxamide, (S)—N—((R)-1-(3-chloro-2,4-difluorophenyl)-2-((trans)-4-(trifluoromethyl)cyclohexyl)ethyl)-2-oxoimidazolidine-4-carboxamide, (S)—N—((S)-1-(3-chloro-2,4-difluorophenyl)-2-((trans)-4-(trifluoromethyl)cyclohexyl)ethyl)-2-oxoimidazolidine-4-carboxamide and (S)—N—((S)-1-(3-chloro-2,4-difluorophenyl)-2-((cis)-4-(trifluoromethyl)cyclohexyl)ethyl)-2-oxoimidazolidine-4-carboxamide

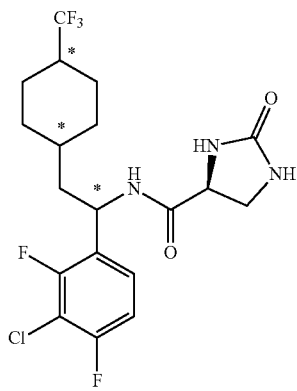 [SMILES: O=C1NC[C@@H](C(=O)NC(CC2CCC(C(F)(F)F)CC2)c2ccc(F)c(Cl)c2F)N1]

Step 1: tert-butyl 2-(4-(trifluoromethyl)cyclohexylidene)acetate. To a mixture of NaH (0.52 g, 13 mmol) in THF (20 mL) was added tert-butyl 2-(diethoxyphosphoryl)acetate (3.0 g, 12 mmol) dropwise at 0° C. The mixture was stirred for 0.5 h at rt, then 4-(trifluoromethyl)-cyclohexan-1-one (1.5 g, 9.0 mmol) was added slowly at 0° C. The reaction was allowed to warm slowly to rt and stirred at rt for 8 h. Then the mixture was concentrated in vacuo. The resulting residue was extracted with DCM. The organic layer was dried over Na$_2$SO$_4$, filtered and concentrated in vacuo. The resulting residue was purified by silica gel chromatography (15% EtOAc:PE) to give the title compound.

Step 2: tert-butyl 2-(4-(trifluoromethyl)cyclohexyl)acetate. To a solution of tert-butyl 2-(4-(trifluoromethyl)cyclohexylidene)acetate (2.3 g, 8.7 mmol) in MeOH (30 mL) was added Pd/C (1.0 g, 10% in activated carbon) under a N$_2$ atmosphere. The mixture was degassed and backfilled with H$_2$ (3 times). The resulting mixture was stirred under H$_2$ (pressure: 50 psi) at rt for 12 h. Then the catalyst was filtered off, and the filtrate was concentrated in vacuo to give the title compound.

Step 3: 2-(4-(trifluoromethyl)cyclohexyl)acetic acid. To a solution of tert-butyl 2-(4-(trifluoromethyl)cyclohexyl)acetate (1.9 g crude) in DCM (15 mL) was added TFA (4.0 mL, 52 mmol) and the resulting mixture was stirred at rt for 3 h. The mixture was then directly concentrated in vacuo to give the title compound.

Step 4: N-methoxy-N-methyl-2-(4-(trifluoromethyl)cyclohexyl)acetamide. To a solution of 2-(4-(trifluoromethyl)cyclohexyl)acetic acid (1.5 g crude) in DCM (20 mL) was added CDI (1.2 g, 7.1 mmol), and the mixture was stirred at rt for 1 h. Then TEA (2.0 mL, 14 mmol) and N,O-dimethylhydroxylamine hydrochloride (0.70 g, 7.1 mmol) were added, and the resulting mixture was stirred at rt for 1 h. Then water was added, and the mixture was extracted with DCM. The combined organic layers were dried over Na$_2$SO$_4$, filtered and concentrated in vacuo. The resulting residue was purified by silica gel chromatography (25% EtOAc:PE) to give the title compound.

Step 5: 1-(3-chloro-2,4-difluorophenyl)-2-(4-(trifluoromethyl)cyclohexyl)ethan-1-one. To a solution of 1-bromo-3-chloro-2,4-difluorobenzene (0.90 g, 4.0 mmol) in THF (1 mL) was added iPrMgCl (1.7 mL, 3.4 mmol, 2 M in THF) at 0° C. The mixture was allowed to stir for 2 h, and added to a solution of N-methoxy-N-methyl-2-(4-(trifluoromethyl)cyclohexyl)acetamide (0.30 g, 1.2 mmol) in THF (2 mL) at 0° C. The resulting mixture was stirred at rt for 12 h, then quenched with sat. NH$_4$Cl and extracted with EtOAc. The combined organic layers were dried over Na$_2$SO$_4$, filtered and concentrated in vacuo. The resulting residue was purified by silica gel chromatography (10% EtOAc:PE) to give the title compound.

Step 6: (R,Z)—N-(1-(3-chloro-2,4-difluorophenyl)-2-(4-(trifluoromethyl)cyclohexyl)ethylidene)-2-methylpropane-2-sulfinamide. A microwave tube was charged with 1-(3-chloro-2,4-difluorophenyl)-2-(4-(trifluoromethyl)cyclohexyl)ethan-1-one (0.31 g, 0.91 mmol), (R)-2-methylpropane-2-sulfinamide (0.16 mg, 1.4 mmol), Ti(OEt)$_4$ (0.37 mL, 1.8 mmol) and toluene (3 mL). The mixture was microwaved at 105° C. for 30 min and then cooled to rt. The reaction was diluted with water and EtOAc. The mixture was filtered and extracted with EtOAc. The combined organic layers were dried over Na$_2$SO$_4$, filtered and concentrated in vacuo to give the title compound.

Step 7: (R)—N-(1-(3-chloro-2,4-difluorophenyl)-2-(4-(trifluoromethyl)cyclohexyl)ethyl)-2-methylpropane-2-sulfinamide. A solution of (R,Z)—N-(1-(3-chloro-2,4-difluorophenyl)-2-(4-(trifluoromethyl)cyclohexyl)ethylidene)-2-methylpropane-2-sulfinamide (0.30 g crude) in THF (3 mL) and water (0.01 mL) was cooled to −78° C. Then NaBH₄ (38 mg, 1.0 mmol) was added, and the mixture was stirred at −78° C. for 20 min. The reaction was then quenched with sat. NaHCO₃ and extracted with EtOAc. The combined organic layers were dried over Na₂SO₄, filtered and concentrated in vacuo. The resulting residue was purified by silica gel chromatography (35% EtOAc:PE) to give the title compound.

Step 8: 1-(3-chloro-2,4-difluorophenyl)-2-(4-(trifluoromethyl)cyclohexyl)ethan-1-amine hydrochloride. To a solution of (R)—N-(1-(3-chloro-2,4-difluorophenyl)-2-(4-(trifluoromethyl)-cyclohexyl)ethyl)-2-methylpropane-2-sulfinamide (0.25 g, 0.56 mmol) in THF (3 mL) was added HCl (0.5 mL, 2 mmol, 4 N in MeOH). The reaction was stirred at rt for 1 h, then directly concentrated to give the title compound.

Step 9: (S)—N-(-1-(3-chloro-2,4-difluorophenyl)-2-(4-(trifluoromethyl)cyclohexyl)ethyl)-2-oxoimidazolidine-4-carboxamide. To a solution of 1-(3-chloro-2,4-difluorophenyl)-2-(4-(trifluoromethyl)cyclohexyl)ethan-1-amine hydrochloride (0.20 g crude), (S)-2-oxoimidazolidine-4-carboxylic acid (70 mg, 0.54 mmol) and DIPEA (0.28 mL, 1.6 mmol) in MeCN (2 mL) was added T₃P® (0.51 g, 0.81 mmol, 50% in EtOAc) at 0° C. The reaction was stirred at rt for 1 h, and then filtered. The filtrate was purified by reverse phase HPLC (44:56 to 24:76; water (0.1% TFA): MeCN (0.1% TFA)) followed by lyophilization to give title compound.

Step 10: (S)—N—((R or S)-1-(3-chloro-2,4-difluorophenyl)-2-((cis or trans)-4-(trifluoromethyl)-cyclohexyl)ethyl)-2-oxoimidazolidine-4-carboxamide. (S)—N-(-1-(3-chloro-2,4-difluorophenyl)-2-(4-(trifluoromethyl)cyclohexyl)ethyl)-2-oxoimidazolidine-4-carboxamide was resolved by chiral-SFC (method O) then chiral-SFC (method P) and then (method Q) to give the title compounds: First eluted isomer 23A (S)—N—((R or S)-1-(3-chloro-2,4-difluorophenyl)-2-((cis or trans)-4-(trifluoromethyl)cyclohexyl)ethyl)-2-oxo-imidazolidine-4-carboxamide, second eluted isomer 23B (S)—N—((R or S)-1-(3-chloro-2,4-difluorophenyl)-2-((cis or trans)-4-(trifluoro-methyl)cyclohexyl)ethyl)-2-oxoimidazolidine-4-carboxamide, third eluted isomer 23C (S)—N—((R or S)-1-(3-chloro-2,4-difluorophenyl)-2-((cis or trans)-4-(trifluoromethyl)cyclohexyl)ethyl)-2-oxoimidazolidine-4-carboxamide, and fourth eluted isomer 23D (S)—N—((R or S)-1-(3-chloro-2,4-difluorophenyl)-2-((cis or trans)-4-(trifluoromethyl)cyclohexyl)ethyl)-2-oxoimidazolidine-4-carboxamide. Isomer 23A: LRMS m/z (M+H): calculated 454.1, observed 454.1. ¹H NMR (400 MHz, CD₃OD) δ 7.36 (dt, J=6.0, 8.4 Hz, 1H), 7.11 (dt, J=1.6, 8.8 Hz, 1H), 5.29-5.33 (m, 1H), 4.27-4.31 (m, 1H), 3.78 (t, J=9.6 Hz, 1H), 3.35-3.39 (m, 1H), 2.01-2.13 (m, 1H), 1.78-2.01 (m, 5H), 1.57-1.63 (m, 1H), 1.29-1.35 (m, 2H), 1.21-1.28 (m, 1H), 0.98-1.15 (m, 2H). Isomer 23B: LRMS m/z (M+H): calculated 454.1, observed 454.1. ¹H NMR (400 MHz, CD₃OD) δ 7.37 (dt, J=5.6, 8.4 Hz, 1H), 7.11 (dt, J=1.6, 8.8 Hz, 1H), 5.24 (t, J=7.6 Hz, 1H), 4.27-4.31 (m, 1H), 3.77 (t, J=9.6 Hz, 1H), 3.35-3.39 (m, 1H), 2.10-2.24 (m, 1H), 1.82-1.89 (m, 2H), 1.54-1.72 (m, 9H). Isomer 23C: LRMS m/z (M+H): calculated 454.1, observed 454.1. ¹H NMR (400 MHz, CD₃OD) δ 7.34 (dt, J=6.0, 8.4 Hz, 1H), 7.10 (dt, J=1.6, 8.8 Hz, 1H), 5.26-5.30 (m, 1H), 4.29-4.33 (m, 1H), 3.77 (t, J=9.6 Hz, 1H), 3.33-3.37 (m, 1H), 1.78-2.10 (m, 6H), 1.57-1.64 (m, 1H), 1.31-1.36 (m, 2H), 1.22-1.28 (m, 1H), 0.98-1.16 (m, 2H). Isomer 23D: LRMS m/z (M+H): calculated 454.1, observed 454.1. ¹H NMR (400 MHz, CD₃OD) δ 7.35 (dt, J=6.0, 8.4 Hz, 1H), 7.11 (dt, J=1.6, 8.8 Hz, 1H), 5.21 (t, J=7.6 Hz, 1H), 4.29-4.33 (m, 1H), 3.76 (t, J=9.6 Hz, 1H), 3.34-3.38 (m, 1H), 2.12-2.24 (m, 1H), 1.81-1.88 (m, 2H), 1.55-1.72 (m, 9H).

TABLE 2

The compounds of Examples 24A-26D were prepared according to a synthetic procedure similar to the synthetic procedure for examples 23A, 23B, 23C and 23D.

| Example | Structure | Name | Calc'd [M + H]+ | Observed [M + H]⁺ | Conditions |
| --- | --- | --- | --- | --- | --- |
| 24A | 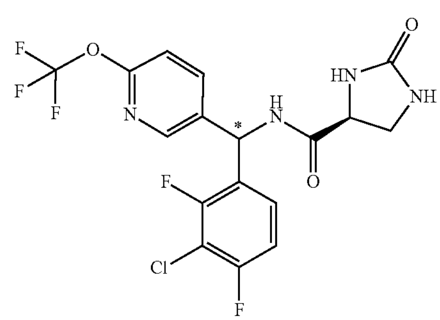 [SMILES: O=C1NC[C@@H](C(=O)NC(c2ccc(OC(F)(F)F)nc2)c2ccc(F)c(Cl)c2F)N1] | (4S)-N-{(R or S)- (3-chloro-2,4-difluorophenyl)[6-(trifluoromethoxy)pyridin-3-yl]methyl}-2-oxoimidazolidine-4-carboxamide | 451.1 | 451.1 | Chiral method D, peak 1 |

TABLE 2-continued

The compounds of Examples 24A-26D were prepared according to a synthetic procedure similar to the synthetic procedure for examples 23A, 23B, 23C and 23D.

| Example | Structure | Name | Calc'd [M + H]+ | Observed [M + H]+ | Conditions |
|---|---|---|---|---|---|
| 24B | 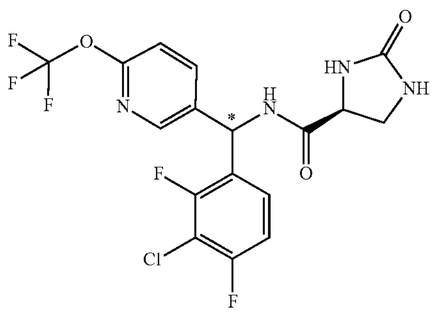 [SMILES: O=C1NC[C@@H](C(=O)NC(c2ccc(OC(F)(F)F)nc2)c2ccc(F)c(Cl)c2F)N1] | (4S)-N-{(R or S)-(3-chloro-2,4-difluorophenyl)[6-(trifluoromethoxy)pyridin-3-yl]methyl}-2-oxoimidazolidine-4-carboxamide | 451.1 | 451.1 | Chiral method D, peak 2 |
| 25A | 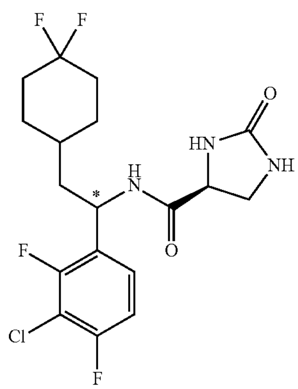 [SMILES: O=C1NC[C@@H](C(=O)NC(CC2CCC(F)(F)CC2)c2ccc(F)c(Cl)c2F)N1] | (S)-N-((R or S)-1-(3-chloro-2,4-difluorophenyl)-2-(4,4-difluorocyclohexyl)ethyl)-2-oxoimidazolidine-4-carboxamide | 422.1 | 422.1 | Chiral method R, peak 1 |
| 25B | 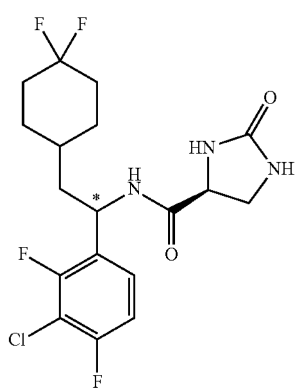 [SMILES: O=C1NC[C@@H](C(=O)NC(CC2CCC(F)(F)CC2)c2ccc(F)c(Cl)c2F)N1] | (S)-N-((R or S)-1-(3-chloro-2,4-difluorophenyl)-2-(4,4-difluorocyclohexyl)ethyl)-2-oxoimidazolidine-4-carboxamide | 422.1 | 422.2 | Chiral method R, peak 2 |
| 26A | 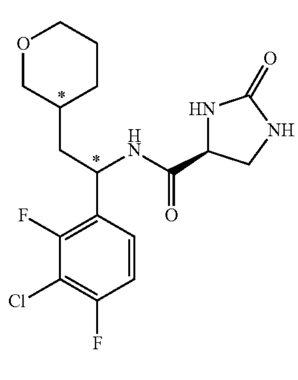 [SMILES: O=C1NC[C@@H](C(=O)NC(CC2CCCOC2)c2ccc(F)c(Cl)c2F)N1] | (S)-N-((R or S)-1-(3-chloro-2,4-difluorophenyl)-2-((R or S)-tetrahydro-2H-pyran-3-yl)ethyl)-2-oxoimidazolidine-4-carboxamide | 388.1 | 388.1 | Chiral method C, Peak 1 |

TABLE 2-continued

The compounds of Examples 24A-26D were prepared according to a synthetic procedure similar to the synthetic procedure for examples 23A, 23B, 23C and 23D.

| Example | Structure | Name | Calc'd [M + H]+ | Observed [M + H]+ | Conditions |
|---------|-----------|------|-----------------|-------------------|------------|
| 26B | 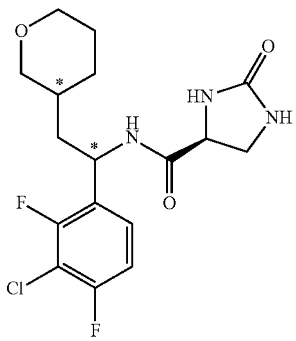 [SMILES: O=C1NC[C@@H](C(=O)NC(CC2CCCOC2)c2ccc(F)c(Cl)c2F)N1] | (S)-N-((R or S)-1-(3-chloro-2,4-difluorophenyl)-2-((R or S)-tetrahydro-2H-pyran-3-yl)ethyl)-2-oxoimidazolidine-4-carboxamide | 388.1 | 388.1 | Chiral method C, Peak 2 |
| 26C | 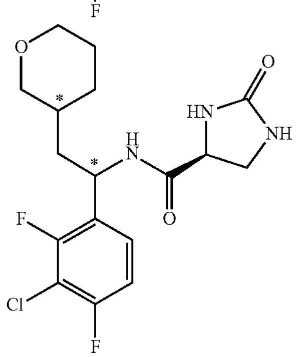 | (S)-N-((R or S)-1-(3-chloro-2,4-difluorophenyl)-2-((R or S)-tetrahydro-2H-pyran-3-yl)ethyl)-2-oxoimidazolidine-4-carboxamide | 388.1 | 388.1 | Chiral method C, Peak 3 |
| 26D | 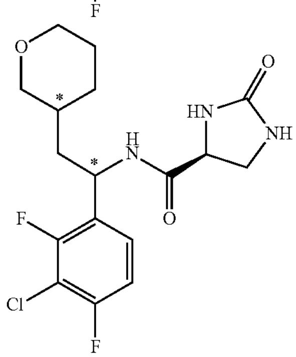 | (S)-N-((R or S)-1-(3-chloro-2,4-difluorophenyl)-2-((R or S)-tetrahydro-2H-pyran-3-yl)ethyl)-2-oxoimidazolidine-4-carboxamide | 388.1 | 388.1 | Chiral method C, Peak 4 |

Examples 27A and 27B (S)—N—((R)-(3-chloro-2,4-difluorophenyl)(3-(trifluoromethyl)bicyclo[1.1.1]pentan-1-yl)methyl)-2-oxoimidazolidine-4-carboxamide and (S)—N—((S)-(3-chloro-2,4-difluorophenyl)(3-(trifluoromethyl)bicyclo[1.1.1]pentan-1-yl)methyl)-2-oxoimidazolidine-4-carboxamide

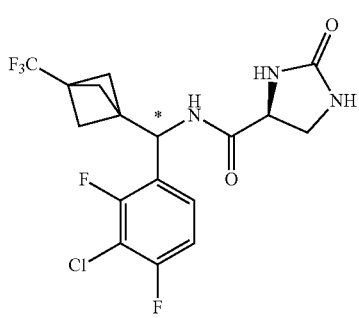 [SMILES: O=C1NC[C@@H](C(=O)NC(c2ccc(F)c(Cl)c2F)C23CC(C(F)(F)F)(C2)C3)N1]

Step 1: N-methoxy-N-methyl-3-(trifluoromethyl)bicyclo[1.1.1]pentane-1-carboxamide. To a mixture of 3-(trifluoromethyl)bicyclo[1.1.1]pentane-1-carboxylic acid (0.30 g, 1.7 mmol) in DCM (20 mL) was added CDI (0.30 g, 1.8 mmol). The reaction was stirred at rt for 1 h, then N,O-dimethylhydroxylamine hydrochloride (0.19 g, 2.0 mmol) and TEA (0.29 mL, 2.0 mmol) were added. The reaction was stirred for 16 h, then diluted with water and extracted with EtOAc. The combined organic layers were washed with brine, dried over $Na_2SO_4$, filtered and concentrated in vacuo. The resulting residue was purified by silica gel chromatography (0-30% EtOAc:PE) to give the title compound.

Step 2: (3-chloro-2,4-difluorophenyl)(3-(trifluoromethyl)bicyclo[1.1.1]pentan-1-yl)methanone. To a mixture of 1-bromo-3-chloro-2,4-difluorobenzene (0.86 g, 3.8 mmol) in THF (2 mL) was added isopropyl magnesium chloride (2.9 mL, 3.8 mmol, 1.3 M toluene solution) at 0° C. The mixture was stirred at 0° C. for 2 h, then N-methoxy-N-methyl-3-(trifluoromethyl)bicyclo-[1.1.1]pentane-1-carboxamide (0.28 g, 1.3 mmol) was added at 0° C. The reaction mixture was stirred at rt for 16 h, then water was added and the mixture was extracted with EtOAc. The combined organic layers were washed with brine, dried over Na$_2$SO$_4$, filtered and concentrated in vacuo. The resulting residue was purified by prep. silica gel TLC (10% EtOAc:PE) to give the title compound.

Step 3: (3-chloro-2,4-difluorophenyl)(3-(trifluoromethyl)bicyclo[1.1.1]pentan-1-yl)methanamine. To a mixture of (3-chloro-2,4-difluorophenyl)(3-(trifluoromethyl)bicyclo[1.1.1]pentan-1-yl)methanone (0.12 g, 0.39 mmol), and NH$_4$OAc (0.45 g, 5.8 mmol) in EtOH (2 mL) was added NaCNBH$_3$ (36 mg, 0.58 mmol) at 25° C. The mixture was stirred under microwave at 130° C. for 10 min. Then the mixture was concentrated in vacuo and treated with 2 N NaOH until pH >10. The mixture was then extracted with EtOAc. The organic layer was separated, dried over Na$_2$SO$_4$, filtered, and concentrated in vacuo to give the title compound.

Step 4: (4S)—N-((3-chloro-2,4-difluorophenyl)(3-(trifluoromethyl)bicyclo[1.1.1]pentan-1-yl)methyl)-2-oxoimidazolidine-4-carboxamide. To a mixture of (S)-2-oxoimidazolidine-4-carboxylic acid (63 mg, 0.48 mmol), (3-chloro-2,4-difluorophenyl)(3-(trifluoromethyl)bicyclo-[1.1.1]pentan-1-yl)methanamine (0.10 g, 0.32 mmol) and DIEA (0.17 mL, 0.96 mmol) in DMF (1 mL) was added T$_3$P® (0.41 g, 0.64 mmol) at 20° C. The mixture was stirred at 20° C. for 12 h. Then the mixture was dissolved in water and extracted with EtOAc. The combined organic layers were washed with brine, dried over Na$_2$SO$_4$, filtered and concentrated in vacuo. The resulting residue was purified by prep. silica gel TLC (90% EtOAc:PE) to give the title compound.

Step 5: (4S)—N—((R or S)-(3-chloro-2,4-difluorophenyl)(3-(trifluoromethyl)bicyclo[1.1.1]pentan-1-yl)methyl)-2-oxoimidazolidine-4-carboxamide. (4S)—N-((3-chloro-2,4-difluorophenyl)(3-(trifluoromethyl)bicyclo[1.1.1]pentan-1-yl)methyl)-2-oxoimidazolidine-4-carboxamide was purified by chiral-SFC (method S) to give the title compounds: first eluted diastereomer 27A (4S)—N—((R or S)-(3-chloro-2,4-difluorophenyl)(3-(trifluoromethyl)bicyclo[1.1.1]pentan-1-yl)methyl)-2-oxoimidazolidine-4-carboxamide, and the second eluted diastereomer 27B (4S)—N—((R or S)-(3-chloro-2,4-difluorophenyl)(3-(trifluoromethyl)bicyclo[1.1.1]pentan-1-yl)methyl)-2-oxoimidazolidine-4-carboxamide. Diastereomer 27A: LRMS m/z (M+H): calculated 424.1, observed 424.1. $^1$H NMR (500 MHz, CD$_3$OD-d$_4$) δ 7.29-7.31 (m, 1H), 7.13-7.17 (m, 1H), 5.41 (s, 1H), 4.35-4.38 (m, 1H), 3.77 (t, J=9.5 Hz, 1H), 3.37-3.40 (m, 1H), 1.84-1.96 (m, 6H). Diastereomer 27B: LRMS m/z (M+H): calculated 424.1, observed 424.1. $^1$H NMR (500 MHz, CD$_3$OD-d$_4$) δ 7.30-7.32 (m, 1H), 7.13-7.17 (m, 1H), 5.35-5.45 (m, 1H), 4.36-4.39 (m, 1H), 3.79 (t, J=9.5 Hz, 1H), 3.41-3.44 (m, 1H), 1.84-1.96 (m, 6H).

TABLE 3

The compounds of Examples 28A-31B were prepared according to a synthetic procedure similar to the synthetic procedure for examples 27A and 27B.

| Example | Structure | Name | Calc'd [M + H]+ | Observed [M + H]+ | Conditions |
| --- | --- | --- | --- | --- | --- |
| 28A | 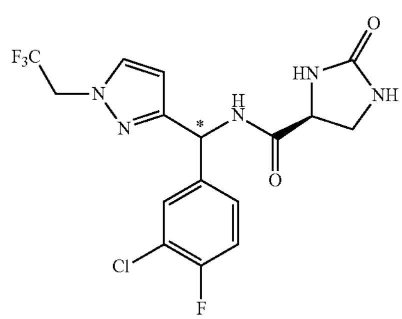 [SMILES: O=C1NC[C@@H](C(=O)NC(c2ccc(F)c(Cl)c2)c2ccn(CC(F)(F)F)n2)N1] | (4S)-N-{(R or S)-(3-chloro-4-fluorophenyl)[1-(2,2,2-trifluoroethyl)-1H-pyrazol-3-yl]methyl}-2-oxoimidazolidine-4-carboxamide | 420.1 | 420.1 | Chiral method D, peak 1 |
| 28B | 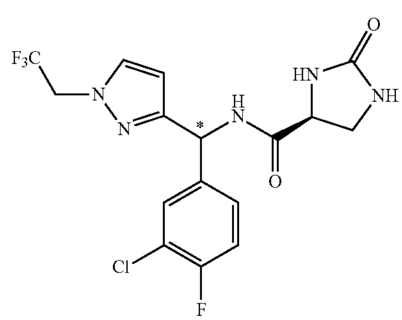 [SMILES: O=C1NC[C@@H](C(=O)NC(c2ccc(F)c(Cl)c2)c2ccn(CC(F)(F)F)n2)N1] | (4S)-N-{(R or S)-(3-chloro-4-fluorophenyl)[1-(2,2,2-trifluoroethyl)-1H-pyrazol-3-yl]methyl}-2-oxoimidazolidine-4-carboxamide | 420.1 | 420.1 | Chiral method D, peak 2 |

TABLE 3-continued

The compounds of Examples 28A-31B were prepared according to a synthetic procedure similar to the synthetic procedure for examples 27A and 27B.

| Example | Structure | Name | Calc'd [M + H]+ | Observed [M + H]+ | Conditions |
|---|---|---|---|---|---|
| 29A | 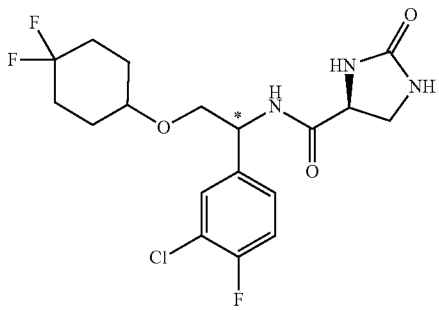 [SMILES: O=C1NC[C@@H](C(=O)NC(COC2CCC(F)(F)CC2)c2ccc(F)c(Cl)c2)N1] | (4S)-N-{1-((R or S)-3-chloro-4-fluorophenyl)-2-[(4,4-difluoro-cyclohexyl)oxy]ethyl}-2-oxoimidazolidine-4-carboxamide | 420.1 | 420.1 | Chiral method C, Peak 1 |
| 29B | 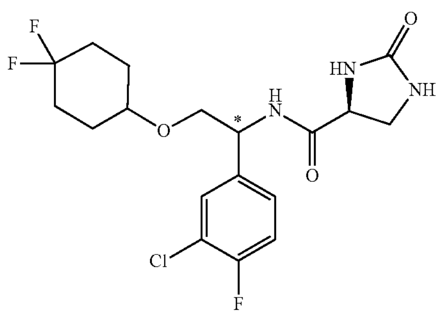 [SMILES: O=C1NC[C@@H](C(=O)NC(COC2CCC(F)(F)CC2)c2ccc(F)c(Cl)c2)N1] | (4S)-N-{1-((R or S)-3-chloro-4-fluorophenyl)-2-[(4,4-difluoro-cyclohexyl)oxy]ethyl}-2-oxoimidazolidine-4-carboxamide | 420.1 | 420.1 | Chiral method C, Peak 2 |
| 30A | 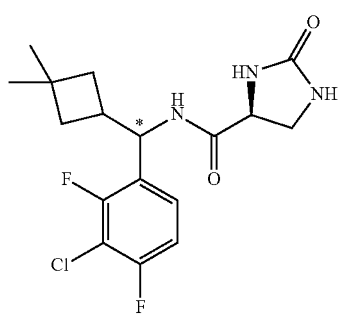 [SMILES: CC1(C)CC(C(NC(=O)[C@@H]2CNC(=O)N2)c2ccc(F)c(Cl)c2F)C1] | (4S)-N-[(R or S)-(3-chloro-2,4-di-fluoro-phenyl)(3,3-dimethylcyclobutyl)meth-yl]-2-oxoimidazolidine-4-carboxamide | 372.1 | 372.1 | Chiral method A, peak 1 |
| 30B | 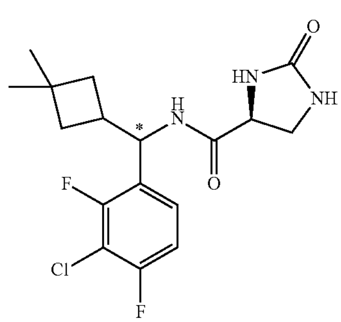 [SMILES: CC1(C)CC(C(NC(=O)[C@@H]2CNC(=O)N2)c2ccc(F)c(Cl)c2F)C1] | (4S)-N-[(R or S)- (3-chloro-2,4-di-fluorophenyl)(3,3-dimethylcyclobutyl)meth-yl]-2-oxoimidazolidine-4-carboxamide | 372.1 | 372.2 | Chiral method A, peak 2 |

TABLE 3-continued

The compounds of Examples 28A-31B were prepared according to a synthetic procedure similar to the synthetic procedure for examples 27A and 27B.

| Example | Structure | Name | Calc'd [M + H]+ | Observed [M + H]+ | Conditions |
|---|---|---|---|---|---|
| 31A | 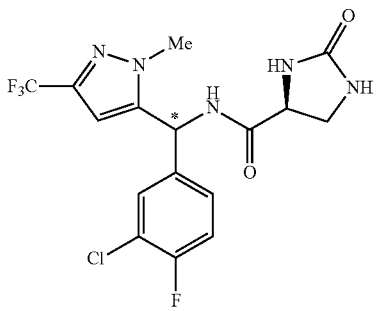 [SMILES: Cn1nc(C(F)(F)F)cc1C(NC(=O)[C@@H]1CNC(=O)N1)c1ccc(F)c(Cl)c1] | (S)-N-((R or S)-(3-chloro-4-fluorophenyl)(1-methyl-3-(trifluoromethyl)-1H-pyrazol-5-yl)methyl)-2-oxoimidazolidine-4-carboxamide | 420.1 | 420.1 | Chiral method T, Peak 1 |
| 31B | 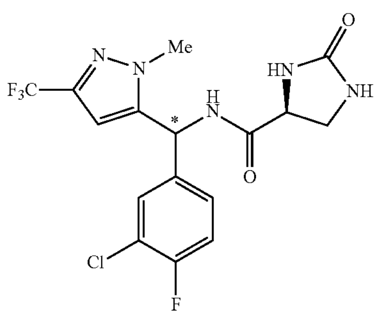 [SMILES: Cn1nc(C(F)(F)F)cc1C(NC(=O)[C@@H]1CNC(=O)N1)c1ccc(F)c(Cl)c1] | (S)-N-((R or S)-(3-chloro-4-fluorophenyl)(1-methyl-3-(trifluoromethyl)-1H-pyrazol-5-yl)methyl)-2-oxoimidazolidine-4-carboxamide | 420.1 | 420 | Chiral method T, Peak 2 |

Example 32A and 32B (S)—N—((R)-(3-chloro-4-fluorophenyl)(trans-4-(trifluoromethyl)cyclohexyl)methyl)-2-oxoimidazolidine-4-carboxamide and (S)—N—((S)-(3-chloro-4-fluorophenyl)(trans-4-(trifluoromethyl)cyclohexyl)methyl)-2-oxoimidazolidine-4-carboxamide

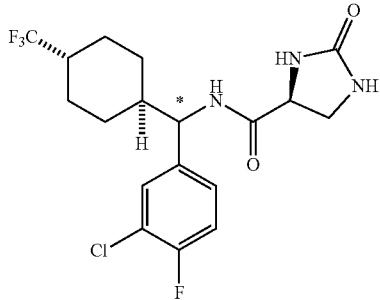 [SMILES: O=C1NC[C@@H](C(=O)NC(c2ccc(F)c(Cl)c2)[C@H]2CC[C@H](C(F)(F)F)CC2)N1]

Step 1: (3-chloro-4-fluorophenyl)(trans-4-(trifluoromethyl)cyclohexyl)methanone. To a solution of trans-4-(trifluoromethyl)cyclohexanecarboxylic acid (0.57 g, 2.9 mmol) in DCM (5 mL) at 0° C. was added (COCl)$_2$ (3.6 mL, 7.3 mmol, 2 M in DCM) and one drop of DMF. The mixture was warmed to rt, stirred for 4 hours, then heated to 40° C. and stirred for 30 minutes. The mixture was then concentrated in vacuo to give a residue, which was dissolved in THF (4 mL, solution A). In a separate flask, CuCN (0.65 g, 7.3 mmol) was suspended in THF (4 mL), cooled to 0° C., followed by the addition of 0.5 M 3-chloro-4-fluorophenylmagnesium bromide in THF (12 mL, 5.8 mmol). The mixture was stirred at 0° C. for 1 hour, then added to solution A and stirred at 0° C. for 4 hours. The reaction was then quenched with sat. NH$_4$Cl and extracted with EtOAc. The combined organic layers were dried over Na$_2$SO$_4$, filtered and concentrated in vacuo to give the title compound.

Step 2: (3-chloro-4-fluorophenyl)(trans-4-(trifluoromethyl)cyclohexyl)methanamine. A microwave tube was charged with (3-chloro-4-fluorophenyl)(trans-4-(trifluoromethyl)cyclohexyl)methanone (1.3 g, 4.2 mmol), NH$_4$OAc (2.6 g, 33 mmol) and EtOH (15 mL). The mixture was microwaved at 130° C. for 20 minutes and then cooled to rt, followed by addition of NaCNBH$_3$ (0.29 g, 4.6 mmol). The mixture was microwaved at 125° C. for 20 minutes and then cooled to rt. The reaction was then quenched with 10% aq. K$_2$CO$_3$ and extracted with EtOAc. The combined organic layers were dried over Na$_2$SO$_4$, filtered and concentrated in vacuo to give the title compound.

Step 3: (4S)—N—((R and S)-(3-chloro-4-fluorophenyl)(trans-4-(trifluoromethyl)cyclohexyl)-methyl)-2-oxoimidazolidine-4-carboxamide. To a solution of (S)-(3-chloro-4-fluorophenyl)-((1R,4S)-4-(trifluoromethyl)cyclohexyl)methanamine (0.10 g, 0.29 mmol) in dry pyridine (3 mL) were added (S)-2-oxoimidazolidine-4-carboxylic acid (56 mg, 0.43 mmol) and EDC (90 mg, 0.58 mmol). The mixture was stirred at rt overnight before being concentrated in vacuo. The residue was purified by silica gel chromatography (0-4% DCM:MeOH) to give title compound.

Step 5: (4S)—N—((R or S)-(3-chloro-4-fluorophenyl)(trans-4-(trifluoromethyl)cyclohexyl)methyl)-2-oxoimidazolidine-4-carboxamide. (S)—N—((R and S)-(3-chloro-4-fluorophenyl)(trans-4-(trifluoromethyl)cyclohexyl)methyl)-2-oxoimidazolidine-4-carboxamide was separated by chiral-SFC (method U) to give the title compounds: first eluted isomer 32A (4S)—N—((R or S)-(3-chloro-4-fluorophenyl)(trans-4-(trifluoromethyl)cyclohexyl)methyl)-2-oxoimidazolidine-4-carboxamide, and second eluted isomer 32B (4S)—N—((R or S)-(3-chloro-4-fluorophenyl)(trans-4-(trifluoro-methyl)cyclohexyl)methyl)-2-oxoimidazolidine-4-carboxamide. Isomer 32A: LRMS m/z (M+H): calculated 422.1, observed 422.2. $^1$H NMR (500 MHz, CD$_3$OD) δ 7.57 (d, J=8.8 Hz, 1H), 7.33 (dd, J=6.9, 2.0 Hz, 1H), 7.17-7.12 (m, 1H), 7.09 (t, J=8.6 Hz, 1H), 4.62 (t, J=9.1 Hz, 1H), 4.21 (dd, J=10.2, 6.1 Hz, 1H), 3.83 (t, J=9.8 Hz, 1H), 3.55 (dd, J=9.3, 6.2 Hz, 1H), 2.02-1.92 (m, 3H), 1.92-1.85 (m, 1H), 1.67 (td, J=11.9, 9.2 Hz, 1H), 1.47 (d, J=13.1 Hz, 1H), 1.33-1.17 (m, 3H), 1.10-0.99 (m, 1H), 0.97-0.84 (m, 1H). Isomer 32B: LRMS m/z (M+H): calculated 422.1, observed 422.2. $^1$H NMR (500 MHz, CD$_3$OD) δ 7.58 (s, 1H), 7.30 (s, 1H), 7.15-7.04 (m, 2H), 4.58 (t, J=8.9 Hz, 1H), 4.28 (dd, J=10.1, 6.6 Hz, 1H), 3.77 (t, J=9.7 Hz, 1H), 3.39-3.33 (m, 1H), 2.05-1.93 (m, 3H), 1.89 (d, J=14.0 Hz, 1H), 1.71-1.61 (m, 1H), 1.47 (d, J=12.8 Hz, 1H), 1.35-1.15 (m, 3H), 1.04 (q, J=12.2, 11.8 Hz, 1H), 0.98-0.78 (m, 2H).

Examples 33A and 33B (S)—N—((R)-(3-chloro-2,4-difluorophenyl)(6-(2,2,2-trifluoroethoxy)pyridin-3-yl)methyl)-2-oxoimidazolidine-4-carboxamide and (S)—N—((S)-(3-chloro-2,4-difluorophenyl)(6-(2,2,2-trifluoroethoxy)pyridin-3-yl)methyl)-2-oxoimidazolidine-4-carboxamide

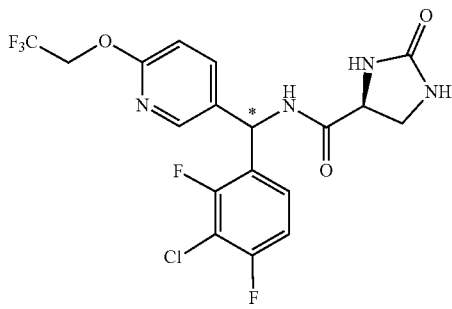 [SMILES: O=C1NC[C@@H](C(=O)NC(c2ccc(OCC(F)(F)F)nc2)c2ccc(F)c(Cl)c2F)N1]

Step 1: (E)-2-methyl-N-((6-(2,2,2-trifluoroethoxy)pyridin-3-yl)methylene)propane-2-sulfinamide. To a solution of 6-(2,2,2-trifluoroethoxy)nicotinaldehyde (2.0 g, 9.6 mmol) and 2-methylpropane-2-sulfinamide (1.2 g, 1.0 mmol) in DCM (8 mL) was added Ti(OiPr)$_4$ (6.0 mL, 20 mmol). The mixture was stirred at rt for 20 hours, then water and EtOAc were added. The mixture was stirred at rt for 20 min, and filtered through a pad of the Celite®. The organic layer was dried over Na$_2$SO$_4$, filtered and concentrated in vacuo to give the title compound.

Step 2: N-((3-chloro-2,4-difluorophenyl)(6-(2,2,2-trifluoroethoxy)pyridin-3-yl)methyl)-2-methyl propane-2-sulfinamide. To a solution of 1-bromo-3-chloro-2,4-difluorobenzene (0.28 g, 1.2 mmol) in THF was added iPrMgCl—LiCl complex (0.94 mL, 1.2 mmol, 1.3M in THF). The mixture was stirred at rt for 5 h, then (E)-2-methyl-N-((6-(2,2,2-trifluoroethoxy)pyridin-3-yl)methylene)propane-2-sulfinamide (0.20 g, 0.65 mmol) was added in one portion. The reaction was stirred at rt for 20 h, then quenched with sat. NH$_4$Cl and extracted with Et$_2$O. The separated organic layer was dried over Na$_2$SO$_4$, filtered and concentrated in vacuo to give the title compound.

Step 3: (3-chloro-2,4-difluorophenyl)(6-(2,2,2-trifluoroethoxy)pyridin-3-yl)methanamine hydrochloride. To a solution of N-((3-chloro-2,4-difluorophenyl)(6-(2,2,2-trifluoroethoxy)pyridin-3-yl)methyl)-2-methylpropane-2-sulfinamide (0.30 g, 0.65 mmol) in DCM (2 mL) and MeOH (1 mL) was added HCl (2.0 mL, 8.0 mmol, 4.0 M in 1,4-dioxane). The mixture was stirred at rt for 2 h and then concentrated in vacuo. The resulting residue was treated with Et$_2$O, and filtered to collect the solid. The solid was washed with extra Et$_2$O, and dried in vacuo to give the title compound.

Step 4: (S)—N—((R and S)-3-chloro-2,4-difluorophenyl)(6-(2,2,2-trifluoroethoxy)pyridin-3-yl)methyl)-2-oxoimidazolidine-4-carboxamide. To a solution of ((3-chloro-2,4-difluorophenyl)-(6-(2,2,2-trifluoroethoxy)pyridin-3-yl)methanamine hydrochloride (0.20 g, 0.51 mmol) and (S)-2-oxoimidazolidine-4-carboxylic acid (87 mg, 0.67 mmol) in pyridine (3 mL) was added EDC (0.16 g, 1.0 mmol). The mixture was heated to 50° C. for 18 hours and then concentrated in vacuo. The resulting residue was purified by silica gel chromatography (0-5% DCM:MeOH) to give the title compound.

Step 5: (S)—N—((R or S)-(3-chloro-2,4-difluorophenyl)(6-(2,2,2-trifluoroethoxy)pyridin-3-yl)methyl)-2-oxoimidazolidine-4-carboxamide. (S)—N—((R and S)-(3-chloro-2,4-difluorophenyl)(6-(2,2,2-trifluoroethoxy)pyridin-3-yl)methyl)-2-oxoimidazolidine-4-carboxamide was separated by chiral-SFC (method V) to give the title compounds: first eluted diastereomer 33A (S)—N—((R or S)-(3-chloro-2,4-difluorophenyl)(6-(2,2,2-trifluoroethoxy)pyridin-3-yl)methyl)-2-oxoimidazolidine-4-carboxamide, and second eluted diastereomer 33B (S)—N—((R or S)-(3-chloro-2,4-difluorophenyl)(6-(2,2,2-trifluoroethoxy)pyridin-3-yl)methyl)-2-oxoimidazolidine-4-carboxamide. Diastereomer 33A: LRMS m/z (M+H): calculated 465.1, observed 465.3. $^1$H NMR (500 MHz, DMSO-d6) δ 8.93 (d, J=7.9 Hz, 1H), 8.14 (d, J=2.3 Hz, 1H), 7.71 (dd, J=8.6, 2.5 Hz, 1H), 7.39 (t, J=7.3 Hz, 2H), 7.02 (d, J=8.6 Hz, 1H), 6.59 (s, 1H), 6.40-6.30 (m, 2H), 5.00 (q, J=9.1 Hz, 2H), 4.29-4.13 (m, 1H), 3.56 (t, J=9.3 Hz, 1H), 3.23 (dd, J=8.6, 6.2 Hz, 1H). Diastereomer 33B: LRMS m/z (M+H): calculated 465.1, observed 465.3. $^1$H NMR (500 MHz, DMSO-d6) δ 8.94 (d, J=7.9 Hz, 1H), 8.14 (d, J=2.3 Hz, 1H), 7.72 (dd, J=8.6, 2.5 Hz, 1H), 7.45-7.33 (m, 2H), 7.01 (d, J=8.6 Hz, 1H), 6.59 (s, 1H), 6.40-6.29 (m, 2H), 5.00 (q, J=9.1 Hz, 2H), 4.25-4.14 (m, 1H), 3.56 (t, J=9.3 Hz, 1H), 3.23 (dd, J=8.4, 6.6 Hz, 1H).

Example 34A (S)—N—((R or S)-(3-chloro-2,4-difluorophenyl)(trans-3-(trifluoromethyl)cyclobutyl)methyl)-2-oxoimidazolidine-4-carboxamide

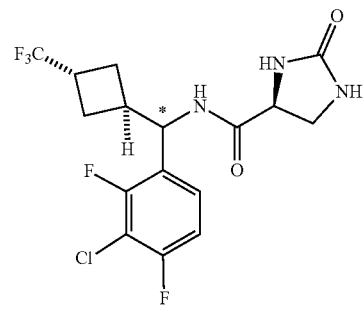 [SMILES: O=C1NC[C@@H](C(=O)NC(c2ccc(F)c(Cl)c2F)[C@H]2C[C@H](C(F)(F)F)C2)N1]

Step 1: (3-chloro-2,4-difluorophenyl)(trans-3-(trifluoromethyl)cyclobutyl)methanone. To a solution of trans-3-(trifluoromethyl)cyclobutane-1-carboxylic acid (1.0 g, 6.0 mmol) in DCM (15 mL) at 0° C. was added (COCl)₂ (3.6 mL, 7.1 mmol, 2.0 M in DCM) and one drop of DMF. The mixture was warmed to rt, stirred at rt for 4 h, then concentrated in vacuo. The resulting residue was dissolved in THF (6 mL; Solution A). In a separate flask, 2-chloro-1,3-difluoro-4-iodobenzene (2.4 g, 8.9 mmol) was dissolved in THF (20 mL) and cooled to −20° C., followed by the addition of iPrMgCl—LiCl complex (6.9 mL, 8.9 mmol, 1.3 M in THF). The mixture was stirred at −20° C. for 2 h, and then warmed to 0° C. Then CuCN (1.1 g, 12 mmol) was added, and the mixture was stirred at 0° C. for 30 min. Solution A was added, and the mixture was stirred at 0° C. for 2 h, and then warmed to rt for 1 h. The mixture was partitioned between EtOAc and sat. NH₄Cl, and filtered through a pad of the Celite®. The separated organic layer was dried over Na₂SO₄, filtered and concentrated in vacuo to give the title compound.

Step 2: (R)—N-((3-chloro-2,4-difluorophenyl)(trans-3-(trifluoromethyl)cyclobutyl)methylene)-2-methylpropane-2-sulfinamide. A microwave tube was charged with (3-chloro-2,4-difluorophenyl)(trans-3-(trifluoromethyl)cyclobutyl)methanone (1.7 g, 5.7 mmol), (R)-2-methylpropane-2-sulfinamide (1.0 g, 8.5 mmol) and Ti(OEt)₄ (10 mL, 11 mmol). The mixture was microwaved at 105° C. for 1 h, and then cooled to rt. Then the mixture was poured into water and EtOAc, stirred for 10 minutes, and filtered through a pad of the Celite®. The separated organic layer was dried over Na₂SO₄, filtered and concentrated in vacuo to give the title compound.

Step 3: (R)—N-((3-chloro-2,4-difluorophenyl)(trans-3-(trifluoromethyl)cyclobutyl)methyl)-2-methylpropane-2-sulfinamide. To a solution of (R)—N-((3-chloro-2,4-difluorophenyl)(trans-3-(trifluoromethyl)cyclobutyl)methylene)-2-methylpropane-2-sulfinamide (2.2 g, 5.5 mmol) in THF (10 mL) and MeOH (2 mL) at 0° C. was added NaBH₄ (0.21 g, 5.5 mmol). The mixture was stirred at 0° C. for 1 h and warmed to rt for 1 hour. Then the mixture was partitioned between EtOAc and sat. NaHCO₃. The separated organic layer was dried over Na₂SO₄, filtered and concentrated in vacuo. The resulting residue was purified by silica gel chromatography (0-40% EtOAc:hex) to give a mixture, which was separated by chiral-SFC (method AM) to give the title compound (first eluted isomer).

Step 4: (3-chloro-2,4-difluorophenyl)(trans-3-(trifluoromethyl)cyclobutyl)methanamine hydrochloride. To a solution of (R)—N-((3-chloro-2,4-difluorophenyl)(trans-3-(trifluoromethyl)-cyclobutyl) methyl)-2-methyl propane-2-sulfinamide (first eluted isomer) (0.12 g, 0.31 mmol) in DCM (1 mL) cooled to 0° C. was added HCl (1.0 mL, 4.0 mmol, 4.0 M in 1,4-dioxane). The mixture was stirred at 0° C. for 2 h and then concentrated in vacuo. The resulting residue was washed with Et₂O and filtered to give the title compound.

Step 5: (S)—N—((R or S)-(3-chloro-2,4-difluorophenyl)(trans-3-(trifluoromethyl)cyclobutyl)-methyl)-2-oxoimidazolidine-4-carboxamide. To a solution of (3-chloro-2,4-difluorophenyl)-(trans-3-(trifluoromethyl)cyclobutyl)methanamine, hydrochloride (70 mg, 0.21 mmol) and (S)-2-oxoimidazolidine-4-carboxylic acid (35 mg, 0.27 mmol) in pyridine (3 mL) was added EDC (65 mg, 0.42 mmol). The mixture was heated to 60° C. for 14 h, and then concentrated in vacuo. The resulting residue was purified by silica gel chromatography (0-5% MeOH:DCM) to give the title compound. LRMS m/z (M+H): calculated 412.1, observed 412.4. ¹H NMR (500 MHz, CD₂Cl₂) δ 7.22 (q, J=8.0 Hz, 1H), 6.98 (t, J=8.3 Hz, 1H), 5.22-5.15 (m, 1H), 4.29 (dd, J=10.1, 6.2 Hz, 1H), 3.90 (t, J=9.7 Hz, 1H), 3.58 (dd, J=9.0, 6.3 Hz, 1H), 2.94 (dq, J=15.3, 9.4, 7.4 Hz, 2H), 2.43-2.30 (m, 1H), 2.20-2.10 (m, 2H), 1.98-1.88 (m, 1H).

TABLE 4

The compounds of Examples 35A-38 were prepared according to a synthetic procedure similar to the synthetic procedure for Example 34A.

| Example | Structure | Name | Calc'd [M + H]+ | Observed [M + H]+ | Conditions |
| --- | --- | --- | --- | --- | --- |
| 35A | 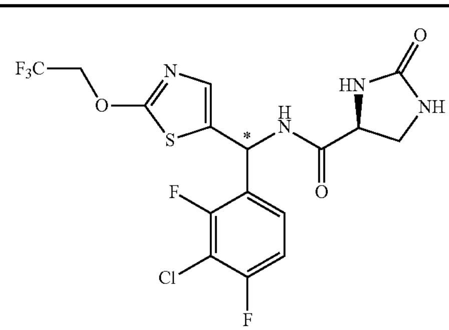 | (S)-N-((R or S)-(3-chloro-2,4-difluorophenyl)(2-(2,2,2-trifluoroethoxy)thiazol-5-yl)methyl)-2-oxoimidazolidine-4-carboxamide | 471.0 | 471.4 | Step 5: Chiral method AK, Peak 1 |

TABLE 4-continued

The compounds of Examples 35A-38 were prepared according to a synthetic procedure similar to the synthetic procedure for Example 34A.

| Example | Structure | Name | Calc'd [M + H]+ | Observed [M + H]+ | Conditions |
|---------|-----------|------|-----------------|-------------------|------------|
| 35B | 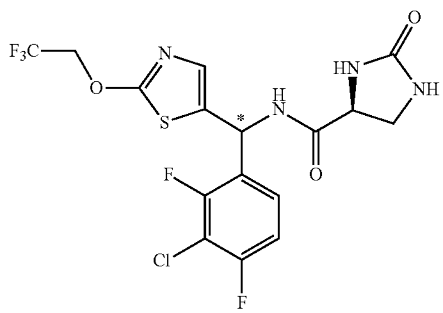 [SMILES: O=C1NC[C@@H](C(=O)NC(c2cnc(OCC(F)(F)F)s2)c2ccc(F)c(Cl)c2F)N1] | (S)-N-((R or S)-(3-chloro-2,4-difluorophenyl)(2-(2,2,2-trifluoroethoxy)thiazol-5-yl)methyl)-2-oxoimidazolidine-4-carboxamide | 471.0 | 471.4 | Step 5: Chiral method AK, Peak 2 |
| 36A | 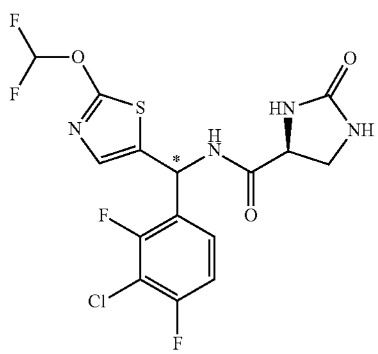 [SMILES: O=C1NC[C@@H](C(=O)NC(c2cnc(OC(F)F)s2)c2ccc(F)c(Cl)c2F)N1] | (S)-N-((R or S)-(3-chloro-2,4-difluorophenyl)(2-(difluoromethoxy)thiazol-5-yl)methyl)-2-oxoimidazolidine-4-carboxamide | 439.0 | 439.4 | Step 5: Chiral method AN, Peak 1 |
| 36B | 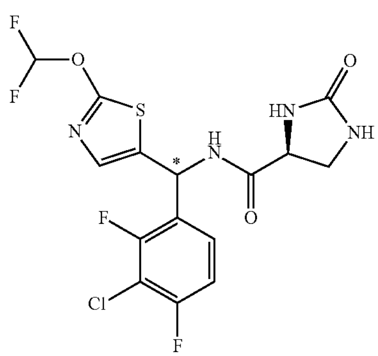 [SMILES: O=C1NC[C@@H](C(=O)NC(c2cnc(OC(F)F)s2)c2ccc(F)c(Cl)c2F)N1] | (S)-N-((R or S)-(3-chloro-2,4-difluorophenyl)(2-(difluoromethoxy)thiazol-5-yl)methyl)-2-oxoimidazolidine-4-carboxamide | 439.0 | 439.4 | Step 5: Chiral method AN, Peak 2 |
| 37 | 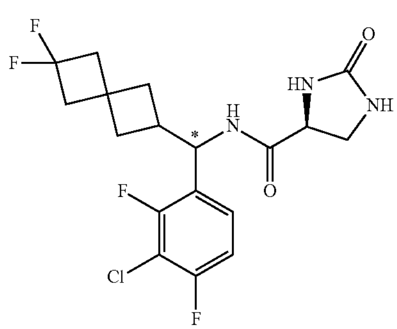 [SMILES: O=C1NC[C@@H](C(=O)NC(c2ccc(F)c(Cl)c2F)C2CC3(C2)CC(F)(F)C3)N1] | (S)-N-((R or S)-(3-chloro-2,4-difluorophenyl)(6,6-difluorospiro[3.3]heptan-2-yl)methyl)-2-oxoimidazolidine-4-carboxamide | 420.1 | 420.4 | Step 3: silica gel chromatography (0-40% EtOAc:hex), Peak 2 |

TABLE 4-continued

The compounds of Examples 35A-38 were prepared according to a synthetic procedure similar to the synthetic procedure for Example 34A.

| Example | Structure | Name | Calc'd [M + H]+ | Observed [M + H]+ | Conditions |
|---|---|---|---|---|---|
| 38 | 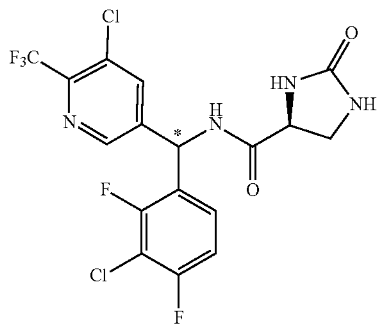 [SMILES: O=C1NC[C@@H](C(=O)NC(c2cnc(C(F)(F)F)c(Cl)c2)c2ccc(F)c(Cl)c2F)N1] | (S)-N-((R or S)-(3-chloro-2,4-difluorophenyl)(5-chloro-6-(trifluoromethyl)pyridin-3-yl)methyl)-2-oxoimidazolidine-4-carboxamide | 469.0 | 469.2 | Step 3, silica gel chromatography (0-25% EtOAc:hex), Peak 1 |

Example 34B (S)—N—((R or S)-(3-chloro-2,4-difluorophenyl)(trans-3-(trifluoromethyl)cyclobutyl)methyl)-2-oxo-imidazolidine-4-carboxamide

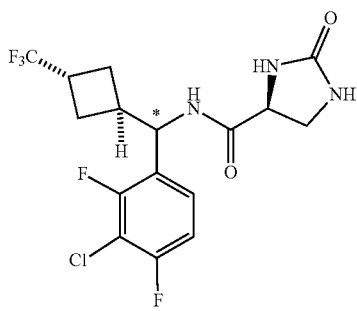 [SMILES: O=C1NC[C@@H](C(=O)NC(c2ccc(F)c(Cl)c2F)[C@H]2C[C@H](C(F)(F)F)C2)N1]

Step 1: (R)—N-((3-chloro-2,4-difluorophenyl)(trans-3-(trifluoromethyl)cyclobutyl)methyl)-2-methylpropane-2-sulfinamide. A solution of (R)—N-((3-chloro-2,4-difluorophenyl)(trans-3-(trifluoromethyl)cyclobutyl)methylene)-2-methylpropane-2-sulfinamide (6.6 g, 17 mmol) in THF (70 mL) and water (1 mL) was cooled to −78° C., then NaBH$_4$ (0.94 g, 25 mmol) was added in one portion. The reaction mixture was slowly warmed to 0° C. over 3 h, and then warmed to rt and stirred at rt overnight. The reaction was quenched with saturated NaHCO$_3$ and extracted with EtOAc. The organic layer was dried over Na$_2$SO$_4$, filtered and concentrated in vacuo. The resulting residue was purified by silica gel chromatography (0-40% EtOAc:hex) to give the title compound (second eluted isomer).

Step 2: (3-chloro-2,4-difluorophenyl)(trans-3-(trifluoromethyl)cyclobutyl)methanamine hydrochloride. To a solution of (R)—N-((3-chloro-2,4-difluorophenyl)(trans-3-(trifluoromethyl)-cyclobutyl)-methyl)-2-methylpropane-2-sulfinamide (second eluted isomer; 0.44 g, 1.1 mmol) in DCM (9 mL) and MeOH (1 mL), cooled to 0° C., was added HCl (8.0 mL, 32 mmol, 4.0 M in 1,4-dioxane). The reaction was stirred at 0° C. for 2 h, and then concentrated in vacuo. The resulting solid was washed with Et$_2$O and filtered to give the title compound.

Step 3: (S)—N—((R or S)-(3-chloro-2,4-difluorophenyl)(trans-3-(trifluoromethyl)cyclobutyl)-methyl)-2-oxoimidazolidine-4-carboxamide. To a solution of (3-chloro-2,4-difluorophenyl)-(trans-3-(trifluoromethyl)cyclobutyl) methanamine hydrochloride (96 mg, 0.29 mmol) and (S)-2-oxoimidazolidine-4-carboxylic acid (48 mg, 0.37 mmol) in pyridine (3 mL) was added EDC (89 mg, 0.57 mmol). The mixture was heated to 60° C. for 14 h, and then concentrated in vacuo. The resulting residue was purified by silica gel chromatography (0-5% MeOH:DCM) to give the title compound. LRMS m/z (M+H): calculated 412.1, observed 412.4. $^1$H NMR (500 MHz, CD$_2$Cl$_2$-d) δ 7.20-7.11 (m, 1H), 6.96-6.90 (m, 1H), 6.23 (s, 1H), 5.25-5.15 (m, 1H), 5.00 (s, 1H), 4.39 (dd, J=10.2, 6.2 Hz, 1H), 3.88 (t, J=9.8 Hz, 1H), 3.52 (dd, J=8.7, 5.7 Hz, 1H), 2.99-2.83 (m, 2H), 2.37 (dt, J=12.1, 6.1 Hz, 1H), 2.23-2.07 (m, 2H), 2.01-1.79 (m, 2H).

Examples 39A and 39B (S)—N—((R)-3-chloro-4-(trifluoromethoxy)phenyl)(5-(trifluoromethoxy)pyridin-2-yl)methyl)-2-oxoimidazolidine-4-carboxamide and (S)—N—((S)-3-chloro-4-(trifluoromethoxy)phenyl)(5-(trifluoromethoxy)pyridin-2-yl)methyl)-2-oxoimidazolidine-4-carboxamide

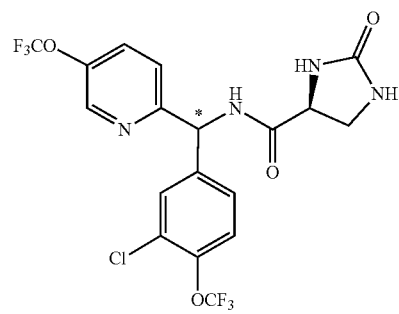 [SMILES: O=C1NC[C@@H](C(=O)NC(c2ccc(OC(F)(F)F)c(Cl)c2)c2ccc(OC(F)(F)F)cn2)N1]

Step 1: N-methoxy-N-methyl-5-(trifluoromethoxy)picolinamide. To a solution of 5-(trifluoromethoxy)picolinic acid (2.7 g, 13 mmol) in THF (20 mL) were added N,O-dimethylhydroxylamine hydrochloride (1.9 g, 19 mmol), DIEA (6.8 mL, 39 mmol) and HATU (7.4 g, 19 mmol). The mixture was stirred at rt for 5 h, then quenched with water and extracted with EtOAc. The organic layer was dried over Na$_2$SO$_4$, filtered and concentrated in vacuo. The resulting residue was purified by silica gel chromatography (0-10 EtOAc:hex) to give the title compound.

Step 2: (3-chloro-4-(trifluoromethoxy)phenyl)(5-(trifluoromethoxy)pyridin-2-yl)methanone. To a solution of 4-bromo-2-chloro-1-(trifluoromethoxy)benzene (0.66 g, 2.4 mmol) in THF (4 mL) was added iPrMgCl—LiCl complex (1.8 mL, 2.4 mmol, 1.3 M in THF) at rt. The mixture was stirred at 40° C. for 1 h, and then cooled to 0° C., followed by addition of N-methoxy-N-methyl-5-(trifluoromethoxy) picolinamide (0.40 g, 1.6 mmol) in THF (1 mL). The reaction was stirred at 0° C. for 2 h, then quenched with sat. NH$_4$Cl and extracted with Et$_2$O. The combined organic layers were dried over Na$_2$SO$_4$, filtered and concentrated in vacuo to give the title compound.

Step 3: N-((3-chloro-4-(trifluoromethoxy)phenyl)(5-(trifluoromethoxy)pyridin-2-yl)methylene)-2-methylpropane-2-sulfinamide. To a solution of (3-chloro-4-(trifluoromethoxy) phenyl)(5-(trifluoromethoxy)pyridin-2-yl)methanone (0.62 g, 1.6 mmol) and (R)-2-methylpropane-2-sulfinamide (0.29 g, 2.4 mmol) in toluene (2 mL) was added Ti(OEt)$_4$ (0.68 mL, 3.2 mmol). The mixture was heated to 105° C. for 1 h, then water and EtOAc was added. The mixture was stirred for 20 minutes and then filtered through a pad of the Celite®. After rinsing the pad with EtOAc, the organic layer was dried over Na$_2$SO$_4$, filtered and concentrated in vacuo. The resulting residue was purified by silica gel chromatography (0-20% EtOAc:hex) to give title compound.

Step 4: N-((3-chloro-4-(trifluoromethoxy)phenyl)(5-(trifluoromethoxy)pyridin-2-yl)methyl)-2-methylpropane-2-sulfinamide. To a solution of N-((3-chloro-4-(trifluoromethoxy)phenyl)(5-(trifluoromethoxy)pyridin-2-yl) methylene)-2-methylpropane-2-sulfinamide (0.51 g, 1.0 mmol) in THF (4 mL) and water (0.2 mL) at 0° C. was added NaBH$_4$ (79 mg, 2.1 mmol). The mixture was stirred at 0° C. for 2 hours and quenched with sat. NH$_4$Cl. The separated organic phase was dried over Na$_2$SO$_4$, filtered and concentrated in vacuo to give title compound.

Step 5: (3-chloro-4-(trifluoromethoxy)phenyl)(5-(trifluoromethoxy)pyridin-2-yl)methanamine hydrochloride. To a solution of ((3-chloro-4-(trifluoromethoxy)phenyl)(5-(trifluoromethoxy) pyridin-2-yl)methyl)-2-methylpropane-2-sulfinamide (0.51 g, 1.0 mmol) in DCM (2 mL) was added HCl (1.5 mL, 6.0 mmol, 4.0 M in 1,4-dioxane). The mixture was stirred at rt for 30 min and then concentrated in vacuo to give the title compound Step 6: (S)—N—((R and S)-(3-chloro-4-(trifluoromethoxy)phenyl)(5-(trifluoromethoxy)pyridin-2-yl) methyl)-2-oxoimidazolidine-4-carboxamide. A mixture of (S)-2-oxoimidazolidine-4-carboxylic acid (69 mg, 0.53 mmol), (3-chloro-4-(trifluoromethoxy)phenyl)(5-(trifluoromethoxy)pyridin-2-yl)methanamine hydrochloride (0.15 g, 0.35 mmol) and EDC (0.14 g, 0.71 mmol) in pyridine (3 mL) was heated to 80° C. and stirred for 4 h. Then the mixture was concentrated in vacuo. The resulting residue was purified by silica gel chromatography (0-4% DCM: MeOH) to give the title compound.

Step 7: (S)—N—((R or S)-(3-chloro-4-(trifluoromethoxy)phenyl)(5-(trifluoromethoxy)pyridin-2-yl) methyl)-2-oxoimidazolidine-4-carboxamide. (S)—N—((R and S)-(3-chloro-4-(trifluoromethoxy)phenyl)(5-(trifluoromethoxy)pyridin-2-yl)methyl)-2-oxoimidazolidine-4-carboxamide was separated by chiral-SFC (method L) to give title compounds: first eluted diastereomer 39A (S)—N—((R or S)-(3-chloro-4-(trifluoromethoxy)phenyl)(5-(trifluoromethoxy)pyridin-2-yl)methyl)-2-oxoimidazolidine-4-carboxamide, and second eluted diastereomer 39B (S)—N—((R or S)-(3-chloro-4-(trifluoromethoxy)phenyl)(5-(trifluoromethoxy)pyridin-2-yl)methyl)-2-oxoimidazolidine-4-carboxamide. Diastereomer 39A: LRMS m/z (M+H): calculated 499.1, observed 499.5. $^1$H NMR (500 MHz, CD$_2$Cl$_2$) δ 8.52 (d, J=2.0 Hz, 1H), 7.61-7.55 (m, 1H), 7.50 (d, J=2.0 Hz, 1H), 7.36-7.26 (m, 4H), 6.17 (t, J=3.6 Hz, 1H), 4.39 (dd, J=10.2, 6.7 Hz, 1H), 3.90 (t, J=9.8 Hz, 1H), 3.57 (dd, J=9.2, 6.8 Hz, 1H). Diastereomer 39B: LRMS m/z (M+H): calculated 499.1, observed 499.5. $^1$H NMR (500 MHz, CD$_2$Cl$_2$) δ 8.55 (d, J=2.1 Hz, 1H), 7.64-7.58 (m, 1H), 7.47 (d, J=1.5 Hz, 1H), 7.35 (d, J=8.6 Hz, 1H), 7.29 (s, 3H), 6.20-6.14 (m, 1H), 4.39 (dd, J=10.1, 6.8 Hz, 1H), 3.91 (t, J=9.7 Hz, 1H), 3.55-3.45 (m, 1H).

TABLE 5

The compounds of Examples 40A and 40B were prepared according to a synthetic procedure similar to the synthetic procedure for Examples 39A and 39B.

| Example | Structure | Name | Calc'd [M + H]$^+$ | Observed [M + H]$^+$ | Conditions |
|---|---|---|---|---|---|
| 40A | 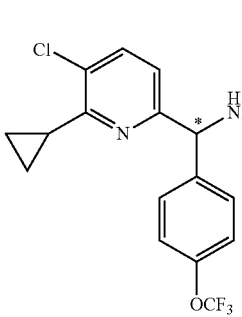 | (S)-N-((R or S)-(5-chloro-6-cyclopropylpyridin-2-yl)(4-(trifluoromethoxy)phenyl) methyl)-2-oxoimidazolidine-4-carboxamide | 455.1 | 455.5 | Step 5: Chiral method V, Peak 1 |

TABLE 5-continued

The compounds of Examples 40A and 40B were prepared according to a synthetic procedure similar to the synthetic procedure for Examples 39A and 39B.

| Example | Structure | Name | Calc'd [M + H]⁺ | Observed [M + H]⁺ | Conditions |
|---|---|---|---|---|---|
| 40B | (structure shown) | (S)-N-((R or S)-(5-chloro-6-cyclopropylpyridin-2-yl)(4-(trifluoromethoxy)phenyl)methyl)-2-oxoimidazolidine-4-carboxamide | 455.1 | 420.4 | Step 5: Chiral method V, Peak 2 |

Examples 41A and 41B (S)—N—((R)-(3-chloro-4-(trifluoromethoxy)phenyl)(1-(trifluoromethyl)-1H-pyrazol-4-yl)-l3-methyl)-2-oxoimidazolidine-4-carboxamide and (S)—N—((S)-(3-chloro-4-(trifluoromethoxy)phenyl)(1-(trifluoromethyl)-1H-pyrazol-4-yl)-l3-methyl)-2-oxoimidazolidine-4-carboxamide

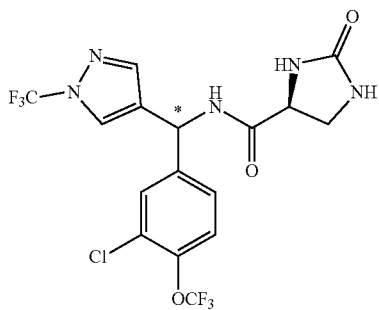 [SMILES: O=C1NC[C@@H](C(=O)NC(c2ccc(OC(F)(F)F)c(Cl)c2)c2cnn(C(F)(F)F)c2)N1]

Step 1: (R)-2-methyl-N-((1-(trifluoromethyl)-1H-pyrazol-4-yl)methylene)propane-2-sulfinamide. To a solution of (R)-2-methylpropane-2-sulfinamide (0.89 g, 7.3 mmol) and 1-(trifluoromethyl)-1H-pyrazole-4-carbaldehyde (1.0 g, 6.1 mmol) in toluene (3 mL) was added Ti(OEt)₄ (2.6 mL, 12 mmol). The mixture was heated to 80° C. for 3 h, and cooled to rt. Then water and EtOAc were added, and the mixture was stirred for 10 min, followed by filtration through a pad of the Celite®. The separated organic layer was dried over Na₂SO₄, filtered and concentrated in vacuo. The resulting residue was purified by silica gel chromatography (0-50% EtOAc:hex) to give the title compound.

Step 2: (R)—N-((3-chloro-4-(trifluoromethoxy)phenyl)(1-(trifluoromethyl)-1H-pyrazol-4-yl)methylene)-2-methylpropane-2-sulfinamide. To a solution of 4-bromo-2-chloro-1-(trifluoromethoxy) benzene (0.99 g, 3.6 mmol) in THF (6 mL) was added iPrMgCl—LiCl complex (2.8 mL, 3.6 mmol, 1.3 M in THF). The mixture was heated to 40° C. for 1.5 h, cooled to 0° C., followed by the addition of (R)-2-methyl-N-((1-(trifluoromethyl)-1H-pyrazol-4-yl)methylene)propane-2-sulfinamide (0.48 g, 1.8 mmol). The reaction was stirred at 0° C. for 2 h, then warmed to rt and stirred overnight. The reaction was then quenched with sat. NH₄Cl and extracted with Et₂O. The separated organic layer was dried over Na₂SO₄, filtered and concentrated in vacuo. The resulting residue was purified by silica gel chromatography (0-50% EtOAc:hex) to give the title compound.

Step 4: (3-chloro-4-(trifluoromethoxy)phenyl)(1-(trifluoromethyl)-1H-pyrazol-4-yl)methanamine hydrochloride. To a solution of (R)—N-((3-chloro-4-(trifluoromethoxy)phenyl)(1-(trifluoro-methyl)-1H-pyrazol-4-yl)methyl)-2-methylpropane-2-sulfinamide (0.42 g, 0.91 mmol) in DCM (1 mL) was added HCl (1.0 mL, 4.0 mmol, 4 M in 1,4-dioxane). The mixture was stirred at 0° C. for 30 minutes and then concentrated in vacuo. The resulting solid was washed with hexane, and then filtered to give the title compound.

Step 5: (S)—N—((R and S)-(3-chloro-4-(trifluoromethoxy)phenyl)(1-(trifluoromethyl)-1H-pyrazol-4-yl)-l3-methyl)-2-oxoimidazolidine-4-carboxamide. A mixture of (3-chloro-4-(trifluoromethoxy)phenyl)(1-(trifluoromethyl)-1H-pyrazol-4-yl)methanamine hydrochloride (90 mg, 0.23 mmol), (S)-2-oxoimidazolidine-4-carboxylic acid (44 mg, 0.34 mmol) and EDC-HCl (87 mg, 0.45 mmol) in pyridine (2 mL) was heated to 80° C. for 4 h. Then the reaction mixture was concentrated in vacuo. The resulting residue was purified by silica gel chromatography (0-4% DCM:MeOH) to give the title compound.

Step 6: (S)—N—((R or S)-(3-chloro-4-(trifluoromethoxy)phenyl)(1-(trifluoromethyl)-1H-pyrazol-4-yl)-l3-methyl)-2-oxoimidazolidine-4-carboxamide. (S)—N—((R and S)-(3-chloro-4-(trifluoromethoxy)phenyl)(1-(trifluoromethyl)-1H-pyrazol-4-yl)-l3-methyl)-2-oxoimidazolidine-4-carboxamide was separated by chiral-SFC (method W) to give the title compounds: first eluted diastereomer 41A (S)—N—((R or S)-(3-chloro-4-(trifluoromethoxy)phenyl)(1-(trifluoromethyl)-1H-pyrazol-4-yl)-l3-methyl)-2-oxoimidazolidine-4-carboxamide, and second eluted diastereomer 41B (S)—N—((R or S)-(3-chloro-4-(trifluoromethoxy)phenyl)(1-(trifluoromethyl)-1H-pyrazol-4-yl)-l3-methyl)-2-oxoimidazolidine-4-carboxamide.

Diastereomer 41A: LRMS m/z (M+H): calculated 472.1, observed 472.2. ¹H NMR (500 MHz, CD₂Cl₂) δ 7.97 (d, J=6.9 Hz, 1H), 7.67 (d, J=11.4 Hz, 2H), 7.54 (d, J=1.5 Hz, 1H), 7.39-7.30 (m, 2H), 6.22 (d, J=5.7 Hz, 1H), 4.37 (s, 1H), 3.88 (t, J=9.1 Hz, 1H), 3.67 (s, 1H). Diastereomer 41B: LRMS m/z (M+H): calculated 472.1, observed 472.2. ¹H NMR (500 MHz, CD₂Cl₂) δ 7.86 (s, 1H), 7.73 (d, J=9.6 Hz, 2H), 7.47 (s, 1H), 7.32 (d, J=8.3 Hz, 1H), 7.26 (d, J=8.5 Hz, 1H), 6.25 (d, J=5.6 Hz, 1H), 4.43 (s, 1H), 3.90 (s, 1H), 3.62 (s, 1H).

TABLE 6

The compounds of Examples 42-49B below were prepared according to a synthetic procedure similar to the synthetic procedure for Examples 41A and 41B.

| Example | Structure | Name | Conditions [M + H]⁺ | Calc'd [M + H]⁺ | Observed |
|---|---|---|---|---|---|
| 42 | 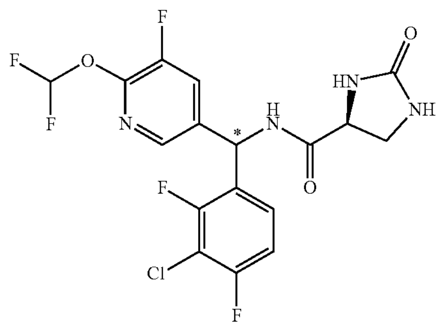 [SMILES: O=C1NC[C@@H](C(=O)NC(c2cnc(OC(F)F)c(F)c2)c2ccc(F)c(Cl)c2F)N1] | (S)-N-((R or S)-(3-chloro-2,4-difluorophenyl)(6-(difluoromethoxy)-5-fluoropyridin-3-yl)methyl)-2-oxoimidazolidine-4-carboxamide | 451.1 | 451.5 | Step 2: silica gel chromatography (0-30% EtOAc:hex), Peak 2 |
| 43 | 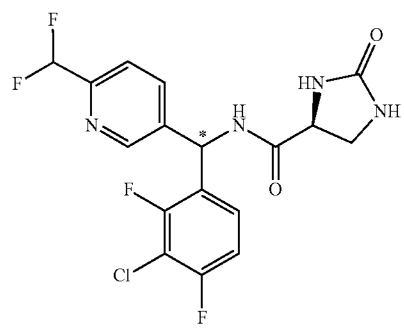 [SMILES: O=C1NC[C@@H](C(=O)NC(c2ccc(C(F)F)nc2)c2ccc(F)c(Cl)c2F)N1] | (S)-N-((R or S)-(3-chloro-2,4-difluorophenyl)(6-(difluoromethyl)pyridin-3-yl)methyl)-2-oxoimidazolidine-4-carboxamide | 417.1 | 417.4 | Step 2: Chiral method W, Peak 2 |
| 44 | 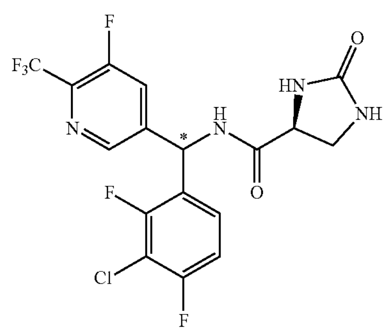 [SMILES: O=C1NC[C@@H](C(=O)NC(c2cnc(C(F)(F)F)c(F)c2)c2ccc(F)c(Cl)c2F)N1] | (S)-N-((R or S)-(3-chloro-2,4-difluorophenyl)(5-fluoro-6-(trifluoromethyl)pyridin-3-yl)methyl)-2-oxoimidazolidine-4-carboxamide | 453.0 | 453.4 | Step 2: Chiral method AO, Peak 1 |
| 45A | 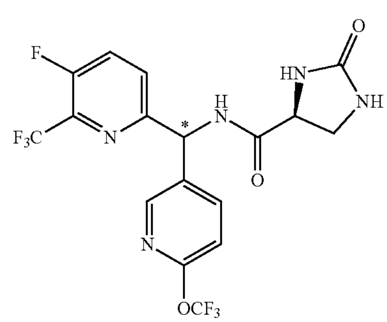 [SMILES: O=C1NC[C@@H](C(=O)NC(c2ccc(OC(F)(F)F)nc2)c2ccc(F)c(C(F)(F)F)n2)N1] | (S)-N-((R or S)-(5-fluoro-6-(trifluoromethyl)pyridin-2-yl)(6-(trifluoromethoxy)pyridin-3-yl)methyl)-2-oxoimidazolidine-4-carboxamide | 468.1 | 468.4 | Chiral method AP, Peak 1 |

TABLE 6-continued

The compounds of Examples 42-49B below were prepared according to a synthetic procedure similar to the synthetic procedure for Examples 41A and 41B.

| Example | Structure | Name | Conditions [M + H]+ | Calc'd [M + H]+ | Observed |
|---------|-----------|------|---------------------|-----------------|----------|
| 45B | 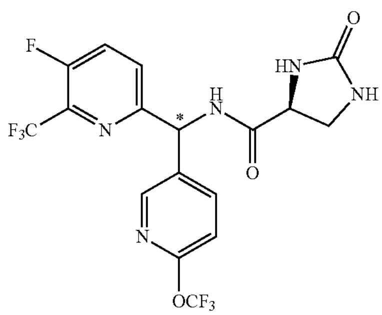 [SMILES: O=C1NC[C@@H](C(=O)NC(c2ccc(OC(F)(F)F)nc2)c2ccc(F)c(C(F)(F)F)n2)N1] | (S)-N-((R or S)-(5-fluoro-6-(trifluoromethyl)pyridin-2-yl)(6-(trifluoromethoxy)pyridin-3-yl)methyl)-2-oxoimidazolidine-4-carboxamide | 468.1 | 468.4 | Chiral method AP, Peak 2 |
| 46A | 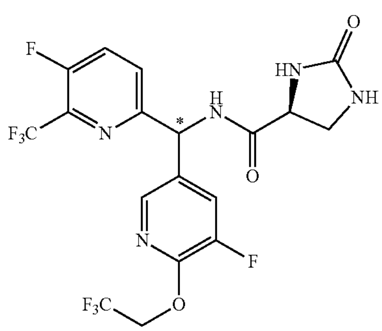 [SMILES: O=C1NC[C@@H](C(=O)NC(c2cnc(OCC(F)(F)F)c(F)c2)c2ccc(F)c(C(F)(F)F)n2)N1] | (S)-N-((R or S)-(5-fluoro-6-(2,2,2-trifluoroethoxy)pyridin-3-yl)(5-fluoro-6-(trifluoromethyl)pyridin-2-yl)methyl)-2-oxoimidazolidine-4-carboxamide | 500.1 | 500.5 | Chiral method AQ, Peak 2 |
| 46B | 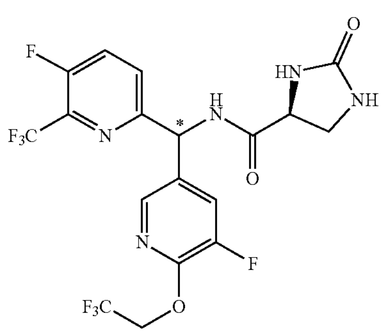 [SMILES: O=C1NC[C@@H](C(=O)NC(c2cnc(OCC(F)(F)F)c(F)c2)c2ccc(F)c(C(F)(F)F)n2)N1] | (S)-N-((R or S)-(5-fluoro-6-(2,2,2-trifluoroethoxy)pyridin-3-yl)(5-fluoro-6-(trifluoromethyl)pyridin-2-yl)methyl)-2-oxoimidazolidine-4-carboxamide | 500.1 | 500.5 | Chiral method AQ, Peak 1 |
| 47A | 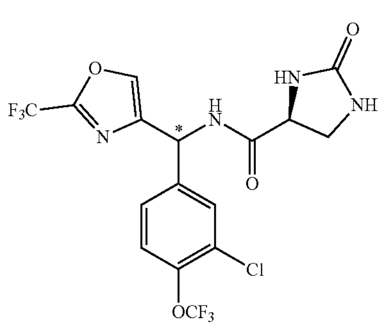 [SMILES: O=C1NC[C@@H](C(=O)NC(c2ccc(OC(F)(F)F)c(Cl)c2)c2coc(C(F)(F)F)n2)N1] | (S)-N-((R or S)-(3-chloro-4-(trifluoromethoxy)phenyl)(2-(trifluoromethyl)oxazol-4-yl)methyl)-2-oxoimidazolidine-4-carboxamide | 473.0 | 473.4 | Chiral method AM, Peak 1 |

TABLE 6-continued

The compounds of Examples 42-49B below were prepared according to a synthetic procedure similar to the synthetic procedure for Examples 41A and 41B.

| Example | Structure | Name | Conditions [M + H]⁺ | Calc'd [M + H]⁺ | Observed |
|---------|-----------|------|---------------------|-----------------|----------|
| 47B | 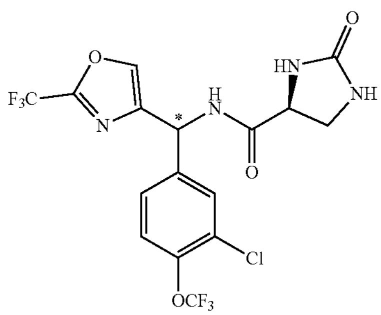 [SMILES: O=C1NC[C@@H](C(=O)NC(c2ccc(OC(F)(F)F)c(Cl)c2)c2coc(C(F)(F)F)n2)N1] | (S)-N-((R or S)-(3-chloro-4-(trifluoro-methoxy)phenyl)(2-(trifluoromethyl)oxazol-4-yl)methyl)-2-oxoimidazolidine-4-carboxamide | 473.0 | 473.4 | Chiral method AM, Peak 2 |
| 48 | 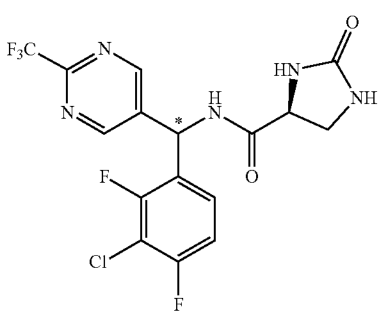 [SMILES: O=C1NC[C@@H](C(=O)NC(c2cnc(C(F)(F)F)nc2)c2ccc(F)c(Cl)c2F)N1] | (S)-N-((R or S)-(3-chloro-2,4-difluorophenyl)(2-(trifluoromethyl)pyrimidin-5-yl)methyl)-2-oxoimidazolidine-4-carboxamide | 436.1 | 436.3 | Step 2: Chiral method AR, Peak 2 |
| 49A | 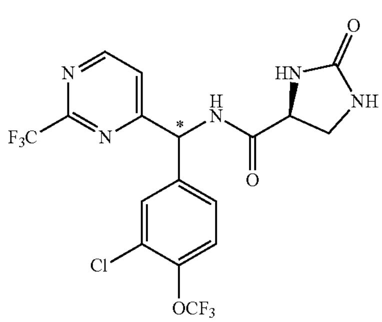 [SMILES: O=C1NC[C@@H](C(=O)NC(c2ccc(OC(F)(F)F)c(Cl)c2)c2ccnc(C(F)(F)F)n2)N1] | (S)-N-((R or S)-3-chloro-4-(trifluoro-methoxy)phenyl)(2-(trifluoromethyl)pyrimidin-4-yl)methyl)-2-oxoimidazolidine-4-carboxamide | 484.1 | 484.2 | Chiral method J, Peak 1 |
| 49B | 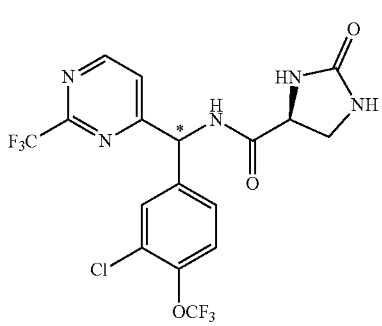 [SMILES: O=C1NC[C@@H](C(=O)NC(c2ccc(OC(F)(F)F)c(Cl)c2)c2ccnc(C(F)(F)F)n2)N1] | (S)-N-((R or S)-3-chloro-4-(trifluoro-methoxy)phenyl)(2-(trifluoromethyl)pyrimidin-4-yl)methyl)-2-oxoimidazolidine-4-carboxamide | 484.1 | 484.2 | Chiral method J, Peak 2 |

Examples 50A and 50B (4S)—N—((R)-(3-chloro-2,4-difluorophenyl)(6-(2,2,2-trifluoroethoxy)pyridazin-3-yl)methyl)-2-oxo-imidazolidine-4-carboxamide and (4S)—N—((S)-(3-chloro-2,4-difluorophenyl)(6-(2,2,2-trifluoroethoxy)pyridazin-3-yl)methyl)-2-oxoimidazolidine-4-carboxamide

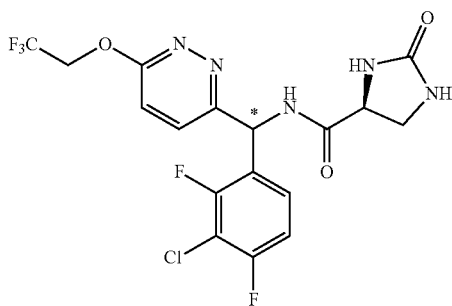

Step 1: N-methoxy-N-methyl-6-(2,2,2-trifluoroethoxy)pyridazine-3-carboxamide. To a solution of 6-(2,2,2-trifluoroethoxy)pyridazine-3-carboxylic acid (0.50 g, 2.3 mmol) and N,O-dimethyl hydroxylamine HCl salt (0.26 g, 2.7 mmol) in DCM (15 mL) were added HOAt (0.40 g, 2.9 mmol), EDC (0.52 g, 2.7 mmol) and DIPEA (1.4 mL, 8.1 mmol) at rt. The reaction mixture was stirred overnight, then the solvent was removed in vacuo. The crude residue was dissolved in DMSO (5 mL) and purified by reverse phase HPLC (90:10 to 100:0; water (0.1% TFA):MeCN (0.1% TFA)), followed by lyophilization to give the title compound.

Step 2. (3-chloro-2,4-difluorophenyl)(6-(2,2,2-trifluoroethoxy)pyridazin-3-yl)methanone. A solution of 2-chloro-1,3-difluoro-4-iodobenzene (0.26 g, 0.94 mmol) in THF (2 mL) was cooled to 0° C. Then iPrMgCl (0.47 mL, 0.94 mmol) was added over 10 min, and the reaction was stirred at 0° C. for 45 min. The reaction mixture was then added to a pre-cooled solution of N-methoxy-N-methyl-6-(2,2,2-trifluoroethoxy)pyridazine-3-carboxamide (0.10 g, 0.38 mmol) in THF (2 mL) at 0° C. The reaction was stirred for 4 h at 0° C., then quenched by the addition of sat. NH$_4$Cl. The mixture was extracted in EtOAc. The combined organic layers were dried, and the resulting crude material was purified by reverse phase HPLC (90:10 to 100:0; water (0.1% TFA):MeCN (0.1% TFA)), followed by lyophilization to give the title compound.

Step 3: (3-chloro-2,4-difluorophenyl)(6-(2,2,2-trifluoroethoxy)pyridazin-3-yl)methanamine. (3-chloro-2,4-difluorophenyl)(6-(2,2,2-trifluoroethoxy)pyridazin-3-yl)methanone (85 mg, 0.24 mmol) and NH$_4$OAc (0.19 g, 2.4 mmol) were combined in EtOH (5 mL) in a 20 mL microwave vial, and then NaBH$_3$CN (38 mg, 0.60 mmol) was added at rt. The vial was sealed, and the mixture was stirred at 140° C. for 1.5 h in a microwave reactor. Then the reaction mixture was quenched by the addition of water, and concentrated in vacuo. The resulting crude material was purified by reverse phase HPLC (90:10 to 100:0; water (0.1% TFA):MeCN (0.1% TFA)), followed by lyophilization to give the title compound.

Step 4: (4S)—N—((R and S)-(3-chloro-2,4-difluorophenyl)(6-(2,2,2-trifluoroethoxy)pyridazin-3-yl)methyl)-2-oxo-imidazolidine-4-carboxamide. To a solution of (S)-2-oxo-imidazolidine-4-carboxylic acid (28 mg, 0.22 mmol), (3-chloro-2,4-difluorophenyl)(6-(2,2,2-trifluoroethoxy)pyridazin-3-yl)-methanamine (76 mg, 0.22 mmol) and HATU (98 mg, 0.26 mmol) in DMSO (5 mL) was added N-methylmorpholine (0.085 mL, 0.78 mmol) at rt. The reaction mixture was stirred at rt for 6 h. The residue was purified by reverse phase HPLC (90:10 to 100:0; water (0.1% TFA):MeCN (0.1% TFA)), followed by lyophilization to give the title compound.

Step 5: (4S)—N—((R or S)-(3-chloro-2,4-difluorophenyl)(6-(2,2,2-trifluoroethoxy)pyridazin-3-yl)methyl)-2-oxo-imidazolidine-4-carboxamide. (4S)—N—((R and S)-(3-chloro-2,4-difluorophenyl)(6-(2,2,2-trifluoroethoxy)pyridazin-3-yl)methyl)-2-oxoimidazolidine-4-carboxamide was separated by chiral-SFC (method L) to give the title compounds: first eluted diastereomer 50A (4S)—N—((R or S)-(3-chloro-2,4-difluorophenyl)(6-(2,2,2-trifluoroethoxy)pyridazin-3-yl)methyl)-2-oxoimidazolidine-4-carboxamide; and second eluted diastereomer 50B (4S)—N—((R or S)-(3-chloro-2,4-difluorophenyl)(6-(2,2,2-trifluoroethoxy)pyridazin-3-yl)methyl)-2-oxoimidazolidine-4-carboxamide. Diastereomer 50A: LRMS m/z (M+H): calculated 466.1, observed 466.5. $^1$H NMR (500 MHz, DMSO-d$_6$) δ 9.11 (d, J=7.9 Hz, 1H), 7.78 (d, J=9.2 Hz, 1H), 7.46 (dd, J=14.5, 8.6 Hz, 2H), 7.36 (t, J=8.7 Hz, 1H), 6.64 (s, 1H), 6.54 (d, J=7.8 Hz, 1H), 6.34 (s, 1H), 5.17 (qd, J=8.9, 2.5 Hz, 2H), 4.23 (dd, J=9.5, 6.0 Hz, 1H), 3.57 (t, J=9.4 Hz, 1H), 3.23 (dd, J=8.7, 6.2 Hz, 1H). Diastereomer 50B: LRMS m/z (M+H): calculated 466.1, observed 466.5. $^1$H NMR (500 MHz, DMSO-d$_6$) δ 9.11 (d, J=7.8 Hz, 1H), 7.79 (d, J=9.2 Hz, 1H), 7.46 (dd, J=17.1, 7.8 Hz, 2H), 7.36 (t, J=8.7 Hz, 1H), 6.59 (s, 1H), 6.53 (d, J=7.8 Hz, 1H), 6.32 (s, 1H), 5.17 (qd, J=8.9, 2.5 Hz, 2H), 4.23 (dd, J=9.0, 6.4 Hz, 1H), 3.56 (t, J=9.3 Hz, 1H), 3.24 (t, J=7.4 Hz, 1H).

Examples 51A and 51B (4S)—N—((R)-(3-chloro-2,4-difluorophenyl)(5-(2,2,2-trifluoroethoxy)pyrazin-2-yl)methyl)-2-oxoimi-dazolidine-4-carboxamide and (4S)—N—((S)-(3-chloro-2,4-difluorophenyl)(5-(2,2,2-trifluoroethoxy)pyrazin-2-yl)methyl)-2-oxoimidazolidine-4-carboxamide

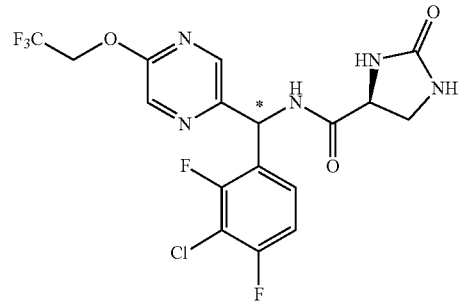 [SMILES: O=C1NC[C@@H](C(=O)NC(c2cnc(OCC(F)(F)F)cn2)c2ccc(F)c(Cl)c2F)N1]

Step 1: N-methoxy-N-methyl-5-(2,2,2-trifluoroethoxy)pyrazine-2-carboxamide. To a solution of 5-(2,2,2-trifluoroethoxy)pyrazine-2-carboxylic acid (470 mg, 2.116 mmol) and N,O-dimethyl hydroxylamine HCl salt (0.25 g, 2.5 mmol) in DCM (15 mL) were added HOAt (0.37 g, 2.8 mmol), EDC (0.49 g, 2.5 mmol) and DIPEA (1.3 mL, 7.6 mmol) at rt. The resulting reaction mixture was stirred for 72 h. Then the solvent was removed in vacuo. The resulting residue was purified via reverse phase HPLC (90:10 to 100:0; water (0.1% TFA):MeCN (0.1% TFA)), followed by lyophilization to give the title compound.

Step 2. (3-chloro-2,4-difluorophenyl)(5-(2,2,2-trifluoroethoxy)pyrazin-2-yl)methanone. A solution of 2-chloro-1,3-difluoro-4-iodobenzene (0.69 g, 2.5 mmol) in THF (6 mL) was cooled to 0° C. Then iPrMgCl (1.2 mL, 2.5 mmol) was added over 10 min, and the reaction was stirred at 0° C. for 45 min. The reaction mixture was then added to a pre-cooled solution of N-methoxy-N-methyl-5-(2,2,2-trifluoroethoxy)pyrazine-2-carboxamide (0.26 g, 1.0 mmol) in THF (9 mL) at 0° C. The reaction was stirred for 1 h at 0° C., then quenched with sat. NH$_4$Cl, and extracted in EtOAc. The combined organic layers were dried, and the resulting crude product was purified by reverse phase HPLC (90:10 to 100:0; water (0.1% TFA):MeCN (0.1% TFA)), followed by lyophilization to give the title compound.

Step 3: (3-chloro-2,4-difluorophenyl)(5-(2,2,2-trifluoroethoxy)pyrazin-2-yl)methanamine: (3-chloro-2,4-difluorophenyl)(5-(2,2,2-trifluoroethoxy)pyrazin-2-yl)methanone (0.22 g, 0.63 mmol), NH$_4$OAc (0.48 g, 6.3 mmol) were combined in EtOH (5 mL) in 20 mL microwave vial. Then NaBH$_3$CN (99 mg, 1.6 mmol) was added at rt. The vial was sealed, and the mixture was stirred at 140° C. for 1 h. The reaction mixture was then quenched by addition of water and concentrated in vacuo. The resulting crude material was purified by reverse phase HPLC (90:10 to 100:0; water (0.1% TFA):MeCN (0.1% TFA)), followed by lyophilization to give the title compound.

Step 4: N—((R and S)-(3-chloro-2,4-difluorophenyl)(5-(2,2,2-trifluoroethoxy)pyrazin-2-yl)methyl)-2-oxoimidazolidine-4-carboxamide. To a mixture of (S)-2-oxoimidazolidine-4-carboxylic acid (26 mg, 0.20 mmol), (3-chloro-2,4-difluorophenyl)(5-(2,2,2-trifluoroethoxy)-pyrazin-2-yl)-methanamine (71 mg, 0.20 mmol) and HATU (91 mg, 0.24 mmol) in DMSO (2 mL) was added N-methylmorpholine (0.079 mL, 0.72 mmol) at rt. The resulting mixture was stirred overnight. Then the residue was purified by reverse phase HPLC (90:10 to 100:0; water (0.1% TFA):MeCN (0.1% TFA)), followed by lyophilization to give the title compound.

Step 5: N—((R or S)-(3-chloro-2,4-difluorophenyl)(5-(2,2,2-trifluoroethoxy)pyrazin-2-yl)methyl)-2-oxoimidazolidine-4-carboxamide. N—((R and S)-(3-chloro-2,4-difluorophenyl)(5-(2,2,2-trifluoroethoxy)pyrazin-2-yl)methyl)-2-oxoimidazolidine-4-carboxamide was separated by chiral-SFC (method X) to give the title compounds: first eluted diastereomer 51A N—((R or S)-(3-chloro-2,4-difluorophenyl)(5-(2,2,2-trifluoroethoxy)pyrazin-2-yl)methyl)-2-oxoimidazolidine-4-carboxamide; and second eluted diastereomer 51B N—((R or S)-(3-chloro-2,4-difluorophenyl)(5-(2,2,2-trifluoroethoxy)pyrazin-2-yl)methyl)-2-oxoimidazolidine-4-carboxamide. Diastereomer 51A: LRMS m/z (M+H): calculated 466.1, observed 466.3. $^1$H NMR (500 MHz, Methanol-d$_4$) δ 8.34 (s, 1H), 8.24 (s, 1H), 7.55-7.30 (m, 1H), 7.13 (t, J=8.7 Hz, 1H), 6.52 (s, 1H), 5.04-4.87 (m, 2H), 4.38 (dd, J=10.1, 6.2 Hz, 1H), 3.79 (t, J=9.7 Hz, 1H), 3.46 (dd, J=9.3, 6.2 Hz, 1H). Diastereomer 51B: LRMS m/z (M+H): calculated 466.1, observed 466.3. $^1$H NMR (500 MHz, Methanol-d$_4$) δ 8.34 (s, 1H), 8.23 (s, 1H), 7.59-7.28 (m, 1H), 7.23-6.90 (m, 1H), 6.51 (s, 1H), 5.14-4.88 (m, 2H), 4.39 (dd, J=10.0, 6.1 Hz, 1H), 3.78 (t, J=9.7 Hz, 1H), 3.45 (dd, J=9.3, 6.1 Hz, 1H).

Examples 52A and 52B (S)—N—((R)-1-(3-chloro-2,4-difluorophenyl)-3-(4-chlorophenyl)propyl)-2-oxoimidazolidine-4-carboxamide and (S)—N—((S)-1-(3-chloro-2,4-difluorophenyl)-3-(4-chlorophenyl)propyl)-2-oxoimidazolidine-4-carboxamide

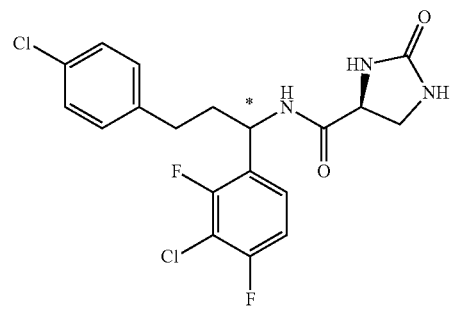 [SMILES: O=C1NC[C@@H](C(=O)NC(CCc2ccc(Cl)cc2)c2ccc(F)c(Cl)c2F)N1]

Step 1: N-(3-chloro-2,4-difluorobenzylidene)-2-methylpropane-2-sulfinamide. To a solution of 3-chloro-2,4-difluorobenzaldehyde (3.0 g, 17 mmol) and 2-methylpropane-2-sulfinamide (2.5 g, 20 mmol) in THF (50 mL) was added Ti(OEt)$_4$ (10 mL, 34 mmol) at rt. After stirring overnight at rt, the reaction mixture was cooled to 0° C., and quenched with sat. NH$_4$Cl. The mixture was then then suspended in EtOAc and filtered. The filtrate was separated, and the organic layer was washed with sat. NH$_4$Cl, sat. NaHCO$_3$, water, and then brine. The organic layer was dried over Na$_2$SO$_4$, filtered and concentrated in vacuo. The resulting residue was purified by silica gel chromatography (0-60% EtOAc:hex) to give the title compound.

Step 2: N-(1-(3-chloro-2,4-difluorophenyl)-3-(4-chlorophenyl)propyl)-2-methylpropane-2-sulfinamide. To a solution of N-(3-chloro-2,4-difluorobenzylidene)-2-methylpropane-2-sulfinamide (0.40 g, 1.4 mmol) in THF (6 mL) was added 4-chlorophenethylmagnesium bromide (6.0 mL, 3.0 mmol) at rt. The reaction was quenched with sat. NaHCO$_3$ and EtOAc and stirred for 20 minutes. Then Celite® was added and the mixture was stirred for 10 minutes before being filtered through Celite®. The filtrate was then concentrated in vacuo to give the title compound.

Step 3: 1-(3-chloro-2,4-difluorophenyl)-3-(4-chlorophenyl)propan-1-amine hydrochloride. To a solution of N-(1-(3-chloro-2,4-difluorophenyl)-3-(4-chlorophenyl)propyl)-2-methylpropane-2-sulfinamide (0.59 g, 1.4 mmol) in DCM (2 mL) and MeOH (2 mL), was added a saturated solution of HCl (8.0 mL, 32 mmol, 4 M in EtOAc). After stirring 2 h, the reaction mixture was diluted with DCM and concentrated in vacuo. The resulting residue was then purified by reverse phase HPLC (90:10 to 80:20; water (0.1% TFA):MeCN (0.1% TFA)), followed by lyophilization. The resulting residue was dissolved in MeOH/DCM, and HCl (6.0 mL, 18 mmol, 3 N in MeOH) was added. The mixture was concentrated to give the title compound.

Step 4: (4S)—N—((R and S)-1-(3-chloro-2,4-difluorophenyl)-3-(4-chlorophenyl)propyl)-2-oxoimidazolidine-4-carboxamide. To a vial containing 1-(3-chloro-2,4-difluorophenyl)-3-(4-chlorophenyl)propan-1-amine hydrochloride (0.10 g, 0.29 mmol) were added (S)-2-oxoimidazolidine-4-carboxylic acid (45 mg, 0.35 mmol), EDC (67 mg, 0.35 mmol), HOBT (47 mg, 0.35 mmol), followed by DMF (2 mL) and DIPEA (75 μL, 0.43 mmol). After stirring overnight at rt, the reaction mixture was then purified by reverse phase HPLC (90:10 to 100:0; water (0.1% TFA):MeCN (0.1% TFA)), followed by lyophilization to give title compound.

Step 5: (4S)—N—((R or S)-1-(3-chloro-2,4-difluorophenyl)-3-(4-chlorophenyl)propyl)-2-oxoimidazolidine-4-carboxamide. (4S)—N—((R and S)-1-(3-chloro-2,4-difluorophenyl)-3-(4-chlorophenyl)propyl)-2-oxoimidazolidine-4-carboxamide was separated by chiral-SFC (method F) to give the title compounds: first eluted diastereomer 52A (4S)—N—((R or S)-1-(3-chloro-2,4-difluorophenyl)-3-(4-chlorophenyl)propyl)-2-oxoimidazolidine-4-carboxamide, and second eluted diastereomer 52B (4S)—N—((R or S)-1-(3-chloro-2,4-difluorophenyl)-3-(4-chlorophenyl)propyl)-2-oxoimidazolidine-4-carboxamide. Diastereomer 52A: LRMS m/z (M+H): calculated 428.1, observed 428.2. $^1$H NMR (500 MHz, DMSO-d6) δ 8.58 (d, J=7.9 Hz, 1H), 7.42 (q, J=8.3 Hz, 1H), 7.35-7.27 (m, 3H), 7.25-7.18 (m, 2H), 6.58 (s, 1H), 6.32 (s, 1H), 5.01-4.89 (m, 1H), 4.17-4.11 (m, 1H), 3.61-3.52 (m, 1H), 3.23-3.13 (m, 1H), 2.73-2.63 (m, 1H), 2.13-2.02 (m, 1H), 1.98-1.87 (m, 1H). Diastereomer 52B: LRMS m/z (M+H): calculated 428.1, observed 428.2. $^1$H NMR (500 MHz, DMSO-d6) δ 8.56 (d, J=8.0 Hz, 1H), 7.47-7.39 (m, 1H), 7.35-7.29 (m, 3H), 7.24-7.19 (m, 2H), 6.58 (s, 1H), 6.32 (s, 1H), 5.01-4.93 (m, 1H), 4.15-4.09 (m, 1H), 3.59-3.51 (m, 1H), 3.19-3.14 (m, 1H), 2.71-2.63 (m, 1H), 2.11-2.02 (m, 1H), 1.97-1.89 (m, 1H).

TABLE 7

The compounds of Examples 53-54B were prepared according to a synthetic procedure similar to the synthetic procedure for Examples 52A and 52B.

| Example | Structure | Name | Calc'd [M + H]$^+$ | Observed [M + H]$^+$ | Conditions |
|---|---|---|---|---|---|
| 53 | 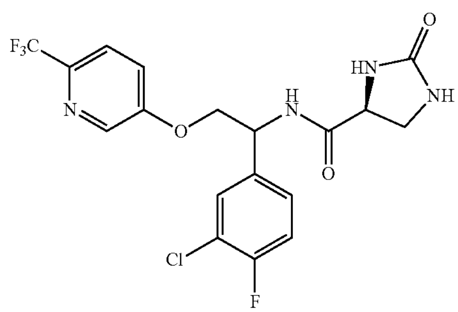 [SMILES: O=C1NC[C@@H](C(=O)NC(COc2ccc(C(F)(F)F)nc2)c2ccc(F)c(Cl)c2)N1] | (4S)-N-(1-(3-chloro-4-fluorophenyl)-2-((6-(trifluoromethyl)pyridin-3-yl)oxy)ethyl)-2-oxoimidazolidine-4-carboxamide | 447.1 | 447.2 | Not Resolved |
| 54A | 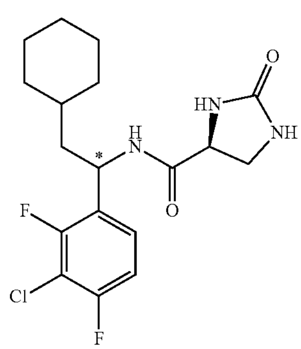 [SMILES: O=C1NC[C@@H](C(=O)NC(CC2CCCCC2)c2ccc(F)c(Cl)c2F)N1] | (S)-N-((R or S)-1-(3-chloro-2,4-difluorophenyl)-2-cyclohexylethyl)-2-oxoimidazolidine-4-carboxamide | 386.1 | 386.4 | Chiral method Y, peak 1 |
| 54B | 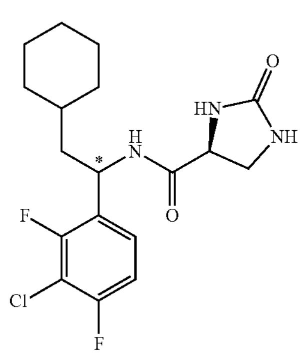 [SMILES: O=C1NC[C@@H](C(=O)NC(CC2CCCCC2)c2ccc(F)c(Cl)c2F)N1] | (S)-N-((R or S)-1-(3-chloro-2,4-difluorophenyl)-2-cyclohexylethyl)-2-oxoimidazolidine-4-carboxamide | 386.1 | 386.4 | Chiral method Y, peak 2 |

Examples 55A and 55B (4S)—N—((R)-(3-chloro-2,4-difluorophenyl)(2-(difluoromethoxy)pyrimidin-5-yl)methyl)-2-oxoimidazolidine-4-carboxamide and (4S)—N—((S)-(3-chloro-2,4-difluorophenyl)(2-(difluoromethoxy)pyrimidin-5-yl)methyl)-2-oxoimidazolidine-4-carboxamide

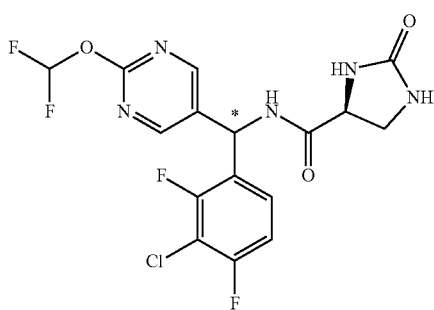 [SMILES: O=C1NC[C@@H](C(=O)NC(c2cnc(OC(F)F)nc2)c2ccc(F)c(Cl)c2F)N1]

Step 1: 5-bromo-2-(difluoromethoxy)pyrimidine. To a solution of 5-bromopyrimidin-2-ol (2.0 g, 11 mmol) in MeCN (50 mL) were added $K_2CO_3$ (6.4 g, 46 mmol) and ethyl 2-bromo-2,2-difluoroacetate (4.6 g, 23 mmol). The reaction mixture was stirred at 80° C. for 13 h, then diluted with water and extracted with EtOAc. The combined organic layers were washed with brine, dried over $Na_2SO_4$, filtered and concentrated in vacuo. The resulting residue was purified by silica gel chromatography (0-10% EtOAc:PE) to give the title compound.

Step 2: 2-(difluoromethoxy)-5-vinylpyrimidine. To a solution of 5-bromo-2-(difluoromethoxy)-pyrimidine (0.45 g, 2.0 mmol) in 1,4-Dioxane (8 mL) and water (2 mL) were added $K_2CO_3$ (0.56 g, 4.0 mmol), potassium trifluoro(vinyl)borate (0.40 g, 3.0 mmol) and Pd(dppf)Cl$_2$ (0.10 g, 0.14 mmol). The reaction mixture was degassed with $N_2$ and stirred at 80° C. for 3 h. Then the mixture was diluted with water and extracted with EtOAc. The combined organic layers were washed with brine, dried over $Na_2SO_4$, filtered and concentrated in vacuo to give title compound.

Step 3: 2-(difluoromethoxy)pyrimidine-5-carbaldehyde. To a solution of 2-(difluoromethoxy)-5-vinylpyrimidine (0.26 g crude) in 1,4-Dioxane (9 mL) and water (3 mL) were added 2,6-dimethylpyridine (0.32 g, 3.0 mmol), OsO$_4$ (38 mg, 0.15 mmol) and NaIO$_4$ (1.3 g, 6.0 mmol). The reaction was stirred at rt for 13 h. Then the mixture was diluted with water and extracted with EtOAc. The combined organic layers were washed with brine, dried over $Na_2SO_4$, filtered and concentrated in vacuo to give the title compound.

Step 4: (R)—N-((2-(difluoromethoxy)pyrimidin-5-yl)methylene)-2-methylpropane-2-sulfinamide. To a solution of 2-(difluoromethoxy)pyrimidine-5-carbaldehyde (0.22 g crude) in THF (10 mL) were added (R)-2-methylpropane-2-sulfinamide (0.31 g, 2.5 mmol) and Ti(OEt)$_4$ (0.58 g, 2.5 mmol). The reaction mixture was stirred at 55° C. for 2 h, then water was added. The mixture was diluted with EtOAc, filtered, and the filtrate was extracted with EtOAc. The combined organic layers were washed with brine, dried over $Na_2SO_4$, filtered and concentrated in vacuo. The resulting residue was purified by preparative silica gel TLC (25% EtOAc:PE) to give the title compound.

Step 5: (R)—N-((3-chloro-2,4-difluorophenyl)(2-(difluoromethoxy)pyrimidin-5-yl)methyl)-2-methylpropane-2-sulfinamide. To 1-bromo-3-chloro-2,4-difluorobenzene (0.37 g, 1.6 mmol) was added iPrMgCl (0.68 mL, 1.4 mmol) in THF (0.68 mL) at 0° C. The mixture was stirred at 0° C. for 2 h. Then (R)—N-((2-(difluoromethoxy)pyrimidin-5-yl)methylene)-2-methylpropane-2-sulfinamide (0.15 g, 0.54 mmol) in toluene (3 mL) was added at −50° C. The reaction was stirred at −50° C. for 1 h, then slowly warmed to 29° C. and stirred at 29° C. for 1 h. Then saturated NH$_4$Cl was added, and the mixture was diluted with water, extracted with EtOAc, and washed with brine. The combined organic layers were dried with $Na_2SO_4$, and the solvent was removed in vacuo. The resulting residue was purified by prep. silica gel TLC (50% EtOAc:PE) to give the title compound.

Step 6: (3-chloro-2,4-difluorophenyl)(2-(difluoromethoxy)pyrimidin-5-yl)methanamine, hydrochloride. To a solution of (R)—N-((3-chloro-2,4-difluorophenyl)(2-(difluoromethoxy)-pyrimidin-5-yl)methyl)-2-methylpropane-2-sulfinamide (80 mg, 0.19 mmol) in THF (2 mL) was added HCl (0.50 mL, 2.0 mmol 4 N in MeOH). The reaction mixture was stirred at 30° C. for 2 h, then concentrated in vacuo to give the title compound.

Step 7: (4S)—N-((R and S)-(3-chloro-2,4-difluorophenyl)(2-(difluoromethoxy)pyrimidin-5-yl)methyl)-2-oxoimidazolidine-4-carboxamide. To a solution of (3-chloro-2,4-difluorophenyl)(2-(difluoromethoxy)pyrimidin-5-yl)methanamine, hydrochloride (50 mg crude) in DMF (1.5 mL) were added TEA (0.024 mL, 0.17 mmol), (S)-2-oxoimidazolidine-4-carboxylic acid (11 mg, 0.085 mmol) and T$_3$P® (81 mg, 0.13 mmol). The reaction was stirred at 30° C. for 2 h, then diluted with MeCN and purified by reverse phase HPLC (73:27 to 43:57; water (0.1% TFA):MeCN (0.1% TFA)), followed by lyophilization. The resulting residue was dissolved in MeOH/DCM, and HCl (6.0 mL, 18 mmol, 3 N in MeOH) was added. The resulting mixture was concentrated to give the title compound.

Step 8: (4S)—N-((R or S)-(3-chloro-2,4-difluorophenyl)(2-(difluoromethoxy)pyrimidin-5-yl)methyl)-2-oxoimidazolidine-4-carboxamide. (4S)—N-((R and S)-(3-chloro-2,4-difluorophenyl)(2-(difluoromethoxy)pyrimidin-5-yl)methyl)-2-oxoimidazolidine-4-carboxamide were separated by chiral SFC (method H) to give the title compounds: first eluted diastereomer 55A (4S)—N-((R or S)-(3-chloro-2,4-difluorophenyl)(2-(difluoromethoxy)pyrimidin-5-yl)methyl)-2-oxoimidazolidine-4-carboxamide, and second eluted diastereomer 55B (4S)—N-((R or S)-(3-chloro-2,4-difluorophenyl)(2-(difluoromethoxy)pyrimidin-5-yl)methyl)-2-oxoimidazolidine-4-carboxamide. Diastereomer 55A: LRMS m/z (M+H): calculated 434.1, observed 434.0. $^1$H NMR (400 MHz, CD3OD) δ 8.58 (s, 2H), 7.57 (t, J=72.0 Hz, 1H), 7.32-7.38 (m, 1H), 7.17-7.22 (m, 1H), 6.51 (s, 1H), 4.36-4.41 (m, 1H), 3.77-3.82 (m, 1H), 3.44-3.48 (m, 1H). Diastereomer 55B: LRMS m/z (M+H): calculated 434.1, observed 434.0. $^1$H NMR (400 MHz, CD3OD) δ 8.59 (s, 2H), 7.57 (t, J=72.0 Hz, 1H), 7.32-7.38 (m, 1H), 7.17-7.22 (m, 1H), 6.50 (s, 1H), 4.36-4.41 (m, 1H), 3.77-3.82 (m, 1H), 3.44-3.48 (m, 1H).

TABLE 8

The compounds of Examples 56A-64B were prepared according to a synthetic procedure similar to the synthetic procedure for Examples 55A and 55B.

| Example | Structure | Name | Calc'd [M + H]+ | Observed [M + H]+ | Conditions |
|---------|-----------|------|-----------------|-------------------|------------|
| 56A | 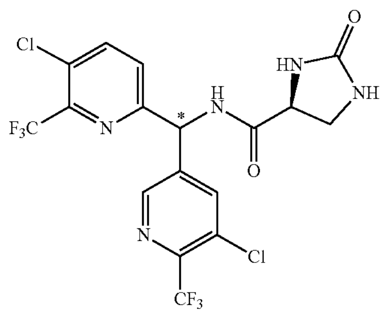 [SMILES: O=C1NC[C@@H](C(=O)NC(c2cnc(C(F)(F)F)c(Cl)c2)c2ccc(Cl)c(C(F)(F)F)n2)N1] | (S)-N-((R or S)-(5-chloro-6-(trifluoromethyl)pyridin-2-yl)(5-chloro-6-(trifluoromethyl)pyridin-3-yl)methyl)-2-oxoimidazolidine-4-carboxamide | 502.0 | 502.0 | Chiral method Z, peak 1 |
| 56B | 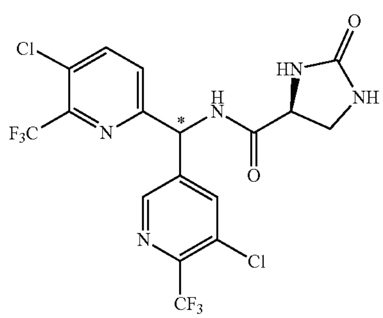 [SMILES: O=C1NC[C@@H](C(=O)NC(c2cnc(C(F)(F)F)c(Cl)c2)c2ccc(Cl)c(C(F)(F)F)n2)N1] | (S)-N-((R or S)-(5-chloro-6-(trifluoromethyl)pyridin-2-yl)(5-chloro-6-(trifluoromethyl)pyridin-3-yl)methyl)-2-oxoimidazolidine-4-carboxamide | 502.0 | 502.0 | Chiral method Z, peak 2 |
| 57A | 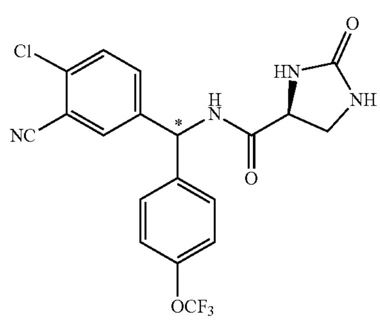 [SMILES: N#Cc1cc(C(NC(=O)[C@@H]2CNC(=O)N2)c2ccc(OC(F)(F)F)cc2)ccc1Cl] | (S)-N-((R or S)-(4-chloro-3-cyanophenyl)(4-(trifluoromethoxy)phenyl)methyl)-2-oxoimidazolidine-4-carboxamide | 439.1 | 439.1 | Chiral method AA, peak 1 |
| 57B | 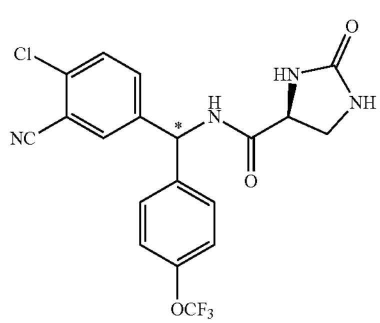 [SMILES: N#Cc1cc(C(NC(=O)[C@@H]2CNC(=O)N2)c2ccc(OC(F)(F)F)cc2)ccc1Cl] | (S)-N-((R or S)-(4-chloro-3-cyanophenyl)(4-(trifluoromethoxy)phenyl)methyl)-2-oxoimidazolidine-4-carboxamide | 439.1 | 439.1 | Chiral method AA, peak 2 |

TABLE 8-continued

The compounds of Examples 56A-64B were prepared according to a synthetic procedure similar to the synthetic procedure for Examples 55A and 55B.

| Example | Structure | Name | Calc'd [M + H]+ | Observed [M + H]+ | Conditions |
|---|---|---|---|---|---|
| 58A | 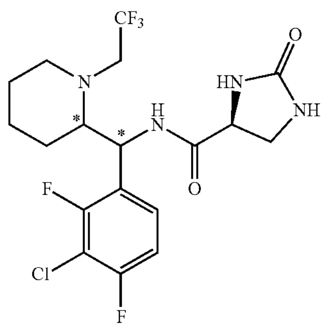 [SMILES: O=C1NC[C@@H](C(=O)NC(c2ccc(F)c(Cl)c2F)C2CCCCN2CC(F)(F)F)N1] | (S)-N-((R or S)-(3-chloro-2,4-difluorophenyl)((R or S)-1-(2,2,2-trifluoroethyl)piperidin-2-yl)methyl)-2-oxoimidazolidine-4-carboxamide | 455.1 | 455.1 | Chiral method C, Peak 1 |
| 58B | 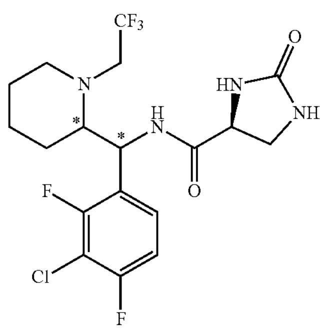 [SMILES: O=C1NC[C@@H](C(=O)NC(c2ccc(F)c(Cl)c2F)C2CCCCN2CC(F)(F)F)N1] | (S)-N-((R or S)-(3-chloro-2,4-difluorophenyl)((R or S)-1-(2,2,2-trifluoroethyl)piperidin-2-yl)methyl)-2-oxoimidazolidine-4-carboxamide | 455.1 | 455.1 | Chiral method C, Peak 2 |
| 58C | 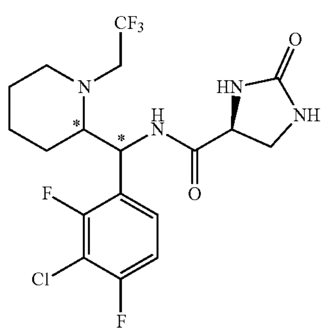 [SMILES: O=C1NC[C@@H](C(=O)NC(c2ccc(F)c(Cl)c2F)C2CCCCN2CC(F)(F)F)N1] | (S)-N-((R or S)-(3-chloro-2,4-difluorophenyl)((R or S)-1-(2,2,2-trifluoroethyl)piperidin-2-yl)methyl)-2-oxoimidazolidine-4-carboxamide | 455.1 | 455.1 | Chiral method C, Peak 3 |
| 58D | 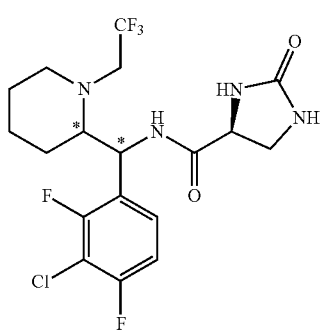 [SMILES: O=C1NC[C@@H](C(=O)NC(c2ccc(F)c(Cl)c2F)C2CCCCN2CC(F)(F)F)N1] | (S)-N-((R or S)-(3-chloro-2,4-difluorophenyl)((R or S)-1-(2,2,2-trifluoroethyl)piperidin-2-yl)methyl)-2-oxoimidazolidine-4-carboxamide | 455.1 | 455.1 | Chiral method C, Peak 4 |

TABLE 8-continued

The compounds of Examples 56A-64B were prepared according to a synthetic procedure similar to the synthetic procedure for Examples 55A and 55B.

| Example | Structure | Name | Calc'd [M + H]+ | Observed [M + H]+ | Conditions |
|---|---|---|---|---|---|
| 59A | 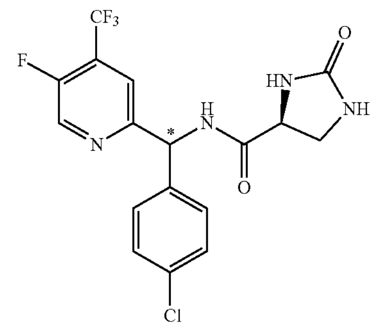 [SMILES: O=C1NC[C@@H](C(=O)NC(c2ccc(Cl)cc2)c2cc(C(F)(F)F)c(F)cn2)N1] | (S)-N-((R or S)-(4-chlorophenyl)(5-fluoro-4-(trifluoromethyl)pyridin-2-yl)methyl)-2-oxoimidazolidine-4-carboxamide | 417.1 | 417.1 | Chiral method AB, Peak 1 |
| 59B | 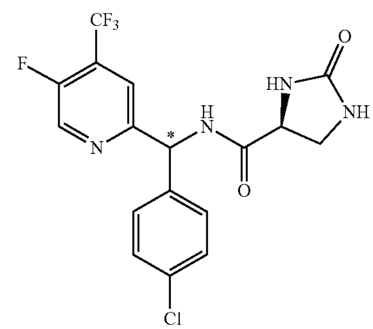 [SMILES: O=C1NC[C@@H](C(=O)NC(c2ccc(Cl)cc2)c2cc(C(F)(F)F)c(F)cn2)N1] | (S)-N-((R or S)-(4-chlorophenyl)(5-fluoro-4-(trifluoromethyl)pyridin-2-yl)methyl)-2-oxo-imidazolidine-4-carboxamide | 417.1 | 417.1 | Chiral method AB, Peak 2 |
| 60A | 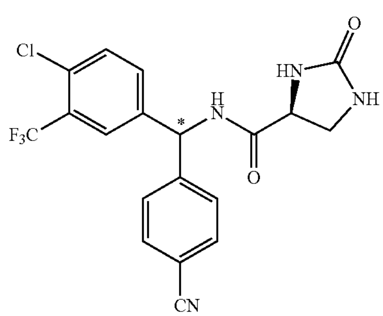 [SMILES: N#Cc1ccc(C(NC(=O)[C@@H]2CNC(=O)N2)c2ccc(Cl)c(C(F)(F)F)c2)cc1] | (S)-N-((R or S)-(4-chloro-3-(trifluoromethyl)-phenyl)(4-cyanophenyl)-methyl)-2-oxo-imidazolidine-4-carboxamide | 423.1 | 423 | Chiral method A, Peak 1 |
| 60B | 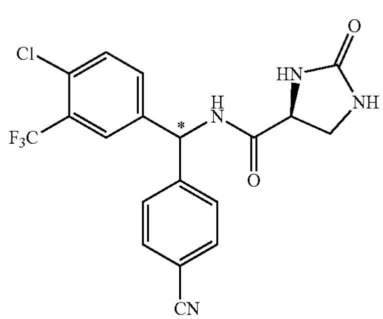 [SMILES: N#Cc1ccc(C(NC(=O)[C@@H]2CNC(=O)N2)c2ccc(Cl)c(C(F)(F)F)c2)cc1] | (S)-N-((R or S)-(4-chloro-3-(trifluoromethyl)-phenyl)(4-cyanophenyl)-methyl)-2-oxo-imidazolidine-4-carboxamide | 423.1 | 423 | Chiral method A, Peak 2 |

TABLE 8-continued

The compounds of Examples 56A-64B were prepared according to a synthetic procedure similar to the synthetic procedure for Examples 55A and 55B.

| Example | Structure | Name | Calc'd [M + H]+ | Observed [M + H]+ | Conditions |
|---|---|---|---|---|---|
| 61 | 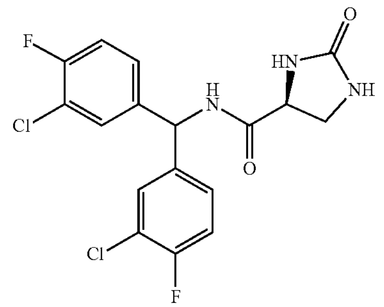 [SMILES: O=C1NC[C@@H](C(=O)NC(c2ccc(F)c(Cl)c2)c2ccc(F)c(Cl)c2)N1] | (S)-N-(bis(3-chloro-4-fluorophenyl)methyl)-2-oxoimidazolidine-4-carboxamide | 400.0 | 400.1 | N/A |
| 62A | 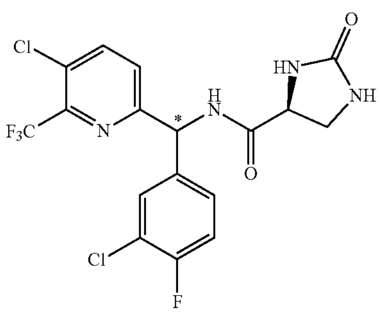 [SMILES: O=C1NC[C@@H](C(=O)NC(c2ccc(F)c(Cl)c2)c2ccc(Cl)c(C(F)(F)F)n2)N1] | (S)-N-((R or S)-(3-chloro-4-fluorophenyl)(5-chloro-6-(trifluoromethyl)pyridin-2-yl)methyl)-2-oxoimidazolidine-4-carboxamide | 451 | 451.1 | Chiral method AC, Peak 1 |
| 62B | 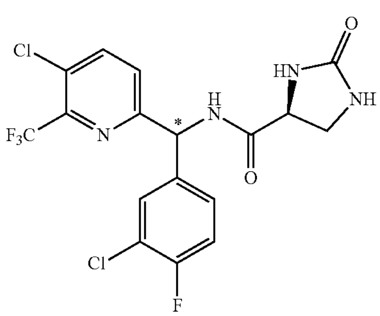 [SMILES: O=C1NC[C@@H](C(=O)NC(c2ccc(F)c(Cl)c2)c2ccc(Cl)c(C(F)(F)F)n2)N1] | (S)-N-((R or S)-(3-chloro-4-fluorophenyl)(5-chloro-6-(trifluoromethyl)pyridin-2-yl)methyl)-2-oxoimidazolidine-4-carboxamide | 451 | 451.0 | Chiral method AC, Peak 2 |
| 63A | 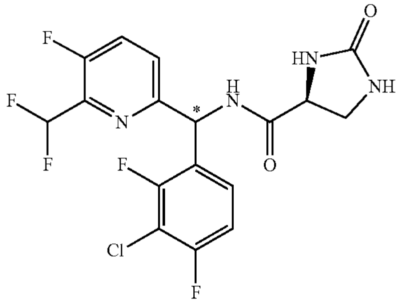 [SMILES: O=C1NC[C@@H](C(=O)NC(c2ccc(F)c(C(F)F)n2)c2ccc(F)c(Cl)c2F)N1] | (S)-N-((R or S)-(3-chloro-2,4-difluorophenyl)(6-(difluoromethyl)-5-fluoropyridin-2-yl)methyl)-2-oxoimidazolidine-4-carboxamide | 435.1 | 435 | Chiral method AA, Peak 1 |

TABLE 8-continued

The compounds of Examples 56A-64B were prepared according to a synthetic procedure similar to the synthetic procedure for Examples 55A and 55B.

| Example | Structure | Name | Calc'd [M + H]+ | Observed [M + H]+ | Conditions |
|---|---|---|---|---|---|
| 63B | 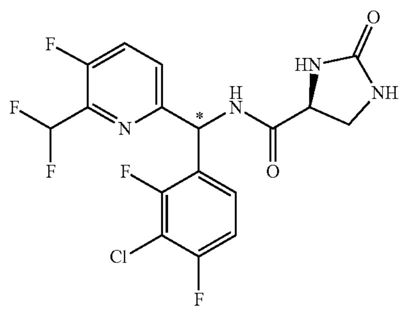 [SMILES: O=C1NC[C@@H](C(=O)NC(c2ccc(F)c(C(F)F)n2)c2ccc(F)c(Cl)c2F)N1] | (S)-N-((R or S)-(3-chloro-2,4-difluorophenyl)(6-(difluoromethyl)-5-fluoropyridin-2-yl)methyl)-2-oxoimidazolidine-4-carboxamide | 435.1 | 435 | Chiral method AA, Peak 2 |
| 64A | 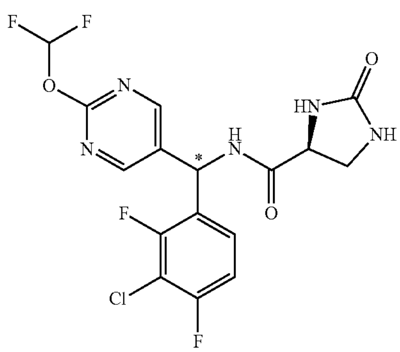 [SMILES: O=C1NC[C@@H](C(=O)NC(c2cnc(OC(F)F)nc2)c2ccc(F)c(Cl)c2F)N1] | (S)-N-((R or S)-(3-chloro-2,4-difluorophenyl)(2-(difluoromethoxy)pyrimidin-5-yl)methyl)-2-oxoimidazolidine-4-carboxamide | 434.1 | 434.0 | Chiral method N, Peak 1 |
| 64B | 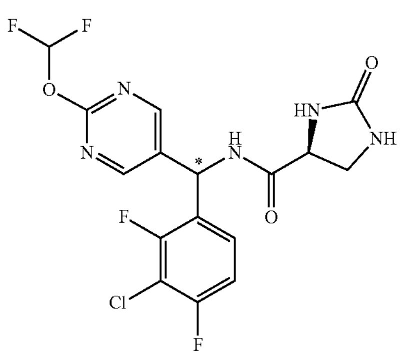 [SMILES: O=C1NC[C@@H](C(=O)NC(c2cnc(OC(F)F)nc2)c2ccc(F)c(Cl)c2F)N1] | (S)-N-((R or S)-(3-chloro-2,4-difluorophenyl)(2-(difluoromethoxy)pyrimidin-5-yl)methyl)-2-oxoimidazolidine-4-carboxamide | 434.1 | 434.0 | Chiral method N, Peak 2 |

Examples 65A, 65B, 65C and 65D (S)—N—((R)-(3-chloro-2,4-difluorophenyl)(3-methyl-1-((S)-1,1,1-trifluoropropan-2-yl)azetidin-3-yl)methyl)-2-oxoimidazolidine-4-carboxamide, (S)—N—((R)-(3-chloro-2,4-difluorophenyl)(3-methyl-1-((R)-1,1,1-trifluoropropan-2-yl)azetidin-3-yl)methyl)-2-oxoimidazolidine-4-carboxamide, (S)—N—((S)-(3-chloro-2,4-difluorophenyl)(3-methyl-1-((S)-1,1,1-trifluoropropan-2-yl)azetidin-3-yl)methyl)-2-oxoimidazolidine-4-carboxamide and (S)—N—((S)-(3-chloro-2,4-difluorophenyl)(3-methyl-1-((R)-1,1,1-trifluoropropan-2-yl)azetidin-3-yl)methyl)-2-oxoimidazolidine-4-carboxamide

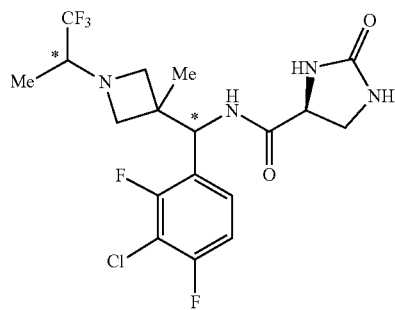 [SMILES: CC(N1CC(C)(C(NC(=O)[C@@H]2CNC(=O)N2)c2ccc(F)c(Cl)c2F)C1)C(F)(F)F]

Step 1: tert-butyl 3-(methoxy(methyl)carbamoyl)-3-methylazetidine-1-carboxylate. To a solution of 1-(boc)-3-methylazetidine-3-carboxylic acid (0.80 g, 3.7 mmol) in DCM (10 mL) was added CDI (1.2 g, 7.4 mmol) at rt for 1 h. Then TEA (1.6 mL, 11 mmol) and N,O-dimethylhydroxylamine hydrochloride (0.72 g, 7.4 mmol) were added, and the mixture was stirred at rt for 10 h. Water was added, and the mixture was extracted with DCM. The combined organic layers were washed with brine, dried over $Na_2SO_4$, filtered and concentrated in vacuo. The resulting residue was purified by silica gel chromatography (25-45% EtOAc:PE) to give the title compound.

Step 2: tert-butyl 3-(3-chloro-2,4-difluorobenzoyl)-3-methylazetidine-1-carboxylate. To a stirred solution of 1-bromo-3-chloro-2,4-difluorobenzene (2.1 g, 9.2 mmol) in THF (5 mL) was added iPrMgCl (4.6 mL, 9.2 mmol, 2.0 M in THF) at 0° C. The mixture was warmed to rt and stirred for 2 h. Then tert-butyl 3-(methoxy(methyl)carbamoyl)-3-methylazetidine-1-carboxylate (0.79 g, 3.1 mmol) in THF (5 mL) was added. The reaction was stirred at 0° C. for 30 min, then allowed to slowly warm to rt. After stirring at rt for 10 h, the reaction was quenched with sat. $NH_4Cl$ and extracted with EtOAc. The combined organic layers were washed with brine, dried over $Na_2SO_4$, filtered and concentrated in vacuo. The resulting crude product was purified by silica gel chromatography (10% EtOAc:PE) to give the title compound.

Step 3: (3-chloro-2,4-difluorophenyl)(3-methylazetidin-3-yl)methanone hydrochloride. A solution of tert-butyl 3-(3-chloro-2,4-difluorobenzoyl)-3-methylazetidine-1-carboxylate (0.20 g, 0.58 mmol) in HCl (10 mL, 40 mmol, 4 N in MeOH) was stirred at rt for 12 h. Then the solvent was removed under reduce pressure to give the title compound.

Step 4: (3-chloro-2,4-difluorophenyl)(3-methyl-1-(1,1,1-trifluoropropan-2-yl)azetidin-3-yl)methanone. To a solution of (3-chloro-2,4-difluorophenyl)(3-methylazetidin-3-yl)methanone hydrochloride (0.14 g crude) in DCE (2 mL) was added $MgSO_4$ (0.14 g, 1.1 mmol), 1,1,1-trifluoropropan-2-one (0.13 g, 1.1 mmol). The reaction was stirred at rt for 12 h, then $NaBH_3CN$ (54 mg, 0.86 mmol) was added in three batches, one hour apart. Then the reaction stirred for 3 h, diluted with water and extracted with EtOAc. The combined organic layers were washed with brine, dried over $Na_2SO_4$, filtered and concentrated in vacuo. The resulting crude product was purified by prep. silica gel TLC (10% EtOAc:PE) to give the title compound.

Step 5: (R)—N-(-(3-chloro-2,4-difluorophenyl)(3-methyl-1-(1,1,1-trifluoropropan-2-yl)azetidin-3-yl)methylene)propane-2-sulfinamide. A mixture of (3-chloro-2,4-difluorophenyl)(3-methyl-1-(1,1,1-trifluoropropan-2-yl)azetidin-3-yl)methanone (0.18 g, 0.53 mmol), $Ti(OEt)_4$ (0.24 g, 1.1 mmol) and (R)-2-methylpropane-2-sulfinamide (77 mg, 0.63 mmol) in toluene (2 mL) was sealed in a 10 mL vial and stirred at 110° C. for 4 h with microwave irradiation. Then the reaction mixture was concentrated, treated with water, and extracted with EtOAc. The combined organic layers were washed with brine, dried over $Na_2SO_4$, filtered and concentrated in vacuo to give the title compound.

Step 6: (R)—N-((3-chloro-2,4-difluorophenyl)(3-methyl-1-(1,1,1-trifluoropropan-2-yl)azetidin-3-yl)methyl)-2-methylpropane-2-sulfinamide. A solution of (R)—N-(-(3-chloro-2,4-difluorophenyl)(3-methyl-1-(1,1,1-trifluoropropan-2-yl)azetidin-3-yl)methylene)propane-2-sulfinamide (0.20 g crude) in THF (2 mL) and water (0.02 mL) was cooled to −78° C., followed by addition of $NaBH_4$ (31 mg, 0.81 mmol). The mixture was stirred at −78° C. for 5 minutes, then diluted with water and extracted with EtOAc. The combined organic layers were washed with brine, dried over $Na_2SO_4$, filtered and concentrated in vacuo to give the title compound.

Step 7: (3-chloro-2,4-difluorophenyl)(3-methyl-1-(1,1,1-trifluoropropan-2-yl)azetidin-3-yl)methanamine. A solution of (R)—N-((3-chloro-2,4-difluorophenyl)(3-methyl-1-(1,1,1-trifluoropropan-2-yl)azetidin-3-yl)methyl)-2-methylpropane-2-sulfinamide (0.17 g, 0.50 mmol) in HCl (2.0 mL, 8.0 mmol, 4 N in MeOH) was stirred at rt for 12 hours. Then the solvent was evaporated to give the title compound.

Step 8: (S)—N—((R and S)-(3-chloro-2,4-difluorophenyl)(3-methyl-1-((R and S)-1,1,1-trifluoropropan-2-yl)azetidin-3-yl)methyl)-2-oxoimidazolidine-4-carboxamide. To a solution of (3-chloro-2,4-difluorophenyl)(3-methyl-1-(1,1,1-trifluoropropan-2-yl)azetidin-3-yl)methanamine (0.12 g, 0.35 mmol) in DMF (2 mL) were added DIEA (0.12 mL, 0.70 mmol), $T_3P$® (0.33 g, 0.52 mmol, 50% in EtOAc) and (S)-2-oxoimidazolidine-4-carboxylic acid (50 mg, 0.38 mmol). The reaction was stirred at rt for 2 h. The residue was purified by reverse phase HPLC (65:35 to 35:65; water (0.1% TFA):MeCN (0.1% TFA)), followed by lyophilization to give the title compound.

Step 9: (S)—N—((R or S)-(3-chloro-2,4-difluorophenyl)(3-methyl-1-((R or S)-1,1,1-trifluoropropan-2-yl)azetidin-3-yl)methyl)-2-oxoimidazolidine-4-carboxamide. (S)—N—((R and S)-(3-chloro-2,4-difluorophenyl)(3-methyl-1-((R and S)-1,1,1-trifluoropropan-2-yl)azetidin-3-yl)methyl)-2-oxoimidazolidine-4-carboxamide was purified by chiral SFC (Phenomenex-Cellulose-2, co-solvent: 35% EtOH (0.1% $NH_3H_2O$) to give the title compounds: first eluted isomer 65A (S)—N—((R or S)-(3-chloro-2,4-difluorophenyl)(3-methyl-1-((R or S)-1,1,1-trifluoropropan-2-yl)azetidin-3-yl)methyl)-2-oxoimidazolidine-4-carboxamide, second eluted isomer 65B (S)—N—((R or S)-(3-chloro-2,4-difluorophenyl)(3-methyl-1-((R or S)-1,1,1-trifluoropropan-2-yl)azetidin-3-yl)methyl)-2-oxoimidazolidine-4-carboxamide, third eluted isomer 65C (S)—N—((R or S)-

(3-chloro-2,4-difluorophenyl)(3-methyl-1-((R or S)-1,1,1-trifluoropropan-2-yl)azetidin-3-yl)methyl)-2-oxoimidazolidine-4-carboxamide, and fourth eluted isomer 65D (S)—N—((R or S)-(3-chloro-2,4-difluorophenyl)(3-methyl-1-((R or S)-1,1,1-trifluoropropan-2-yl)azetidin-3-yl)methyl)-2-oxoimidazolidine-4-carboxamide. Isomer 65A: LRMS m/z (M+H): calculated 455.1, observed 455.2. $^1$H NMR (400 MHz, CD$_3$OD) δ 7.30-7.41 (m, 1H), 7.10-7.19 (m, 1H), 5.34 (s, 1H), 4.37 (dd, J=6.4, 10.4 Hz, 1H), 3.80 (t, J=9.6 Hz, 1H), 3.47 (d, J=8.0 Hz, 1H), 3.39-3.45 (m, 2H), 3.17 (d, J=8.0 Hz, 1H), 3.11 (d, J=7.6 Hz, 1H), 2.94-3.05 (m, 1H), 1.23 (s, 3H), 1.13 (d, J=6.8 Hz, 3H). Isomer 65B: LRMS m/z (M+H): calculated 455.1, observed 455.1. $^1$H NMR (500 MHz, CD$_3$OD) δ 7.31-7.40 (m, 1H), 7.13 (t, J=8.5 Hz, 1H), 5.31 (s, 1H), 4.32 (dd, J=6.0, 10.0 Hz, 1H), 3.79 (t, J=9.5 Hz, 1H), 3.50 (d, J=7.5 Hz, 1H), 3.41 (dd, 9.5 Hz, 1H), 3.35 (d, J=7.5 Hz, 1H), 3.12 (dd, J=7.5, 12.0 Hz, 2H), 2.92-3.02 (m, 1H), 1.22 (s, 3H), 1.12 (d, J=6.5 Hz, 3H). Isomer 65C: LRMS m/z (M+H): calculated 455.1, observed 455.1. $^1$H NMR (400 MHz, CD$_3$OD) δ 7.32-7.37 (m, 1H), 7.10-7.15 (m, 1H), 5.32 (s, 1H), 4.32 (dd, J=6.8, 10.0 Hz, 1H), 3.78 (t, J=9.6 Hz, 1H), 3.48 (d, J=8.0 Hz, 1H), 3.35-3.42 (m, 2H), 3.16 (d, J=7.6 Hz, 1H), 3.09 (d, J=7.4 Hz, 1H), 2.94-3.01 (m, 1H), 1.22 (s, 3H), 1.11 (d, J=6.8 Hz, 3H). Isomer 65D: LRMS m/z (M+H): calculated 455.1, observed 455.1. $^1$H NMR (500 MHz, CD$_3$OD) δ 7.32-7.37 (m, 1H), 7.11-7.15 (m, 1H), 5.33 (s, 1H), 4.35 (dd, J=6.5, 10.0 Hz, 1H), 3.78 (t, J=9.5 Hz, 1H), 3.48 (d, J=7.5 Hz, 1H), 3.42 (dd, J=6.5, 9.0 Hz, 1H), 3.36 (d, J=7.5 Hz, 1H), 3.12 (dd, J=8.0, 10.0 Hz, 2H), 2.94-3.00 (m, 1H), 1.22 (s, 3H), 1.12 (d, J=6.5 Hz, 3H).

Examples 66A and 66B (S)—N—((R)-(3-chloro-4-fluorophenyl)(2-methylbenzo[d]thiazol-5-yl)methyl)-2-oxoimidazolidine-4-carboxamide and (S)—N—((S)-(3-chloro-4-fluorophenyl)(2-methylbenzo[d]thiazol-5-yl)methyl)-2-oxoimidazolidine-4-carboxamide

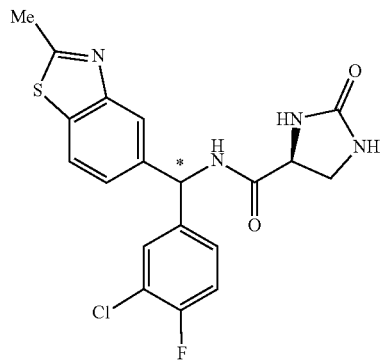 [SMILES: Cc1nc2cc(C(NC(=O)[C@@H]3CNC(=O)N3)c3ccc(F)c(Cl)c3)ccc2s1]

Step 1: N-methoxy-N,2-dimethylbenzo[d]thiazole-5-carboxamide. 2-methylbenzo[d]thiazole-5-carboxylic acid (1.0 g, 5.2 mmol), N-Methylmorpholine (0.57 mL, 5.2 mmol), and N,O-dimethylhydroxylamine hydrochloride (0.50 g, 5.2 mmol) were dissolved in DMF (10 mL) at rt, then HATU (2.5 g, 6.5 mmol) was added. Then the reaction was extracted with EtOAc and washed with sat. NaHCO$_3$, brine, dried over MgSO$_4$, filtered and concentrated in vacuo. The resulting residue was purified by silica gel chromatography (0-100% (3:1 EtOAc:EtOH):hex to give the title compound.

Step 2: (3-chloro-4-fluorophenyl)(2-methylbenzo[d]thiazol-5-yl)methanone. To a solution of 2-chloro-1-fluoro-4-iodobenzene (0.87 mL, 6.8 mmol) in THF (5.6 mL) at 0° C. was slowly added iPrMgCl (2.3 mL, 4.5 mmol) dropwise over 5 minutes. The mixture was allowed to stir for 15 minutes before being slowly added to a solution of N-methoxy-N,2-dimethylbenzo[d]thiazole-5-carboxamide (0.53 g, 2.3 mmol) in toluene (28 mL) at 0° C. The reaction was then allowed to warm to room temperature and stirred overnight. The reaction was quenched with 1 M HCl stirred for 10 minutes, then extracted with EtOAc. The combined organic layers were washed with sat. NaHCO$_3$ and brine, dried over MgSO$_4$, and concentrated in vacuo. The resulting residue was purified by silica gel chromatography (0-100% EtOAc:hex) to give the title compound.

Step 3: (3-chloro-4-fluorophenyl)(2-methylbenzo[d]thiazol-5-yl)methanamine. A solution of (3-chloro-4-fluorophenyl)(2-methylbenzo[d]thiazol-5-yl)methanone (0.39 g, 1.3 mmol), NH$_4$OAc (2.0 g, 26 mmol) and NaCNBH$_3$ (0.24 g, 3.8 mmol) in EtOH (8 mL) was heated via microwave irradiation for 15 min at 130° C. Then the reaction was quenched with excess TFA (9.8 mL, 0.13 mol), and concentrated in vacuo. The resulting residue was purified by reverse phase HPLC (95:5 to 5:95; water (0.1% TFA):MeCN (0.1% TFA)), followed by lyophilization to give the title compound.

Step 4: (S)—N—((R and S)-(3-chloro-4-fluorophenyl)(2-methylbenzo[d]thiazol-5-yl)methyl)-2-oxoimidazolidine-4-carboxamide. To a solution of (S)-2-oxoimidazolidine-4-carboxylic acid (21 mg, 0.16 mmol), (3-chloro-4-fluorophenyl)(2-methylbenzo[d]thiazol-5-yl)methanamine (75 mg, 0.18 mmol), and DIEA (0.093 mL, 0.54 mmol) in DMF (1 mL) was added HATU (88 mg, 0.23 mmol) at rt. The reaction stirred for 1 h. Then MeOH was added and the reaction was purified by reverse phase HPLC (95:5 to 5:95; water (0.1% TFA):MeCN (0.1% TFA)), followed by lyophilization to give the title compound.

Step 5: (S)—N—((R)-(3-chloro-4-fluorophenyl)(2-methylbenzo[d]thiazol-5-yl)methyl)-2-oxoimidazolidine-4-carboxamide. (S)—N—((R and S)-(3-chloro-4-fluorophenyl)(2-methylbenzo[d]thiazol-5-yl)methyl)-2-oxoimidazolidine-4-carboxamide was separated by chiral SFC (method AD) to give the title compounds: first eluted diastereomer 66A (S)—N—((R or S)-(3-chloro-4-fluorophenyl)(2-methylbenzo[d]thiazol-5-yl)methyl)-2-oxoimidazolidine-4-carboxamide, and second eluted diastereomer 66B (S)—N—((R or S)-(3-chloro-4-fluorophenyl)(2-methylbenzo[d]thiazol-5-yl)methyl)-2-oxoimidazolidine-4-carboxamide. Diastereomer 66A: LRMS m/z (M+H): calculated 419.1, observed 419.2. $^1$H NMR (500 MHz, DMSO-d$_6$) δ 8.90 (d, J=8.4 Hz, 1H), 7.99 (d, J=8.3 Hz, 1H), 7.86 (s, 1H), 7.57 (dd, J=7.1, 1.8 Hz, 1H), 7.42-7.32 (m, 3H), 6.60 (s, 1H), 6.32-6.27 (m, 2H), 4.23 (dd, J=9.2, 6.3 Hz, 1H), 3.56 (t, J=9.2 Hz, 1H), 3.26-3.21 (m, 1H), 2.78 (s, 3H). Diastereomer 66B: LRMS m/z (M+H): calculated 419.1, observed 419.2. $^1$H NMR (500 MHz, DMSO-d$_6$) δ 8.87 (d, J=8.3 Hz, 1H), 7.99 (d, J=8.3 Hz, 1H), 7.86 (s, 1H), 7.58 (dd, J=7.1, 1.6 Hz, 1H), 7.42-7.31 (m, 3H), 6.60 (s, 1H), 6.32-6.28 (m, 2H), 4.23 (dd, J=9.6, 6.0 Hz, 1H), 3.56 (t, J=9.3 Hz, 1H), 3.24 (dd, J=8.4, 6.3 Hz, 1H), 2.78 (s, 3H).

TABLE 9

The compounds of Examples 67A-79H were prepared according to a synthetic procedure similar to the synthetic procedure for Example 66A and 66B.

| Example | Structure | Name | Calc'd [M + H]+ | Observed [M + H]+ | Conditions |
|---|---|---|---|---|---|
| 67A | 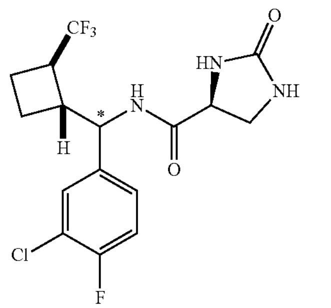 [SMILES: O=C1NC[C@@H](C(=O)NC(c2ccc(F)c(Cl)c2)[C@@H]2CC[C@H]2C(F)(F)F)N1] | (S)-N-((R or S)-(3-chloro-4-fluorophenyl)(trans-2-(trifluoromethyl)cyclobutyl)methyl)-2-oxoimidazolidine-4-carboxamide | 394.1 | 394.3 | Step 2 run at -20° C. Final purification by silica gel chromatography, peak 1 |
| 67B | 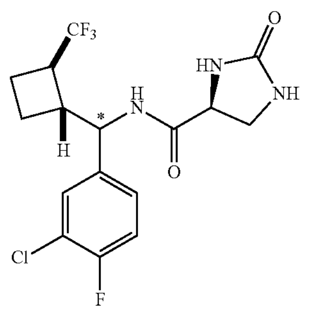 [SMILES: O=C1NC[C@@H](C(=O)NC(c2ccc(F)c(Cl)c2)[C@@H]2CC[C@H]2C(F)(F)F)N1] | (S)-N-((R or S)-(3-chloro-4-fluorophenyl)(trans-2-(trifluoromethyl)cyclobutyl)methyl)-2-oxoimidazolidine-4-carboxamide | 394.1 | 394.3 | Step 2 run at -20° C. Final purification by silica gel chromatography, peak 2 |
| 68 | 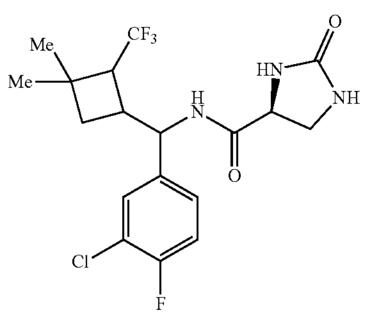 [SMILES: CC1(C)CC(C(NC(=O)[C@@H]2CNC(=O)N2)c2ccc(F)c(Cl)c2)C1C(F)(F)F] | (4S)-N-((3-chloro-4-fluorophenyl)(3,3-dimethyl-2-(trifluoromethyl)cyclobutyl)methyl)-2-oxoimidazolidine-4-carboxamide | 422.1 | 422.2 | Not resolved |
| 69 | 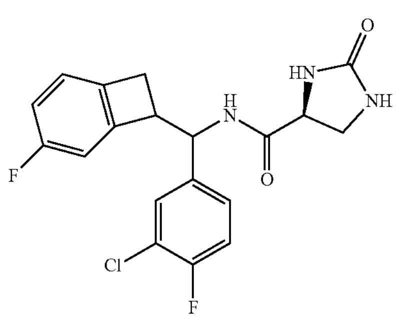 [SMILES: O=C1NC[C@@H](C(=O)NC(c2ccc(F)c(Cl)c2)C2Cc3ccc(F)cc32)N1] | (4S)-N-((3-chloro-4-fluorophenyl)(4-fluorobicyclo[4.2.0]octa-1(6),2,4-trien-7-yl)methyl)-2-oxoimidazolidine-4-carboxamide | 392.1 | 392.2 | Not resolved |

TABLE 9-continued

The compounds of Examples 67A-79H were prepared according to a synthetic procedure similar to the synthetic procedure for Example 66A and 66B.

| Example | Structure | Name | Calc'd [M + H]+ | Observed [M + H]+ | Conditions |
|---|---|---|---|---|---|
| 70A | 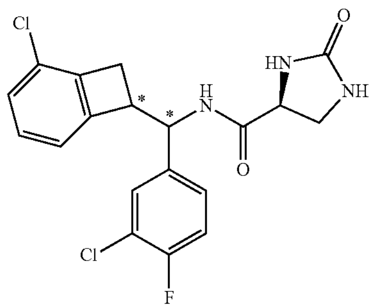 [SMILES: O=C1NC[C@@H](C(=O)NC(c2ccc(F)c(Cl)c2)C2Cc3c(Cl)cccc32)N1] | (S)-N-((R or S)-(3-chloro-4-fluoro-phenyl)((R or S)-2-chlorobicyclo[4.2.0]-octa-1(6),2,4-trien-7-yl)methyl)-2-oxoimidazolidine-4-carboxamide | 408.1 | 408.2 | Chiral method L, Peak 1 |
| 70B | 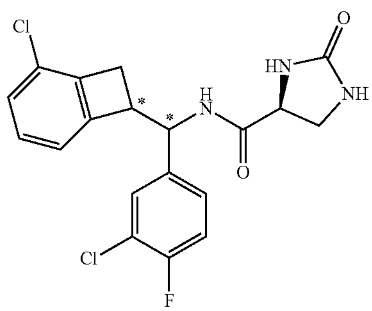 [SMILES: O=C1NC[C@@H](C(=O)NC(c2ccc(F)c(Cl)c2)C2Cc3c(Cl)cccc32)N1] | (S)-N-((R or S)-(3-chloro-4-fluoro-phenyl)((R or S)-2-chlorobicyclo[4.2.0]-octa-1(6),2,4-trien-7-yl)methyl)-2-oxoimidazolidine-4-carboxamide | 408.1 | 408.2 | Chiral method L, Peak 2 |
| 70C | 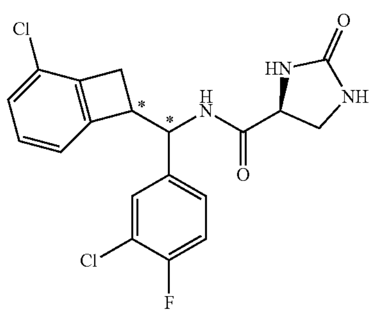 [SMILES: O=C1NC[C@@H](C(=O)NC(c2ccc(F)c(Cl)c2)C2Cc3c(Cl)cccc32)N1] | (S)-N-((R or S)-(3-chloro-4-fluoro-phenyl)((R or S)-2-chlorobicyclo[4.2.0]-octa-1(6),2,4-trien-7-yl)methyl)-2-oxoimidazolidine-4-carboxamide | 408.1 | 408.2 | Chiral method L, Peak 3 |
| 70D | 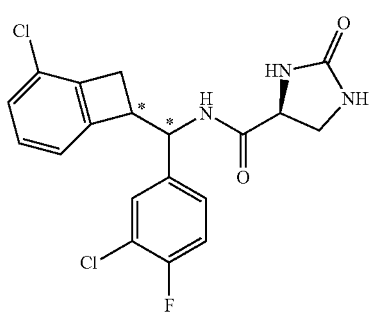 [SMILES: O=C1NC[C@@H](C(=O)NC(c2ccc(F)c(Cl)c2)C2Cc3c(Cl)cccc32)N1] | (S)-N-((R or S)-(3-chloro-4-fluoro-phenyl)((R or S)-2-chlorobicyclo[4.2.0]-octa-1(6),2,4-trien-7-yl)methyl)-2-oxoimidazolidine-4-carboxamide | 408.1 | 408.2 | Chiral method L, Peak 4 |

TABLE 9-continued

The compounds of Examples 67A-79H were prepared according to a synthetic procedure similar to the synthetic procedure for Example 66A and 66B.

| Example | Structure | Name | Calc'd [M + H]+ | Observed [M + H]+ | Conditions |
|---|---|---|---|---|---|
| 71 | 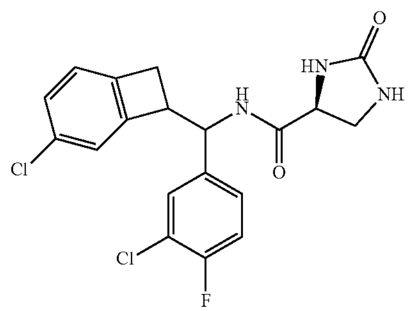 [SMILES: O=C1NC[C@@H](C(=O)NC(c2ccc(F)c(Cl)c2)C2Cc3ccc(Cl)cc32)N1] | (4S)-N-((3-chloro-4-fluorophenyl)(4-chlorobicyclo[4.2.0]-octa-1(6),2,4-trien-7-yl)methyl)-2-oxoimidazolidine-4-carboxamide | 408.1 | 408.1 | Not resolved |
| 72 | 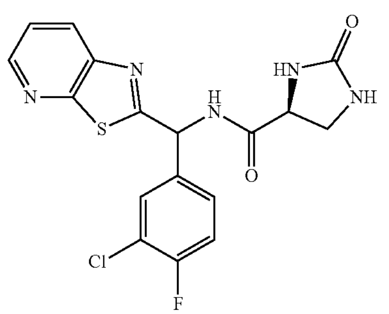 [SMILES: O=C1NC[C@@H](C(=O)NC(c2ccc(F)c(Cl)c2)c2nc3cccnc3s2)N1] | (4S)-N-((3-chloro-4-fluorophenyl)(thiazolo[5,4-b]pyridin-2-yl)methyl)-2-oxoimidazolidine-4-carboxamide | 406.1 | 406.1 | Not resolved |
| 73A | 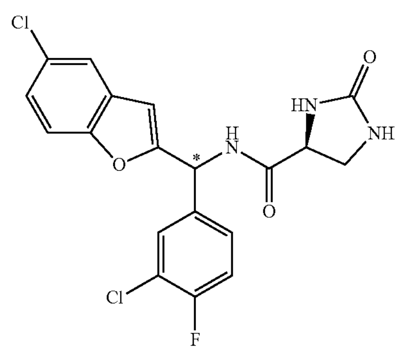 [SMILES: O=C1NC[C@@H](C(=O)NC(c2ccc(F)c(Cl)c2)c2cc3cc(Cl)ccc3o2)N1] | (S)-N-((R or S)-(3-chloro-4-fluorophenyl)(5-chlorobenzofuran-2-yl)methyl)-2-oxoimidazolidine-4-carboxamide | 422 | 422.1 | Chiral method AE, peak 1 |
| 73B | 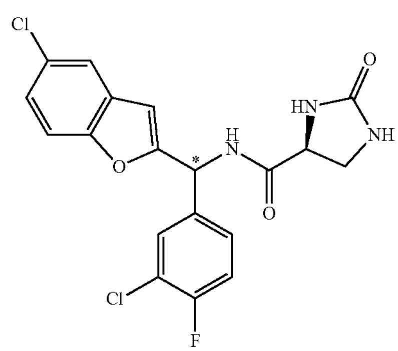 [SMILES: O=C1NC[C@@H](C(=O)NC(c2ccc(F)c(Cl)c2)c2cc3cc(Cl)ccc3o2)N1] | (S)-N-((R or S)-(3-chloro-4-fluorophenyl)(5-chlorobenzofuran-2-yl)methyl)-2-oxoimidazolidine-4-carboxamide | 422 | 422.1 | Chiral method AE, peak 2 |

TABLE 9-continued

The compounds of Examples 67A-79H were prepared according to a synthetic procedure similar to the synthetic procedure for Example 66A and 66B.

| Example | Structure | Name | Calc'd [M + H]+ | Observed [M + H]+ | Conditions |
|---|---|---|---|---|---|
| 74A | 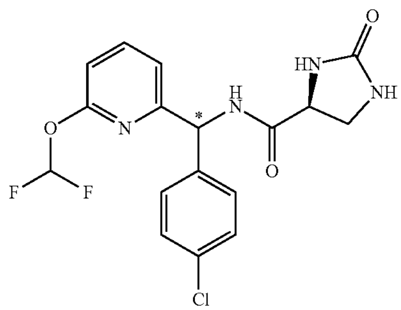 [SMILES: O=C1NC[C@@H](C(=O)NC(c2ccc(Cl)cc2)c2cccc(OC(F)F)n2)N1] | (S)-N-((R or S)-(4-chlorophenyl)(6-(difluoromethoxy)pyridin-2-yl)methyl)-2-oxoimidazolidine-4-carboxamide | 397.1 | 397.3 | Chiral method M, peak 1 |
| 74B | 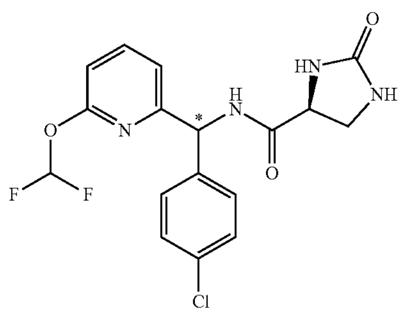 [SMILES: O=C1NC[C@@H](C(=O)NC(c2ccc(Cl)cc2)c2cccc(OC(F)F)n2)N1] | (S)-N-((R or S)-(4-chlorophenyl)(6-(difluoromethoxy)pyridin-2-yl)methyl)-2-oxoimidazolidine-4-carboxamide | 397.1 | 397.3 | Chiral method M, peak 2 |
| 75A | 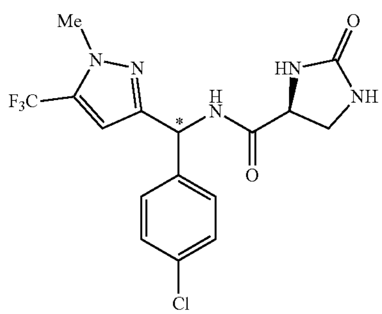 [SMILES: Cn1nc(C(NC(=O)[C@@H]2CNC(=O)N2)c2ccc(Cl)cc2)cc1C(F)(F)F] | (S)-N-((R or S)-(4-chlorophenyl)(1-methyl-5-(trifluoromethoxyl)-1H-pyrazol-3-yl)methyl)-2-oxoimidazolidine-4-carboxamide | 402.1 | 402.1 | Chiral method AF, peak 1 |
| 75B | 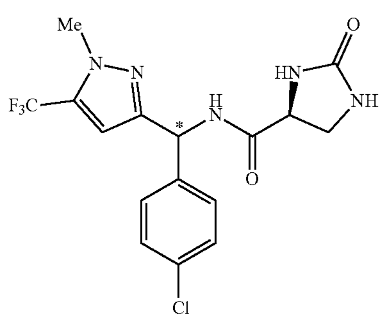 [SMILES: Cn1nc(C(NC(=O)[C@@H]2CNC(=O)N2)c2ccc(Cl)cc2)cc1C(F)(F)F] | (S)-N-((R or S)-(4-chlorophenyl)(1-methyl-5-(trifluoromethoxyl)-1H-pyrazol-3-yl)methyl)-2-oxoimidazolidine-4-carboxamide | 402.1 | 402.1 | Chiral method AF, peak 2 |

TABLE 9-continued

The compounds of Examples 67A-79H were prepared according to a synthetic procedure similar to the synthetic procedure for Example 66A and 66B.

| Example | Structure | Name | Calc'd [M + H]+ | Observed [M + H]+ | Conditions |
|---|---|---|---|---|---|
| 76 | 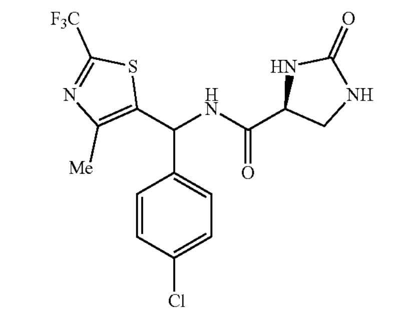 [SMILES: Cc1nc(C(F)(F)F)sc1C(NC(=O)[C@@H]1CNC(=O)N1)c1ccc(Cl)cc1] | (4S)-N-((4-chlorophenyl)(4-methyl-2-(trifluoromethyl)thiazol-5-yl)methyl)-2-oxoimidazolidine-4-carboxamide | 419.1 | 419.1 | Not resolved |
| 77A | 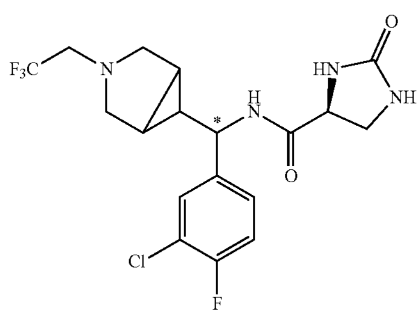 [SMILES: O=C1NC[C@@H](C(=O)NC(c2ccc(F)c(Cl)c2)C2C3CN(CC(F)(F)F)CC32)N1] | (4S)-N-((1(R or S))-(3-chloro-4-fluorophenyl)(3-(2,2,2-trifluoroethyl)-3-azabicyclo[3.1.0]hexan-6-yl)methyl)-2-oxoimidazolidine-4-carboxamide | 435.1 | 435.4 | Chiral method L, Peak 1 |
| 77B | 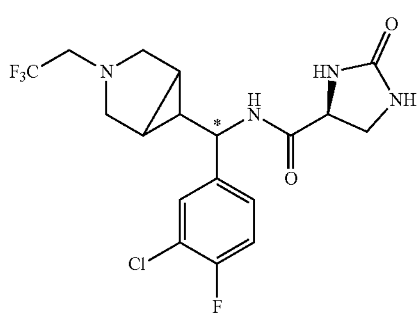 [SMILES: O=C1NC[C@@H](C(=O)NC(c2ccc(F)c(Cl)c2)C2C3CN(CC(F)(F)F)CC32)N1] | (4S)-N-((1(R or S))-(3-chloro-4-fluorophenyl)(3-(2,2,2-trifluoroethyl)-3-azabicyclo[3.1.0]hexan-6-yl)methyl)-2-oxoimidazolidine-4-carboxamide | 435.1 | 435.4 | Chiral method L, Peak 2 |
| 78A | 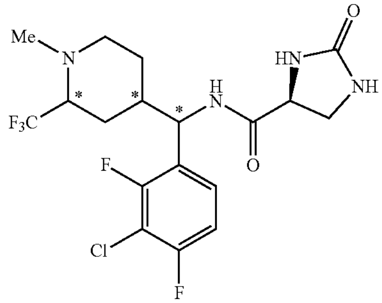 [SMILES: CN1CCC(C(NC(=O)[C@@H]2CNC(=O)N2)c2ccc(F)c(Cl)c2F)CC1C(F)(F)F] | (S)-N-((R or S)-(3-chloro-2,4-difluorophenyl)((cis or trans)-1-methyl-2-(trifluoromethyl)piperidin-4-yl)methyl)-2-oxoimidazolidine-4-carboxamide | 455.1 | 455.5 | Chiral method AG, Peak 1 |

TABLE 9-continued

The compounds of Examples 67A-79H were prepared according to a synthetic procedure similar to the synthetic procedure for Example 66A and 66B.

| Example | Structure | Name | Calc'd [M + H]+ | Observed [M + H]+ | Conditions |
|---|---|---|---|---|---|
| 78B | 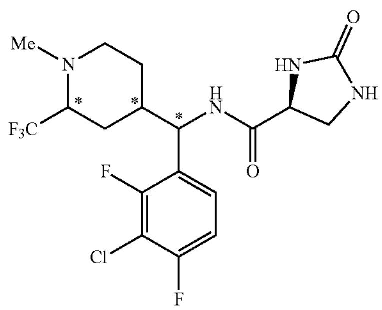 [SMILES: CN1CCC(C(NC(=O)[C@@H]2CNC(=O)N2)c2ccc(F)c(Cl)c2F)CC1C(F)(F)F] | (S)-N-((R or S)-(3-chloro-2,4-difluorophenyl)((cis or trans)-1-methyl-2-(trifluoromethyl)piperidin-4-yl)methyl)-2-oxoimidazolidine-4-carboxamide | 455.1 | 455.4 | Chiral method AG, Peak 2 |
| 78C | 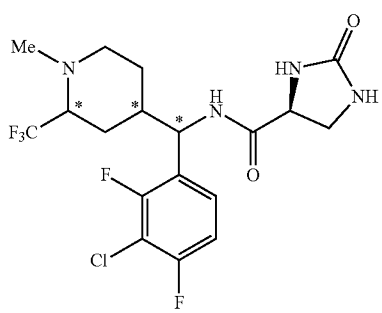 [SMILES: CN1CCC(C(NC(=O)[C@@H]2CNC(=O)N2)c2ccc(F)c(Cl)c2F)CC1C(F)(F)F] | (S)-N-((R or S)-(3-chloro-2,4-difluorophenyl)((cis or trans)-1-methyl-2-(trifluoromethyl)piperidin-4-yl)methyl)-2-oxoimidazolidine-4-carboxamide | 455.1 | 455.4 | Chiral method AG, Peak 3 |
| 78D | 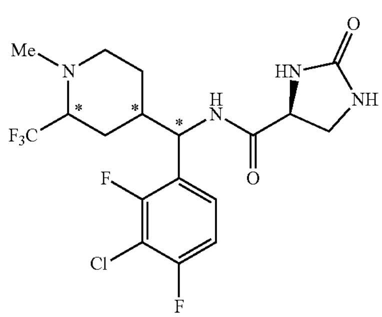 [SMILES: CN1CCC(C(NC(=O)[C@@H]2CNC(=O)N2)c2ccc(F)c(Cl)c2F)CC1C(F)(F)F] | (S)-N-((R or S)-(3-chloro-2,4-difluorophenyl)((cis or trans)-1-methyl-2-(trifluoromethyl)piperidin-4-yl)methyl)-2-oxoimidazolidine-4-carboxamide | 455.1 | 455.4 | Chiral method AG, Peak 4 |
| 78E | 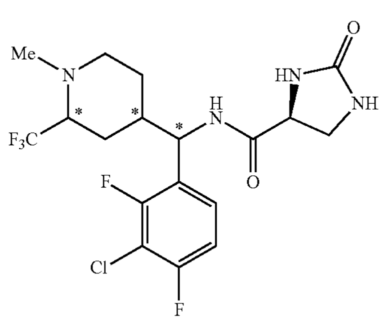 [SMILES: CN1CCC(C(NC(=O)[C@@H]2CNC(=O)N2)c2ccc(F)c(Cl)c2F)CC1C(F)(F)F] | (S)-N-((R or S)-(3-chloro-2,4-difluorophenyl)((cis or trans)-1-methyl-2-(trifluoromethyl)piperidin-4-yl)methyl)-2-oxoimidazolidine-4-carboxamide | 455.1 | 455.4 | Chiral method AG, Peak 5 |

TABLE 9-continued

The compounds of Examples 67A-79H were prepared according to a synthetic procedure similar to the synthetic procedure for Example 66A and 66B.

| Example | Structure | Name | Calc'd [M + H]+ | Observed [M + H]+ | Conditions |
|---|---|---|---|---|---|
| 79A | 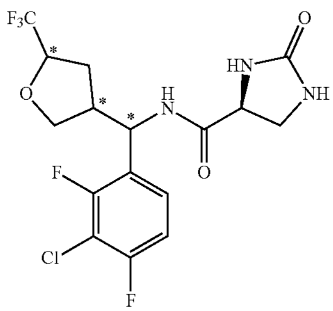 [SMILES: O=C1NC[C@@H](C(=O)NC(c2ccc(F)c(Cl)c2F)C2COC(C(F)(F)F)C2)N1] | (S)-N-((R or S)-(3-chloro-2,4-difluorophenyl)((cis or trans)-5-(trifluoromethyl)-tetrahydrofuran-3-yl)methyl)-2-oxoimidazolidine-4-carboxamide | 428.1 | 428.4 | Chiral method AH, Peak 1; then Chiral method AI, Peak 1A |
| 79B | 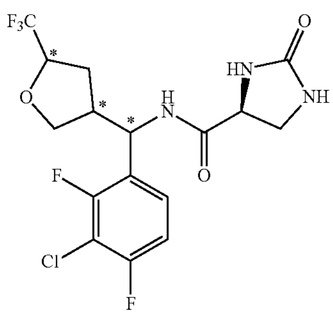 [SMILES: O=C1NC[C@@H](C(=O)NC(c2ccc(F)c(Cl)c2F)C2COC(C(F)(F)F)C2)N1] | (S)-N-((R or S)-(3-chloro-2,4-difluorophenyl)((cis or trans)-5-(trifluoromethyl)tetrahydrofuran-3-yl)methyl)-2-oxoimidazolidine-4-carboxamide | 428.1 | 428.4 | Chiral method AH, Peak 1; then Chiral method AI, Peak 1B |
| 79C | 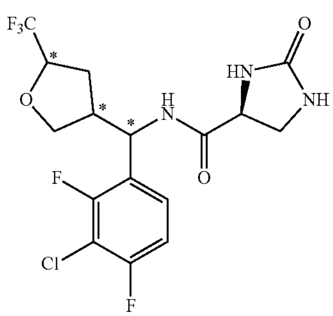 [SMILES: O=C1NC[C@@H](C(=O)NC(c2ccc(F)c(Cl)c2F)C2COC(C(F)(F)F)C2)N1] | (S)-N-((R or S)-(3-chloro-2,4-difluorophenyl)((cis or trans)-5-(trifluoromethyl)tetrahydrofuran-3-yl)methyl)-2-oxoimidazolidine-4-carboxamide | 428.1 | 428.4 | Chiral method AH, Peak 2; then Chiral method AJ, Peak 2A; then Chiral method AK, Peak 2A1 |
| 79D | 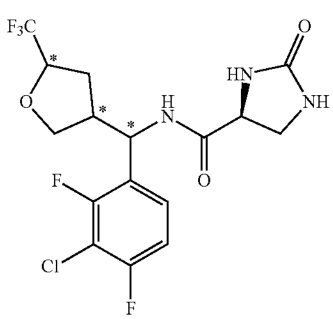 [SMILES: O=C1NC[C@@H](C(=O)NC(c2ccc(F)c(Cl)c2F)C2COC(C(F)(F)F)C2)N1] | (S)-N-((R or S)-(3-chloro-2,4-difluorophenyl)((cis or trans)-5-(trifluoromethyl)tetrahydrofuran-3-yl)methyl)-2-oxoimidazolidine-4-carboxamide | 428.1 | 428.4 | Chiral method AH, Peak 2; then Chiral method AJ, Peak 2A; then Chiral method AK, Peak 2A2 |

TABLE 9-continued

The compounds of Examples 67A-79H were prepared according to a synthetic procedure similar to the synthetic procedure for Example 66A and 66B.

| Example | Structure | Name | Calc'd [M + H]+ | Observed [M + H]+ | Conditions |
| --- | --- | --- | --- | --- | --- |
| 79E | 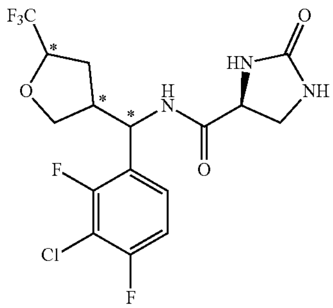 [SMILES: O=C1NC[C@@H](C(=O)NC(c2ccc(F)c(Cl)c2F)C2COC(C(F)(F)F)C2)N1] | (S)-N-((R or S)-(3-chloro-2,4-difluorophenyl)((cis or trans)-5-(trifluoromethyl)tetrahydrofuran-3-yl)methyl)-2-oxoimidazolidine-4-carboxamide | 428.1 | 428.4 | Chiral method AH, Peak 2; then Chiral method AJ, Peak 2B |
| 79F | 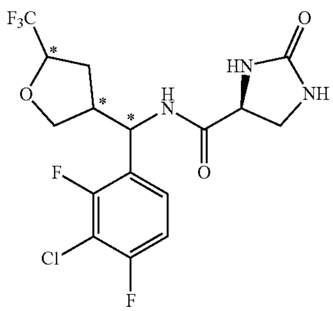 [SMILES: O=C1NC[C@@H](C(=O)NC(c2ccc(F)c(Cl)c2F)C2COC(C(F)(F)F)C2)N1] | (S)-N-((R or S)-(3-chloro-2,4-difluorophenyl)((cis or trans)-5-(trifluoromethyl)tetrahydrofuran-3-yl)methyl)-2-oxoimidazolidine-4-carboxamide | 428.1 | 428.4 | Chiral method AH, Peak 2; then Chiral method AJ, Peak 2C |
| 79G | 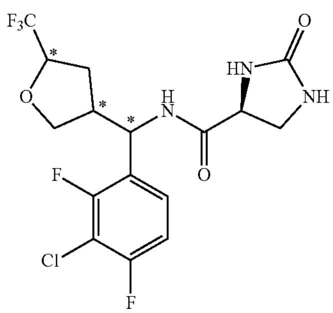 [SMILES: O=C1NC[C@@H](C(=O)NC(c2ccc(F)c(Cl)c2F)C2COC(C(F)(F)F)C2)N1] | (S)-N-((R or S)-(3-chloro-2,4-difluorophenyl)((cis or trans)-5-(trifluoromethyl)tetrahydrofuran-3-yl)methyl)-2-oxoimidazolidine-4-carboxamide | 428.1 | 428.4 | Chiral method AH, Peak 3 |
| 79H | 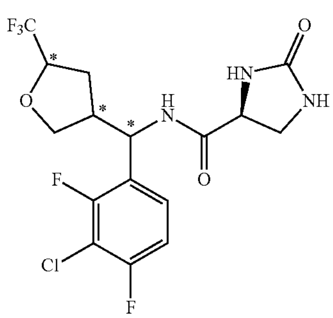 [SMILES: O=C1NC[C@@H](C(=O)NC(c2ccc(F)c(Cl)c2F)C2COC(C(F)(F)F)C2)N1] | (S)-N-((R or S)-(3-chloro-2,4-difluorophenyl)((cis or trans)-5-(trifluoromethyl)tetrahydrofuran-3-yl)methyl)-2-oxoimidazolidine-4-carboxamide | 428.1 | 428.4 | Chiral method AH, Peak 4 |

Example 80A (S)—N—((R or S)-(4-chlorophenyl)(pyrazolo[1,5-a]pyridin-5-yl)methyl)-2-oxoimidazolidine-4-carboxamide

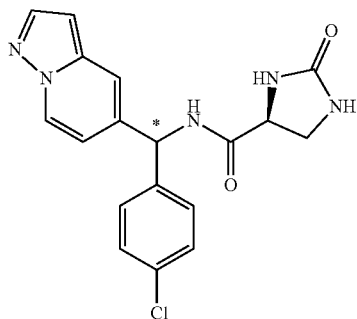

Step 1: (R)-2-methyl-N-(pyrazolo[1,5-a]pyridin-5-ylmethylene)propane-2-sulfinamide. (R)-2-methylpropane-2-sulfinamide (0.46 g, 3.8 mmol) and pyrazolo[1,5-a]pyridine-5-carbaldehyde (0.50 g, 3.4 mmol) were dissolved in THF (12 mL) at rt and treated with Ti(OEt)$_4$ (1.6 mL, 6.8 mmol). The reaction was stirred overnight, then quenched with sat. NaHCO$_3$ and extracted with EtOAc. The combined organic layers were washed with brine, dried over MgSO$_4$, filtered and concentrated in vacuo. The resulting residue was purified by silica gel chromatography (0-100% EtOAc:hex) to give the title compound.

Step 2: (R)—N-((4-chlorophenyl)(pyrazolo[1,5-a]pyridin-5-yl)methyl)-2-methylpropane-2-sulfinamide. To a solution of (R)-2-methyl-N-(pyrazolo[1,5-a]pyridin-5-ylmethylene)propane-2-sulfinamide (0.74 g, 3.0 mmol) in toluene (20 mL) at −20° C. was added (4-chlorophenyl)-magnesium bromide (4.5 mL, 4.5 mmol, 1 M in THF) dropwise over 1 minute. The reaction was stirred for 48 h, then quenched with sat. NaHCO$_3$ and extracted with EtOAc. The combined organic layers were washed with brine, dried over MgSO$_4$, filtered and concentrated in vacuo. The resulting residue was purified by silica gel chromatography (0-100% EtOAc:hex) to give the title compound. The major isomer of the title compound was used in the next step.

Step 3: (4-chlorophenyl)(pyrazolo[1,5-a]pyridin-5-yl)methanamine hydrochloride. (R)—N-((4-chlorophenyl)(pyrazolo[1,5-a]pyridin-5-yl)methyl)-2-methylpropane-2-sulfinamide (0.77 mg, 2.1 mmol) was dissolved in ethyl acetate (8.5 mL), and sat. HCl (7.7 mL, 53 mmol) was added. The mixture was stirred for 2 h, then concentrated in vacuo and azeotroped with EtOAc to give the title compound.

Step 4: (S)—N—((R or S)-(4-chlorophenyl)(pyrazolo[1,5-a]pyridin-5-yl)methyl)-2-oxo-imidazolidine-4-carboxamide. (S)-2-oxoimidazolidine-4-carboxylic acid (30 mg, 0.23 mmol), (4-chlorophenyl)(pyrazolo[1,5-a]pyridin-5-yl)methanamine hydrochloride (75 mg, 0.26 mmol), and DIEA (0.13 mL, 0.77 mmol) were dissolved in DMF (1 mL), then HATU (0.13 g, 0.33 mmol) was added at rt. The reaction stirred overnight, then MeOH was added. The mixture was purified by reverse phase HPLC (95:5 to 5:95; water (0.1% TFA): MeCN (0.1% TFA)). The fractions containing product were combined, basified with sat. NaHCO$_3$, and extracted with DCM. The organic layer was dried with MgSO$_4$ and concentrated in vacuo to give the title compound. LRMS m/z (M+H): calculated 370.1, observed 370.2. $^1$H NMR (500 MHz, DMSO-d$_6$) δ 8.85 (d, J=8.2 Hz, 1H), 8.63 (d, J=7.1 Hz, 1H), 7.98 (s, 1H), 7.53 (s, 1H), 7.43 (d, J=8.3 Hz, 2H), 7.37 (d, J=7.8 Hz, 2H), 6.74 (d, J=7.1 Hz, 1H), 6.65-6.51 (m, 2H), 6.30 (s, 1H), 6.18 (d, J=8.1 Hz, 1H), 4.27-4.20 (m, 1H), 3.56 (t, J=9.2 Hz, 1H), 3.28-3.23 (m, 1H).

TABLE 10

The compounds of Examples 81-88 were prepared according to a synthetic procedure similar to the synthetic procedure for Example 80A.

| Example | Structure | Name | Calc'd [M + H]$^+$ | Observed [M + H]$^+$ | Conditions |
|---|---|---|---|---|---|
| 81 | 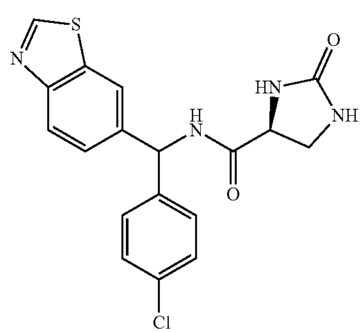 [SMILES: O=C1NC[C@@H](C(=O)NC(c2ccc(Cl)cc2)c2ccc3ncsc3c2)N1] | (4S)-N-(benzo[d]thiazol-6-yl(4-chlorophenyl)methyl)-2-oxoimidazolidine-4-carboxamide | 387.1 | 387.2 | Step 2 run at 0° C. Racemic |

TABLE 10-continued

The compounds of Examples 81-88 were prepared according to a synthetic procedure similar to the synthetic procedure for Example 80A.

| Example | Structure | Name | Calc'd [M + H]+ | Observed [M + H]+ | Conditions |
|---|---|---|---|---|---|
| 82A | 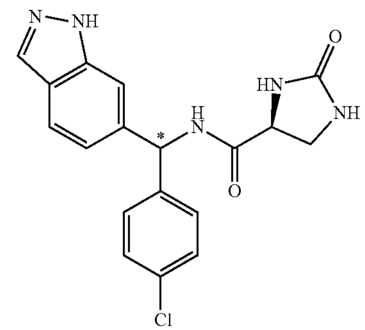 [SMILES: O=C1NC[C@@H](C(=O)NC(c2ccc(Cl)cc2)c2ccc3cn[nH]c3c2)N1] | (S)-N-((R or S)-(4-chlorophenyl)(1H-indazol-6-yl)methyl)-2-oxoimidazolidine-4-carboxamide | 370.1 | 370.2 | Major isomer using S-sulfianmide |
| 82B | 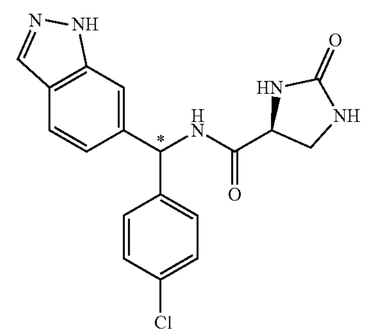 [SMILES: O=C1NC[C@@H](C(=O)NC(c2ccc(Cl)cc2)c2ccc3cn[nH]c3c2)N1] | (S)-N-((R or S)-(4-chlorophenyl)(1H-indazol-6-yl)methyl)-2-oxoimidazolidine-4-carboxamide | 370.1 | 370.2 | Major isomer using R-sulfianmide |
| 80B | 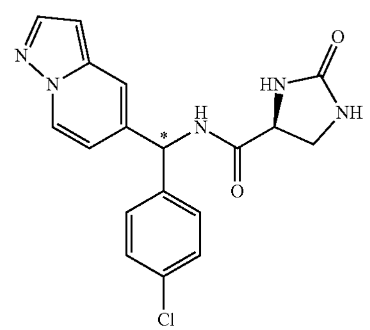 [SMILES: O=C1NC[C@@H](C(=O)NC(c2ccc(Cl)cc2)c2ccn3nccc3c2)N1] | (S)-N-((R or S)-(4-chlorophenyl)(pyrazolo[1,5-a]pyridin-5-yl)methyl)-2-oxoimidazolidine-4-carboxamide | 370.1 | 370.2 | Major isomer using S-sulfianmide |
| 83A | 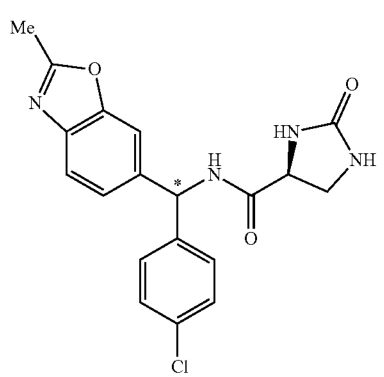 [SMILES: Cc1nc2ccc(C(NC(=O)[C@@H]3CNC(=O)N3)c3ccc(Cl)cc3)cc2o1] | (S)-N-((R or S)-(4-chlorophenyl)(2-methylbenzo[d]oxazol-6-yl)methyl)-2-oxoimidazolidine-4-carboxamide | 385.1 | 385.2 | Major isomer using S-sulfianmide |

TABLE 10-continued

The compounds of Examples 81-88 were prepared according to a synthetic procedure similar to the synthetic procedure for Example 80A.

| Example | Structure | Name | Calc'd [M + H]⁺ | Observed [M + H]⁺ | Conditions |
|---|---|---|---|---|---|
| 83B | 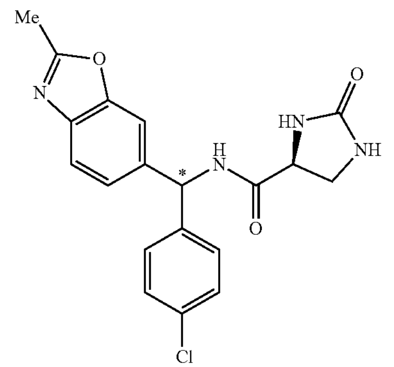 [SMILES: Cc1nc2ccc(C(NC(=O)[C@@H]3CNC(=O)N3)c3ccc(Cl)cc3)cc2o1] | (S)-N-((R or S)-(4-chlorophenyl)(2-methylbenzo[d]oxazol-6-yl)methyl)-2-oxoimidazolidine-4-carboxamide | 385.1 | 385.2 | Major isomer using R-sulfianmide |
| 84 | 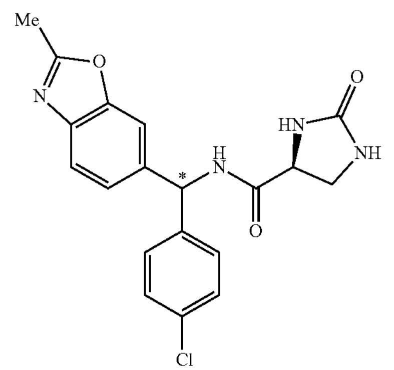 [SMILES: Cc1nc2ccc(C(NC(=O)[C@@H]3CNC(=O)N3)c3ccc(Cl)cc3)cc2o1] | (S)-N-((R or S)-(4-chlorophenyl)(2-methylbenzo[d]thiazol-6-yl)methyl)-2-oxoimidazolidine-4-carboxamide | 419.1 | 419.2 | Step 2 run at 0° C. Major isomer using R-sulfianmide |
| 85A | 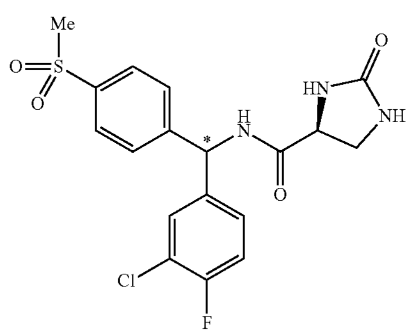 [SMILES: CS(=O)(=O)c1ccc(C(NC(=O)[C@@H]2CNC(=O)N2)c2ccc(F)c(Cl)c2)cc1] | (S)-N-((R or S)-(3-chloro-4-fluorophenyl)(4-(methylsulfonyl)phenyl)methyl)-2-oxoimidazolidine-4-carboxamide | 426.1 | 426.1 | Step 2 run at 0° C. Major isomer using S-sulfianmide |
| 85B | 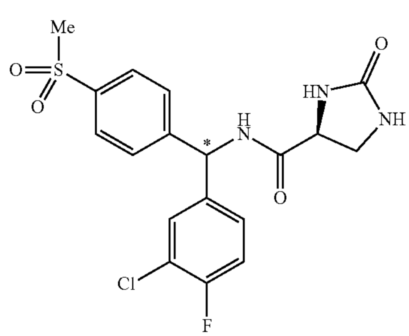 [SMILES: CS(=O)(=O)c1ccc(C(NC(=O)[C@@H]2CNC(=O)N2)c2ccc(F)c(Cl)c2)cc1] | (S)-N-((R or S)-(3-chloro-4-fluorophenyl)(4-(methylsulfonyl)phenyl)methyl)-2-oxoimidazolidine-4-carboxamide | 426.1 | 426.2 | Step 2 run at 0° C. Major isomer using S-sulfianmide |

TABLE 10-continued

The compounds of Examples 81-88 were prepared according to a synthetic procedure similar to the synthetic procedure for Example 80A.

| Example | Structure | Name | Calc'd [M + H]+ | Observed [M + H]+ | Conditions |
|---------|-----------|------|-----------------|-------------------|------------|
| 86 | 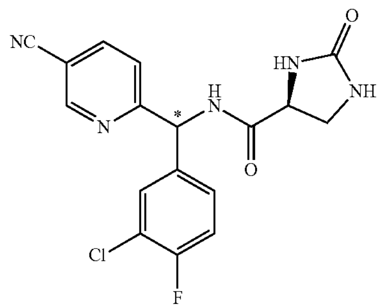 [SMILES: N#Cc1ccc(C(NC(=O)[C@@H]2CNC(=O)N2)c2ccc(F)c(Cl)c2)nc1] | (4S)-N-[(3-chloro-4-fluorophenyl)(5-cyanopyridin-2-yl)methyl]-2-oxoimidazolidine-4-carboxamide | 374.1 | 374.2 | Step 2 run at 0° C. Major isomer using S-sulfianmide |
| 87 | 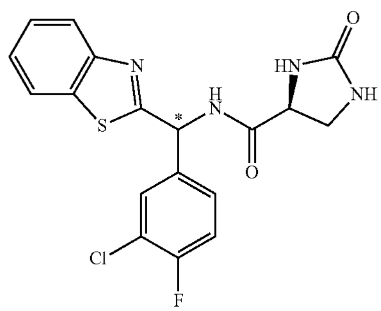 [SMILES: O=C1NC[C@@H](C(=O)NC(c2ccc(F)c(Cl)c2)c2nc3ccccc3s2)N1] | (S)-N-((R or S)-benzo[d]thiazol-2-yl(3-chloro-4-fluorophenyl)methyl)-2-oxoimidazolidine-4-carboxamide | 405.1 | 405.2 | Step 2 run at 0° C. Major isomer using R-sulfianmide |
| 88 | 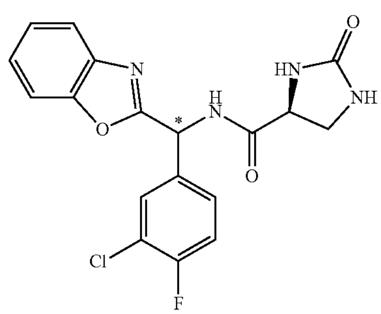 [SMILES: O=C1NC[C@@H](C(=O)NC(c2ccc(F)c(Cl)c2)c2nc3ccccc3o2)N1] | (S)-N-((R or S)-benzo[d]oxazol-2-yl(3-chloro-4-fluorophenyl)methyl)-2-oxoimidazolidine-4-carboxamide | 389.1 | 389.2 | Step 2 run at 0° C. Major isomer using R-sulfianmide |

Example 89

(S)—N—((R or S)-(8,8-difluorobicyclo[4.2.0]octa-1(6),2,4-trien-3-yl)(4-(trifluoromethoxy)phenyl)methyl)-2-oxoimidazolidine-4-carboxamide

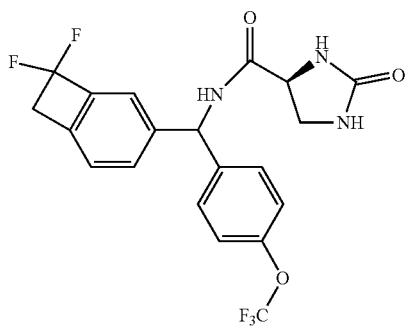 [SMILES: O=C1NC[C@@H](C(=O)NC(c2ccc(OC(F)(F)F)cc2)c2ccc3c(c2)C(F)(F)C3)N1]

Step 1: (5-bromo-2-methylphenyl)(4,8-di-tert-butyl-2,10-dimethyl-6-oxido-12H-dibenzo[d,g]-[1,3,2]dioxaphosphocin-6-yl)methanone. To a solution of 5-bromo-2-methylbenzoic acid (3.2 g, 15 mmol) in DCM (15 mL) was added (COCl)₂ (7.4 mL, 15 mmol, 2 M in DCM), followed by two drops of DMF. The reaction heated at reflux for 1 h. Then the solvent was removed in vacuo. The resulting residue dissolved in DCM (15 mL) and added dropwise over 1 h to a solution of 4,8-di-tert-butyl-2,10-dimethyl-12H-dibenzo[d,g][1,3,2]dioxaphosphocine 6-oxide (2.9 g, 7.4 mmol) and DIEA (6.5 mL, 37 mmol) in DCM (15 mL) at rt. The reaction was stirred for 6 h at rt, then diluted with DCM, washed with aq. HCl (1 M), and then sat. NaHCO₃. The combined organic layers were dried over MgSO₄, filtered, and concentrated in vacuo. The resulting residue was purified by silica gel chromatography (0-5% EtOAc:hex) to give the title compound.

Step 2: 4-bromobicyclo[4.2.0]octa-1(6),2,4-trien-7-one. A solution of (5-bromo-2-methylphenyl)(4,8-di-tert-butyl-2,10-dimethyl-6-oxido-12H-dibenzo[d,g][1,3,2] dioxaphosphocin-6-yl)methanone (3.6 g, 6.1 mmol) in toluene (60 mL) was irradiated at 420 nM in a Penn OC photoreactor (100% intensity) for 8 h. Alumina (6.2 g, 61 mmol) was added, and the reaction was heated to 45° C. for 18 h. Then the reaction was filtered, and the filtrate was purified via silica gel chromatography (0-15% EtOAc:hex) to give the title compound.

Step 3: 3-bromo-8,8-difluorobicyclo[4.2.0]octa-1(6),2,4-triene. Deoxofluor® (3.1 mL, 17 mmol) was added to 4-bromobicyclo[4.2.0]octa-1(6),2,4-trien-7-one (0.66 g, 3.3 mmol), and the reaction heated at 50° C. overnight. The reaction was quenched by slowly adding to ice cold sat. Na$_2$HCO$_3$, and the mixture was extracted with DCM. The combined organic layers were dried over MgSO$_4$, filtered, and concentrated in vacuo. The resulting residue was purified via silica gel chromatography (hexanes) to give the title compound.

Step 4: 8,8-difluorobicyclo[4.2.0]octa-1(6),2,4-triene-3-carbaldehyde. A mixture of 3-bromo-8,8-difluorobicyclo[4.2.0]octa-1(6),2,4-triene (0.47 g, 2.1 mmol), sodium formate (0.22 g, 3.2 mmol), and PdCl$_2$(PPh$_3$)$_2$ (0.15 g, 0.22 mmol) in DMF (8.6 mL) was placed under 20 psi CO and heated to 110° C. for 16 h. Then the reaction mixture was allowed to cool to rt, diluted with hexanes, washed with water, brine, dried over MgSO$_4$, filtered, and concentrated in vacuo to give the title compound.

Step 5: (S)—N-((8,8-difluorobicyclo[4.2.0]octa-1(6),2,4-trien-3-yl)methylene)-2-methylpropane-2-sulfinamide. To a mixture of 8,8-difluorobicyclo[4.2.0]octa-1(6),2,4-triene-3-carbaldehyde (0.38 g, 2.3 mmol) and (S)-2-methylpropane-2-sulfinamide (0.28 g, 2.3 mmol) in THF (9 mL) was added Ti(OEt)$_4$ (0.96 mL, 4.6 mmol) at rt. The reaction was stirred at rt for 18 h, then quenched with sat. NaHCO$_3$. The mixture was filtered, washed with EtOAc, and the filtrate was extracted with EtOAc. The organic layer was separated, washed with brine, dried over MgSO$_4$, filtered, and concentrated in vacuo to give the title compound.

Step 6: (S)—N-((8,8-difluorobicyclo[4.2.0]octa-1(6),2,4-trien-3-yl)(4-(trifluoromethoxy)phenyl)-methyl)2-methylpropane-2-sulfinamide. To a mixture of ((S)—N-((8,8-difluorobicyclo[4.2.0]-octa-1(6),2,4-trien-3-yl)methylene)-2-methylpropane-2-sulfinamide (48 mg, 0.18 mmol), bis(acetonitrile)(1,5-cyclooctadiene) rhodium(I) tetrafluoroborate (6.7 mg, 0.018 mmol), (4-(trifluoromethoxy)phenyl)boronic acid (0.11 g, 0.53 mmol) and dioxane (0.4 mL) was added TEA (74 µl, 0.53 mmol), followed by water (0.8 mL). The mixture was stirred for 18 h, then quenched with water and extracted with EtOAc. The combined organic layers were dried over MgSO$_4$, filtered and concentrated in vacuo. The resulting residue was purified via silica gel chromatography (0-100% EtOAc:hex) to give the title compound.

Step 7: (8,8-difluorobicyclo[4.2.0]octa-1(6),2,4-trien-3-yl)(4-(trifluoromethoxy)phenyl)-methanamine hydrochloride. (S)—N-((8,8-difluorobicyclo[4.2.0]octa-1(6),2,4-trien-3-yl)(4-(trifluoromethoxy)phenyl)methyl)-2-methylpropane-2-sulfinamide (28 mg, 0.065 mmol) was taken up in EtOAc (0.25 mL) and cooled to 0° C. Then HCl gas was bubbled through this mixture for 15 seconds until saturated. The mixture was concentrated in vacuo to give the title compound.

Step 8: (S)—N—((R or S)-(8,8-difluorobicyclo[4.2.0]octa-1(6),2,4-trien-3-yl)(4-(trifluoromethoxy)phenyl)methyl)-2-oxoimidazolidine-4-carboxamide. To a mixture of (8,8-difluorobicyclo[4.2.0]octa-1(6),2,4-trien-3-yl)(4-(trifluoromethoxy)phenyl)methanamine hydrochloride (23 mg crude), (S)-2-oxoimidazolidine-4-carboxylic acid (10 mg, 0.079 mmol) and DIEA (0.033 mL, 0.19 mmol) in DMF (0.25 mL) was added HATU (31 mg, 0.082 mmol) at ambient temperature. The reaction mixture was stirred at rt for 18 h. The residue was purified by reverse phase HPLC (95:5 to 5:95; water (0.1% TFA):MeCN (0.1% TFA)). The fractions containing product were combined and basified with sat. NaHCO$_3$, then extracted with DCM. The organic layer was dried over MgSO$_4$, filtered and concentrated in vacuo to give the title compound. LRMS m/z (M+H): calculated 442.1, observed 442.2. $^1$H NMR (500 MHz, DMSO-d$_6$) δ 8.83 (d, J=8.1 Hz, 1H), 7.55-7.32 (m, 7H), 6.58 (s, 1H), 6.30 (s, 1H), 6.23 (d, J=7.9 Hz, 1H), 4.22 (dd, J=9.0, 6.0 Hz, 1H), 3.92-3.67 (m, 2H), 3.55 (t, J=9.3 Hz, 1H), 3.27-3.19 (m, 1H).

TABLE 11

The compound of Example 90 was prepared according to a synthetic procedure similar to the synthetic procedure for Example 89.

| Example | Structure | IUPAC Name | Calc'd [M + H]$^+$ | Observed [M + H]$^+$ |
|---|---|---|---|---|
| 90 | 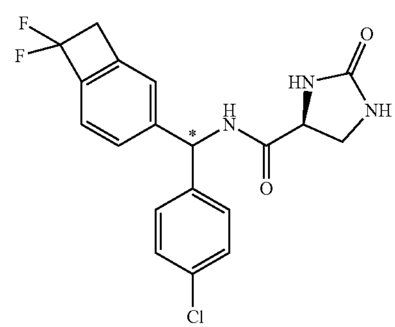 [SMILES: O=C1NC[C@@H](C(=O)NC(c2ccc(Cl)cc2)c2ccc3c(c2)CC3(F)F)N1] | (S)-N-((R or S)-(4-chlorophenyl)(7,7-difluorobicyclo[4.2.0]octa-1(6),2,4-trien-3-yl)methyl)-2-oxoimidazolidine-4-carboxamide | 392.1 | 392.2 |

Examples 91A, 91B, 91C and 91D (4S)—N—((R)(4-chlorophenyl)((R)2,2-dimethyl-1-(2,2,2-trifluoroethyl)piperidin-4-yl)methyl)-2-oxoimidazolidine-4-carboxamide, (4S)—N—((R)(4-chlorophenyl)((S)2,2-dimethyl-1-(2,2,2-trifluoroethyl)piperidin-4-yl)methyl)-2-oxoimidazolidine-4-carboxamide, (4S)—N—((S)(4-chlorophenyl)((S)2,2-dimethyl-1-(2,2,2-trifluoroethyl)piperidin-4-yl)methyl)-2-oxoimidazolidine-4-carboxamide and (4S)—N—((S)(4-chlorophenyl)((R)2,2-dimethyl-1-(2,2,2-trifluoroethyl)piperidin-4-yl)methyl)-2-oxoimidazolidine-4-carboxamide

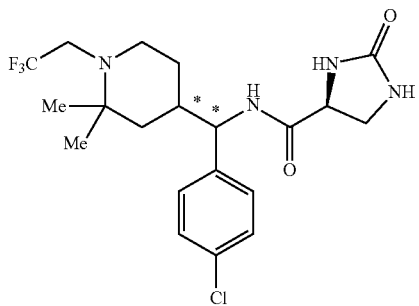 [SMILES: CC1(C)CC(C(NC(=O)[C@@H]2CNC(=O)N2)c2ccc(Cl)cc2)CCN1CC(F)(F)F]

Step 1: tert-butyl 4-(methoxy(methyl)carbamoyl)-2,2-dimethylpiperidine-1-carboxylate. To a solution of 1-(tert-butoxycarbonyl)-2,2-dimethylpiperidine-4-carboxylic acid (0.50 g, 1.9 mmol) and N,O-dimethylhydroxylamine HCl salt (0.23 g, 2.3 mmol) in DCM (15 mL) were added HOAt (0.34 g, 2.5 mmol), EDC (0.45 g, 2.3 mmol) and DIEA (1.2 mL, 7.0 mmol) at rt. The resulting reaction mixture was stirred for 20 h, then the solvent was removed in vacuo. The resulting residue was purified by reverse phase HPLC (90:10 to 100:0; water (0.1% TFA):MeCN (0.1% TFA)), followed by lyophilization to give the title compound.

Step 2: tert-butyl 4-(4-chlorobenzoyl)-2,2-dimethylpiperidine-1-carboxylate. A solution of tert-butyl 4-(methoxy(methyl)carbamoyl)-2,2-dimethylpiperidine-1-carboxylate (0.32 g, 1.1 mmol) in dry THF (10 mL) was cooled to 0° C., then (4-chlorophenyl)magnesium bromide (6.5 mL, 6.5 mmol) was added at 0° C. The reaction mixture was stirred at at 0° C. for 30 min, then gradually allowed to warm to rt and stirred for 18 h. Then the reaction was quenched with water and extracted with EtOAc. The combined organic layers were dried, and the resulting residue was purified by reverse phase HPLC (90:10 to 100:0; water (0.1% TFA):MeCN (0.1% TFA)), followed by lyophilization to give the title compound.

Step 3: tert-butyl-4-(amino(4-chlorophenyl)methyl)-2,2-dimethylpiperidine-1-carboxylate. Tert-butyl 4-(4-chlorobenzoyl)-2,2-dimethylpiperidine-1-carboxylate (0.20 g, 0.57 mmol), and NH$_4$OAc (0.44 g, 5.7 mmol) were combined in EtOH (5 mL) in 20 mL microwave vial and then NaBH$_3$CN (89 mg, 1.4 mmol) was added at rt. The vial was sealed, and the mixture was stirred and heated at 140° C. for 2 h. Then the reaction mixture was quenched by the addition of water and concentrated in vacuo. The resulting residue was purified by reverse phase HPLC (90:10 to 100:0; water (0.1% TFA):MeCN (0.1% TFA)), followed by lyophilization to give the title compound.

Step 4: tert-butyl 4-((4-chlorophenyl)((S)-2-oxoimidazolidine-4-carboxamido)methyl)-2,2-dimethylpiperidine-1-carboxylate. To a solution of tert-butyl-4-(amino(4-chlorophenyl)methyl)-2,2-dimethylpiperidine-1-carboxylate (81 mg, 0.23 mmol) and HATU (88 mg, 0.23 mmol) in DMSO (3 mL) was added N-methylmorpholine (0.076 mL, 0.69 mmol) at rt. The resulting mixture was stirred for 2 h. The residue was purified by reverse phase HPLC (90:10 to 100:0; water (0.1% TFA):MeCN (0.1% TFA)), followed by lyophilization to give the title compound.

Step 5: (4S)—N-((4-chlorophenyl)(2,2-dimethylpiperidin-4-yl)methyl)-2-oxoimidazolidine-4-carboxamide. To a stirred solution of tert-butyl 4-((4-chlorophenyl)((S)-2-oxoimidazolidine-4-carboxamido)methyl)-2,2-dimethylpiperidine-1-carboxylate (80 mg, 0.17 mmol) in MeOH (5 mL) was added HCl (0.22 mL, 0.86 mmol, 4 M in dioxane) at rt. The reaction mixture was stirred for 16 h at rt, then heated to 50° C. for 2 h. Then the mixture was concentrated in vacuo to give the title compound.

Step 6: (4S)—N—((R and S)(4-chlorophenyl)((R and S)2,2-dimethyl-1-(2,2,2-trifluoroethyl)-piperidin-4-yl)methyl)-2-oxoimidazolidine-4-carboxamide: (4S)—N-((4-chlorophenyl)(2,2-dimethylpiperidin-4-yl)methyl)-2-oxoimidazolidine-4-carboxamide (65 mg, 0.18 mmol) and 2,2,2-trifluoroethyl trifluoromethanesulfonate (0.051 mL, 0.36 mmol) were combined in MeCN (3 mL) in a microwave vial and DIEA (0.062 mL, 0.36 mmol) was added. The vial was sealed, and the reaction was heated to 80° C. for 5 h. The residue was purified by reverse phase HPLC (90:10 to 100:0; water (0.1% TFA):MeCN (0.1% TFA)), followed by lyophilization to give the title compound.

Step 7: (4S)—N—((R or S)(4-chlorophenyl)((R or S)2,2-dimethyl-1-(2,2,2-trifluoroethyl)piperidin-4-yl)methyl)-2-oxoimidazolidine-4-carboxamide. (4S)—N—((R and S)(4-chlorophenyl)((R and S)2,2-dimethyl-1-(2,2,2-trifluoroethyl)piperidin-4-yl)methyl)-2-oxoimidazolidine-4-carboxamide was separated by chiral-SFC (OD-H, co-solvent: 15% IPA) to give 3 peaks: The first peak was further separated by chiral-SFC (AS-H, co-solvent: 15% IPA) to give title compounds: diastereomer 91A (4S)—N—((R or S)(4-chlorophenyl)((R or S)2,2-dimethyl-1-(2,2,2-trifluoroethyl)piperidin-4-yl)methyl)-2-oxoimidazolidine-4-carboxamide and diastereomer 91B (4S)—N—((R or S)(4-chlorophenyl)((R or S)2,2-dimethyl-1-(2,2,2-trifluoroethyl)piperidin-4-yl)methyl)-2-oxoimidazolidine-4-carboxamide, diastereomer 91C (4S)—N—((R or S)(4-chlorophenyl)((R or S)2,2-dimethyl-1-(2,2,2-trifluoroethyl)piperidin-4-yl)methyl)-2-oxoimidazolidine-4-carboxamide; and diastereomer 91D (4S)—N—((R or S)(4-chlorophenyl)((R or S)2,2-dimethyl-1-(2,2,2-trifluoroethyl)piperidin-4-yl)methyl)-2-oxoimidazolidine-4-carboxamide. Diastereomer 91A: LRMS m/z (M+H): calculated 447.2, observed 447.5. $^1$H NMR (600 MHz, Methanol-d4) δ 7.37-7.25 (m, 4H), 4.57 (d, J=9.6 Hz, 1H), 4.26 (dd, J=10.1, 6.2 Hz, 1H), 3.77-3.72 (m, 1H), 3.39-3.33 (m, 2H), 2.88 (dt, J=11.9, 4.0 Hz, 1H), 2.69-2.63 (m, 1H), 2.62-2.51 (m, 1H), 2.05 (dtt, J=18.8, 7.1, 3.3 Hz, 1H), 1.84 (dd, J=10.1, 2.7 Hz, 1H), 1.33-1.28 (m, 1H), 1.17-1.09 (m, 1H), 1.05 (dd, J=7.9, 5.1 Hz, 1H), 1.03 (s, 3H), 0.88 (s, 3H). Diastereomer 91B: LRMS m/z (M+H): calculated 447.2, observed 447.5. $^1$H NMR (500 MHz, Methanol-d4) δ 7.37-7.26 (m, 4H), 4.58 (d, J=9.3 Hz, 1H), 4.27 (dd, J=10.0, 6.2 Hz, 1H), 3.81-3.68 (m, 1H), 3.41-3.32 (m, 2H), 2.75 (d, J=11.6 Hz, 1H), 2.61-2.49 (m, 2H), 2.06-1.96 (m, 1H), 1.65 (d, J=12.3 Hz, 1H), 1.31-1.17 (m, 3H), 1.13 (s, 3H), 0.99 (s, 3H). Diastereomer 91C: LRMS m/z (M+H): calculated 447.2, observed 447.4. $^1$H NMR (500 MHz, Methanol-d4) δ 7.36-7.23 (m, 4H), 4.57 (d, J=9.1

Hz, 1H), 4.30 (dd, J=10.1, 6.5 Hz, 1H), 3.79-3.67 (m, 1H), 3.37 (dd, J=16.2, 10.6 Hz, 2H), 2.79-2.72 (m, 1H), 2.55 (ddt, J=18.0, 12.4, 6.3 Hz, 2H), 2.07-1.95 (m, 1H), 1.68-1.61 (m, 1H), 1.30-1.16 (m, 3H), 1.13 (s, 3H), 0.99 (s, 3H). Diastereomer 91D: LRMS m/z (M+H): calculated 447.2, observed 447.5. $^1$H NMR (500 MHz, Methanol-d4) δ 7.35-7.26 (m, 4H), 4.54 (d, J=9.5 Hz, 1H), 4.28 (dd, J=10.0, 6.5 Hz, 1H), 3.78-3.70 (m, 1H), 3.40-3.33 (m, 2H), 2.92-2.84 (m, 1H), 2.65 (s, 1H), 2.57 (dd, J=15.8, 9.2 Hz, 1H), 2.09-1.98 (m, 1H), 1.84 (d, J=13.3 Hz, 1H), 1.36-1.25 (m, 1H), 1.13 (t, J=12.6 Hz, 1H), 1.08-1.03 (m, 1H), 1.02 (s, 3H), 0.88 (s, 3H).

Example of a Pharmaceutical Composition

As a specific embodiment of an oral pharmaceutical composition, a 100 mg potency tablet is composed of 100 mg of any one of the Examples, 268 mg microcrystalline cellulose, 20 mg of croscarmellose sodium, and 4 mg of magnesium stearate. The active, microcrystalline cellulose, and croscarmellose are blended first. The mixture is then lubricated by magnesium stearate and pressed into tablets.

Biological Assays

Qube® Assay Experimental Procedure

Compounds were tested on human $Na_V1.8$ and $Na_V1.5$ channels stably expressed in human embryo kidney (HEK) 293 cells. Sodium current measurements on Qube® were conducted as follows: automated 384-well patch-clamp assays on the Qube® platform (Sophion Biosciences) were used to measure the inhibition of sodium flow through human $Na_V1.8$ and $Na_V1.5$ channels. Whole-cell voltage-clamp recordings were performed in QChips® (Sophion Biosciences) at room temperature. $Na_V1.8$ current measurements on Qube® were obtained as follows: $Na_V1.8$ currents were elicited with a 10 second 1 Hertz (Hz) pulse train from a holding potential of −90 millivolts (mV), delivered to the cells once per minute in the control condition (DMSO only) and after compound addition. The 1 hertz pulse train stimulation consisted of ten test pulses to 10 millivolt (mV) for 20 milliseconds (ms), each of which was followed by a 980 millisecond repolarization to −67 millivolts. At the end of the 10 second pulse train stimulation, a 5 second hyperpolarization step to −100 millivolt (mV) was used to recover $Na_V1.8$ from fast inactivation. The peak currents elicited by the $1^{st}$ and $10^{th}$ test pulses were used to determine $IC_{50}$ values for resting inhibition and inactivated state inhibition. $Na_V1.5$ current measurements on Qube® were obtained as follows: $Na_V1.5$ currents were elicited with a 20 second 3 Hertz pulse train in the control condition (DMSO only) and after compound addition. The pulse train consisted of sixty 20 millisecond test pulses to 0 millivolt from a holding potential of −80 millivolt (mV). The average peak currents elicited by the last 3 test pulses were used to determine $IC_{50}$ values for $Na_V1.5$ inhibition.

The following buffers were used for the Qube® recordings: External buffer for $Na_V1.8$ Qube® recording: 150 NaCl, 2 $CaCl_2$, 5 KCl, 1 Mg $Cl_2$, 10 HEPES, 12 Dextrose; External buffer for Qube® $Na_V1.5$ recording: 120 N-Methyl-D-Glucamine, 40 NaCl, 1 KCl, 2.7 $CaCl_2$, 5 HEPES, 0.5 $MgCl_2$; and Internal buffer for Qube® recording: 120 CsF, 30 CsCl, 10 EGTA, 5 HEPES, 5 NaF, 2 $MgCl_2$.

For all Qube® experiments offline analysis was used to determine percent inhibition as a function of drug concentration. $IC_{50}$ values were determined by fitting to the Hill equation.

The compounds of the present invention have Nav1.8 $IC_{50}$ values in the Qube® Assay of less than 25 micromolar. Preferred compounds of the present invention have Nav1.8 $IC_{50}$ values in the Qube® Assay of less than 5 micromolar. More preferred compounds of the present invention have Nav1.8 $IC_{50}$ values in the Qube® Assay of less than 1 micromolar. Specific $IC_{50}$ values of the compounds of Examples 1A-91D in the Qube® Assay are listed in Table I.

TABLE I $IC_{50}$ values (nM) for Examples in the Nav1.8 Qube ® Assay

| Example | $IC_{50}$ (nM) | Example | $IC_{50}$ (nM) |
|---|---|---|---|
| 1A | 4.0 | 47B | 3.9 |
| 1B | 22 | 48 | 16 |
| 2A | 34 | 49A | 7.6 |
| 2B | 8100 | 49B | 6.8 |
| 3A | 9.7 | 50A | 45 |
| 3B | 2.7 | 50B | 206 |
| 4A | 203 | 51A | 9.2 |
| 4B | 6.2 | 51B | 166 |
| 5A | 1.6 | 52A | 46 |
| 5B | 74 | 52B | 4.3 |
| 6 | 28 | 53 | 219 |
| 7A | 1.1 | 54A | 3.2 |
| 7B | 44 | 54B | 50 |
| 8A | 1140 | 55A | 79 |
| 8B | 8.4 | 55B | 805 |
| 8C | 23 | 56A | 2.5 |
| 9A | 2.0 | 56B | 4.5 |
| 9B | 2.0 | 57A | 3.5 |
| 10A | 1070 | 57B | 2.4 |
| 10B | 504 | 58A | 2010 |
| 11A | 50 | 58C | 130 |
| 11B | 3.9 | 58B | 35 |
| 12A | 81 | 58D | 787 |
| 12B | 1420 | 59A | 44 |
| 13A | 1.1 | 59B | 62 |
| 13B | 38 | 60A | 3.1 |
| 14A | 2.4 | 60B | 3.8 |
| 14B | 21 | 61 | 0.7 |
| 15A | 31 | 62A | 8.0 |
| 15B | 965 | 62B | 0.4 |
| 16A | 1.1 | 63A | 4.2 |
| 16B | 14 | 63B | 16 |
| 17A | 0.6 | 64A | 79 |
| 17B | 7 | 64B | 805 |
| 18A | 18 | 65A | 16200 |
| 18B | 17 | 65B | 302 |
| 19 | 116 | 65C | 309 |
| 20A | 19200 | 65D | 7760 |
| 20B | 9480 | 66A | 63 |
| 21A | 209 | 66B | 3.8 |
| 21B | 14700 | 67A | 182 |
| 22A | 373 | 67B | 965 |
| 22B | 6410 | 68 | 604 |
| 23A | 15 | 69 | 141 |
| 23B | 4.9 | 70A | 26 |
| 23C | 62 | 70B | 9.0 |
| 23D | 190 | 70C | 117 |
| 24A | 3.1 | 70D | 650 |
| 24B | 41 | 71 | 44 |
| 25A | 22 | 72 | 74 |
| 25B | 189 | 73A | 0.2 |
| 26A | 413 | 73B | 0.2 |
| 26B | 22200 | 74A | 19 |
| 26C | 386 | 74B | 244 |
| 26D | 7830 | 75A | 58 |
| 27A | 5.8 | 75B | 115 |
| 27B | 244 | 76 | 35 |
| 28A | 633 | 77A | 26 |
| 28B | 436 | 77B | 267 |
| 29A | 110 | 78A | 4070 |
| 29B | 161 | 78B | 9500 |
| 30A | 4.6 | 78C | 8630 |
| 30B | 458 | 78D | 4660 |
| 31A | 5.2 | 78E | 24 |
| 31B | 268 | 79A | 39 |
| 32A | 3.4 | 79B | 190 |
| 32B | 67 | 79C | 886 |

TABLE I-continued

IC$_{50}$ values (nM) for Examples in the Nav1.8 Qube ® Assay

| Example | IC$_{50}$ (nM) | Example | IC$_{50}$ (nM) |
|---|---|---|---|
| 33A | 1.3 | 79D | 3680 |
| 33B | 39 | 79E | 49 |
| 34A | 3.8 | 79F | 520 |
| 34B | 76 | 79G | 2330 |
| 35A | 2.4 | 79H | 3860 |
| 35B | 64 | 80A | 100 |
| 36A | 12 | 80B | 107 |
| 36B | 186 | 81 | 54 |
| 37 | 11 | 82A | 255 |
| 38 | 1.1 | 82B | 93 |
| 39A | 1.3 | 83A | 147 |
| 39B | 2.5 | 83B | 201 |
| 40A | 21 | 84 | 29 |
| 40B | 3.5 | 85A | 372 |
| 41A | 1.7 | 85B | 1280 |
| 41B | 16 | 86 | 320 |
| 42 | 190 | 87 | 2.9 |
| 43 | 13 | 88 | 8.6 |
| 44 | 3.1 | 89 | 4.9 |
| 45A | 10 | 90 | 3.8 |
| 45B | 125 | 91A | 289 |
| 46B | 27 | 91B | 899 |
| 46B | 6.0 | 91C | 2960 |
| 47A | 5.2 | 91D | 458 |

The scope of the claims should not be limited by the preferred embodiments set forth in the examples, but should be given the broadest interpretation consistent with the description as a whole.

While the invention has been described and illustrated with reference to certain particular embodiments thereof, those skilled in the art will appreciate that various adaptations, changes, modifications, substitutions, deletions, or additions of procedures and protocols may be made without departing from the scope of the invention. For example, effective dosages other than the particular dosages as set forth herein above may be applicable as a consequence of variations in responsiveness of the mammal being treated for any of the indications with the compounds of the invention indicated above. The specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention.

What is claimed is:

1. A compound of structural Formula I:

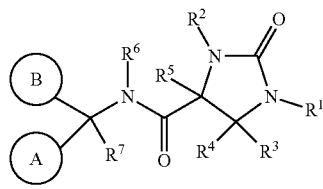

or a pharmaceutically acceptable salt thereof, wherein
A is selected from:
  1) phenyl, and
  2) pyridine, wherein each phenyl and pyridine is unsubstituted or substituted with one to five substituents selected from R$^a$;

B is selected from:
  1) phenyl,
  2) pyridine,
  3) thiazole,
  4) pyrimidine,
  5) pyrazine,
  6) pyridazine,
  7) imidazole,
  8) pyrazole,
  9) oxazole,
  10) benzofuran,
  11) benzo[d]oxazole,
  12) benzo[d]thiazole,
  13) indazole,
  14) thiazolo[5,4-b]pyridine,
  15) pyrazolo[1,5-a]pyridine,
  16) —(CH$_2$)$_2$-phenyl,
  17) —CH$_2$—O-phenyl,
  18) —CH$_2$—O-pyridine,
  19) cyclobutane,
  20) cyclohexane,
  21) bicyclo[1.1.1]pentane,
  22) spiro[3.3]heptane,
  23) azetidine,
  24) piperidine,
  25) tetrahydropyran,
  26) tetrahydrofuran,
  27) azabicyclo[3.1.0]hexane,
  28) —CH$_2$-cyclohexane,
  29) —CH$_2$-tetrahydropyran,
  30) —CH$_2$—O-cyclohexane, and
  31) bicyclo[4.2.0]octatriene, wherein B is unsubstituted or substituted with one to five substituents selected from R$^b$;

R$^1$ is selected from:
  1) hydrogen, and
  2) C$_{1-6}$alkyl, wherein alkyl is unsubstituted or substituted with one to five substituents selected from R$^c$;

R$^2$ is selected from:
  1) hydrogen, and
  2) —C$_{1-6}$alkyl, wherein alkyl is unsubstituted or substituted with one to five substituents selected from R$^d$;

R$^3$ is selected from:
  1) hydrogen, and
  2) —C$_{1-6}$alkyl, wherein alkyl is unsubstituted or substituted with one to five substituents selected from R$^f$;

R$^4$ is selected from:
  1) hydrogen, and
  2) —C$_{1-6}$alkyl, wherein alkyl is unsubstituted or substituted with one to five substituents selected from R$^g$;

R$^5$ is selected from:
  1) hydrogen, and
  2) —C$_{1-6}$alkyl, wherein alkyl is unsubstituted or substituted with one to five halogen substituents;

R$^6$ is hydrogen;

R$^7$ is selected from:
  1) hydrogen, and
  2) —C$_{1-6}$alkyl, wherein alkyl is unsubstituted or substituted with one to five halogen substituents;

each $R^a$ is independently selected from:
1) —$CF_3$,
2) —$OCF_3$,
3) —$CHF_2$,
4) —$OCHF_2$,
5) —$CH_2CF_3$,
6) —$OCH_2CF_3$,
7) —$CF_2CH_3$,
8) CN,
9) oxo,
10) halogen,
11) —$S(O)_2C_{1-6}$alkyl,
12) —$C_{1-6}$alkyl,
13) —$C_{2-6}$alkenyl,
14) —$C_{2-6}$alkynyl,
15) —$C_{3-6}$cycloalkyl,
16) —$C_{2-6}$cycloheteroalkyl,
17) aryl,
18) heteroaryl,
19) —$C_{1-6}$alkyl-aryl,
20) —$C_{1-6}$alkyl-heteroaryl,
21) —$C_{1-6}$alkyl-$C_{3-6}$cycloalkyl,
22) —$C_{1-6}$alkyl-$C_{2-6}$cycloheteroalkyl,
23) —$C_{2-6}$alkenyl-$C_{3-6}$cycloalkyl,
24) —$C_{2-6}$alkenyl-$C_{2-6}$cycloheteroalkyl,
25) —$C_{2-6}$alkenyl-aryl,
26) —$C_{2-6}$alkenyl-heteroaryl,
27) —$C_{2-6}$alkynyl-$C_{3-6}$cycloalkyl,
28) —$C_{2-6}$alkynyl-$C_{2-6}$cycloheteroalkyl,
29) —$C_{2-6}$alkynyl-aryl,
30) —$C_{2-6}$alkynyl-heteroaryl,
31) —OH,
32) —$(CH_2)_p$—O—$C_{1-6}$alkyl,
33) —$(CH_2)_p$—O—$C_{2-6}$alkenyl,
34) —$(CH_2)_p$—O—$C_{2-6}$alkynyl,
35) —$(CH_2)_p$—O—$C_{3-6}$cycloalkyl,
36) —$(CH_2)_p$—O—$C_{2-6}$heterocycloalkyl,
37) —$(CH_2)_p$—O-aryl,
38) —$(CH_2)_p$—O-heteroaryl,
39) —$OC_{1-6}$alkyl-$C_{3-6}$cycloalkyl,
40) —$OC_{1-6}$alkyl-$C_{2-6}$heterocycloalkyl,
41) —$OC_{1-6}$alkyl-aryl,
42) —$OC_{1-6}$alkyl-heteroaryl,
43) —$S(O)_mR^i$,
44) —$C_{1-6}$alkyl-$S(O)_mR^i$,
45) —$N(R^k)_2$, and
46) —$NR^kR^L$,
wherein each $R^a$ is unsubstituted or substituted with one to six substituents selected from halogen, $CF_3$, OH, $C_{1-6}$alkyl, and —$OC_{1-6}$alkyl;

each $R^b$ is independently selected from:
1) —$CF_3$,
2) —$OCF_3$,
3) —$CHF_2$,
4) —$OCHF_2$,
5) —$CH_2CF_3$,
6) —$OCH_2CF_3$,
7) —$CF_2CH_3$—,
8) CN,
9) oxo,
10) halogen,
11) —$S(O)_2C_{1-6}$alkyl,
12) —$C_{1-6}$alkyl,
13) —$C_{2-6}$alkenyl,
14) —$C_{2-6}$alkynyl,
15) —O—$C_{1-6}$alkyl,
16) —$C_{3-6}$cycloalkyl,
17) —O—$C_{3-6}$cycloalkyl,
18) —$C_{2-6}$cycloheteroalkyl,
19) aryl,
20) heteroaryl,
21) —$C_{1-6}$alkyl-aryl,
22) —$C_{1-6}$alkyl-heteroaryl,
23) —$C_{1-6}$alkyl-$C_{3-6}$cycloalkyl,
24) —$C_{1-6}$alkyl-$C_{2-6}$cycloheteroalkyl,
25) —$C_{2-6}$alkenyl-$C_{3-6}$cycloalkyl,
26) —$C_{2-6}$alkenyl-$C_{2-6}$cycloheteroalkyl,
27) —$C_{2-6}$alkenyl-aryl,
28) —$C_{2-6}$alkenyl-heteroaryl,
29) —$C_{2-6}$alkynyl-$C_{3-6}$cycloalkyl,
30) —$C_{2-6}$alkynyl-$C_{2-6}$cycloheteroalkyl,
31) —$C_{2-6}$alkynyl-aryl,
32) —$C_{2-6}$alkynyl-heteroaryl,
33) —OH,
34) —$(CH_2)_q$—$OC_{1-6}$alkyl,
35) —$(CH_2)_q$—$OC_{2-6}$alkenyl,
36) —$(CH_2)_q$—$OC_{2-6}$alkynyl,
37) —$(CH_2)_q$—$OC_{3-6}$cycloalkyl,
38) —$(CH_2)_q$—$OC_{2-6}$heterocycloalkyl,
39) —$(CH_2)_q$—O-aryl,
40) —$(CH_2)_q$—O-heteroaryl,
41) —$OC_{1-6}$alkyl-$C_{3-6}$cycloalkyl,
42) —$OC_{1-6}$alkyl-$C_{2-6}$heterocycloalkyl,
43) —$OC_{1-6}$alkyl-aryl,
44) —$OC_{1-6}$alkyl-heteroaryl,
45) —$S(O)_mR^i$,
46) —$C_{1-6}$alkyl-$S(O)_mR^i$,
47) —$C(O)R^L$, and
48) —$NR^kR^L$,
wherein each $R^b$ is unsubstituted or substituted with one to six substituents selected from halogen, $CF_3$, $OCF_3$, CN, $CH_2CF_3$, $CF_2CH_3$, —$C_{1-6}$alkyl, and —$OC_{1-6}$alkyl;

$R^c$ is selected from:
1) —$C_{1-6}$alkyl,
2) OH,
3) halogen, and
4) —$OC_{1-6}$alkyl,
wherein alkyl can be unsubstituted or substituted with one to three halogens;

$R^d$ is selected from:
1) —$C_{1-6}$alkyl,
2) OH,
3) halogen, and
4) —$OC_{1-6}$alkyl,
wherein alkyl can be unsubstituted or substituted with one to three halogens;

$R^f$ is selected from:
1) —$C_{1-6}$alkyl,
2) OH,
3) halogen, and
4) —$OC_{1-6}$alkyl,
wherein alkyl can be unsubstituted or substituted with one to three halogens;

$R^g$ is selected from:
1) —$C_{1-6}$alkyl,
2) OH,
3) halogen, and
4) —$OC_{1-6}$alkyl,
wherein alkyl can be unsubstituted or substituted with one to three halogens;

$R^i$ is selected from:
1) hydrogen,
2) $C_{1-6}$alkyl,
3) $C_{3-6}$cycloalkyl,
4) aryl, and
5) heteroaryl;

$R^k$ is selected from:
1) hydrogen, and
2) $C_{1-6}$alkyl;

$R^L$ is selected from:
1) hydrogen,
2) $C_{1-6}$alkyl,
3) $C_{3-6}$cycloalkyl,
4) aryl, and
5) heteroaryl;

m is independently selected from 0 to 2;
p is independently selected from 0 to 3; and
q is independently selected from 0 to 3.

2. The compound according to claim 1 wherein A is phenyl unsubstituted or substituted with one to five substituents selected from $R^a$; or a pharmaceutically acceptable salt thereof.

3. The compound according to claim 1 wherein B is selected from:
1) phenyl,
2) pyridine,
3) thiazole, and
4) cyclobutane,
wherein B is unsubstituted or substituted with one to five substituents selected from $R^b$;
or a pharmaceutically acceptable salt thereof.

4. The compound according to claim 1 wherein $R^1$, $R^2$, $R^3$, $R^4$, $R^5$, $R^6$ and $R^7$ are each hydrogen; or a pharmaceutically acceptable salt thereof.

5. The compound according to claim 1 wherein each $R^a$ is independently selected from:
1) —$CF_3$,
2) —$OCF_3$,
3) —$CHF_2$,
4) —$OCH_2CF_3$,
5) CN,
6) halogen, and
7) —$C_{2-6}$alkynyl,
wherein each $R^a$ is unsubstituted or substituted with one to six substituents selected from halogen, $CF_3$, OH, $C_{1-6}$alkyl, and $OC_{1-6}$alkyl, or a pharmaceutically acceptable salt thereof.

6. The compound according to claim 1 wherein each $R^a$ is independently selected from:
1) —$CF_3$,
2) —$OCF_3$, and
3) halogen;
or a pharmaceutically acceptable salt thereof.

7. The compound according to claim 1 wherein each $R^b$ is independently selected from:
1) —$CF_3$,
2) —$OCF_3$,
3) —$CHF_2$,
4) —$OCHF_2$,
5) —$CH_2CF_3$,
6) —$CH(CF_3)CH_3$,
7) —$OCH_2CF_3$,
8) CN,
9) halogen,
10) —$S(O)_2C_{1-6}$alkyl,
11) —$C_{1-6}$alkyl, and
12) —$C_{3-6}$cycloalkyl, wherein each $R^b$ is unsubstituted or substituted with one to six substituents selected from halogen, $CF_3$, $OCF_3$, CN, $CH_2CF_3$, $CF_2CH_3$, —$C_{1-6}$alkyl, and O—$C_{1-6}$alkyl; or a pharmaceutically acceptable salt thereof.

8. The compound according to claim 1 wherein each $R^b$ is independently selected from:
(1) —$CF_3$,
(2) —$OCF_3$,
(3) —$OCH_2CF_3$, and
(4) halogen,
wherein each $R^b$ is unsubstituted or substituted with one to six substituents selected from halogen, $CF_3$, $OCF_3$, CN, $CH_2CF_3$, $CF_2CH_3$, —$C_{1-6}$alkyl, and O—$C_{1-6}$alkyl; or a pharmaceutically acceptable salt thereof.

9. The compound according to claim 1 wherein
A is selected from:
1) phenyl, and
2) pyridine,
wherein each phenyl and pyridine is unsubstituted or substituted with one to five substituents selected from $R^a$;

B is selected from:
1) phenyl,
2) pyridine,
3) thiazole,
4) pyrimidine,
5) pyrazine,
6) pyridazine,
7) imidazole,
8) pyrazole,
9) oxazole,
10) benzofuran,
11) benzo[d]oxazole,
12) benzo[d]thiazole,
13) indazole,
14) thiazolo[5,4-b]pyridine,
15) pyrazolo[1,5-a]pyridine,
16) —$(CH_2)_2$-phenyl,
17) —$CH_2$—O-phenyl,
18) —$CH_2$—O-pyridine,
19) cyclobutane,
20) cyclohexane,
21) bicyclo[1.1.1]pentane,
22) spiro[3.3]heptane,
23) azetidine,
24) piperidine,
25) tetrahydropyran,
26) tetrahydrofuran,
27) azabicyclo[3.1.0]hexane,
28) —$CH_2$-cyclohexane,
29) —$CH_2$-tetrahydropyran,
30) —$CH_2$—O-cyclohexane, and
31) bicyclo[4.2.0]octatriene,
wherein B is unsubstituted or substituted with one to five substituents selected from $R^b$;

$R^1$ is selected from:
(1) hydrogen, and
(2) —$C_{1-6}$alkyl,
wherein alkyl is unsubstituted or substituted with one to five substituents selected from $R^c$;

$R^2$ is selected from:
(1) hydrogen, and
(2) —$C_{1-6}$alkyl,
wherein alkyl is unsubstituted or substituted with one to five substituents selected from $R^d$;

R³ is selected from:
1) hydrogen, and
2) —C₁₋₆alkyl,
wherein alkyl is unsubstituted or substituted with one to five substituents selected from R^f;
R⁴ is selected from:
1) hydrogen, and
2) —C₁₋₆alkyl,
wherein alkyl is unsubstituted or substituted with one to five substituents selected from R^g;
R⁶ is hydrogen;
R⁷ is selected from:
1) hydrogen, and
2) —C₁₋₆alkyl,
wherein alkyl is unsubstituted or substituted with one to five halogen substituents;
each R^a is independently selected from:
1) —CF₃,
2) —OCF₃,
3) —CHF₂,
4) —OCH₂CF₃,
5) CN,
6) halogen, and
7) —C₂₋₆alkynyl,
wherein each R^a is unsubstituted or substituted with one to six substituents selected from halogen, CF₃, OH, C₁₋₆alkyl, and —OC₁₋₆alkyl;
each R^b is independently selected from:
1) —CF₃,
2) —OCF₃,
3) —CHF₂,
4) —OCHF₂,
5) —CH₂CF₃,
6) —CH(CF₃)CH₃,
7) —OCH₂CF₃,
8) CN,
9) halogen,
10) —S(O)₂C₁₋₆alkyl,
11) —C₁₋₆alkyl, and
12) —C₃₋₆cycloalkyl,
wherein each R^b is unsubstituted or substituted with one to six substituents selected from halogen, CF₃, OCF₃, CN, CH₂CF₃, CF₂CH₃, —C₁₋₆alkyl, and O—C₁₋₆alkyl;
or a pharmaceutically acceptable salt thereof.

10. The compound according to claim 1 wherein
A is phenyl unsubstituted or substituted with one to five substituents selected from R^a;
B is selected from:
1) phenyl,
2) pyridine,
3) thiazole, and
4) cyclobutane,
wherein B is unsubstituted or substituted with one to five substituents selected from R^b;
R¹, R², R³, R⁴, R⁵, R⁶ and R⁷ are hydrogen;
each R^a is independently selected from:
1) —CF₃,
2) —OCF₃, and
3) halogen;
each R^b is independently selected from:
1) —CF₃,
2) —OCF₃,
3) —OCH₂CF₃, and
4) halogen,
wherein each R^b is unsubstituted or substituted with one to six substituents selected from halogen, CF₃, OCF₃, CN, CH₂CF₃, CF₂CH₃, —C₁₋₆alkyl, and O—C₁₋₆alkyl;
or a pharmaceutically acceptable salt thereof.

11. The compound according to claim 1 selected from:
1) (S)—N—((R)-2-(3-chloro-4-fluorophenoxy)-1-(3-chloro-4-fluorophenyl)ethyl)-2-oxoimidazolidine-4-carboxamide;
2) (S)—N—((S)-2-(3-chloro-4-fluorophenoxy)-1-(3-chloro-4-fluorophenyl)ethyl)-2-oxoimidazolidine-4-carboxamide;
3) (R)—N-(bis(4-chlorophenyl)methyl)-3-methyl-2-oxo-imidazolidine-4-carboxamide and (S)—N-(bis(4-chlorophenyl)methyl)-3-methyl-2-oxoimidazolidine-4-carboxamide;
4) (S)—N—((R)-(5-chloro-6-(difluoromethyl)pyridin-2-yl)(5-chloro-6-(trifluoromethyl)pyridin-3-yl)methyl)-2-oxoimidazolidine-4-carboxamide;
5) (S)—N—((S)-(5-chloro-6-(difluoromethyl)pyridin-2-yl)(5-chloro-6-(trifluoromethyl)pyridin-3-yl)methyl)-2-oxoimidazolidine-4-carboxamide;
6) (S)—N—((R)-(3-chloro-4-fluorophenyl)(5-(trifluoromethyl)-1H-pyrazol-3-yl)methyl)-2-oxoimidazolidine-4-carboxamide;
7) (S)—N—((S)-(3-chloro-4-fluorophenyl)(5-(trifluoromethyl)-1H-pyrazol-3-yl)methyl)-2-oxoimidazolidine-4-carboxamide;
8) (S)—N—((R)-(3-chloro-2,4-difluorophenyl)(1-(1-(trifluoromethyl)cyclopropyl)piperidin-4-yl)methyl)-2-oxoimidazolidine-4-carboxamide;
9) (S)—N—((S)-(3-chloro-2,4-difluorophenyl)(1-(1-(trifluoromethyl)cyclopropyl)piperidin-4-yl)methyl)-2-oxoimidazolidine-4-carboxamide;
10) (S)—N-((5-chloro-4-(trifluoromethyl)pyrimidin-2-yl)(4-chlorophenyl)methyl)-2-oxoimidazolidine-4-carboxamide;
11) (S)—N—((R)-(5-fluoro-6-(trifluoromethyl)pyridin-2-yl)(4-(trifluoromethoxy)phenyl)-methyl)-2-oxoimidazolidine-4-carboxamide;
12) (S)—N—((S)-(5-fluoro-6-(trifluoromethyl)pyridin-2-yl)(4-(trifluoromethoxy)phenyl)-methyl)-2-oxoimidazolidine-4-carboxamide;
13) (S)—N—((R)-(3-chloro-2,4-difluorophenyl)((trans)-5-(trifluoromethyl)tetrahydro-2H-pyran-2-yl)methyl)-2-oxoimidazolidine-4-carboxamide;
14) (S)—N—((S)-(3-chloro-2,4-difluorophenyl)((trans)-5-(trifluoromethyl)tetrahydro-2H-pyran-2-yl)methyl)-2-oxoimidazolidine-4-carboxamide;
15) (S)—N—((R)-(3-chlorophenyl)(4-(trifluoromethoxy)phenyl)methyl)-2-oxoimidazolidine-4-carboxamide;
16) (S)—N—((S)-(3-chlorophenyl)(4-(trifluoromethoxy)phenyl)methyl)-2-oxoimidazolidine-4-carboxamide;
17) (R)—N-[bis(4-chlorophenyl)methyl]-1-methyl-2-oxoimidazolidine-4-carboxamide;
18) (S)-N-[bis(4-chlorophenyl)methyl]-1-methyl-2-oxoimidazolidine-4-carboxamide;
19) (4S)—N—{((R)-3-chloro-4-fluorophenyl)[5-fluoro-6-(2,2,2-trifluoro-ethoxy)pyridin-2-yl]methyl}-2-oxoimidazolidine-4-carboxamide;
20) (4S)—N—{((S)-3-chloro-4-fluorophenyl)[5-fluoro-6-(2,2,2-trifluoro-ethoxy)pyridin-2-yl]methyl}-2-oxoimidazolidine-4-carboxamide;
21) (4S)—N—[((R)-3-chloro-4-fluorophenyl)(6-cyano-pyridin-2-yl)methyl]-2-oxoimidazolidine-4-carboxamide;

22) (4S)—N—[((S)-3-chloro-4-fluorophenyl)(6-cyano-pyridin-2-yl)methyl]-2-oxoimidazolidine-4-carboxamide;
23) (4S)—N—[((R)-5-chloro-6-cyclopropylpyridin-3-yl)(3-chloro-2,4-difluoro-phenyl)methyl]-2-oxoimidazolidine-4-carboxamide;
24) (4S)—N—[((S)-5-chloro-6-cyclo-propylpyridin-3-yl)(3-chloro-2,4-difluoro-phenyl)methyl]-2-oxoimidazolidine-4-carboxamide;
25) (4S)—N—{[(R)-5-chloro-6-(trifluoromethyl)pyridin-3-yl][5-fluoro-6-(trifluoro-methyl)pyridin-2-yl]methyl}-2-oxoimidazolidine-4-carboxamide;
26) (4S)—N—{[(S)-5-chloro-6-(trifluoromethyl)pyridin-3-yl][5-fluoro-6-(trifluoro-methyl)pyridin-2-yl]methyl}-2-oxoimidazolidine-4-carboxamide;
27) (S)—N—((R)-(3-chloro-4-fluorophenyl)(cis-2,6-dimethyl-1-(2,2,2-trifluoroethyl)-piperidin-4-yl)methyl)-2-oxoimidazolidine-4-carboxamide;
28) (S)—N—((S)-(3-chloro-4-fluorophenyl)(cis-2,6-dimethyl-1-(2,2,2-trifluoroethyl)-piperidin-4-yl)methyl)-2-oxoimidazolidine-4-carboxamide;
29) (S)—N—((R)-(3-chloro-4-fluorophenyl)(2-(1-(trifluoromethyl)cyclopropyl)thiazol-4-yl)methyl)-2-oxoimidazolidine-4-carboxamide;
30) (S)—N—((S)-(3-chloro-4-fluorophenyl)(2-(1-(trifluoromethyl)cyclopropyl)thiazol-4-yl)methyl)-2-oxoimidazolidine-4-carboxamide;
31) (S)—N—((R)-(4-chlorophenyl)(4-fluoro-3-(trifluoro-methyl)phenyl)methyl)-2-oxoimidazolidine-4-carboxamide;
32) (S)—N—((S)-(4-chlorophenyl)(4-fluoro-3-(trifluoromethyl)phenyl)methyl)-2-oxoimidazolidine-4-carboxamide;
33) (S)—N—((R)-(3-chloro-4-fluoro-phenyl)(4-cyanophenyl)methyl)-2-oxoimidazolidine-4-carboxamide;
34) (S)—N—((S)-(3-chloro-4-fluoro-phenyl)(4-cyanophenyl)methyl)-2-oxoimidazolidine-4-carboxamide;
35) (S)-2-oxo-N—((R)-(6-(trifluoromethyl)pyridin-3-yl)(2-(trifluoromethyl)thiazol-4-yl)methyl)imidazolidine-4-carboxamide;
36) (S)-2-oxo-N—((S)-(6-(trifluoromethyl)pyridin-3-yl)(2-(trifluoromethyl)thiazol-4-yl)methyl)imidazolidine-4-carboxamide;
37) (R)—N-(bis(4-chlorophenyl)methyl)-4-methyl-2,5-dioxoimidazolidine-4-carboxamide;
38) (S)—N-(bis(4-chlorophenyl)methyl)-4-methyl-2,5-dioxoimidazolidine-4-carboxamide;
39) (R)—N-(bis(4-chlorophenyl)methyl)-3-(2-hydroxyethyl)-2-oxoimidazolidine-4-carboxamide;
40) (S)—N-(bis(4-chlorophenyl)methyl)-3-(2-hydroxyethyl)-2-oxoimidazolidine-4-carboxamide;
41) (S)—N—((R)-(4-chlorophenyl)(2-(trifluoromethyl)-1H-imidazol-4-yl)methyl)-2-oxoimidazolidine-4-carboxamide;
42) (S)—N—((S)-(4-chlorophenyl)(2-(trifluoromethyl)-1H-imidazol-4-yl)methyl)-2-oxoimidazolidine-4-carboxamide;
43) (S)—N—((R)-1-(3-chloro-2,4-difluorophenyl)-2-((cis)-4-(trifluoromethyl)cyclohexyl)ethyl)-2-oxoimidazolidine-4-carboxamide;
44) (S)—N—((R)-1-(3-chloro-2,4-difluorophenyl)-2-((trans)-4-(trifluoromethyl)cyclohexyl)-ethyl)-2-oxoimidazolidine-4-carboxamide;
45) (S)—N—((S)-1-(3-chloro-2,4-difluorophenyl)-2-((trans)-4-(trifluoromethyl)cyclohexyl)-ethyl)-2-oxoimidazolidine-4-carboxamide;
46) (S)—N—((S)-1-(3-chloro-2,4-difluorophenyl)-2-((cis)-4-(trifluoromethyl)cyclohexyl)ethyl)-2-oxoimidazolidine-4-carboxamide;
47) (4S)—N—{(R)-(3-chloro-2,4-difluorophenyl)[6-(trifluoromethoxy)pyridin-3-yl]methyl}-2-oxoimidazolidine-4-carboxamide;
48) (4S)—N—{(S)-(3-chloro-2,4-difluorophenyl)[6-(trifluoromethoxy)pyridin-3-yl]methyl}-2-oxoimidazolidine-4-carboxamide;
49) (S)—N—((R)-1-(3-chloro-2,4-difluorophenyl)-2-(4,4-difluorocyclohexyl)ethyl)-2-oxoimidazolidine-4-carboxamide;
50) (S)—N—((S)-1-(3-chloro-2,4-difluorophenyl)-2-(4,4-difluorocyclohexyl)ethyl)-2-oxoimidazolidine-4-carboxamide;
51) (S)—N—((R)-1-(3-chloro-2,4-difluorophenyl)-2-((R)-tetrahydro-2H-pyran-3-yl)ethyl)-2-oxoimidazolidine-4-carboxamide;
52) (S)—N—((R)-1-(3-chloro-2,4-difluorophenyl)-2-((S)-tetrahydro-2H-pyran-3-yl)ethyl)-2-oxoimidazolidine-4-carboxamide;
53) (S)—N—((S)-1-(3-chloro-2,4-difluorophenyl)-2-((R)-tetrahydro-2H-pyran-3-yl)ethyl)-2-oxoimidazolidine-4-carboxamide;
54) (S)—N—((S)-1-(3-chloro-2,4-difluorophenyl)-2-((S)-tetrahydro-2H-pyran-3-yl)ethyl)-2-oxoimidazolidine-4-carboxamide;
55) (S)—N—((R)-(3-chloro-2,4-difluorophenyl)(3-(trifluoromethyl)bicyclo[1.1.1]pentan-1-yl)methyl)-2-oxoimidazolidine-4-carboxamide;
56) (S)—N—((S)-(3-chloro-2,4-difluorophenyl)(3-(trifluoromethyl)bicyclo[1.1.1]pentan-1-yl)methyl)-2-oxoimidazolidine-4-carboxamide;
57) ((4S)—N—{(R)-(3-chloro-4-fluorophenyl)[1-(2,2,2-trifluoroethyl)-1H-pyrazol-3-yl]methyl}-2-oxoimidazolidine-4-carboxamide;
58) (4S)—N—{(S)-(3-chloro-4-fluorophenyl)[1-(2,2,2-trifluoroethyl)-1H-pyrazol-3-yl]methyl}-2-oxoimidazolidine-4-carboxamide;
59) (4S)—N—{1-((R)-3-chloro-4-fluorophenyl)-2-[(4,4-difluoro-cyclohexyl)oxy]ethyl}-2-oxoimidazolidine-4-carboxamide;
60) (4S)—N—{1-((S)-3-chloro-4-fluorophenyl)-2-[(4,4-difluoro-cyclohexyl)oxy]ethyl}-2-oxoimidazolidine-4-carboxamide;
61) (4S)—N—[(R)-(3-chloro-2,4-di-fluorophenyl)(3,3-dimethylcyclobutyl)methyl]-2-oxoimidazolidine-4-carboxamide;
62) (4S)—N—[(S)-(3-chloro-2,4-di-fluorophenyl)(3,3-dimethylcyclobutyl)methyl]-2-oxoimidazolidine-4-carboxamide;
63) (S)—N—((R)-(3-chloro-4-fluorophenyl)(1-methyl-3-(trifluoromethyl)-1H-pyrazol-5-yl)methyl)-2-oxoimidazolidine-4-carboxamide;
64) (S)—N—((S)-(3-chloro-4-fluorophenyl)(1-methyl-3-(trifluoromethyl)-1H-pyrazol-5-yl)methyl)-2-oxoimidazolidine-4-carboxamide;
65) (S)—N—((R)-(3-chloro-4-fluorophenyl)(trans-4-(trifluoromethyl)cyclohexyl)methyl)-2-oxoimidazolidine-4-carboxamide;
66) (S)—N—((S)-(3-chloro-4-fluorophenyl)(trans-4-(trifluoromethyl)cyclohexyl)methyl)-2-oxoimidazolidine-4-carboxamide;
67) (S)—N—((R)-(3-chloro-2,4-difluorophenyl)(6-(2,2,2-trifluoroethoxy)pyridin-3-yl)methyl)-2-oxoimidazolidine-4-carboxamide;

68) (S)—N—((S)-(3-chloro-2,4-difluorophenyl)(6-(2,2,2-trifluoroethoxy)pyridin-3-yl)methyl)-2-oxoimidazolidine-4-carboxamide;
69) (S)—N—((R)-(3-chloro-2,4-difluorophenyl)(trans-3-(trifluoromethyl)cyclobutyl)-methyl)-2-oxoimidazolidine-4-carboxamide;
70) (S)—N—((S)-(3-chloro-2,4-difluorophenyl)(trans-3-(trifluoromethyl)cyclobutyl)-methyl)-2-oxoimidazolidine-4-carboxamide;
71) (S)—N—((R)-(3-chloro-2,4-difluorophenyl)(2-(2,2,2-trifluoroethoxy)thiazol-5-yl)-methyl)-2-oxoimidazolidine-4-carboxamide;
72) (S)—N—((S)-(3-chloro-2,4-difluorophenyl)(2-(2,2,2-trifluoroethoxy)thiazol-5-yl)-methyl)-2-oxoimidazolidine-4-carboxamide;
73) (S)—N—((R)-(3-chloro-2,4-difluorophenyl)(2-(difluoromethoxy)thiazol-5-yl)methyl)-2-oxoimidazolidine-4-carboxamide;
74) (S)—N—((S)-(3-chloro-2,4-difluorophenyl)(2-(difluoromethoxy)thiazol-5-yl)methyl)-2-oxoimidazolidine-4-carboxamide;
75) (S)—N—((R)-(3-chloro-2,4-difluorophenyl)(6,6-difluorospiro[3.3]heptan-2-yl)methyl)-2-oxoimidazolidine-4-carboxamide;
76) (S)—N—((S)-(3-chloro-2,4-difluorophenyl)(6,6-difluorospiro[3.3]heptan-2-yl)methyl)-2-oxoimidazolidine-4-carboxamide;
77) (S)—N—((R)-(3-chloro-2,4-difluorophenyl)(5-chloro-6-(trifluoromethyl)pyridin-3-yl)methyl)-2-oxoimidazolidine-4-carboxamide;
78) (S)—N—((S)-(3-chloro-2,4-difluorophenyl)(5-chloro-6-(trifluoromethyl)pyridin-3-yl)methyl)-2-oxoimidazolidine-4-carboxamide;
79) (S)—N—((R)-(3-chloro-2,4-difluorophenyl)(trans-3-(trifluoromethyl)cyclobutyl)-methyl)-2-oxoimidazolidine-4-carboxamide;
80) (S)—N—((S)-(3-chloro-2,4-difluorophenyl)(trans-3-(trifluoromethyl)cyclobutyl)-methyl)-2-oxoimidazolidine-4-carboxamide;
81) (S)—N—((R)-3-chloro-4-(trifluoromethoxy)phenyl)(5-(trifluoromethoxy)pyridin-2-yl)methyl)-2-oxoimidazolidine-4-carboxamide;
82) (S)—N—((S)-3-chloro-4-(trifluoromethoxy)phenyl)(5-(trifluoromethoxy)pyridin-2-yl)methyl)-2-oxoimidazolidine-4-carboxamide;
83) (S)—N—((R)-(5-chloro-6-cyclopropylpyridin-2-yl)(4-(trifluoromethoxy)phenyl)-methyl)-2-oxoimidazolidine-4-carboxamide;
84) (S)—N—((S)-(5-chloro-6-cyclopropylpyridin-2-yl)(4-(trifluoromethoxy)phenyl)-methyl)-2-oxoimidazolidine-4-carboxamide;
85) (S)—N—((R)-(3-chloro-4-(trifluoromethoxy)phenyl)(1-(trifluoromethyl)-1H-pyrazol-4-yl)-13-methyl)-2-oxoimidazolidine-4-carboxamide;
86) (S)—N—((S)-(3-chloro-4-(trifluoromethoxy)phenyl)(1-(trifluoromethyl)-1H-pyrazol-4-yl)-13-methyl)-2-oxoimidazolidine-4-carboxamide;
87) (S)—N—((R)-(3-chloro-2,4-difluorophenyl)(6-(difluoromethoxy)-5-fluoropyridin-3-yl)methyl)-2-oxoimidazolidine-4-carboxamide;
88) (S)—N—((S)-(3-chloro-2,4-difluorophenyl)(6-(difluoromethoxy)-5-fluoropyridin-3-yl)methyl)-2-oxoimidazolidine-4-carboxamide;
89) (S)—N—((R)-(3-chloro-2,4-difluorophenyl)(6-(difluoromethyl)pyridin-3-yl)methyl)-2-oxoimidazolidine-4-carboxamide;
90) (S)—N—((S)-(3-chloro-2,4-difluorophenyl)(6-(difluoromethyl)pyridin-3-yl)methyl)-2-oxoimidazolidine-4-carboxamide;
91) (S)—N—((R)-(3-chloro-2,4-difluorophenyl)(5-fluoro-6-(trifluoromethyl)pyridin-3-yl)methyl)-2-oxoimidazolidine-4-carboxamide;
92) (S)—N—((S)-(3-chloro-2,4-difluorophenyl)(5-fluoro-6-(trifluoromethyl)pyridin-3-yl)methyl)-2-oxoimidazolidine-4-carboxamide;
93) (S)—N—((R)-(5-fluoro-6-(trifluoro-methyl)pyridin-2-yl)(6-(trifluoromethoxy)pyridin-3-yl)methyl)-2-oxoimidazolidine-4-carboxamide;
94) (S)—N—((S)-(5-fluoro-6-(trifluoromethyl)pyridin-2-yl)(6-(trifluoromethoxy)pyridin-3-yl)methyl)-2-oxoimidazolidine-4-carboxamide;
95) (S)—N—((R)-(5-fluoro-6-(2,2,2-trifluoroethoxy)pyridin-3-yl)(5-fluoro-6-(trifluoro-methyl)pyridin-2-yl)methyl)-2-oxoimidazolidine-4-carboxamide;
96) (S)—N—((S)-(5-fluoro-6-(2,2,2-trifluoroethoxy)pyridin-3-yl)(5-fluoro-6-(trifluoro-methyl)-pyridin-2-yl)methyl)-2-oxoimidazolidine-4-carboxamide;
97) (S)—N—((R)-(3-chloro-4-(trifluoromethoxy)phenyl)(2-(trifluoromethyl)oxazol-4-yl)methyl)-2-oxoimidazolidine-4-carboxamide
98) (S)—N—((S)-(3-chloro-4-(trifluoromethoxy)phenyl)(2-(trifluoromethyl)oxazol-4-yl)methyl)-2-oxoimidazolidine-4-carboxamide;
99) (S)—N—((R)-(3-chloro-2,4-difluorophenyl)(2-(trifluoromethyl)pyrimidin-5-yl)methyl)-2-oxoimidazolidine-4-carboxamide;
100) (S)—N—((S)-(3-chloro-2,4-difluorophenyl)(2-(trifluoromethyl)pyrimidin-5-yl)methyl)-2-oxoimidazolidine-4-carboxamide;
101) (S)—N—((R)-3-chloro-4-(trifluoromethoxy)phenyl)(2-(trifluoromethyl)pyrimidin-4-yl)methyl)-2-oxoimidazolidine-4-carboxamide;
102) (S)—N—((S)-3-chloro-4-(trifluoromethoxy)phenyl)(2-(trifluoromethyl)pyrimidin-4-yl)methyl)-2-oxoimidazolidine-4-carboxamide;
103) (4S)—N—((R)-(3-chloro-2,4-difluorophenyl)(6-(2,2,2-trifluoroethoxy)pyridazin-3-yl)-methyl)-2-oxoimidazolidine-4-carboxamide;
104) (4S)—N—((S)-(3-chloro-2,4-difluorophenyl)(6-(2,2,2-trifluoroethoxy)pyridazin-3-yl)-methyl)-2-oxoimidazolidine-4-carboxamide;
105) (4S)—N—((R)-(3-chloro-2,4-difluorophenyl)(5-(2,2,2-trifluoroethoxy)pyrazin-2-yl)methyl)-2-oxoimidazolidine-4-carboxamide;
106) (4S)—N—((S)-(3-chloro-2,4-difluorophenyl)(5-(2,2,2-trifluoroethoxy)pyrazin-2-yl)methyl)-2-oxoimidazolidine-4-carboxamide;
107) (S)—N—((R)-1-(3-chloro-2,4-difluorophenyl)-3-(4-chlorophenyl)propyl)-2-oxo-imidazolidine-4-carboxamide;
108) (S)—N—((S)-1-(3-chloro-2,4-difluorophenyl)-3-(4-chlorophenyl)propyl)-2-oxo-imidazolidine-4-carboxamide;
109) (4S)—N-(1-(3-chloro-4-fluorophenyl)-2-((6-(trifluoromethyl)pyridin-3-yl)oxy)ethyl)-2-oxoimidazolidine-4-carboxamide;
110) (S)—N—((R)-1-(3-chloro-2,4-difluorophenyl)-2-cyclohexylethyl)-2-oxoimidazolidine-4-carboxamide;
111) (S)—N—((S)-1-(3-chloro-2,4-difluorophenyl)-2-cyclohexylethyl)-2-oxoimidazolidine-4-carboxamide;
112) (4S)—N—((R)-(3-chloro-2,4-difluorophenyl)(2-(difluoromethoxy)pyrimidin-5-yl)methyl)-2-oxoimidazolidine-4-carboxamide;

113) (4S)—N—((S)-(3-chloro-2,4-difluorophenyl)(2-(difluoromethoxy)pyrimidin-5-yl)methyl)-2-oxoimidazolidine-4-carboxamide;
114) (S)—N—((R)-(5-chloro-6-(trifluoromethyl)pyridin-2-yl)(5-chloro-6-(trifluoromethyl)-pyridin-3-yl)methyl)-2-oxoimidazolidine-4-carboxamide;
115) (S)—N—((S)-(5-chloro-6-(trifluoromethyl)pyridin-2-yl)(5-chloro-6-(trifluoromethyl)-pyridin-3-yl)methyl)-2-oxoimidazolidine-4-carboxamide;
116) (S)—N—((R)-(4-chloro-3-cyanophenyl)(4-(trifluoromethoxy)phenyl)methyl)-2-oxoimidazolidine-4-carboxamide;
117) (S)—N—((S)-(4-chloro-3-cyanophenyl)(4-(trifluoromethoxy)phenyl)methyl)-2-oxoimidazolidine-4-carboxamide;
118) (S)—N—((R)-(3-chloro-2,4-difluorophenyl)((R)-1-(2,2,2-trifluoroethyl)piperidin-2-yl)methyl)-2-oxoimidazolidine-4-carboxamide;
119) (S)—N—((R)-(3-chloro-2,4-difluorophenyl)((S)-1-(2,2,2-trifluoroethyl)piperidin-2-yl)methyl)-2-oxoimidazolidine-4-carboxamide;
120) (S)—N—((S)-(3-chloro-2,4-difluorophenyl)((S)-1-(2,2,2-trifluoroethyl)piperidin-2-yl)methyl)-2-oxoimidazolidine-4-carboxamide;
121) (S)—N—((S)-(3-chloro-4-fluoro-phenyl)((S)-2-chlorobicyclo[4.2.0]-octa-1(6),2,4-trien-7-yl)methyl)-2-oxoimidazolidine-4-carboxamide;
122) (S)—N—((R)-(4-chlorophenyl)(5-fluoro-4-(trifluoromethyl)pyridin-2-yl)methyl)-2-oxo-imidazolidine-4-carboxamide;
123) (S)—N—((S)-(4-chlorophenyl)(5-fluoro-4-(trifluoromethyl)pyridin-2-yl)methyl)-2-oxo-imidazolidine-4-carboxamide;
124) (S)—N—((R)-(4-chloro-3-(trifluoromethyl)-phenyl)(4-cyanophenyl)-methyl)-2-oxo-imidazolidine-4-carboxamide;
125) (S)—N—((S)-(4-chloro-3-(trifluoromethyl)-phenyl)(4-cyanophenyl)-methyl)-2-oxo-imidazolidine-4-carboxamide;
126) (S)—N-(bis(3-chloro-4-fluorophenyl)methyl)-2-oxoimidazolidine-4-carboxamide;
127) (S)—N—((R)-(3-chloro-4-fluorophenyl)(5-chloro-6-(trifluoromethyl)pyridin-2-yl)methyl)-2-oxoimidazolidine-4-carboxamide;
128) (S)—N—((S)-(3-chloro-4-fluorophenyl)(5-chloro-6-(trifluoromethyl)pyridin-2-yl)methyl)-2-oxoimidazolidine-4-carboxamide;
129) (S)—N—((R)-(3-chloro-2,4-difluorophenyl)(6-(difluoromethyl)-5-fluoropyridin-2-yl)methyl)-2-oxoimidazolidine-4-carboxamide;
130) (S)—N—((S)-(3-chloro-2,4-difluorophenyl)(6-(difluoromethyl)-5-fluoropyridin-2-yl)methyl)-2-oxoimidazolidine-4-carboxamide;
131) (S)—N—((R)-(3-chloro-2,4-difluorophenyl)(2-(difluoromethoxy)pyrimidin-5-yl)methyl)-2-oxoimidazolidine-4-carboxamide;
132) (S)—N—((S)-(3-chloro-2,4-difluorophenyl)(2-(difluoromethoxy)pyrimidin-5-yl)methyl)-2-oxoimidazolidine-4-carboxamide;
133) (S)—N—((R)-(3-chloro-2,4-difluorophenyl)(3-methyl-1-((S)-1,1,1-trifluoropropan-2-yl)azetidin-3-yl)methyl)-2-oxoimidazolidine-4-carboxamide;
134) (S)—N—((R)-(3-chloro-2,4-difluorophenyl)(3-methyl-1-((R)-1,1,1-trifluoropropan-2-yl)azetidin-3-yl)methyl)-2-oxoimidazolidine-4-carboxamide;
135) (S)—N—((S)-(3-chloro-2,4-difluorophenyl)(3-methyl-1-((S)-1,1,1-trifluoropropan-2-yl)azetidin-3-yl)methyl)-2-oxoimidazolidine-4-carboxamide;
136) (S)—N—((S)-(3-chloro-2,4-difluorophenyl)(3-methyl-1-((R)-1,1,1-trifluoropropan-2-yl)azetidin-3-yl)methyl)-2-oxoimidazolidine-4-carboxamide;
137) (S)—N—((R)-(3-chloro-4-fluorophenyl)(2-methylbenzo[d]thiazol-5-yl)methyl)-2-oxoimidazolidine-4-carboxamide;
138) (S)—N—((S)-(3-chloro-4-fluorophenyl)(2-methylbenzo[d]thiazol-5-yl)methyl)-2-oxoimidazolidine-4-carboxamide;
139) (S)—N—((R)-(3-chloro-4-fluorophenyl)(trans-2-(trifluoromethyl)cyclobutyl)methyl)-2-oxoimidazolidine-4-carboxamide;
140) (S)—N—((S)-(3-chloro-4-fluorophenyl)(trans-2-(trifluoromethyl)cyclobutyl)methyl)-2-oxoimidazolidine-4-carboxamide;
141) (4S)—N-((3-chloro-4-fluorophenyl)(3,3-dimethyl-2-(trifluoromethyl)cyclobutyl)methyl)-2-oxoimidazolidine-4-carboxamide;
142) (4S)—N-((3-chloro-4-fluorophenyl)(4-fluorobicyclo[4.2.0]octa-1(6),2,4-trien-7-yl)methyl)-2-oxoimidazolidine-4-carboxamide;
143) (S)—N—((R)-(3-chloro-4-fluoro-phenyl)((R)-2-chlorobicyclo[4.2.0]-octa-1(6),2,4-trien-7-yl)methyl)-2-oxoimidazolidine-4-carboxamide;
144) (S)—N—((R)-(3-chloro-4-fluoro-phenyl)((S)-2-chlorobicyclo[4.2.0]-octa-1(6),2,4-trien-7-yl)methyl)-2-oxoimidazolidine-4-carboxamide;
145) (S)—N—((S)-(3-chloro-4-fluoro-phenyl)((R)-2-chlorobicyclo[4.2.0]-octa-1(6),2,4-trien-7-yl)methyl)-2-oxoimidazolidine-4-carboxamide;
146) (S)—N—((S)-(3-chloro-4-fluoro-phenyl)((S)-2-chlorobicyclo[4.2.0]-octa-1(6),2,4-trien-7-yl)methyl)-2-oxoimidazolidine-4-carboxamide;
147) (S)—N—((R)-(3-chloro-4-fluoro-phenyl)((R)-2-chlorobicyclo[4.2.0]-octa-1(6),2,4-trien-7-yl)methyl)-2-oxoimidazolidine-4-carboxamide;
148) (S)—N—((R)-(3-chloro-4-fluoro-phenyl)((S)-2-chlorobicyclo[4.2.0]-octa-1(6),2,4-trien-7-yl)methyl)-2-oxoimidazolidine-4-carboxamide;
149) (S)—N—((S)-(3-chloro-4-fluoro-phenyl)((R)-2-chlorobicyclo[4.2.0]-octa-1(6),2,4-trien-7-yl)methyl)-2-oxoimidazolidine-4-carboxamide;
150) (S)—N—((S)-(3-chloro-4-fluoro-phenyl)((S)-2-chlorobicyclo[4.2.0]-octa-1(6),2,4-trien-7-yl)methyl)-2-oxoimidazolidine-4-carboxamide;
151) (4S)—N-((3-chloro-4-fluorophenyl)(4-chlorobicyclo[4.2.0]-octa-1(6),2,4-trien-7-yl)-methyl)-2-oxoimidazolidine-4-carboxamide;
152) (4S)—N-((3-chloro-4-fluorophenyl)(thiazolo[5,4-b]pyridin-2-yl)methyl)-2-oxo-imidazolidine-4-carboxamide;
153) (S)—N—((R)-(3-chloro-4-fluorophenyl)(5-chlorobenzofuran-2-yl)methyl)-2-oxo-imidazolidine-4-carboxamide;
154) (S)—N—((S)-(3-chloro-4-fluorophenyl)(5-chlorobenzofuran-2-yl)methyl)-2-oxo-imidazolidine-4-carboxamide;
155) (S)—N—((R)-(4-chlorophenyl)(6-(difluoromethoxy)pyridin-2-yl)methyl)-2-oxo-imidazolidine-4-carboxamide;
156) (S)—N—((S)-(4-chlorophenyl)(6-(difluoromethoxy)pyridin-2-yl)methyl)-2-oxo-imidazolidine-4-carboxamide;

157) (S)—N—((R)-(4-chlorophenyl)(1-methyl-5-(trifluoromethyl)-1H-pyrazol-3-yl)methyl)-2-oxoimidazolidine-4-carboxamide;
158) (S)—N—((S)-(4-chlorophenyl)(1-methyl-5-(trifluoromethyl)-1H-pyrazol-3-yl)methyl)-2-oxoimidazolidine-4-carboxamide;
159) (4S)—N-((4-chlorophenyl)(4-methyl-2-(trifluoromethyl)thiazol-5-yl)methyl)-2-oxoimidazolidine-4-carboxamide;
160) (4S)—N-((1(R))-(3-chloro-4-fluorophenyl)(3-(2,2,2-trifluoroethyl)-3-azabicyclo-[3.1.0]hexan-6-yl)methyl)-2-oxoimidazolidine-4-carboxamide;
161) (4S)—N-((1(S))-(3-chloro-4-fluorophenyl)(3-(2,2,2-trifluoroethyl)-3-azabicyclo-[3.1.0]-hexan-6-yl)methyl)-2-oxoimidazolidine-4-carboxamide;
162) (S)—N—((R)-(3-chloro-2,4-difluorophenyl)((cis)-1-methyl-2-(trifluoro-methyl)piperidin-4-yl)methyl)-2-oxoimidazolidine-4-carboxamide;
163) (S)—N—((R)-(3-chloro-2,4-difluorophenyl)((trans)-1-methyl-2-(trifluoro-methyl)piperidin-4-yl)methyl)-2-oxoimidazolidine-4-carboxamide;
164) (S)—N—((S)-(3-chloro-2,4-difluorophenyl)((cis)-1-methyl-2-(trifluoro-methyl)-piperidin-4-yl)methyl)-2-oxoimidazolidine-4-carboxamide;
165) (S)—N—((S)-(3-chloro-2,4-difluorophenyl)((trans)-1-methyl-2-(trifluoro-methyl)-piperidin-4-yl)methyl)-2-oxoimidazolidine-4-carboxamide;
166) (S)—N—((R)-(3-chloro-2,4-difluorophenyl)((cis)-5-(trifluoromethyl)-tetrahydrofuran-3-yl)methyl)-2-oxoimidazolidine-4-carboxamide;
167) S)—N—((R)-(3-chloro-2,4-difluorophenyl)((trans)-5-(trifluoromethyl)-tetrahydrofuran-3-yl)methyl)-2-oxoimidazolidine-4-carboxamide;
168) (S)—N—((S)-(3-chloro-2,4-difluorophenyl)((cis)-5-(trifluoromethyl)-tetrahydrofuran-3-yl)methyl)-2-oxoimidazolidine-4-carboxamide;
169) (S)—N—((S)-(3-chloro-2,4-difluorophenyl)((trans)-5-(trifluoromethyl)-tetrahydrofuran-3-yl)methyl)-2-oxoimidazolidine-4-carboxamide;
170) (S)—N—((R)-(4-chlorophenyl)(pyrazolo[1,5-a]pyridin-5-yl)methyl)-2-oxo-imidazolidine-4-carboxamide;
171) (S)—N—((S)-(4-chlorophenyl)(pyrazolo[1,5-a]pyridin-5-yl)methyl)-2-oxo-imidazolidine-4-carboxamide;
172) (4S)—N-(benzo[d]thiazol-6-yl)(4-chlorophenyl)methyl)-2-oxoimidazolidine-4-carboxamide;
173) (S)—N—((R)-(4-chlorophenyl)(1H-indazol-6-yl)methyl)-2-oxoimidazolidine-4-carboxamide;
174) (S)—N—((S)-(4-chlorophenyl)(1H-indazol-6-yl)methyl)-2-oxoimidazolidine-4-carboxamide;
175) (S)—N—((R)-(4-chlorophenyl)(pyrazolo[1,5-a]pyridin-5-yl)methyl)-2-oxo-imidazolidine-4-carboxamide;
176) (S)—N—((S)-(4-chlorophenyl)(pyrazolo[1,5-a]pyridin-5-yl)methyl)-2-oxo-imidazolidine-4-carboxamide;
177) (S)—N—((R)-(4-chlorophenyl)(2-methylbenzo[d]oxazol-6-yl)methyl)-2-oxo-imidazolidine-4-carboxamide;
178) (S)—N—((S)-(4-chlorophenyl)(2-methylbenzo[d]oxazol-6-yl)methyl)-2-oxo-imidazolidine-4-carboxamide;
179) (S)—N—((R)-(4-chlorophenyl)(2-methylbenzo[d]thiazol-6-yl)methyl)-2-oxo-imidazolidine-4-carboxamide;
180) (S)—N—((S)-(4-chlorophenyl)(2-methylbenzo[d]thiazol-6-yl)methyl)-2-oxo-imidazolidine-4-carboxamide;
181) (S)—N—((R)-(3-chloro-4-fluorophenyl)(4-(methylsulfonyl)phenyl)methyl)-2-oxoimidazolidine-4-carboxamide;
182) (S)—N—((S)-(3-chloro-4-fluorophenyl)(4-(methylsulfonyl)phenyl)methyl)-2-oxo-imidazolidine-4-carboxamide;
183) (4S)—N-[(3-chloro-4-fluorophenyl)(5-cyanopyridin-2-yl)methyl]-2-oxoimidazolidine-4-carboxamide;
184) (S)—N—((R)-benzo[d]thiazol-2-yl(3-chloro-4-fluoro-phenyl)methyl)-2-oxo-imidazolidine-4-carboxamide;
185) (S)—N—((S)-benzo[d]thiazol-2-yl(3-chloro-4-fluoro-phenyl)methyl)-2-oxo-imidazolidine-4-carboxamide;
186) (S)—N—((R)-benzo[d]oxazol-2-yl(3-chloro-4-fluoro-phenyl)methyl)-2-oxo-imidazolidine-4-carboxamide;
187) (S)—N—((S)-benzo[d]oxazol-2-yl(3-chloro-4-fluoro-phenyl)methyl)-2-oxo-imidazolidine-4-carboxamide;
188) (S)—N—((R)-(8,8-difluorobicyclo[4.2.0]octa-1(6),2,4-trien-3-yl)(4-(trifluoromethoxy)-phenyl)methyl)-2-oxoimidazolidine-4-carboxamide;
189) (S)—N—((S)-(8,8-difluorobicyclo[4.2.0]octa-1(6),2,4-trien-3-yl)(4-(trifluoromethoxy)-phenyl)methyl)-2-oxoimidazolidine-4-carboxamide;
190) (S)—N—((R)-(4-chlorophenyl)(7,7-difluorobicyclo[4.2.0]octa-1(6),2,4-trien-3-yl)methyl)-2-oxoimidazolidine-4-carboxamide;
191) (S)—N—((S)-(4-chlorophenyl)(7,7-difluorobicyclo[4.2.0]octa-1(6),2,4-trien-3-yl)methyl)-2-oxoimidazolidine-4-carboxamide;
192) (4S)—N—((R)(4-chlorophenyl)((R)2,2-dimethyl-1-(2,2,2-trifluoroethyl)piperidin-4-yl)methyl)-2-oxoimidazolidine-4-carboxamide;
193) (4S)—N—((R)(4-chlorophenyl)((S)2,2-dimethyl-1-(2,2,2-trifluoroethyl)piperidin-4-yl)methyl)-2-oxoimidazolidine-4-carboxamide;
194) (4S)—N—((S)(4-chlorophenyl)((S)2,2-dimethyl-1-(2,2,2-trifluoroethyl)piperidin-4-yl)methyl)-2-oxoimidazolidine-4-carboxamide; and
195) (4S)—N—((S)(4-chlorophenyl)((R)2,2-dimethyl-1-(2,2,2-trifluoroethyl)piperidin-4-yl)methyl)-2-oxoimidazolidine-4-carboxamide;

or a pharmaceutically acceptable salt thereof.

12. A compound selected from:
1) (S)—N—((R)-(5-fluoro-6-(trifluoromethyl)pyridin-2-yl)(4-(trifluoromethoxy)-phenyl)-methyl)-2-oxoimidazolidine-4-carboxamide;
2) (S)—N—((S)-(5-fluoro-6-(trifluoromethyl)pyridin-2-yl)(4-(trifluoromethoxy)-phenyl)-methyl)-2-oxoimidazolidine-4-carboxamide;
3) (S)—N—((R)-(3-chlorophenyl)(4-(trifluoromethoxy)phenyl)methyl)-2-oxoimidazolidine-4-carboxamide;
4) (S)—N—((S)-(3-chlorophenyl)(4-(trifluoromethoxy)phenyl)methyl)-2-oxoimidazolidine-4-carboxamide;
5) (S)—N—((R)-(3-chloro-2,4-difluorophenyl)(6-(2,2,2-trifluoroethoxy)pyridin-3-yl)methyl)-2-oxoimidazolidine-4-carboxamide;
6) (S)—N—((S)-(3-chloro-2,4-difluorophenyl)(6-(2,2,2-trifluoroethoxy)pyridin-3-yl)methyl)-2-oxoimidazolidine-4-carboxamide;

7) (S)—N—((R)-(3-chloro-2,4-difluorophenyl)(trans-3-(trifluoromethyl)cyclobutyl)-methyl)-2-oxoimidazolidine-4-carboxamide; and
8) (S)—N—((S)-(3-chloro-2,4-difluorophenyl)(trans-3-(trifluoromethyl)cyclobutyl)-methyl)-2-oxoimidazolidine-4-carboxamide;

or a pharmaceutically acceptable salts thereof.

13. A composition comprising a compound of claim 1, or a pharmaceutically acceptable salt thereof, and a pharmaceutically acceptable carrier.

14. A method of treating a disorder selected from: a pain disorder, a cough disorder, an acute itch disorder or a chronic itch disorder in a patient in need thereof comprising administration of a therapeutically effective amount of a compound according to claim 1, or a pharmaceutically acceptable salt thereof.

15. The method of claim 14 wherein the disorder is a pain disorder.

16. The method of claim 15 wherein the pain disorder is selected from: acute pain, inflammatory pain, and neuropathic pain.

17. The compound according to claim 12 which is: (S)—N—((R)-(3-chlorophenyl)(4-(trifluoromethoxy)phenyl)methyl)-2-oxoimidazolidine-4-carboxamide; or a pharmaceutically acceptable salt thereof.

18. The compound according to claim 12 which is: (S)—N—((S)-(3-chlorophenyl)(4-(trifluoromethoxy)phenyl)methyl)-2-oxoimidazolidine-4-carboxamide; or a pharmaceutically acceptable salt thereof.

19. The compound according to claim 12 which is: (S)—N—((R)-(5-fluoro-6-(trifluoromethyl)pyridin-2-yl)(4-(trifluoromethoxy)phenyl)methyl)-2-oxoimidazolidine-4-carboxamide; or a pharmaceutically acceptable salt thereof.

20. The compound according to claim 12 which is: (S)—N—((S)-(5-fluoro-6-(trifluoromethyl)pyridin-2-yl)(4-(trifluoromethoxy)phenyl)methyl)-2-oxoimidazolidine-4-carboxamide; or a pharmaceutically acceptable salt thereof.

21. The compound according to claim 12 which is: (S)—N—((R)-(3-chloro-2,4-difluorophenyl)(trans-3-(trifluoromethyl)cyclobutyl)-methyl)-2-oxoimidazolidine-4-carboxamide; or a pharmaceutically acceptable salt thereof.

22. The compound according to claim 12 which is: (S)—N—((S)-(3-chloro-2,4-difluorophenyl)(trans-3-(trifluoromethyl)cyclobutyl)-methyl)-2-oxoimidazolidine-4-carboxamide; or a pharmaceutically acceptable salt thereof.

23. A method of treating a disorder selected from: nociception, osteoarthritis, peripheral neuropathy, inherited erythromelalgia, multiple sclerosis, asthma, itch, atopy, allergic dermatitis, contact dermatitis, renal failure, cholestasis, pruritus, migraine, neurodegeneration following ischemia, epilepsy, spontaneous pain, acute pain due to fractures, musculoskeletal damage, pancreatitis and renal colic, pre-operative pain, peri-operative pain, post-operative pain, post herpetic neuralgia, trigeminal neuralgia, diabetic neuropathy, chronic lower back pain, phantom limb pain, sciatica, pain caused by 2° or 3° burn injury, burning mouth syndrome, optic neuritis, pain resulting from cancer and chemotherapy, chronic pelvic pain, pain syndromes, and complex regional pain syndromes, central pain syndromes, post surgical pain syndromes, post mastectomy syndrome, post thoracotomy syndrome, stump pain, bone and joint pain, vulvodynia, pain associated with HIV, and HIV treatment-induced neuropathy, nerve injury, root avulsions, painful traumatic mononeuropathy, painful polyneuropathy, erythromyelalgia, paroxysmal extreme pain disorder, small fiber neuropathy, repetitive motion pain, dental pain, myofascial pain, muscular injury, fibromyalgia, chronic pain, dysmennorhea, pain associated with angina, shoulder tendonitis, bursitis, gouty arthritis, aolymyalgia rheumatica, primary hyperalgesia, secondary hyperalgesia, primary allodynia, secondary allodynia, pain caused by central sensitization, chronic arthritic pain, cluster headache, non-vascular headache, traumatic nerve injury, nerve compression, nerve entrapment, and neuroma pain in a patient in need thereof comprising administration of a therapeutically effective amount of a compound according to claim 1.

24. The method of claim 23 wherein the disorder is selected from: osteoarthritis, peripheral neuropathy, acute pain due to fractures, musculoskeletal damage, pancreatitis and renal colic, pre-operative pain, peri-operative pain, post-operative pain, diabetic neuropathy, chronic lower back pain, pain resulting from chemotherapy, bone and joint pain, myofascial pain, muscular injury, fibromyalgia, shoulder tendonitis, and bursitis.

25. The method of claim 23 wherein the disorder is chronic pain.

26. The compound according to claim 12 which is: (S)-N-((R)-(3-chlorophenyl)(4-(trifluoromethoxy)phenyl)methyl)-2-oxoimidazolidine-4-carboxamide.

27. A composition comprising a compound of claim 26, and a pharmaceutically acceptable carrier.

28. A method of treating a disorder selected from: osteoarthritis, peripheral neuropathy, acute pain due to fractures, musculoskeletal damage, pancreatitis and renal colic, pre-operative pain, peri-operative pain, post-operative pain, diabetic neuropathy, chronic lower back pain, pain resulting from chemotherapy, bone and joint pain, myofascial pain, muscular injury, fibromyalgia, shoulder tendonitis, and bursitis in a patient in need thereof comprising administration of a therapeutically effective amount of a compound according to claim 26.

29. The compound according to claim 12 which is: (S)-N-((S)-(3-chlorophenyl)(4-(trifluoromethoxy)phenyl)methyl)-2-oxoimidazolidine-4-carboxamide.

30. A composition comprising a compound of claim 29, and a pharmaceutically acceptable carrier.

31. A method of treating a disorder selected from: osteoarthritis, peripheral neuropathy, acute pain due to fractures, musculoskeletal damage, pancreatitis and renal colic, pre-operative pain, peri-operative pain, post-operative pain, diabetic neuropathy, chronic lower back pain, pain resulting from chemotherapy, bone and joint pain, myofascial pain, muscular injury, fibromyalgia, shoulder tendonitis, and bursitis in a patient in need thereof comprising administration of a therapeutically effective amount of a compound according to claim 29.

32. The compound according to claim 12 which is: (S)-N4R)-(5-fluoro-6-(trifluoromethyl)pyridin-2-yl)(4-(trifluoromethoxy)phenyl)methyl)-2-oxoimidazolidine-4-carboxamide.

33. A composition comprising a compound of claim 32, and a pharmaceutically acceptable carrier.

34. A method of treating a disorder selected from: osteoarthritis, peripheral neuropathy, acute pain due to fractures, musculoskeletal damage, pancreatitis and renal colic, pre-operative pain, peri-operative pain, post-operative pain, diabetic neuropathy, chronic lower back pain, pain resulting from chemotherapy, bone and joint pain, myofascial pain, muscular injury, fibromyalgia, shoulder tendonitis, and bursitis in a patient in need thereof comprising administration of a therapeutically effective amount of a compound according to claim 32.

35. The compound according to claim 12 which is: (S)-N-((S)-(5-fluoro-6-(trifluoromethyl)pyridin-2-yl)(4-(trifluoromethoxy)phenyl)methyl)-2-oxoimidazolidine-4-carboxamide.

36. A composition comprising a compound of claim 35, and a pharmaceutically acceptable carrier.

37. A method of treating a disorder selected from: osteoarthritis, peripheral neuropathy, acute pain due to fractures, musculoskeletal damage, pancreatitis and renal colic, pre-operative pain, peri-operative pain, post-operative pain, diabetic neuropathy, chronic lower back pain, pain resulting from chemotherapy, bone and joint pain, myofascial pain, muscular injury, fibromyalgia, shoulder tendonitis, and bursitis in a patient in need thereof comprising administration of a therapeutically effective amount of a compound according to claim 35.

38. The compound according to claim 12 which is: (S)-N-((R)-(3-chloro-2,4-difluorophenyl)(trans-3-(trifluoromethyl)cyclobutyl)-methyl)-2-oxoimidazolidine-4-carboxamide.

39. A composition comprising a compound of claim 38, and a pharmaceutically acceptable carrier.

40. A method of treating a disorder selected from: osteoarthritis, peripheral neuropathy, acute pain due to fractures, musculoskeletal damage, pancreatitis and renal colic, pre-operative pain, peri-operative pain, post-operative pain, diabetic neuropathy, chronic lower back pain, pain resulting from chemotherapy, bone and joint pain, myofascial pain, muscular injury, fibromyalgia, shoulder tendonitis, and bursitis in a patient in need thereof comprising administration of a therapeutically effective amount of a compound according to claim 38.

41. The compound according to claim 12 which is: (S)-N-((S)-(3-chloro-2,4-difluorophenyl)(trans-3-(trifluoromethyl)cyclobutyl)-methyl)-2-oxoimidazolidine-4-carboxamide.

42. A composition comprising a compound of claim 41, and a pharmaceutically acceptable carrier.

43. A method of treating a disorder selected from: osteoarthritis, peripheral neuropathy, acute pain due to fractures, musculoskeletal damage, pancreatitis and renal colic, pre-operative pain, peri-operative pain, post-operative pain, diabetic neuropathy, chronic lower back pain, pain resulting from chemotherapy, bone and joint pain, myofascial pain, muscular injury, fibromyalgia, shoulder tendonitis, and bursitis in a patient in need thereof comprising administration of a therapeutically effective amount of a compound according to claim 41.

44. A method of treating a disorder selected from: nociception, osteoarthritis, peripheral neuropathy, inherited erythromelalgia, multiple sclerosis, asthma, itch, atopy, allergic dermatitis, contact dermatitis, renal failure, cholestasis, pruritus, migraine, neurodegeneration following ischemia, epilepsy, spontaneous pain, acute pain due to fractures, musculoskeletal damage, pancreatitis and renal colic, pre-operative pain, peri-operative pain, post-operative pain, post herpetic neuralgia, trigeminal neuralgia, diabetic neuropathy, chronic lower back pain, phantom limb pain, sciatica, pain caused by 2° or 3° burn injury, burning mouth syndrome, optic neuritis, pain resulting from cancer and chemotherapy, chronic pelvic pain, pain syndromes, and complex regional pain syndromes, central pain syndromes, post surgical pain syndromes, post mastectomy syndrome, post thoracotomy syndrome, stump pain, bone and joint pain, vulvodynia, pain associated with HIV, and HIV treatment-induced neuropathy, nerve injury, root avulsions, painful traumatic mononeuropathy, painful polyneuropathy, erythromyelalgia, paroxysmal extreme pain disorder, small fiber neuropathy, repetitive motion pain, dental pain, myofascial pain, muscular injury, fibromyalgia, chronic pain, dysmennorhea, pain associated with angina, shoulder tendonitis, bursitis, gouty arthritis, aolymyalgia rheumatica, primary hyperalgesia, secondary hyperalgesia, primary allodynia, secondary allodynia, pain caused by central sensitization, chronic arthritic pain, cluster headache, non-vascular headache, traumatic nerve injury, nerve compression, nerve entrapment, and neuroma pain in a patient in need thereof comprising administration of a therapeutically effective amount of a compound according to claim 12.

45. The method of claim 44 wherein the disorder is selected from:
osteoarthritis, peripheral neuropathy, acute pain due to fractures, musculoskeletal damage, pancreatitis and renal colic, pre-operative pain, peri-operative pain, post-operative pain, diabetic neuropathy, chronic lower back pain, pain resulting from chemotherapy, bone and joint pain, myofascial pain, muscular injury, fibromyalgia, shoulder tendonitis, and bursitis.

46. The method of claim 44 wherein the disorder is chronic pain.

* * * * *

UNITED STATES PATENT AND TRADEMARK OFFICE
CERTIFICATE OF CORRECTION

PATENT NO. : 11,802,122 B2
APPLICATION NO. : 17/347639
DATED : October 31, 2023
INVENTOR(S) : Ashok Arasappan et al.

It is certified that error appears in the above-identified patent and that said Letters Patent is hereby corrected as shown below:

In the Claims

Claim 1, Column 193, Lines 28-49: under variable "each Ra is independently selected from" please indent 25)-46) as shown below:
    25) –C2-6alkenyl-aryl,
    26) –C2-6alkenyl-heteroaryl,
    27) –C2-6alkynyl-C3-6cycloalkyl,
    28) –C2-6alkynyl-C2-6cycloheteroalkyl,
    29) –C2-6alkynyl-aryl,
    30) –C2-6alkynyl-heteroaryl,
    31) –OH,
    32) –(CH2)p-O-C1-6alkyl,
    33) –(CH2)p -O-C2-6alkenyl,
    34) –(CH2)p -O-C2-6alkynyl,
    35) –(CH2)p -O-C3-6cycloalkyl,
    36) –(CH2)p -O-C2-6heterocycloalkyl,
    37) –(CH2)p -O-aryl,
    38) –(CH2)p -O-heteroaryl,
    39) –OC1-6alkyl-C3-6cycloalkyl,
    40) –OC1-6alkyl-C2-6heterocycloalkyl,
    41) –OC1-6alkyl-aryl,
    42) –OC1-6alkyl-heteroaryl,
    43) –S(O)mRi,
    44) –C1-6alkyl-S(O)mRi,
    45) –N(Rk)2, and
    46) –NRkRL, Claim 5, Column 195, Line 46, after "and OC1-6alkyl" delete "," replace with ";"

Signed and Sealed this
Twenty-sixth Day of March, 2024

Katherine Kelly Vidal
*Director of the United States Patent and Trademark Office*

CERTIFICATE OF CORRECTION (continued)
U.S. Pat. No. 11,802,122 B2

Claim 11, Column 202, Line 24, add a ";" after "97) (S)-N-((R)-(3-chloro-4-(trifluoromethoxy) phenyl) (2-(trifluoromethyl)oxazol-4-yl)methyl)-2-oxoimidazolidine-4-carboxamide"

Claim 32, Column 208, Line 53, delete "(S)-N4R)" replace with "(S)-N-((R)-"

Claim 45, Column 210, Line 36, after "osteoarthritis," delete the extra space